(12) United States Patent
Shi et al.

(10) Patent No.: US 10,174,033 B2
(45) Date of Patent: Jan. 8, 2019

(54) $N^6$-SUBSTITUTED ADENOSINE DERIVATIVES AND $N^6$-SUBSTITUTED ADENINE DERIVATIVES AND USES THEREOF

(75) Inventors: Jiangong Shi, Beijing (CN); Jianjun Zhang, Beijing (CN); Zhenggang Yue, Beijing (CN); Min Li, Beijing (CN); Chenggen Zhu, Beijing (CN); Ying Zhang, Beijing (CN); Jiachen Zi, Beijing (CN); Yafang Wang, Beijing (CN); Xiaona Fan, Beijing (CN); Ruiming Xu, Beijing (CN); Sheng Lin, Beijing (CN); Yan Li, Beijing (CN); Yongchun Yang, Beijing (CN); Li Sheng, Beijing (CN)

(73) Assignee: INSTITUTE OF MATERIA MEDICA, CHINESE ACADEMY OF MEDICAL SCIENCES, Beijing (CN)

( * ) Notice: Subject to any disclaimer, the term of this patent is extended or adjusted under 35 U.S.C. 154(b) by 24 days.

(21) Appl. No.: 13/515,152

(22) PCT Filed: Dec. 10, 2009

(86) PCT No.: PCT/CN2009/075478
§ 371 (c)(1),
(2), (4) Date: Sep. 18, 2012

(87) PCT Pub. No.: WO2011/069294
PCT Pub. Date: Jun. 16, 2011

(65) Prior Publication Data
US 2013/0045942 A1    Feb. 21, 2013

(51) Int. Cl.
*C07D 473/34*    (2006.01)
*C07H 19/167*    (2006.01)

(52) U.S. Cl.
CPC ......... *C07D 473/34* (2013.01); *C07H 19/167* (2013.01)

(58) Field of Classification Search
None
See application file for complete search history.

(56) References Cited

U.S. PATENT DOCUMENTS

| | | | | |
|---|---|---|---|---|
| 3,502,649 A * | 3/1970 | Dietmann | ............... | A61K 31/70 536/27.62 |
| 2005/0153989 A1 * | 7/2005 | Grotzfeld | ............. | A61K 31/519 514/260.1 |
| 2012/0295863 A1 † | 11/2012 | Lin | | |

FOREIGN PATENT DOCUMENTS

| CN | 1217952 C | 9/2005 | |
|---|---|---|---|
| EP | 0179630 A2 * | 4/1986 | ........... C07H 19/167 |
| WO | 02/18404 A2 | 3/2002 | |
| WO | 2004/058791 A2 | 7/2004 | |

OTHER PUBLICATIONS

Koszalka, G. W., Averett, D. R., Fyfe, J. A., Roberts, G. B., Spector, T. H. O. M. A. S., Biron, K. A. R. E. N., & Krenitsky, T. A. (1991). 6-N-substituted derivatives of adenine arabinoside as selective inhibitors of varicella-zoster virus. Antimicrobial agents and chemotherapy, 35(7), 1437-1443.*
Gao, Z. G., Blaustein, J. B., Gross, A. S., Melman, N., & Jacobson, K. A. (2003). N 6-Substituted adenosine derivatives: selectivity, efficacy, and species differences at A 3 adenosine receptors. Biochemical pharmacology, 65(10), 1675-1684.*
Ukena, D., Olsson, R. A., & Daly, J. W. (1987). Definition of subclasses of adenosine receptors associated with adenylate cyclase: interaction of adenosine analogs with inhibitory A1 receptors and stimulatory A2 receptors. Canadian journal of physiology and pharmacology.*
PubChem record for 1-phenyl-1-aminopropane and 1-phenyl-1-aminobutane, retrieved from https://pubchem.ncbi.nlm.nih.gov/compound on Apr. 12, 2107.*
Dolezal, K. et al., "Preparation, biological activity and endogenous occurrence of $N^6$-benzyladenosines" *Bioorganic & Medicinal Chemistry* (2007) pp. 3737-3747, vol. 15.
Kwatra, M.M. et al., "$N^6$-phenyladenosines: Pronounced Effect of Phenyl Substituents on Affinity for $A_2$ Adenosine Receptors" *Journal of Med. Chem.* (May 1987) pp. 954-956, vol. 30, No. 5.
Huang, N.K., et al., "Neuroprotective Principles from *Gastrodia elata*" *J. Nat. Prod.* (2007) pp. 571-574, vol. 70.
International Search Report dated Oct. 8, 2012, issued in International Application No. PCT/CN2009/075478.
Kusachi S et al. "Dog coronary artery adenosine receptor: structure of the N6-aryl subregion" J Med Chem. Jun. 1986;29(6):989-96.†

* cited by examiner
† cited by third party

*Primary Examiner* — Shaojia A Jiang
*Assistant Examiner* — Dale R Miller
(74) *Attorney, Agent, or Firm* — Scully Scott Murphy & Presser

(57) ABSTRACT

The present invention provides $N^6$-substituted adenosine derivatives and $N^6$-substituted adenine derivatives, manufacturing methods thereof, a pharmaceutical composition comprising the said compounds above, and uses of these compounds in manufacturing medicaments and health-care products for treating insomnia, convulsion, epilepsy, and Parkinson's diseases, and preventing and treating dementia.

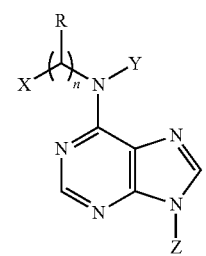

6 Claims, No Drawings

$N^6$-SUBSTITUTED ADENOSINE DERIVATIVES AND $N^6$-SUBSTITUTED ADENINE DERIVATIVES AND USES THEREOF

FIELD OF THE INVENTION

The invention belongs to the field of pharmaceuticals and therapeutics. The invention relates to $N^6$-substituted adenosine derivatives and $N^6$-substituted adenine derivatives, manufacturing methods, pharmaceutical compositions comprising such compounds, and uses of these compounds in manufacturing medicaments and health care products for treating insomnia, convulsion, epilepsy, and Parkinson's diseases, and for preventing and treating dementia.

BACKGROUND OF THE INVENTION $N^6$-substituted adenosine derivatives and $N^6$-substituted adenine derivatives are important bioactive compounds. Some of them are present as trace ingredients in plants as cytokinin to promote plant cell division and differentiation, and have important biological functions on promotion of seed germination, bud differentiation, and branch formation, as well as on production of chlorophyll and starch. In addition, they have been widely used in plant biotechnological research. Recent research shows that histidine kinases AHK2, AHK3 and AHK4 act as cytokinin receptor and play an important role in cytokinin signal transduction. Among them, research was focused on $N^6$-isopentenyl-adenine derivaties, but less on $N^6$-isopentenyl-adenosine. Meanwhile, due to the important physiological role, investigations were focused on antitumor and antivirus activities of these compounds, and some researchers conducted studies of $N^6$-phenyl-adenosine derivatives, $N^6$-phenylisopropyl-adenosine derivatives, and $N^6$-cyclohexyl-adenosine derivatives, and activation of adenylate cyclase by these compounds through inhibiting adenosine receptor $A_1$ and $A_2$. However, so far, there is no experimental report of whether $N^6$-substituted-adenosine derivatives have any sedative, hypnotic, anticonvulsant, or antiepileptic effects, or effects in treating Parkinson's disease or in prevention of dementia. See, Karel Dolezal; Igor Popa; Eva Hauserova; Lukas Spichal; Kuheli Chakrabarty; Ondrej Novak; Vladimir Krystof; Jiri Voller; Jan Holub and Miroslav Strnad, Preparation, biological activity and endogenous occurrence of $N^6$-benzyladenosines, Bioorganic & Medicinal Chemistry, 2007, 15, 3737-3747 (as well as the references in this article); Substitution Derivatives of $N^6$-benzyladenosine, Methods of Their Preparation, Their Use for Preparation of Drugs, Cosmetic Preparations and Growth Regulations Containing This Compounds, WO 2004/058791 A2, 15 Jul. 2004; Madan M. Kwatra; Edward Leung; M. Marlene Hosey, Richrad D. Dreen, $N^6$-phenyladenosines: Pronounced Effect of Phenyl Substituents on Affinity for $A_2$ Adenosine Receptors, 1987, 30, 954-956 (as well as the references in this article).

Recently, $N^6$-(4-hydroxybenzyl)-adenosine was reported from *Rhizoma Gastrodiae*, and was found to be effective in preventing PC12 cell apoptosis and binding to adenosine $A_{2A}$ receptor. However, there is no report of whether this compound and its analogues have any sedative and hypnotic effects in the central nervous and mental systems. Nai-Kuei Huang, Yijuang Chem, Jim-Min Fang, Chia-I Lin, Wang-Ping Chen, and Yun-Lian Lin, Neuroprotective Principles from *Gastrodia elata*, J. Nat. Prod., 2007, 70, 571-574 (references cited therein).

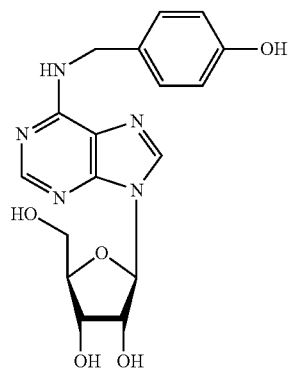

$N^6$-(4-hydroxybenzyl)-adenine riboside

DISCLOSURE OF THE INVENTION

Firstly, this invention provides a group of $N^6$-substituted-adenosine and $N^6$-substituted-adenine compounds.

Secondly, this invention provides preparation methods of the $N^6$-substituted-adenosine and $N^6$-substituted-adenine compounds.

Thirdly, this invention provides pharmaceutical compositions containing $N^6$-substituted-adenosine and $N^6$-substituted-adenine compounds.

Additionally, this invention provides uses of the $N^6$-substituted-adenosine and $N^6$-substituted-adenine compounds.

Through bioassay-guided fractionation, the inventors isolated $N^6$-(4-hydroxy-benzyl)-adenosine with significant sedative and hypnotic effects from Rhizomes of *Gastrodia elata* and *Gymnadenia conopsea* in the studies of bioactive constituents of the two materials. On the basis of this finding, the synthesis and structural modification of $N^6$-(4-hydroxybenzyl)-adenosine and further evaluations of the sedative, hypnotic, anticonvulsant, and antiepileptic activities of the compounds were carried out, which confirmed the activities of these compounds, in particularly the sedative and hypnotic activities. Because clinical and practical experiences demonstrate that a lack of sleep or psychological stress is closely related to diseases of the nervous and mental systems, such as depression, convulsion, epilepsy, Parkinson's disease, senile dementia, etc., the compounds of the invention can also be used as drugs and health care products to treat depression, convulsion, epilepsy, Parkinson's disease and to prevent and treat dementia.

In this invention, the general structure of the $N^6$-substituted adenosine derivatives and $N^6$-substituted adenine derivatives is shown by formula VI, including the derived esters, stereoisomers, and ethers, as well as pharmaceutically acceptable salts.

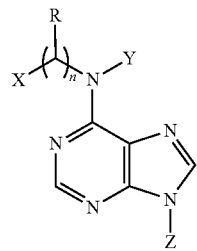

(VI)

Wherein n is an integer selected from 0-4, preferably from 1-3, more preferably from 1-2.

X is selected from the group consisting of substituted and unsubstituted phenyls, substituted and unsubstituted furyls, substituted and unsubstituted thiopheneyls, substituted and unsubstituted pyrrolyls, substituted and unsubstituted naphthyls, substituted and unsubstituted tetrahydro-naphthyls, substituted and unsubstituted fluoreneyls, substituted and unsubstituted imidazolyls, substituted and unsubstituted indyls, substituted and unsubstituted 1H-imidazolyls, substituted and unsubstituted 1H-indyls, substituted and unsubstituted C3-8cycloalkyls, and substituted and unsubstituted C1-16 alkyls with straight and branched chains.

Y is selected from the group consisting of H, substituted and unsubstituted C1-16 alkyls with a straight chain, substituted and unsubstituted C1-16 alkyls with a branched chain; preferably from H, C1-4 alkyls a straight chain, and C1-4 alkyls with a branched chain; more preferably from H, C1-2 alkyls with a straight chain, and C1-2 alkyls with a branched chain; and most preferably from H.

R is selected from the group consisting of H, hydroxyl, substituted and unsubstituted C1-6 alkyls with a straight chain, substituted and unsubstituted C1-6 alkyls with a branched chain, substituted and unsubstituted C3-8cycloalkyls, substituted and unsubstituted phenyls (Ph), and COOR' (wherein, R' is selected from the group consisting of H and C1-6 alkyls).

When R' is selected as H, COOR' is a carboxyl group (COOH). When R' is selected from the group consisting of C1-6 alkyls, COOR' are alkoxylformyl groups with C1-6 alkyl chains.

R is preferably selected from H, hydroxyl, C1-6 alkyls, hydroxy substituted C1-6 alkyls, cyclohexyl, and COOR' (wherein R' is selected from the group consisting of H and C1-4 alkyls); more preferably from H, hydroxyl, methyl (Me), ethyl (Et), propyl (Pr), cyclohexyl, hydroxymethyl (CH$_2$OH), 2-hydroxypropyl [CH$_2$CH(CH$_3$)OH], carboxyl (COOH), and C1-2 alkoxylformyls [COOR' (wherein, R' is selected from the group consisting of methyl and ethyl)]; and most preferably from H, hydroxyl, methyl, ethyl, propyl, and hydroxymethyl.

Z is selected from the group consisting of ribosyl, esterified ribosyls, etherified ribosyls, 2'-deoxyribosyl, esterified 2'-deoxy ribosyls, etherified 2'-deoxyribosyls, tetrahydrofuranyl, and substituted and unsubstituted aliphatic groups. Z is preferably selected from ribosyl, esterified ribosyls, etherified ribosyls, 2'-deoxyribosyl, esterified 2'-deoxyribosyls, and etherified 2'-deoxyribosyl; more preferably from ribosyl, esterified ribosyls, and etherified ribosyls.

When n is not 0, e.g. an integer selected from 0-4, and when both R and X are not selected as H, the configuration at the carbon atom connected with R and X includes both R and S (a mixture of epimers at the carbon atom), R (an optical pure compound with the R configuration at the carbon atom), and S (an optical pure compound with the S configuration at the carbon atom).

The structural moiety, represented by

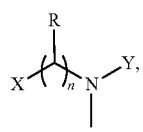

can also be selected from the group consisting of (5R)-5-carboxy-2-pyrrolyl, (5S)-5-carboxy-2-pyrrolyl, (5R)-5-hydroxymethyl-2-pyrrolyl, (5S)-5-hydroxymethyl-2-pyrroleyl, and substituted and unsubstituted phenylpiperazinyls, amino acid units, and amino acid ester units.

When the structural moiety

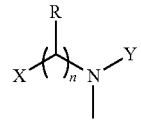

is selected from the group consisting of amino acid units, it can be any known amino acid unit with the D or L configuration. The amino acid unit is preferably selected from phenylalanine, tyrosine, tryptophane, histidine, proline, valine, threonine, serine, glycine, and prolinol. The COOH of amino acid unit can be esterified with any alcohol, preferably esterified with C1-16 alkyl alcohols; more preferably esterified with methanol and ethanol.

The structural moiety

can also be selected from the group consisting of substituted and unsubstituted furanyls, substituted and unsubstituted thienyls, substituted and unsubstituted pyrrolyls, substituted and unsubstituted imidazolyls, substituted and unsubstituted naphthyls, substituted and unsubstituted tetrahydro-naphthyls, substituted and unsubstituted indyls, substituted and unsubstituted fluoreneyls, and substituted and unsubstituted C3-8 cycloalkyls.

Wherein, the substitution group(s) in the above structural moiety is selected from the group consisting of H, hydroxyl (OH), amino (NH$_2$), nitro (NO$_2$), phenyl (Ph), methylenedioxy (OCH$_2$O), halogens, C1-16 alkyls, C1-16 alkoxyls, C1-16 alkthioyl, and C1-16 alkacyloxoyls. The alkyl in C1-16 alkyls, C1-16 alkoxyls, C1-16 alkthioyl, and C1-16 alkacyloxoyls can have straight and branched chains which are unsubstituted or substituted by halogen, hydroxyl, and amino group(s).

The substitution groups is preferably selected from H, hydroxyl, amino, phenyl, methylenedioxy, halogen(s) (F, Cl, Br, and I), C1-10 alkyls, C1-10 alkoxyls, C1-10 alkthioyl, and C1-10 alkacyloxoyls. The alkyl in C1-10 alkyls, C1-10 alkoxyls, C1-10 alkthioyl, and C1-10 alkacyloxoyls can have straight and branched chains which are unsubstituted or substituted by halogen, hydroxyl, and amino group(s).

The substitution groups is more preferably selected from H, hydroxyl, amino, phenyl, methylenedioxy, halogen(s) (F, Cl, Br, and I), C1-6 alkyls, C1-6 alkoxyls, C1-6 alkthioyl, and C1-6 alkacyloxoyls. The alkyl in C1-6 alkyls, C1-6 alkoxyls, C1-6 alkthioyl, and C1-6 alkacyloxoyls can have straight and branched chains which are unsubstituted or substituted by halogen, hydroxyl, and amino group(s).

The substitution groups is most preferably selected from H, methyl, ethyl, propyl, isopropyl, methoxy, ethoxy, propoxy, isopropoxy, methylthio, acetoxy, propionyloxy, trifluoromethyl, trifluoromethoxyl, fluoro, chloro, bromo, and methylenedioxy.

R is selected from the group consisting of H, hydroxy, substituted and unsubstituted C1-16 alkyls with a straight or branched chain, substituted and unsubstituted C3-8 cycloalkyls, substituted and unsubstituted phenyl (Ph), and COOR' (R' is selected from the group consisting of H and C1-6 alkyls). The further substitution group(s) of R is selected from the group consisting of hydroxyl, amino, nitro, methylenedioxy, and halogens; more preferably from hydroxyl, methylenedioxy and halogen; and most preferably from hydroxyl.

For the substituted or unsubstituted furyl(s), the $N^6$ atom of the parent structure can connect with any suitable position of the furyls, e.g. position 2 [2-furyl(s)] and position 3 [3-furyl(s)].

For the substituted or unsubstituted thienyls, the $N^6$ atom of the parent structure can connect with any suitable position of the thienyl(s), e.g. position 2 [2-thienyl(s)] and position 3 [3-thienyl(s)].

For the substituted or unsubstituted pyrrolyl(s), the $N^6$ atom of the parent structure can connect with any suitable position of the pyrrolyl(s), e.g. position 2 [2-pyrrolyl(s)] and position 3 [3-pyrrolyl(s)].

For the substituted or unsubstituted imidazolyl(s), the $N^6$ atom of the parent structure can connect with any suitable position of the imidazolyl(s), and preferably with position 4.

For the substituted or unsubstituted naphthyl(s), the $N^6$ atom of the parent structure can connect with any suitable position of the napthyl(s), and preferably with position 1.

For the substituted or unsubstituted tetranaphthyl(s), the $N^6$ atom of the parent structure can connect with any suitable position of the tetranapthyl(s), and preferably with position 1.

For the substituted or unsubstituted indyl(s), the $N^6$ atom of the parent structure can connect with any suitable position of the indyl(s), and preferably with positions 1 and 3.

For the substituted or unsubstituted fluoren(s), the $N^6$ atom of the parent structure can connect with any suitable position of the fluoren(s), and preferably with position 9.

For the substituted or unsubstituted C3-8 cycloalkyl(s), the $N^6$ atom of the parent structure can connect with any suitable position of the C3-8 cycloalkyl(s).

For the substituted phenyl group(s), the substituted position(s) can be position(s) 2~6, the number of the substitution group(s) can be 1~5; and the substituted position for methylenedioxy ($OCH_2O$) is preferably at ortho position.

Thereof, the straight-chain alkyl(s) includes saturated and unsaturated aliphatic chains containing one to sixteen carbons. The unsaturated group(s) in the unsaturated straight alophatic chain(s) includes the 1~4 unconjugated and/or conjugated double bond(s), and/or a terminal triple bond.

Thereof, the branched-chain alkyl(s) includes the saturated and unsaturated aliphatic branched chains containing one to sixteen carbons, the number of branched chain is selected form 1~2. The unsaturated group(s) in the unsaturated straight alophatic chain(s) includes the 1~4 unconjugated and/or conjugated double bond(s), and/or a terminal triple bond.

Thereof, the esterified ribosyl and 2'-deoxyribosyl refer to esterification of the hydroxyl group(s) in the ribosyl and 2'-deoxyribosyl. Wherein, the acids used for esterification are saturated C1-16 aliphatic acids, unsaturated C1-16 aliphatic acids [containing 1-4 unconjugated and/or conjugated double bond(s), and a terminal triple bond], phenylpropionic acid, p-methyl-phenylacrylic acid, p-hydroxyphenylpropionic acid, phenylacrylic acid, p-phenylacrylic acid, and ferulic acid. The esterified position(s) is at 2'-, 3'- and/or 5'-hydroxyl group(s) for the ribosyl and at 3'- and/or 5'-hydroxyl group(s) for the for 2'-deoxyribosyl.

Thereof, the etherified ribosyl(s) and 2'-deoxyribosyl(s) imply that the hydroxyl group(s) of the ribosyl and 2'-deoxyribosyl is etherified. Wherein, the group(s) used for the etherification includes saturated C1-16 aliphatic groups, unsaturated C1-16 aliphatic groups [containing 1~4 unconjugated and/or conjugated double bond(s), and/or terminal triple bond], phenylpropyl, p-methyl-phenylpropyl, phenylpropenyl, p-hydroxyphenylpropenyl, and nitrophenyl. The etherified position(s) is at 2'-, 3'- and/or 5'-hydroxyl group(s) for the ribosyl and at 3'- and/or 5'-hydroxyl group(s) for the for 2'-deoxyribosyl.

The preferable compounds, represented by the formula VI, include but are not limited to the compounds represented by the general structure I.

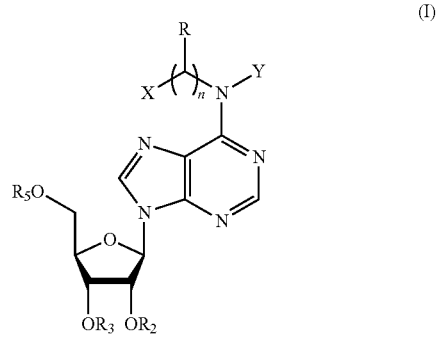

(I)

Wherein n is an integer selected from 0-4.

X is selected from the group consisting of substituted and unsubstituted phenyls, substituted and unsubstituted furyls, substituted and unsubstituted thiopheneyls, substituted and unsubstituted pyrrolyls, substituted and unsubstituted naphthyls, substituted and unsubstituted tetrahydro-naphthyls, substituted and unsubstituted fluoreneyls, substituted and unsubstituted imidazolyls, substituted and unsubstituted indyls, substituted and unsubstituted 1H-imidazolyls, substituted and unsubstituted 1H-indyls, substituted and unsubstituted C3-8 cycloalkyls, and substituted and unsubstituted C1-16 alkyls with straight and branched chains.

Y is selected from the group consisting of H and substituted and unsubstituted C1-6 alkyls with a straight or branched chain.

R is selected from the group consisting of H, hydroxy, substituted and unsubstituted C1-16 alkyls with a straight chain or a branched-chain, substituted or unsubstituted C3-8cycloalkyls, substituted or unsubstituted phenyls, and COOR' (R' is selected from the group consisting of H and C1-6 alkyls).

The structural moiety, represented by

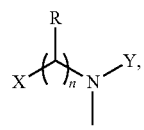

can also be selected from the group consisting of (5R)-5-carboxy-2-pyrrolyl, (5S)-5-carboxy-2-pyrrolyl, (5R)-5-hydroxymethyl-2-pyrrolyl, (5S)-5-hydroxymethyl-2-pyrroleyl, substituted and unsubstituted phenylpiperazinyls, amino acid units, and amino acid ester units.

The structural moiety, represented by

can also be selected from the group consisting of substituted and unsubstituted furanyls, substituted and unsubstituted thienyls, substituted and unsubstituted pyrrolyls, substituted and unsubstituted imidazolyls, substituted and unsubstituted naphthyls, substituted and unsubstituted tetrahydro-naphthyls, substituted and unsubstituted indyls, substituted and unsubstituted fluoreneyls, and C3-8 cycloalkyls.

Thereof, the substitution group(s) in the above structural moiety is selected from the group consisting of H, hydroxy (OH), amino ($NH_2$), nitro ($NO_2$), phenyl (Ph), methylenedioxy ($OCH_2O$), halogens, C1-16 alkyls, C1-16 alkoxyls, C1-16 alkthioyls, and C1-16 alkacyloxoyls. Wherein, the alkyl in the said C1-16 alkyls, C1-16 alkoxyls, C1-16 alkthioyls, and C1-16 alkacyloxoyls can be straight, breached, unsubstituted, and substituted, thereof the further substitution group(s) can be selected from the group consisting of halogens, hydroxyl, and amino groups.

$R_2$, $R_3$, and $R_5$ are independently selected from the group consisting of H, saturated and unsaturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxy-phenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

$R_2$, $R_3$, and $R_5$ are independently and preferably selected from saturated C7-12 alkyls, phenylpropyl, p-hydroxyphenylpropyl, p-methylphenylpropyl, phenylpropenyl, p-hydroxyphenylpropenyl, nitrophenyl, saturated C7-12 alkylacyls, phenylpropionyl, p-hydroxy-phenylpropionyl, p-methyl-phenylpropionyl, phenylpropenionyl, p-hydroxyphenylpropenionyl, and nitrophenylacyl.

$R_2$, $R_3$, and $R_5$ are independently and most preferably selected from propyl, o-nitrophenyl, decyl ($C_{10}H_{21}$), acetyl, propionyl, p-methylphenylpropenionyl, p-methoxyl-phenyl-propionyl, octanoyl, dodecanoyl ($C_{11}H_{23}CO$), thereof, $R_2$ and $R_3$ can be an isopropylidene.

The preferable compounds, represented by the formula I, include but are not limited to the compounds represented by the structure A.

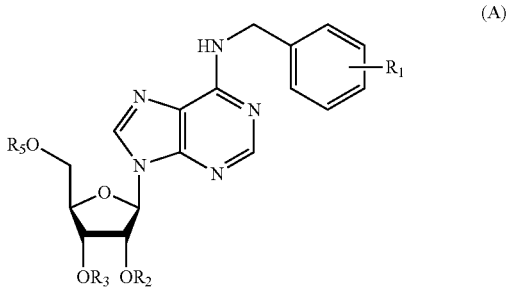

(A)

Wherein, $R_1$ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. Wherein, the alkyl in the said C1-16 alkyls, C1-16 alkoxyls, C1-16 alkthioyls, and C1-16 alkacyloxoyls can be straight, breached, unsubstituted, and substituted; thereof the further substitution group(s) can be selected from the group consisting of halogens, hydroxyl, and amino groups.

$R_2$, $R_3$, and $R_5$ are independently selected from the group consisting of H, saturated and unsaturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxy-phenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

The preferable compounds, represented by the formula A, include but are not limited to the compounds represented by formula Aa.

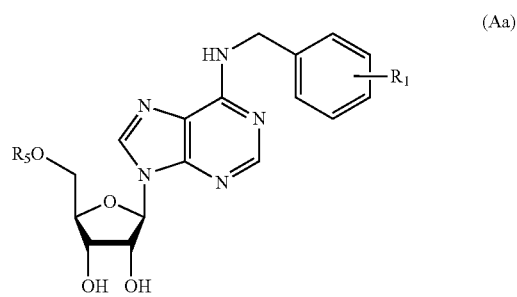

(Aa)

Wherein, $R_1$ is selected from the group consisting of H, hydroxy, amino, nitro, phenyl, methylenedioxy, halogens, C1-10 alkyls, C1-10 alkoxyls, C1-10 alkthioyls, and C1-10 alkacyloxoyls. Wherein, the alkyl in the said C1-10 alkyls, C1-10 alkoxyls, C1-10 alkthioyls, and C1-10 alkacyloxoyls can be straight, breached, unsubstituted, and substituted, thereof the further substitution group(s) can be selected from the group consisting of halogens, hydroxyl, and amino groups.

$R_5$ is selected from the group consisting of H, saturated C1-7 alkyls, phenylpropyl, p-hydroxy-phenylpropyl, p-methylphenylpropyl, phenylpropenyl, p-hydroxyphenylpropenyl, nitrophenyl, saturated C1-7 alkylacyls, phenylpropionyl, p-hydroxy-phenylpropionyl, p-methyl-phenylpropionyl, phenylpropenionyl, p-hydroxyphenylpropenionyl, and nitrophenylacyl.

The preferable compounds, represented by the formula Aa, include but are not limited to the compounds represented by the formula Aa1.

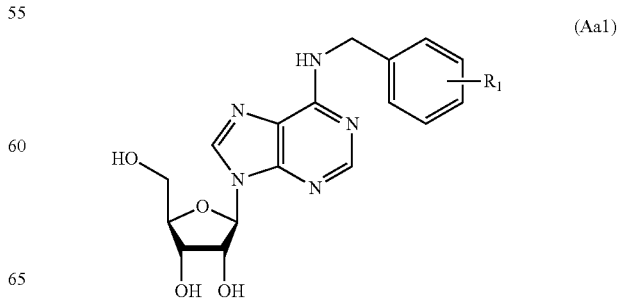

(Aa1)

Wherein,

R₁ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. Wherein, the alkyl in the said C1-6 alkyls, C1-6 alkoxyls, C1-6 alkthioyls, and C1-6 alkacyloxoyls can be straight, breached, unsubstituted, and substituted, thereof the further substitution group(s) can be selected from the group consisting of halogens, hydroxyl, and amino groups.

The preferable compounds, represented by the formula Aa, include but are not limited to the compounds represented by the formula Aa2.

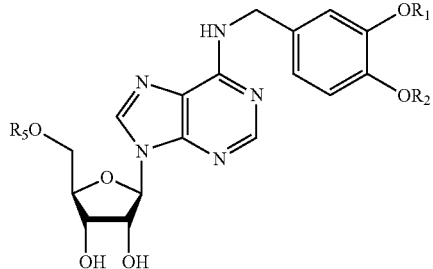

(Aa2)

Wherein,

R₁ and R₂ are independently selected from the group consisting of H, C1-6 alkyls, and C1-6 alkoxyls.

R₅ is selected from the group consisting of H, saturated C1-7 alkyls, phenylpropyl, p-hydroxy-phenylpropyl, p-methyl-phenylpropyl, phenylpropenyl, p-hydroxyphenylpropenyl, nitrophenyl, saturated C1-7 alkylacyls, phenylpropionyl, p-hydroxy-phenylpropionyl, p-methyl-phenylpropionyl, phenylpropenionyl, p-hydroxyphenylpropenionyl, and nitrophenylacyl.

The preferable compounds, represented by the formula A, include but are not limited to the compounds represented by the formula Ab.

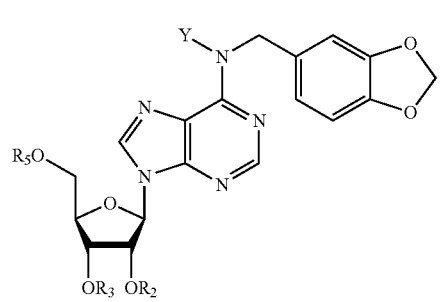

(Ab)

Wherein,

Y is selected from the group consisting of H, and C1-7 alkyls.

R₂, R₃, and R₅ are independently selected from the group consisting of H, saturated $C_1$-$C_{12}$ alkyls, phenylpropyl, p-hydroxy-phenylpropyl, p-methyl-phenylpropyl, phenylpropenyl, p-hydroxyphenylpropenyl, nitrophenyl, saturated and unsaturated $C_1$-$C_{12}$ alkylacyls, phenylpropionyl, p-hydroxy-phenylpropionyl, p-methyl-phenylpropionyl, phenylpropenionyl, p-hydroxyphenylpropenionyl, nitrophenylacyl, thereof, R₂ and R₃ can be interconnected to form a ring.

The preferable compounds represented by the formula Ab, include but are not limited to the compounds represented by the formula Ab1.

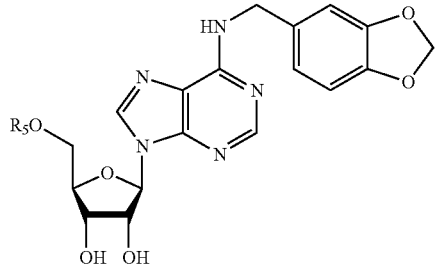

(Ab1)

Wherein,

R₅ is selected from the group consisting of H, saturated C7-12 alkyls, phenylpropyl, p-hydroxy-phenylpropyl, p-methyl-phenylpropyl, phenylpropenyl, p-hydroxyphenylpropenyl, nitrophenyl, saturated C7-12 alkylacyls, phenylpropionyl, p-hydroxy-phenylpropionyl, p-methyl-phenylpropionyl, phenylpropenionyl, p-hydroxyphenylpropenionyl, and nitrophenylacyl.

The preferable compounds represented by the formula 1, include but are not limited to the compounds represented by the formula B.

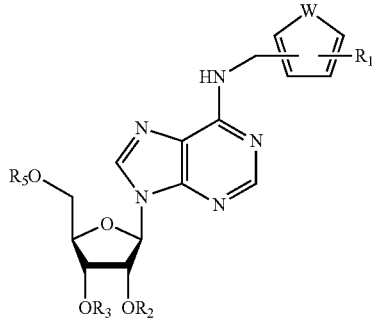

(B)

Wherein,

W is selected from the group consisting of oxygen (O), sulfur (S), and nitrogen (N) atoms.

R₁ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. Wherein, the alkyl in the said C1-16 alkyls, C1-16 alkoxyls, C1-16 alkthioyls, and C1-16 alkacyloxoyls can be straight, breached, unsubstituted, and substituted, thereof the further substitution group(s) can be selected from the group consisting of halogens, hydroxyl, and amino groups.

R₂, R₃, and R₅ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxyphenylpropionyl, p-methyl-phenylpropionyl, phenylpropenionyl, p-hydroxyphenylpropenionyl, nitrophenylacyl, thereof, R₂ and R₃ can be interconnected to form a ring.

The preferable compounds represented by the formula B, include but are not limited to the compounds represented by the formula Ba.

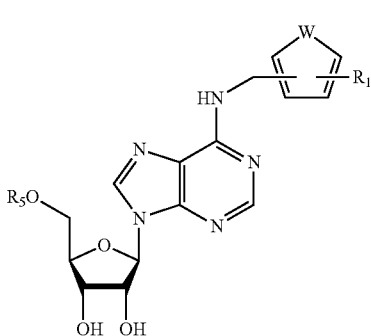

(Ba)

Wherein,
W is selected from the group consisting of oxygen (O), sulfur (S), and nitrogen (N) atoms.
$R_1$ is selected from the group consisting of H, hydroxy, amino, nitro, phenyl, methylenedioxy, halogens, C1-10 alkyls, C1-10 alkoxyls, C1-10 alkthioyls, and C1-10 alkacyloxoyls. Wherein, the alkyl in the said C1-10 alkyls, C1-10 alkoxyls, C1-10 alkthioyls, and C1-10 alkacyloxoyls can be straight, breached, unsubstituted, and substituted, thereof the further substitution group(s) can be selected from the group consisting of halogens, hydroxyl, and amino groups.
$R_5$ is selected from the group consisting of H, saturated C7-12 alkyls, phenylpropyl, p-hydroxy-phenylpropyl, p-methyl-phenylpropyl, phenylpropenyl, p-hydroxyphenyl-propenyl, nitrophenyl, saturated C7-12 alkylacyls, phenylpropionyl, p-hydroxy-phenylpropionyl, p-methyl-phenyl-propionyl, phenylpropenionyl, p-hydroxyphenylpropenionyl, and nitrophenylacyl.
The preferable compounds represented by the formula Ba, include but are not limited to the compounds represented by formula Ba1.

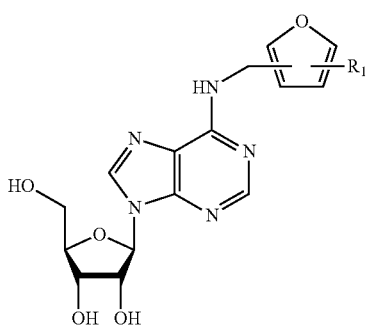

(Ba1)

Wherein,
$R_1$ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.
The preferable compounds represented by the formula Ba1, include but are not limited to the compounds represented by the formula Ba11

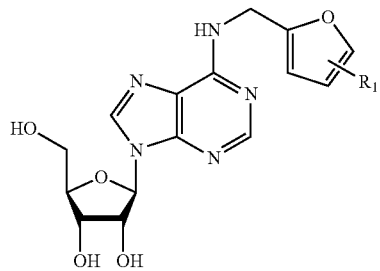

(Ba11)

Wherein,
$R_1$ is selected from the group consisting of H, methyl, ethyl, propyl, isopropyl, methoxyl, ethoxyl, propoxy, isopropoxy, methylthio, acetoxy, propionyloxy, trifluoromethyl, trifluoromethoxyl, fluoro, chloro, bromo, and methylenedioxy.
The preferable compounds represented by the formula Ba1, include but are not limited to the compounds represented by the formula Ba12.

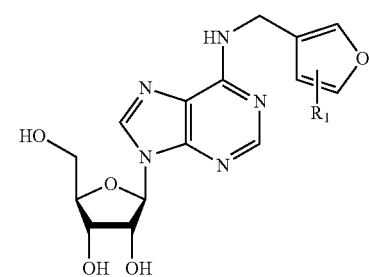

(Ba12)

Wherein,
$R_1$ is selected from the group consisting of H, methyl, ethyl, propyl, isopropyl, methoxyl, ethoxyl, propoxy, isopropoxy, methylthio, acetoxy, propionyloxy, trifluoromethyl, trifluoromethoxyl, fluoro, chloro, bromo, methylenedioxy.
The preferable compounds Ba represented by the formula, include but are not limited to the compounds represented the formula Ba2.

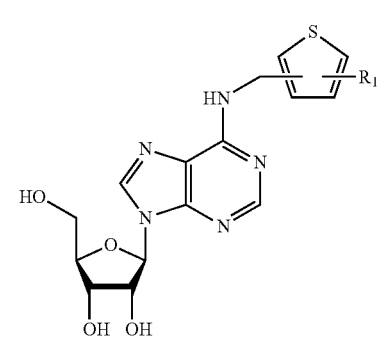

(Ba2)

Wherein,
$R_1$ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

The preferable compounds represented by the formula Ba2, include but are not limited to the compounds represented by the formula Ba21.

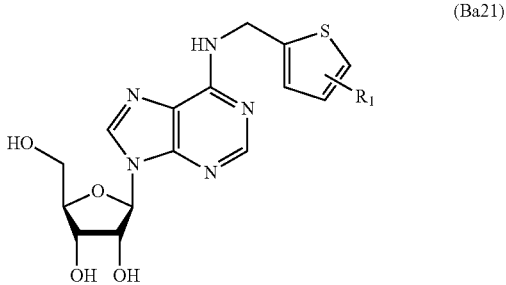
(Ba21)

Wherein,

R₁ is selected from the group consisting of H, methyl, ethyl, propyl, isopropyl, methoxyl, ethoxyl, propoxy, isopropoxy, methylthio, acetoxy, propionyloxy, trifluoromethyl, trifluoromethoxyl, fluoro, chloro, bromo, methylenedioxy.

The preferable compounds, represented by the formula Ba2, include but are not limited to the compounds represented the formula Ba22.

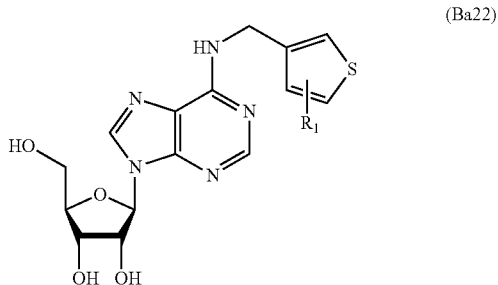
(Ba22)

Wherein,

R₁ is selected from the group consisting of H, methyl, ethyl, propyl, isopropyl, methoxyl, ethoxyl, propoxy, isopropoxy, methylthio, acetoxy, propionyloxy, trifluoromethyl, trifluoromethoxyl, fluoro, chloro, bromo, methylenedioxy.

The preferable compounds represented by the formula Ba, include but are not limited to the compounds represented by the formula Ba3.

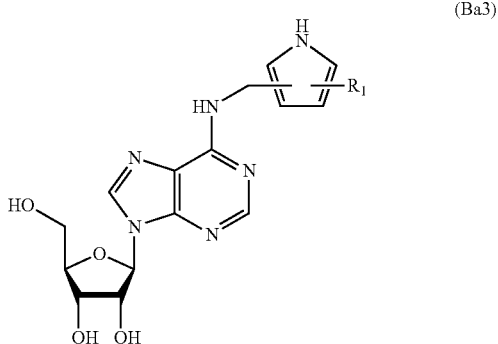
(Ba3)

Wherein,

R₁ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

The preferable compounds represented by the formula Ba3, include but are not limited to the compounds represented by the formula Ba31.

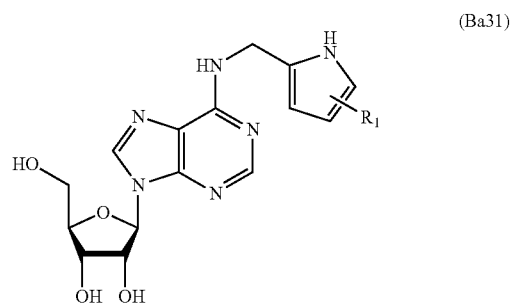
(Ba31)

Wherein,

R₁ is selected from the group consisting of H, methyl, ethyl, propyl, isopropyl, methoxyl, ethoxyl, propoxy, isopropoxy, methylthio, acetoxy, propionyloxy, trifluoromethyl, trifluoromethoxyl, fluoro, chloro, bromo, and methylenedioxy.

The preferable compounds, represented by the formula Ba3, include but are not limited to the compounds represented by the formula Ba32.

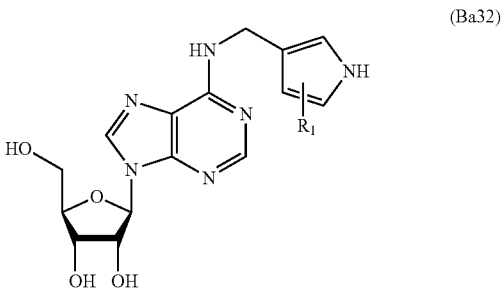
(Ba32)

Wherein,

R₁ is selected from the group consisting of H, methyl, ethyl, propyl, isopropyl, methoxyl, ethoxyl, propoxy, isopropoxy, methylthio, acetoxy, propionyloxy, trifluoromethyl, trifluoromethoxyl, fluoro, chloro, bromo, and methylenedioxy.

The preferable compounds represented by the formula I, include but are not limited to the compounds represented by the formula C.

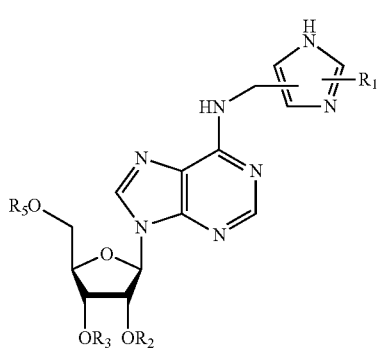

(C)

Wherein,
R₁ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups. R₂, R₃, and R₅ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxy-phenylpropionyl, p-methyl-phenylpropionyl, phenylpropenionyl, p-hydroxyphenylpropenionyl, nitrophenylacyl, thereof, R₂ and R₃ can be interconnected to form a ring.

The preferable compounds, represented by the formula I, include but are not limited to the compounds represented by formula D.

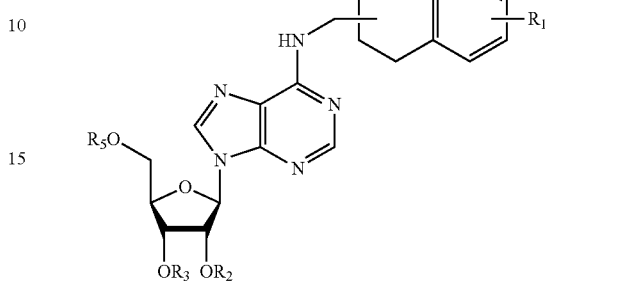

(D)

Wherein,
R₁ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups. R₂, R₃, and R₅ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxy-phenylpropionyl, p-methyl-phenylpropionyl, phenylpropenionyl, p-hydroxyphenylpropenionyl, nitrophenylacyl, thereof, R₂ and R₃ can be interconnected to form a ring.

The preferable compounds, represented by the formula I, include but are not limited to the compounds represented by the formula E.

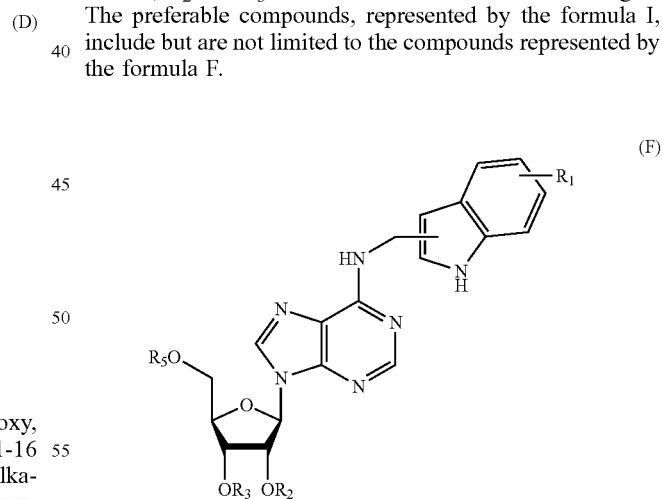

(E)

Wherein,
R₁ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups. R₂, R₃, and R₅ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxy-phenylpropionyl, p-methyl-phenylpropionyl, phenylpropenionyl, p-hydroxyphenylpropenionyl, nitrophenylacyl, thereof, R₂ and R₃ can be interconnected to form a ring.

The preferable compounds, represented by the formula I, include but are not limited to the compounds represented by the formula F.

(F)

Wherein,
R₁ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.

$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxyphenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

The preferable compounds, represented by the formula I, include but are not limited to the compounds represented by the formula G

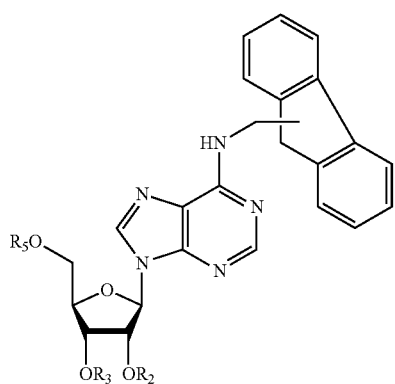

(G)

Wherein, $R_1$ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.

$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxyphenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

The preferable compounds, represented by the formula I, include but are not limited to the compounds represented by the formula H.

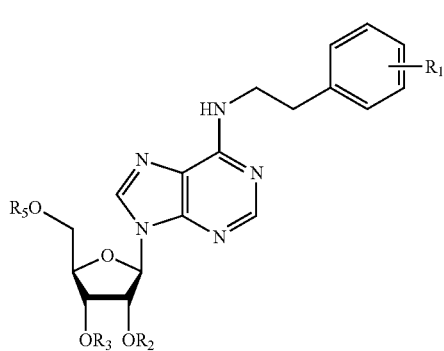

(H)

Wherein, $R_1$ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.

$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxyphenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

The preferable compounds, represented by the formula H, include but are not limited to the compounds represented by the formula Ha.

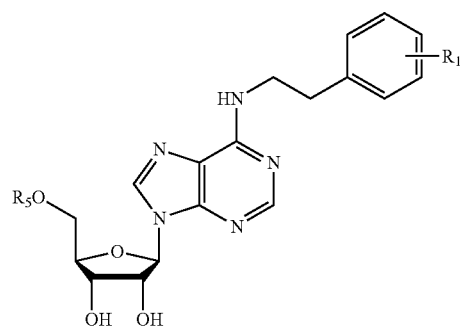

(Ha)

Wherein, $R_1$ is selected from the group consisting of H, hydroxy, amino, nitro, phenyl, methylenedioxy, halogens, C1-10 alkyls, C1-10 alkoxyls, C1-10 alkthioyls, and C1-10 alkacyloxoyls. The alkyl in the said C1-10 alkyls, C1-10 alkoxyls, C1-10 alkthioyls, and C1-10 alkacyloxoyls can be straight, breached, unsubstituted, and substituted, thereof, the further substitution group(s) can be selected from the group consisting of halogens, hydroxyl, and amino groups.

$R_5$ is selected from the group consisting of H, saturated C7-12 alkyls, phenylpropyl, p-hydroxy-phenylpropyl, p-methyl-phenylpropyl, phenylpropenyl, p-hydroxyphenylpropenyl, nitrophenyl, saturated and unsaturated C7-12 alkyl acyls, phenylpropionyl, p-hydroxy-phenylpropionyl, p-methyl-phenylpropionyl, phenylpropenionyl, p-hydroxyphenylpropenionyl, and nitrophenylacyl.

The preferable compounds, represented by the formula Ha, include but are not limited to the compounds represented by the formula Ha1.

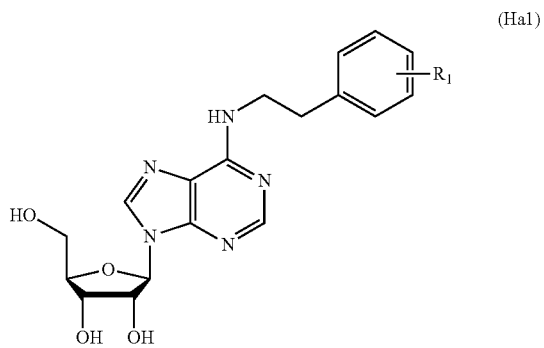

(Hal)

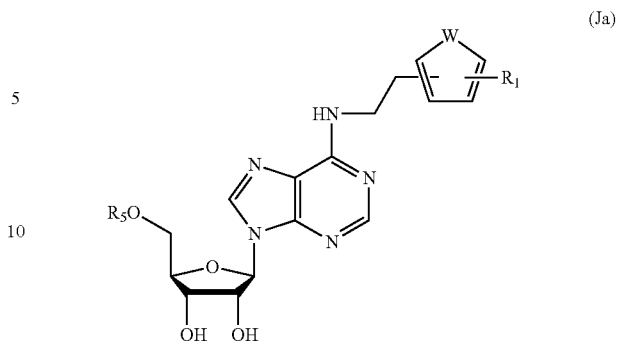

(Ja)

Wherein,

R₁ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

The preferable compounds, represented by the formula I, include but are not limited to the compounds represented by the formula J.

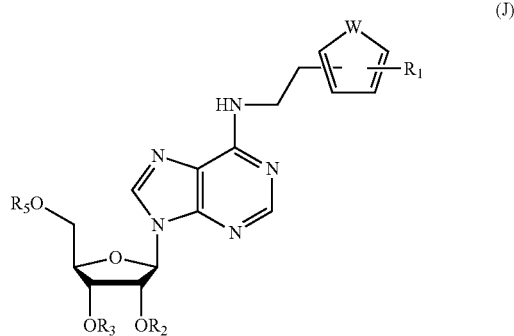

(J)

Wherein,

W is selected from the group consisting of oxygen (O), sulfur (S), and nitrogen (N) atoms.

R₁ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.

R₂, R₃, and R₅ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxyphenylpropionyl, p-methyl-phenylpropionyl, phenylpropenionyl, p-hydroxyphenylpropenionyl, nitrophenylacyl, thereof, R₂ and R₃ can be interconnected to form a ring.

The preferable compounds represented by the formula J include but are not limited to the compounds represented by the formula Ja.

Wherein,

W is selected from the group consisting of oxygen (O), sulfur (S), and nitrogen (N) atoms.

R₁ is selected from the group consisting of H, hydroxy, amino, nitro, phenyl, methylenedioxy, halogens, C1-10 alkyls, C1-10 alkoxyls, C1-10 alkthioyls, and C1-10 alkacyloxoyls. The alkyl in the said C1-10 alkyls, C1-10 alkoxyls, C1-10 alkthioyls, and C1-10 alkacyloxoyls can be straight, breached, unsubstituted, and substituted, thereof, the further substitution group(s) can be selected from the group consisting of halogens, hydroxyl, and amino groups.

R₅ are independently selected from the group consisting of H, saturated C7-12 alkyls, phenylpropyl, p-hydroxy-phenylpropyl, p-methyl-phenylpropyl, phenylpropenyl, p-hydroxyphenylpropenyl, nitrophenyl, saturated and unsaturated C7-12 alkylacyls, phenylpropionyl, p-hydroxyphenylpropionyl, p-methyl-phenylpropionyl, phenylpropenionyl, p-hydroxyphenylpropenionyl, nitrophenylacyl, thereof, R₂ and R₃ can be interconnected to form a ring.

The preferable compounds, represented by the formula Ja, include but are not limited to the compounds represented by formula Ja1.

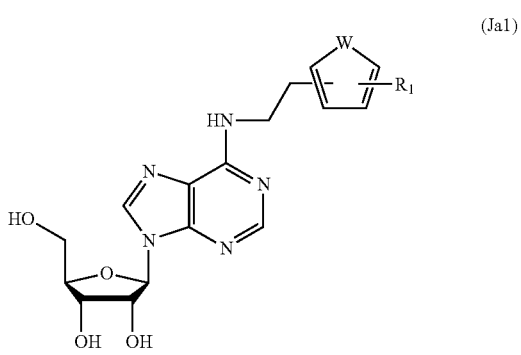

(Ja1)

Wherein,

W is selected from the group consisting of oxygen (O), sulfur (S), and nitrogen (N) atoms.

R₁ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

The preferable compounds, represented by the formula I, include but are not limited to the compounds represented by the formula K.

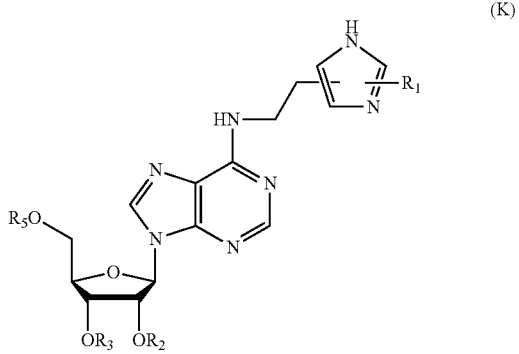

Wherein,
$R_1$ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.
$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxy-phenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

The preferable compounds represented by the formula I, include but are not limited to the compounds represented by the formula M.

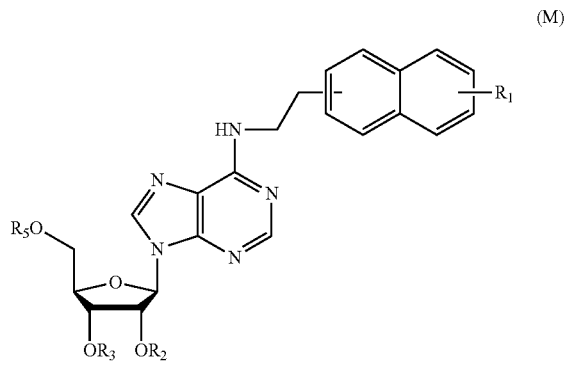

Wherein,
$R_1$ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.
$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxy-phenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

The preferable compounds, represented by the formula I, include but are not limited to the compounds represented by the formula N.

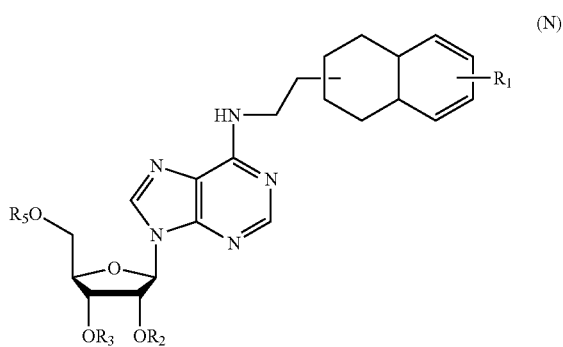

Wherein,
$R_1$ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.
$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxy-phenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

The preferable compounds, represented by the formula I, include but are not limited to the compounds represented by the formula O.

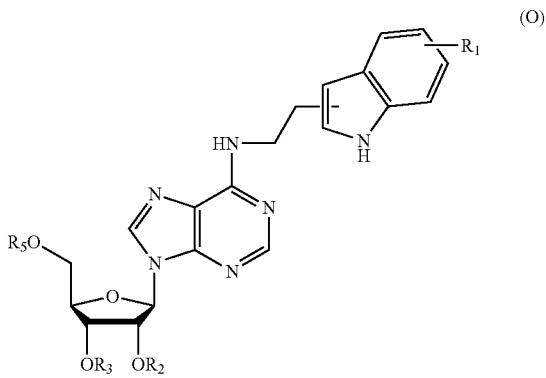

Wherein,

R₁ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.

$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxyphenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

The preferable compounds, represented by the formula I, include but are not limited to the compounds represented by the formula P.

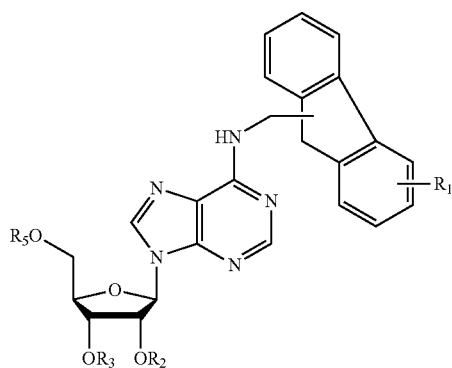

(P)

Wherein,

R₁ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.

$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxyphenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

The preferable compounds, represented by the formula I, include but are not limited to the compounds represented by the formula Q.

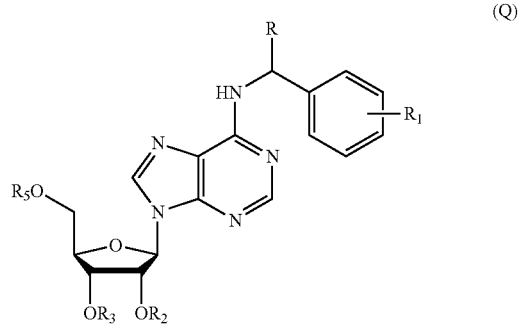

(Q)

Wherein,

R is selected from the group consisting of C1-4 alkyls and hydroxy substituted C1-4 alkyls.

R₁ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.

$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxyphenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

The preferable compounds, represented by the formula Q, include but are not limited to the compounds represented by the formula Qa.

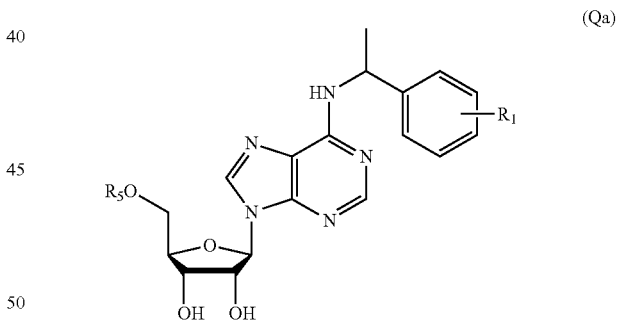

(Qa)

Wherein,

R₁ is selected from the group consisting of H, hydroxy, amino, nitro, phenyl, methylenedioxy, halogens, C1-10 alkyls, C1-10 alkoxyls, C1-10 alkthioyls, and C1-10 alkacyloxoyls. The alkyl in the said C1-10 alkyls, C1-10 alkoxyls, C1-10 alkthioyls, and C1-10 alkacyloxoyls can be straight, breached, unsubstituted, and substituted, thereof, the further substitution group(s) can be selected from the group consisting of halogens, hydroxyl, and amino groups.

$R_5$ is selected from the group consisting of H, saturated C7-12 alkyls, phenylpropyl, p-hydroxy-phenylpropyl, p-methyl-phenylpropyl, phenylpropenyl, p-hydroxyphenylpropenyl, nitrophenyl, saturated and unsaturated C7-12 alkylacyls, phenylpropionyl, p-hydroxy-phenylpropionyl, p-methyl-phenylpropionyl, phenylpropenionyl, p-hydroxyphenylpropenionyl, nitrophenylacyl.

The preferable compounds, represented by the formula Qa, include but are not limited to the compounds represented by the formula Qa1.

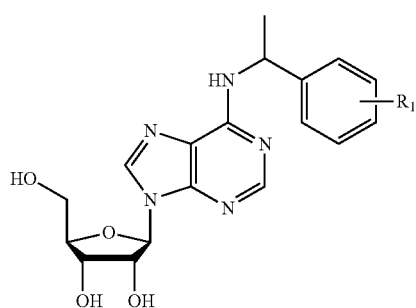

(Qa1)

Wherein,
$R_1$ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

The preferable compounds, represented by the formula Qa1, include but are not limited to the compounds represented by the formula Qa11.

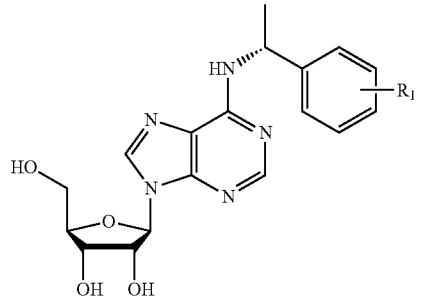

(Qa11)

Wherein,
$R_1$ is selected from the group consisting of H, methyl, ethyl, propyl, isopropyl, methoxyl, ethoxyl, propoxy, isopropoxy, methylthio, acetoxy, propionyloxy, trifluoromethyl, trifluoromethoxyl, fluoro, chloro, bromo, methylenedioxy.

The preferable compounds, represented by the formula Qa1, include but are not limited to the compounds represented by the formula Qa12.

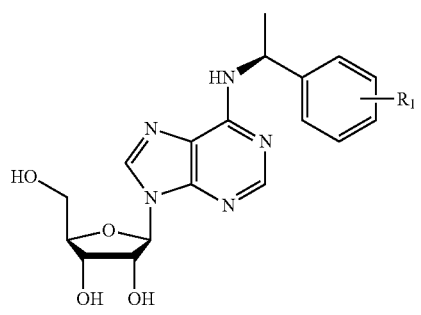

(Qa12)

Wherein,
$R_1$ is selected from the group consisting of H, methyl, ethyl, propyl, isopropyl, methoxyl, ethoxyl, propoxy, isopropoxy, methylthio, acetoxy, propionyloxy, trifluoromethyl, trifluoromethoxyl, fluoro, chloro, bromo, methylenedioxy.

The preferable compounds, represented by the formula Q, include but are not limited to the compounds represented by the formula Qb.

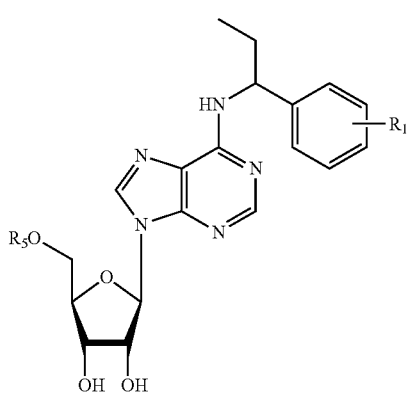

(Qb)

Wherein,
$R_1$ is selected from the group consisting of H, hydroxy, amino, nitro, phenyl, methylenedioxy, halogens, C1-10 alkyls, C1-10 alkoxyls, C1-10 alkthioyls, and C1-10 alkacyloxoyls. The alkyl in the said C1-10 alkyls, C1-10 alkoxyls, C1-10 alkthioyls, and C1-10 alkacyloxoyls can be straight, breached, unsubstituted, and substituted, thereof, the further substitution group(s) can be selected from the group consisting of halogens, hydroxyl, and amino groups.
$R_5$ is selected from the group consisting of H, saturated C7-12 alkyls, phenylpropyl, p-hydroxy-phenylpropyl, p-methyl-phenylpropyl, phenylpropenyl, p-hydroxyphenylpropenyl, nitrophenyl, saturated and unsaturated C7-12 alkylacyls, phenylpropionyl, p-hydroxy-phenylpropionyl, p-methyl-phenylpropionyl, phenylpropenionyl, p-hydroxy-phenylpropenionyl, nitrophenylacyl.

The preferable compounds, represented by the formula Qb, include but are not limited to the compounds represented by the formula Qb1.

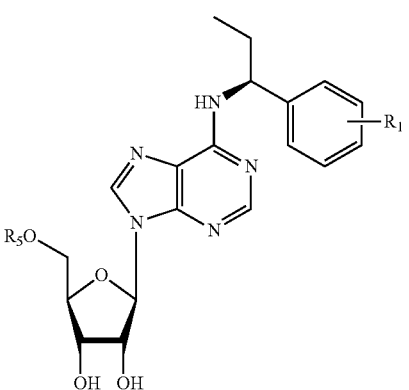

(Qb1)

Wherein,
$R_1$ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

The preferable compounds, represented by the formula Qb, include but are not limited to the compounds represented by the formula Qb2.

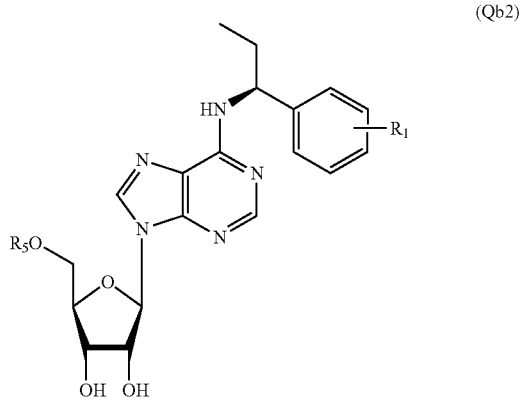

(Qb2)

Wherein,
R₁ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

The preferable compounds, represented by the formula Q, include but are not limited to the compounds represented by the formula Qc.

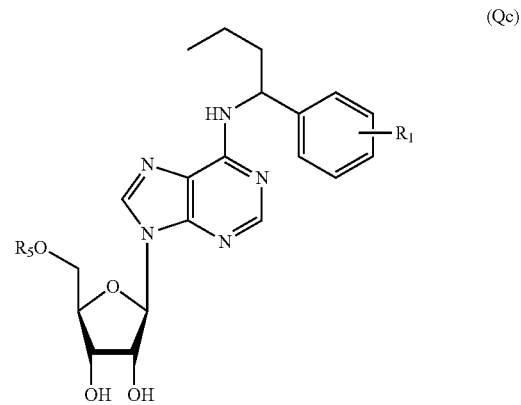

(Qc)

Wherein,
R₁ is selected from the group consisting of H, hydroxy, amino, nitro, phenyl, methylenedioxy, halogens, C1-10 alkyls, C1-10 alkoxyls, C1-10 alkthioyls, and C1-10 alkacyloxoyls. The alkyl in the said C1-10 alkyls, C1-10 alkoxyls, C1-10 alkthioyls, and C1-10 alkacyloxoyls can be straight, breached, unsubstituted, and substituted, thereof, the further substitution group(s) can be selected from the group consisting of halogens, hydroxyl, and amino groups.

R₅ is selected from the group consisting of H, saturated C7-12 alkyls, phenylpropyl, p-hydroxy-phenylpropyl, p-methyl-phenylpropyl, phenylpropenyl, p-hydroxyphenylpropenyl, nitrophenyl, saturated and unsaturated C7-12 alkylacyls, phenylpropionyl, p-hydroxy-phenylpropionyl, p-methyl-phenylpropionyl, phenylpropenionyl, p-hydroxyphenylpropenionyl, nitrophenylacyl.

The preferable compounds, represented by the formula Qc, include but are not limited to the compounds represented by the formula Qc1.

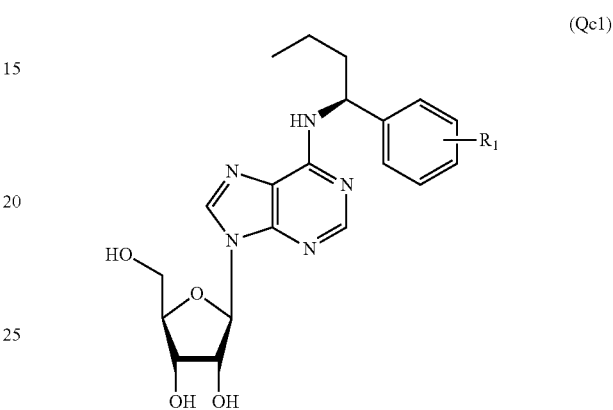

(Qc1)

Wherein,
R₁ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

The preferable compounds, represented by the formula Qc, include but are not limited to the compounds represented by the formula Qc2.

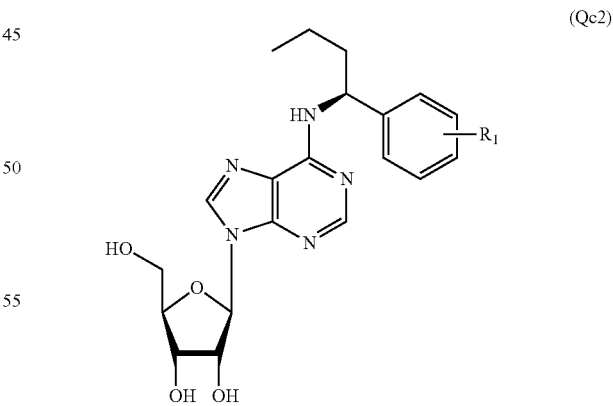

(Qc2)

Wherein,
R₁ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

The preferable compounds represented by the formula I, include but are not limited to the compounds represented by the formula R.

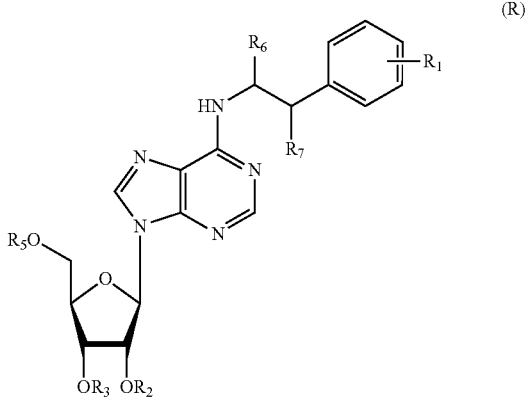

(R)

Wherein, $R_6$ and $R_7$ are independently selected from the group consisting of hydroxy and hydroxymethyl.

$R_1$ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.

$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxy-phenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

The preferable compounds, represented by the formula R, include but are not limited to the compounds represented by the formula Ra.

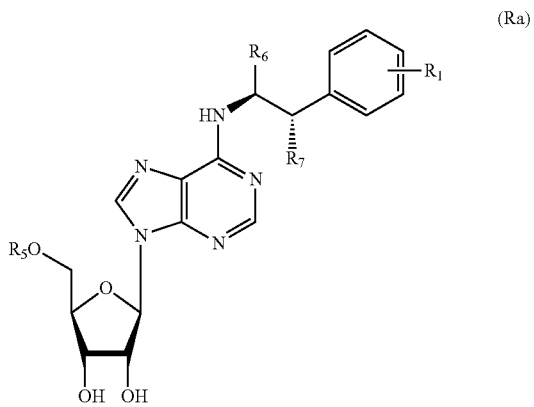

(Ra)

Wherein, $R_6$ and $R_7$ are independently selected from the group consisting of hydroxy and hydroxymethyl.

$R_1$ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

$R_5$ is selected from the group consisting of H, saturated C7-12 alkyls, phenylpropyl, p-hydroxy-phenylpropyl, p-methyl-phenylpropyl, phenylpropenyl, p-hydroxyphenylpropenyl, nitrophenyl, saturated and unsaturated C7-12 alkylacyls, phenylpropionyl, p-hydroxy-phenylpropionyl, p-methyl-phenylpropionyl, phenylpropenionyl, p-hydroxyphenylpropenionyl, nitrophenylacyl.

The preferable compounds, represented by the formula R, include but are not limited to the compounds represented by the formula Rb.

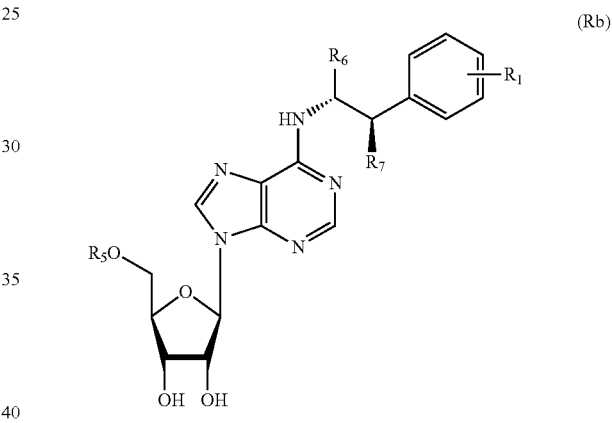

(Rb)

Wherein, $R_6$ and $R_7$ are independently selected from the group consisting of hydroxy and hydroxymethyl.

$R_1$ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

$R_5$ is selected from the group consisting of H, saturated C7-12 alkyls, phenylpropyl, p-hydroxy-phenylpropyl, p-methyl-phenylpropyl, phenylpropenyl, p-hydroxyphenylpropenyl, nitrophenyl, saturated and unsaturated C7-12 alkylacyls, phenylpropionyl, p-hydroxy-phenylpropionyl, p-methyl-phenylpropionyl, phenylpropenionyl, p-hydroxyphenylpropenionyl, nitrophenylacyl.

The preferable compounds, represented by the formula I, include but are not limited to the compounds represented by the formula S.

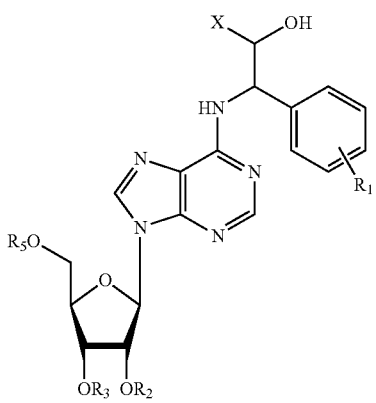

(S)

Wherein,

X is selected from the group consisting of substituted and unsubstituted cyclohexyls and substituted and unsubstituted phenyls.

$R_1$ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.

$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxy-phenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

The preferable compounds, represented by the formula S, include but are not limited to the compounds represented by the formula Sa.

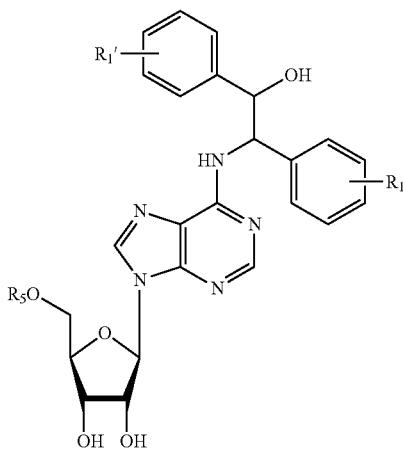

(Sa)

Wherein, $R_1$ and $R_1'$ are independently selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

$R_5$ is selected from the group consisting of H, saturated C7-12 alkyls, phenylpropyl, p-hydroxy-phenylpropyl, p-methyl-phenylpropyl, phenylpropenyl, p-hydroxyphenylpropenyl, nitrophenyl, saturated and unsaturated C7-12 alkyl acyls, phenylpropionyl, p-hydroxy-phenylpropionyl, p-methyl-phenylpropionyl, phenylpropenionyl, p-hydroxyphenylpropenionyl, nitrophenylacyl.

The preferable compounds represented by the formula Sa, include but are not limited to the compounds represented by the formula Sa1.

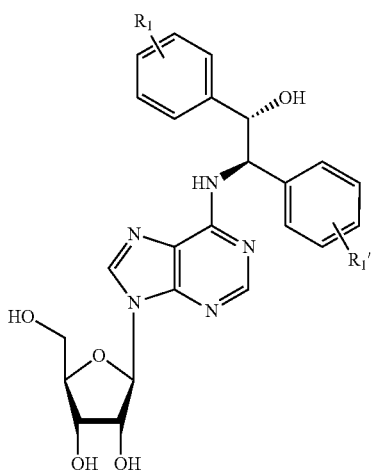

(Sa1)

$R_1$ and $R_1'$ are independently selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

The preferable compounds, represented by the formula Sa, include but are not limited to the compounds represented by the formula Sa2.

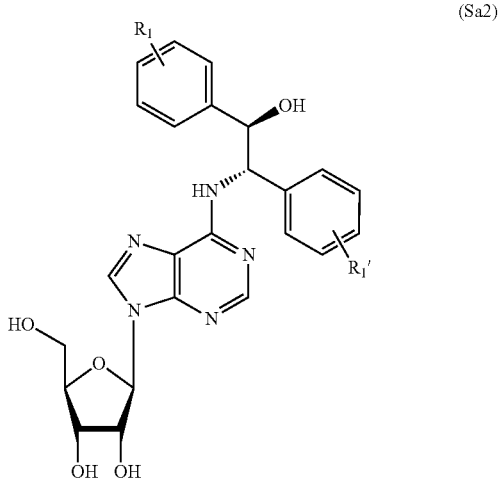

(Sa2)

Wherein, $R_1$ and $R_1'$ are independently selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

The preferable compounds, represented by the formula I, include but are not limited to the compounds represented by the formula T.

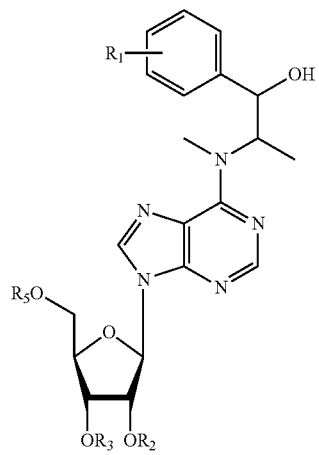
(T)

Wherein, $R_1$ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.

$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxy-phenylpropionyl, p-methyl-phenylpropionyl, phenylpropenionyl, p-hydroxyphenylpropenionyl, nitrophenylacyl, thereof, $R_2$ and $R_3$ can be interconnected to form a ring.

The preferable compounds, represented by the formula T, include but are not limited to the compounds represented by the formula Ta.

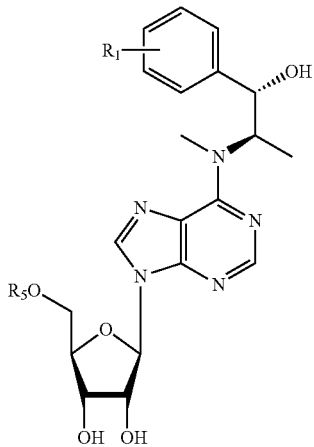
(Ta)

Wherein, $R_1$ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

$R_5$ is selected from the group consisting of H, saturated C7-12 alkyls, phenylpropyl, p-hydroxy-phenylpropyl, p-methyl-phenylpropyl, phenylpropenyl, p-hydroxyphenylpropenyl, nitrophenyl, saturated and unsaturated C7-12 alkyl acyls, phenylpropionyl, p-hydroxy-phenylpropionyl, p-methyl-phenylpropionyl, phenylpropenionyl, p-hydroxyphenylpropenionyl, nitrophenylacyl.

The preferable compounds, represented by the formula T, include but are not limited to the compounds by represented the formula Tb.

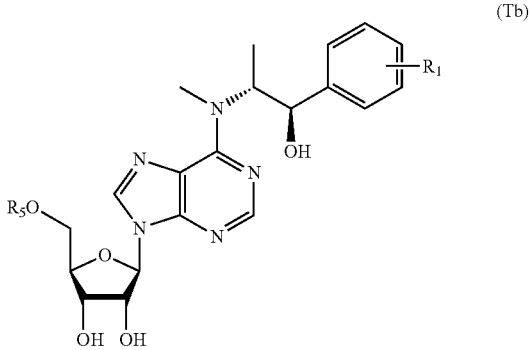
(Tb)

Wherein, $R_1$ is selected from the group consisting of H, hydroxy, amino, nitro, phenyl, methylenedioxy, halogens, C1-6 alkyls, C1-6 alkoxyls, C1-6 alkthioyls, and C1-6 alkacyloxoyls. The alkyl in the said C1-6 alkyls, C1-6 alkoxyls, C1-6 alkthioyls, and C1-6 alkacyloxoyls can be straight, breached, unsubstituted, and substituted, thereof, the further substitution group(s) can be selected from the group consisting of halogens, hydroxyl, and amino groups.

$R_5$ is selected from the group consisting of H, saturated C7-12 alkyls, phenylpropyl, p-hydroxy-phenylpropyl, p-methyl-phenylpropyl, phenylpropenyl, p-hydroxyphenylpropenyl, nitrophenyl, saturated and unsaturated C7-12 alkylacyls, phenylpropionyl, p-hydroxy-phenylpropionyl, p-methyl-phenylpropionyl, phenylpropenionyl, p-hydroxyphenylpropenionyl, nitrophenylacyl.

The preferable compounds, represented by the formula I, include but are not limited to the compounds represented by the formula U.

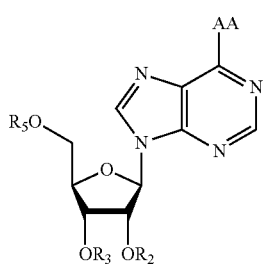

(U)

Wherein,
AA is selected from the group consisting of amino acids, thereof attached to the formula by nitrogen atom of the amino acids.
$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxyphenylpropionyl, p-methyl-phenylpropionyl, phenylpropenionyl, p-hydroxyphenylpropenionyl, nitrophenylacyl, thereof, $R_2$ and $R_3$ can be interconnected to form a ring.
The preferable AA is selected from the group consisting of phenylalanine, tyrosine, tryptophane, histidine, praline, valine, threonine, serine, and glycine.
The preferable compounds represented by the formula VI, include but are not limited to the compounds represented by the formula II.

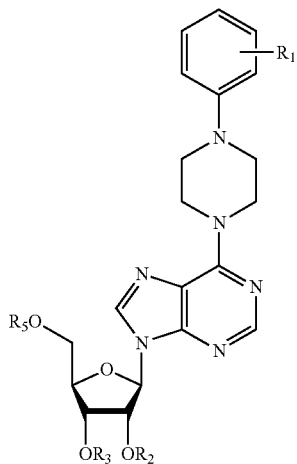

(II)

Wherein,
$R_1$ is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.
$R_2$, $R_3$, and $R_5$ are independently selected from the group consisting of H, saturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxyphenylpropionyl, p-methyl-phenylpropionyl, phenylpropenionyl, p-hydroxyphenylpropenionyl, nitrophenylacyl, thereof, $R_2$ and $R_3$ can be interconnected to form a ring.
The preferable compounds represented by the formula VI, include but are not limited to the compounds represented by the formula III.

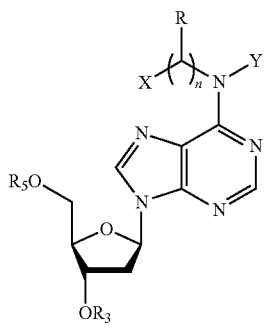

(III)

Wherein,
n is an integer selected from 0-4.
X is selected from the group consisting of substituted and unsubstituted phenyls, substituted and unsubstituted furyls, substituted or unsubstituted thiopheneyls, substituted and unsubstituted pyrrolyls, substituted or unsubstituted naphthyls, substituted and unsubstituted tetrahydro-naphthyls, substituted and unsubstituted fluoreneyls, substituted and unsubstituted imidazolyls, substituted and unsubstituted indyls, substituted and unsubstituted 1H-imidazolyls, substituted and unsubstituted 1H-indyls, substituted and unsubstituted C3-8 cycloalkyls, and C1-16 alkyls with straight and/or branched chains.
Y is selected from the group consisting of H and unsubstituted C1-6 alkyls with straight and/or branched chains.
R is selected from the group consisting of H, hydroxy, substituted and unsubstituted C1-16 alkyls with straight and/or branched chains., substituted and unsubstituted C3-8cycloalkyls, substituted and unsubstituted phenyls, COOR' (R' is selected H or C1-6 alkyls).
The structural moiety, represented by

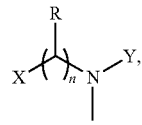

can also be selected from the group consisting of (5R)-5-carboxy-2-pyrrolyl, (5S)-5-carboxy-2-pyrrolyl, (5R)-5-hydroxymethyl-2-pyrrolyl, (5S)-5-hydroxymethyl-2-pyrroleyl, substituted and unsubstituted phenylpiperazinyls, amino acid units, and amino acid ester units.

The structural moiety, represented by

can also be selected from the group consisting of substituted and unsubstituted furanyls, substituted and unsubstituted thienyls, substituted and unsubstituted pyrrolyls, substituted and unsubstituted imidazolyls, substituted and unsubstituted naphthyls, substituted and unsubstituted tetrahydro-naphthyls, substituted and unsubstituted indyls, substituted and unsubstituted fluoreneyls, and substituted and unsubstituted C3-8 cycloalkyls.

In addition, the above mentioned substituent is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.

$R_3$ and $R_5$ are independently selected from the group consisting of H, saturated and unsaturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxy-phenylpropionyl, p-methyl-phenylpropionyl, phenylpropenionyl, p-hydroxyphenylpropenionyl, nitrophenylacyl.

The preferable compounds, represented by the formula III, include but are not limited to the compounds represented by the formula IIIA.

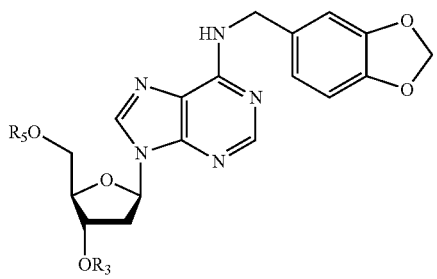

(IIIA)

Wherein,
$R_3$ and $R_5$ are independently selected from the group consisting of H, saturated and unsaturated C1-16 alkyls, phenylpropyl, p-hydroxy-phenylpropyl, p-methyl-phenylpropyl, phenylpropenyl, p-hydroxyphenylpropenyl, nitrophenyl, saturated and unsaturated C1-16 alkylacyls, phenylpropionyl, p-hydroxy-phenylpropionyl, p-methyl-phenylpropionyl, phenylpropenionyl, p-hydroxyphenylpropenionyl, nitrophenylacyl.

The preferable compounds, represented by the formula VI, include but are not limited to the compounds represented by the formula IV.

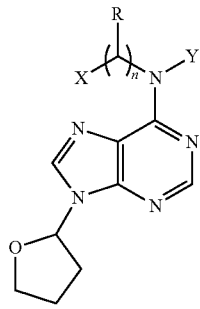

(IV)

Wherein,
n is an integer selected from 0-4.
X is selected from the group consisting of substituted and unsubstituted phenyls, substituted and unsubstituted furyls, substituted or unsubstituted thiopheneyls, substituted and unsubstituted pyrrolyls, substituted or unsubstituted naphthyls, substituted and unsubstituted tetrahydro-naphthyls, substituted and unsubstituted fluoreneyls, substituted and unsubstituted imidazolyls, substituted and unsubstituted indyls, substituted and unsubstituted 1H-imidazolyls, substituted and unsubstituted 1H-indyls, substituted and unsubstituted C3-8 cycloalkyls, and C1-16 alkyls with straight and/or branched chains.
Y is selected from the group consisting of H and unsubstituted C1-6 alkyls with straight and/or branched chains.
R is selected from the group consisting of H, hydroxy, substituted and unsubstituted C1-16 alkyls with straight and/or branched chains, substituted and unsubstituted C3-8cycloalkyls, substituted and unsubstituted phenyls, COOR' (R' is selected H or C1-6 alkyls).

The structural moiety, represented by

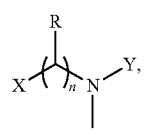

can also be selected from the group consisting of (5R)-5-carboxy-2-pyrrolyl, (5S)-5-carboxy-2-pyrrolyl, (5R)-5-hydroxymethyl-2-pyrrolyl, (5S)-5-hydroxymethyl-2-pyrroleyl, substituted and unsubstituted phenylpiperazinyls, amino acid units, and amino acid ester units.

The structural moiety, represented by

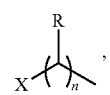

can also be selected from the group consisting of substituted and unsubstituted furanyls, substituted and unsubstituted thienyls, substituted and unsubstituted pyrrolyls, substituted and unsubstituted imidazolyls, substituted and unsubstituted naphthyls, substituted and unsubstituted tetrahydro-naphthyls, substituted and unsubstituted indyls, substituted and unsubstituted fluoreneyls, and substituted and unsubstituted C3-8 cycloalkyls.

The preferable compounds represented by the formula VI, include but are not limited to the compounds represented by the formula V.

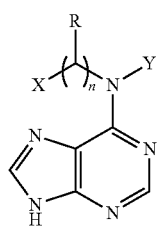

(V)

Wherein, n is an integer selected from 0-4.

X is selected from the group consisting of substituted and unsubstituted phenyls, substituted and unsubstituted furyls, substituted or unsubstituted thiopheneyls, substituted and unsubstituted pyrrolyls, substituted or unsubstituted naphthyls, substituted and unsubstituted tetrahydro-naphthyls, substituted and unsubstituted fluoreneyls, substituted and unsubstituted imidazolyls, substituted and unsubstituted indyls, substituted and unsubstituted 1H-imidazolyls, substituted and unsubstituted 1H-indyls, substituted and unsubstituted C3-8 cycloalkyls, and C1-16 alkyls with straight and/or branched chains.

Y is selected from the group consisting of H and unsubstituted C1-6 alkyls with straight and/or branched chains.

R is selected from the group consisting of H, hydroxy, substituted and unsubstituted C1-16 alkyls with straight and/or branched chains, substituted and unsubstituted C3-8cycloalkyls, substituted and unsubstituted phenyls, COOR' (R' is selected H or C1-6 alkyls).

The structural moiety, represented by

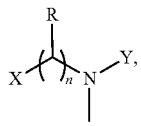

can also be selected from the group consisting of (5R)-5-carboxy-2-pyrrolyl, (5S)-5-carboxy-2-pyrrolyl, (5R)-5-hydroxymethyl-2-pyrrolyl, (5S)-5-hydroxymethyl-2-pyrroleyl, substituted and unsubstituted phenylpiperazinyls, amino acid units, and amino acid ester units.

The structural moiety, represented by

can also be selected from the group consisting of substituted and unsubstituted furanyls, substituted and unsubstituted thienyls, substituted and unsubstituted pyrrolyls, substituted and unsubstituted imidazolyls, substituted and unsubstituted naphthyls, substituted and unsubstituted tetrahydro-naphthyls, substituted and unsubstituted indyls, substituted and unsubstituted fluoreneyls, and substituted and unsubstituted C3-8 cycloalkyls.

In addition, the above mentioned substituent is selected from the group consisting of H, hydroxy, amino, nitro, phenyl, methylenedioxy, halogens, C1-16 alkyls, C1-16 alkoxyls, C1-16 alkthioyls, and C1-16 alkacyloxoyls. The alkyl in the said C1-16 alkyls, C1-16 alkoxyls, C1-16 alkthioyls, and C1-16 alkacyloxoyls can be straight, breached, unsubstituted, and substituted, thereof, the further substitution group(s) can be selected from the group consisting of halogens, hydroxyl, and amino groups.

The above compounds can be synthesized through the following steps and methods:

(1) The raw materials used in the synthesis, 6-cholopurine, can be synthesized by hypoxanthine (6-hydroxypurine) and phosphorus oxychloride (POCl$_3$) according to the method in the literature (LaMontagne and Maurice P., Journal of Heterocyclic Chemistry 1983, 20, 295). 6-Chloropurine riboside can be synthesized by inosine and SO$_2$Cl$_2$ according to the method in the literature (Lakshmi P. Kotra, Konstantine K. Manouilov, Journal of Medicinal Chemistry 1996, 39, 5202), or purchased directly from commercial companies (such as Sigma, Aldrich and Fluka). 6-Bromo-adenine-2'-dexoriboside can be synthesized by 3',5'-diacetyl-adenine-2'-dexoriboside, tert-butyl nitrite, and bromoform.

(2) The other raw materials used in the synthesis are commercially available aldehydes, ketones, and amines.

(3) The two synthesis methods are described below.

Basic steps of the first method include:

The first step, various aldehyde derivatives, hydroxyamine hydrochloride, and NaOAc are independently stirred in an alcohol solvent at room temperature. After the solvent is removed, H$_2$O is added to the residue, and extracted with EtOAc. The EtOAc of the combined organic layer is removed to yield various aldehyde oxime as the first step product.

The second step, a solution of the first step product and concentrated HCl is subjected to hydrogenation in an alcohol solvent and the presence of Pd/C at atmospheric pressure. The reaction mixture is filtered, and the filtrate is concentrated to yield the corresponding amine hydrochloride. Selectively, the first step product and zinc dust are stirred in HOAc at room temperature. The reaction solution is filtered to remove the excess zinc dust and ZnOAc residue, and the filtrate is concentrated to yield the corresponding amine.

The third step, a mixture of the amine derivative (or the amine hydrochloride), 6-chloropurine riboside (or 6-chloropurine, N$^9$-substituted-6-chloropurine or 3',5'-diacetyl-2'-deoxy-6-bromo-adenosine) and N,N-diisopropylethylamine (or triethylamine) is heated in an alcohol solvent to react. After evaporation of the solvent, the residue is purified by recrystallization or separated by column chromatography over chromatography to yield the target product.

Basic steps of the second method include:

The first step, benzotriazole, benzaldehyde derivative, and adenosine are heated with a catalycal amount of acid in anhydrous alcohol solvent. After the solvent is removed, the residue is purified by recrystallization or separated by column chromatography over chromatography to yield the product as a white solid.

The second step, the first step product and NaBH$_4$ are heated in anhydrous tetrahydrofuran. After the reaction solution was cooled to the room temperature, it is poured into a mixture of ice and water, then neutralized with acid, and extracted with chloroform. The chloroform layer is concentrated, and the residue is purified by recrystallization or separated by column chromatography over chromatography to yield the target product.

In addition, a triester derivative is prepared by a reaction of the N$^6$-substituted adenosine derivative obtained from the above steps with acid anhydride or acyl chloride in pyridine, respectively. Monoester and diester derivatives are prepared as follows: An N$^6$-substituted adenosine derivative is reacted with 2,2-dimethoxypropane to protect 2',3'-hydroxy of the ribosyl unit, then esterified with the corresponding acid under EDCI and DMAP catalysis, and finally deprotected in formic acid.

A further object of this invention is to provide the preparation methods of $N^6$-substituted adenosine derivatives and $N^6$-substituted adenine derivatives; the pharmaceutical compositions containing therapeutically effective doses of the $N^6$-substituted adenosine derivatives and the $N^6$-substituted adenine derivatives; as well as any selectable pharmaceutical carrier, thereof, the pharmaceutical carriers referring to common carriers used in pharmaceutical field, and the preparation methods of the pharmaceutical compositions referring to the common pharmaceutical methods used in the field.

This invention involves in another aspect the pharmaceutical compositions containing these compounds covered by the invention as the active components. The pharmaceutical compositions can be prepared by commonly acknowledged pharmaceutical preparation methods in the area. The compounds of this invention can be combined with one or more pharmaceutical acceptable solid or liquid excipient(s) and (or) adjuvant(s) to produce any dosage form suitable for human or animals applications. In the pharmaceutical compositions, the compounds normally constitute weight percentages of 0.1~95%.

The compounds in this invention and the pharmaceutical compositions containing these compounds can be administrated in a unit dose form, and the suitable route for administration can be intestinal and parenteral, such as oral, intravenous, intramuscular, intradermal, nasal, buccal and sublingual, ocular, rectal, pneumonic and respiratory, dermal, vaginal, rectal, etc. Drug delivery formulations can be liquid, solid and semisolid dose forms. The liquid dose form can be liquors (including molecular solution and colloidal solution), emulsion (including o/w type, w/o type, and multiple emulsion), suspensions, injections (including injection, injectable powder, and transfusion), eye drops, nasal drops, lotions, liniments, etc. The solid dose form can be tablets (including general tablets, enteric-coated tablets, buccal tablets, dispersible tablets, mastication tablets, effervescent tablets, and orally disintegrating tablets), capsules (including saussaurea capsules, soft capsules, and enteric capsule), granules, pulvis, pellets, dropping pills, suppositorys, films, patches, aerosols, powders, and sprays, etc. The semisolid dose form can be ointments, gels, and pastes, etc. Compounds of this invention can be manufactured to common preparations, sustained-release preparations, controlled-release preparations, target-oriented preparations, and all kinds of particulate delivery system.

In order to manufacture compounds of this invention to the tablets, various kinds of commonly acknowledged excipient(s) in the area can be used, including diluent agents, adhesive agents, moistening agents, disintegrating agents, lubricant agents, and glidant agents. The diluent agent(s) can be, for example, starch, dextrin, sucrose, glucose, lactose, mannitol, sorbitol, xylitol, microcrystalline cellulose, calcium sulfate, calcium phosphate dibasic, and calcium carbonate; the moistening agent(s) can be, for example, water, ethanol, and isopropyl alcohol; the adhesive agent(s) can be, for example, starch paste, dextrin, syrup, honey, the glucose solution, microcrystalline cellulose, acacia mucilage, gelatin mucilage, sodium carboxymethylcellulose, methyl cellulose, hydroxypropylmethyl cellulose, ethyl cellulose, acrylic resin, carbomer, polyvidone, and macrogol; the disintegrating agent(s) can be anhydrous starch, microcrystalline cellulose, low-substituted hydroxypropyl cellulose, crospolyvinylpyrrolidone, croscarmellose sodium, sodium carboxymethyl starch, sodium bicarbonate and citric acid, polyoxyethylene sorbitol fatty acid ester, sodium dodecylsulphate; the lubricant agent(s) and glidant agent(s) can be, for example, talcum powder, silicon dioxide, stearate, tartaric acid, liquid paraffin, and macrogol.

The tablet forms can be further manufactured to coated tablets such as sugar coated tablets, film coated tablet and enteric-coated tablet, double-deck tablet and multideck tablet.

In order to manufacture units of administration to capsules, the effective component(s), the compound(s) of this invention, can be mixed with lubricant agent(s) and glidant agent(s), and place the mixture(s) in soft elastic capsules or hard gelatin capsules. The effective component(s), the compound(s) of this invention, can also be manufactured to granules or pellets with lubricant agent(s), adhesive agent(s), disintegrating agent(s), and are made in soft elastic capsules or hard gelatin capsules. A variety of the diluent agent(s), adhesive agent(s), moistening agent(s), disintegrating agent(s) and glidant agent(s) used for the preparation of the tablets in this invention can also be used in the preparation of the capsules.

In order to manufacture compounds of this invention to injections, water, ethanol, isopropanol, propylene glycol, and a mixture of them can be solvents, adding an appropriate amount of the solubilizing agent(s), auxiliary solvent(s), pH conditioner(s), and osmotic pressure conditioner(s) which are commonly acknowledged in this field. The solubilizing agent(s) and auxiliary solvent(s) can be, for example, poloxamer, lecithin, and hydroxypropyl-β-cyclodextrin, etc.; the pH conditioner can be, for example, phosphates, acetates, hydrochloric acid, and sodium hydroxide, etc.; the osmotic pressure conditioners can be sodium chloride, mannitol, glucose, phosphates, and acetates, etc. In the preparation of a freeze-dried powder injection mannitol and/or glucose etc can be added to serve as support agent(s).

In addition, if it is necessary, coloring agent(s), preservative agent(s), aromatic agent(s), taste correctant(s), and other additives can be added in the pharmaceutical preparations.

In order to achieve the pharmaceutical administration goal and enhancing the therapeutic efficacy, the pharmaceuticals or pharmaceutical compositions of this invention can be used for administration in any commonly acknowledged medication method.

Therefore, the other object of this invention is to provide the uses of $N^6$-substituted adenosine derivatives and $N^6$-substituted adenine derivatives in manufacturing medicaments and health-care products, especially, the uses of $N^6$-substituted adenosine derivatives and $N^6$-substituted adenine derivatives in manufacturing medicaments used for sedative-hypnotic, anticonvulsant, antiepileptic, and anti-Parkinson's diseases, and for prevention and treatment of dementia. The $N^6$-substituted adenosine derivatives and the $N^6$-substituted adenine derivatives of this invention can be used to manufacture medicaments and health care products used for sedative, hypnotic, anti-convulsant, anti-epileptic, anti-Parkinson's diseases, and for prevention and treatment of dementia.

In uses of $N^6$-substituted adenosine derivatives and $N^6$-substituted adenine derivatives and the compositions of this invention to treat the above mentioned diseases, the dosage uses can refer to the doses of $N^6$-substituted adenosine derivatives and $N^6$-substituted adenine derivatives in the treatments. In uses of $N^6$-substituted adenosine derivatives and $N^6$-substituted adenine derivatives and the compositions of this invention as the health-care products, and in uses of $N^6$-substituted adenosine derivatives and $N^6$-substituted adenine derivatives and the compositions of this invention to add in the health-care products, the dose can be less than those used in the common treatments.

The inventors have carried out many pharmaceutical experiments and proved that the $N^6$-substituted adenosine derivatives and the $N^6$-substituted adenine derivatives had sedative, hypnotic, anticonvulsant, and antiepileptic functions, as well as and anti-Parkinson's disease function, and had fine curative effects in treating insomnia, convulsion, epilepsy, and Parkinson's disease, as well as in treating and preventing dementia; and they can be added in the health-care products to improve health status and enhance immunity.

The administration doses of the compounds and the pharmaceutical compositions of this invention depend on the property and severity of the diseases to be prevented and treated. The administration toutes and dosage types etc can be in a large range of variation. Generally, appropriate daily doses of the compounds in this invention are 0.001-150 mg/kg (body weight), preferable doses are 0.1-100 mg/kg (body weight), more preferable doses are 1-60 mg/kg (body weight), and the most preferable doses are 2-30 mg/kg (body weight). The above said dosages can be administrated in one dosage unit and in several divided dosage units, depending on the clinical experience of the doctors and administration strategies including an application of other treatment methods.

The compounds and the pharmaceutical compositions of this invention can be taken independently and be used in a combination with other therapeutical medicines as well as symptomatic drugs. In the cases that the compounds of this invention have synergistic effects with other therapeutical medicines, the doses can be adjusted according to the practical situations.

EXAMPLES

The following examples serve to illustrate the invention without limiting the scope thereof.

Example 1: Preparation of $N^6$-(benzyl)-adenosine

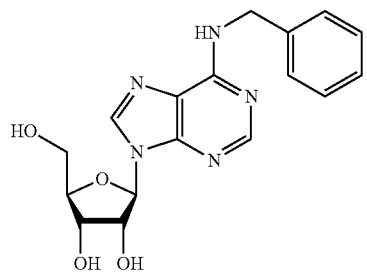

First step, benzaldehyde (1.08 g), hydroxyamine hydrochloride (1.29 g), and NaOAc (1.67 g) were dissolved in EtOH (40 ml). The reaction mixture was stirred at room temperature for 6 h. EtOH was removed under reduced pressure. $H_2O$ (20 ml) was added to the residue, and extracted with EtOAc (3×20 ml). The EtOAc of the combined organic layer was removed by a rotary evaporation under reduced pressure to yield benzaldehyde oxime (1.13 g) as a pale yellowish solid.

Second step, a solution of benzaldehyde oxime (1.13 g) and concentrated HCl (1 ml) in EtOH (40 ml) was subjected to hydrogenation at atmospheric pressure in the presence of 10% Pd/C (85 mg). The reaction mixture was filtered and the filtrate was concentrated to yield benzylamine hydrochloride (1.29 g) as a white solid.

Third step, a mixture of benzylamine (355 mg, the hydrochloride), 6-chloropurine riboside (143 mg), and N,N-diisopropylethylamine (2 ml) in PrOH (40 ml) was heated to 70° C. and reacted for 8 h. After evaporation of the reaction mixture, the residue was separated by column chromatography over silica gel eluting with $CHCl_3$—$CH_3OH$ (30:1) to yield $N^6$-(benzyl)-adenosine (151 mg) as a colorless solid: positive ESIMS at m/z 358 [M+H]$^+$: negative ESIMS at 356 [M−H]$^−$ and 392 [M+Cl]$^−$; $^1$H NMR (300 MHz, $CD_3OD$): the adenosine moiety δ 8.20 (1H, s, H-2), 8.18 (1H, brs, H-8), 5.90 (1H, d, J=6.6 Hz, H-1, H-1'), 4.69 (1H, dd, J=6.6, 5.4 Hz, H-2'), 4.26 (1H, dd, J=5.4 and 2.4 Hz, H-3'), 4.11 (1H, q, J=2.4 Hz, H-4'), 3.83 (1H, dd, J=12.6 and 2.4 Hz, H-5'a), 3.68 (1H, dd, J=12.6 and 2.4 Hz, H-5'b); the benzyl moiety δ 7.14-7.34 (5H, m, H-2"~H-6"), 4.77 (2H, brs, H-7"); $^{13}$C NMR (75 MHz, DMSO-d$_6$): the adenosine moiety δ 154.6 (C-6), 152.4 (C-2), 148.5 (C-4), 140.0 (C-8), 119.8 (C-5), 88.0 (C-1'), 85.9 (C-4'), 73.5 (C-2'), 70.7 (C-3'), 61.7 (C-5'); the benzyl moiety δ 128.2 (C-3", C-5"), 127.1 (C-2", C-6"), 126.6 (C-4"), 42.9 (C-7").

Example 2: Preparation of $N^6$-(p-hydroxybenzyl)-adenosine

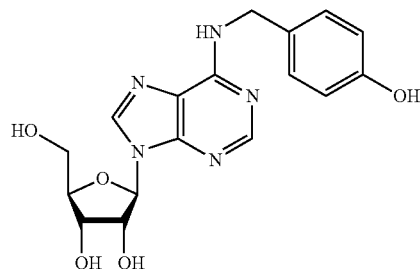

First step, p-hydroxybenzaldehyde (2.55 g) hydroxyamine hydrochloride (2.60 g) and NaOAc (3.40 g) were dissolved in EtOH (80 ml). The reaction mixture was stirred at room temperature for 6 h. EtOH was removed under reduced pressure. $H_2O$ (40 ml) was added to the residue, and extracted with EtOAc (3×40 ml). The EtOAc of the combined organic layer was removed by rotary evaporation under reduced pressure to yield p-hydroxybenzaldehyde oxime (2.66 g) as a pale yellowish solid.

Second step, a solution of p-hydroxybenzaldehyde oxime (2.66 g) and concentrated HCl (8 ml) in EtOH (70 ml) was subjected to hydrogenation at atmospheric pressure in the presence of 10% Pd/C (300 mg). The reaction mixture was filtered, and the filtrate was concentrated to yield p-hydroxybenzylamine hydrochloride (3.02 g) as a white solid.

Third step, a mixture of p-hydroxybenzylamine (3.02 g, the hydrochloride), 6-chloropurine riboside (1 g), and N,N-diisopropylethylamine (14 ml) in PrOH (40 ml) was heated to 70° C. and reacted for 8 h. After evaporation of the reaction mixture, the residue was crystallised in ethanol to yield $N^6$-(p-hydroxybenzyl)-adenosine (1.07 g) as a colorless crystal: positive ESIMS m/z 374 [M+H]$^+$, 396 [M+Na]$^+$ and 412 [M+K]$^+$; negative ESIMS m/z 372 [M−H]$^−$ and 408 [M+Cl]$^−$; $^1$H NMR (400 MHz, $CD_3OD$): the adenosine moiety δ 8.19 (2H, s, H-2, H-8), 5.89 (1H, d, J=6.4 Hz, H-1'), 4.69 (1H, dd, J=6.4 and 5.2 Hz, H-2'), 4.26 (1H, dd, J=5.2 and 2.4 Hz, H-3'), 4.11 (1H, q, J=2.4 Hz, H-4'), 3.83 (1H, dd, J=12.8 and 2.4 Hz, H-5'a), 3.68 (1H, dd, J=12.8 nd 2.4 Hz, H-5'b); the p-hydroxybenzyl moiety δ 7.16 (2H, d, J=8.4 Hz, H-2" and H-6"), 6.68 (2H, d, J=8.4 Hz, H-3" and H-5"), 4.64 (2H, brs, H-7"); $^{13}$C NMR (100 MHz, CD$_3$OD): the adenosine moiety δ 154.4 (C-6), 152.3 (C-2), 148.4 (C-4), 139.8 (C-8), 119.7 (C-5), 87.9 (C-1'), 85.8 (C-4'), 73.3 (C-2'), 70.6 (C-3'), 61.6 (C-5'); the p-hydroxybenzyl moiety δ 156.1 (C-4"), 130.1 (C-1"), 128.5 (C-2", C-6"), 114.8 (C-3", C-5"), 42.3 (C-7").

Example 3: Preparation of
N$^6$-(o-hydroxybenzyl)-adenosine

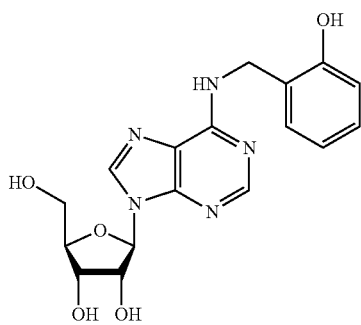

First step, a solution of o-hydroxybenzaldehyde oxime (1.0 g) and concentrated HCl (2.8 ml) in EtOH (50 ml) was subjected to hydrogenation at atmospheric pressure in the presence of 10% Pd/C (150 mg). The reaction mixture was filtered, and the filtrate was concentrated. The residue was suspended in EtOAc, and the suspension was filtered to yield o-hydroxybenzylamine hydrochloride (1.1 g) as a white solid.

Second step, a mixture of o-hydroxybenzylamine (223 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with CHCl$_3$—CH$_3$OH (10:1) to yield N$^6$-(o-hydroxybenzyl)-adenosine (210 mg) as a white solid: positive ESIMS m/z 374 [M+H]$^+$ and 396 [M+Na]$^+$; negative ESIMS m/z 372[M−H]$^-$; $^1$H NMR (300 MHz, DMSO-d$_6$): the adenosine moiety δ8.38 (1H, s, H-2), 8.26 (1H, brs, —NH), 8.20 (1H, s, H-8), 5.88 (1H, d, J=6.0 Hz, H-1'), 5.44 (1H, d, J=6.0 Hz, —OH), 5.35 (1H, m, —OH), 5.17 (1H, m, —OH), 4.60 (1H, m, H-2'), 4.13 (1H, m, H-3'), 3.95 (1H, m, H-4'), 3.67 (1H, m, H-5'a), 3.54 (1H, m, H-5'b); the o-hydroxybenzyl moiety δ 9.87 (1H, brs, —OH), 7.08 (1H, d, J=7.8 Hz, H-6"), 7.03 (1H, d, J=7.8 Hz, H-4"), 6.79 (1H, d, J=7.8 Hz, H-3"), 6.70 (1H, t, J=7.8 Hz, H-5"), 4.60 (2H, brs, H-7"); $^{13}$C NMR (75 MHz, DMSO-d$_6$): the adenosine moiety δ154.7 (s, C-6), 152.4 (d, C-2), 148.5 (s, C-4), 140.3 (d, C-8), 120.0 (s, C-5), 88.2 (d, C-1'), 86.1 (d, C-4'), 73.8 (d, C-2'), 70.8 (d, C-3'), 61.8 (t, C-5'); the o-hydroxybenzyl moiety δ155.1 (s, C-2"), 128.4 (s, C-1"), 128.1 (d, C-6"), 125.7 (s, C-4"), 119.1 (d, C-3"), 115.5 (d, C-5"), 40.0 (t, C-7").

Example 4: Preparation of
N$^6$-(p-methylbenzyl)-adenosine

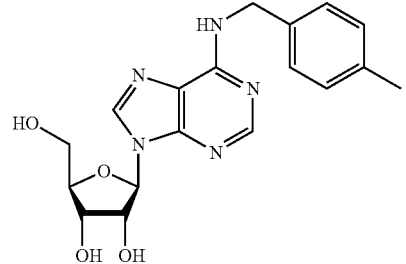

First step, hydroxyamine hydrochloride (2.04 g) and NaOAc (2.73 g) were added to a solution of p-metheylbenzylaldehyde (2 g) in EtOH (80 ml). The reaction mixture was stirred at room temperature for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield p-methylbenzaldehyde oxime (2.02 g) as a pale yellowish solid.

Second step, p-methylbenzaldehyde oxime (2.02 g) and concentrated HCl (6 ml) in EtOH (50 ml) was subjected to hydrogenation at atmospheric pressure in the presence of 10% Pd/C (318 mg). The reaction solution was filtered and the filtrate was concentrated. The residue was suspended in EtOAc, and the suspension was filtered to yield p-methylbenzylamine hydrochloride (2.0 g) as a white solid.

Third step, a mixture of p-methylbenzylamine (221 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with CHCl$_3$—CH$_3$OH (20:1) to yield N$^6$-(o-hydroxybenzyl)-adenosine (195 mg) as a white solid: positive ESIMS m/z 372 [M+H]$^+$ and 394 [M+Na]$^+$; negative ESIMS m/z 370[M−H]$^-$; $^1$H NMR (300 MHz, DMSO-d$_6$): the adenosine moiety δ 8.40 (1H, brs, —NH), 8.36 (1H, s, H-2), 8.18 (1H, s, H-8), 5.87 (1H, d, J=6.0 Hz, H-1'), 5.43 (1H, d, J=6.3 Hz, —OH), 5.37 (1H, m, —OH), 5.17 (1H, d, J=4.5 Hz, —OH), 4.60 (1H, m, H-2'), 4.14 (1H, m, H-3'), 3.95 (1H, m, H-4'), 3.66 (1H, m, H-5'a), 3.54 (1H, m, H-5'b); the p-methylbenzyl moiety δ 7.20 (2H, d, J=8.1 Hz, H-2", H-6"), 7.08 (2H, d, J=8.1 Hz, H-3", H-5"), 4.67 (2H, brs, H-7"), 2.24 (3H, s, —CH$_3$). $^{13}$C NMR (75 MHz, DMSO-d$_6$): the adenosine moiety δ 154.7 (s, C-6), 152.6 (d, C-2), 148.6 (s, C-4), 140.1 (d, C-8), 120.0 (s, C-5), 88.2 (d, C-1'), 86.2 (d, C-4'), 73.7 (d, C-2'), 70.9 (d, C-3'), 61.9 (t, C-5'); the p-methylbenzyl moiety δ 137.0 (s, C-1"), 135.9 (s, C-4"), 129.0 (d, C-2", C-6"), 127.3 (d, C-3", C-5"), 42.8 (t, C-7"), 20.8 (q, —CH$_3$).

Example 5: Preparation of N[6]-(m-methylbenzyl)-adenosine

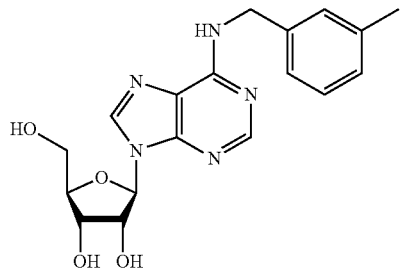

First step, hydroxyamine hydrochloride (1.22 g) and NaOAc (1.64 g) were added to a solution of m-metheylbenzaldehyde (1.2 g) in EtOH (80 ml). The reaction mixture was stirred at room temperature for 6 h. EtOH was removed under reduced pressure. $H_2O$ (40 ml) was added to the residue, and extracted with EtOAc (3×40 ml). The EtOAc of the combined organic layer was removed by rotary evaporation under reduced pressure to yield m-methylbenzaldehyde oxime (1.2 g) as a pale yellowish solid.

Second step, m-methylbenzaldehyde oxime (1.2 g) and concentrated HCl (3.6 ml) in EtOH (50 ml) was subjected to hydrogenation at atmospheric pressure in the presence of 10% Pd/C (188 mg). The reaction mixture was filtered and the filtrate was concentrated. The residue was suspended in EtOAc, and the suspension was filtered to yield m-methylbenzylamine hydrochloride (1.2 g) as a white solid.

Third step, a mixture of m-methylbenzylamine (221 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with $CHCl_3$—$CH_3OH$ (20:1) to yield N[6]-(o-hydroxybenzyl)-adenosine (208 mg) as a white solid: positive ESIMS m/z 372 [M+H]+, 394 [M+Na]+ and 410 [M+K]+; negative ESIMS m/z 370 [M−H]− and 406 [M+Cl]−; $^1$H NMR (300 MHz, DMSO-$d_6$): the adenosine moiety δ 8.40 (1H, brs, —NH), 8.37 (1H, s, H-2), 8.19 (1H, s, H-8), 5.88 (1H, d, J=6.3 Hz, H-1'), 5.43 (1H, d, J=6.3 Hz, —OH), 5.37 (1H, m, —OH), 5.17 (1H, d, J=4.8 Hz, —OH), 4.61 (1H, m, H-2'), 4.14 (1H, m, H-3'), 3.96 (1H, m, H-4'), 3.66 (1H, m, H-5'a), 3.56 (1H, m, H-5'b); the m-methylbenzyl moiety δ 7.16-7.09 (3H, m, H-2", H-4", H-5"), 7.00 (1H, d, J=7.2 Hz, H-6"), 4.67 (2H, brs, H-7"), 2.25 (3H, s, —$CH_3$); $^{13}$C NMR (75 MHz, DMSO-$d_6$): the adenosine moiety δ 154.6 (s, C-6), 152.5 (d, C-2), 148.5 (s, C-4), 140.1 (d, C-8), 119.9 (s, C-5), 88.2 (d, C-1'), 86.1 (d, C-4'), 73.7 (d, C-2'), 70.8 (d, C-3'), 61.8 (t, C-5'); the m-methylbenzyl moiety δ 140.1 (s, C-1"), 137.4 (s, C-3"), 128.3 (d, C-2"), 127.8 (d, C-5"), 127.4 (d, C-4"), 124.3 (d, C-6"), 43.0 (t, C-7"), 21.2 (q, —$CH_3$).

Example 6: Preparation of N[6]-(p-aminobenzyl)-adenosine

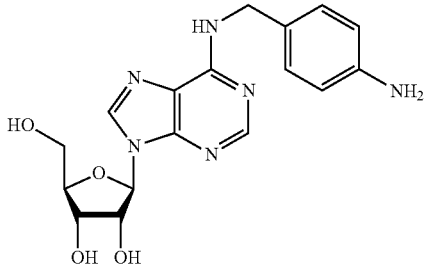

First step, p-aminobenzaldehyde (2 g), hydroxyamine hydrochloride (2.04 g), and NaOAc (2.73 g) were dissolved in EtOH (80 ml). The reaction mixture was stirred at room temperature for 6 h. EtOH was removed under reduced pressure. $H_2O$ (40 ml) was added to the residue, and extracted with EtOAc (3×40 ml). The EtOAc of the combined organic layer was removed by rotary evaporation under reduced pressure to yield p-aminobenzaldehyde oxime (2.02 g) as a pale yellowish solid.

Second step, p-aminobenzaldehyde oxime (2.02 g) and concentrated HCl (6 ml) in EtOH (50 ml) was subjected to hydrogenation at atmospheric pressure in the presence of 10% Pd/C (318 mg). The reaction mixture was filtered and the filtrate was concentrated. The residue was suspended in EtOAc, and the suspension was filtered to yield the p-aminobenzylamine hydrochloride (2.0 g) as a white solid.

Third step, a mixture of p-aminobenzylamine (221 mg, the hydrochloride), 6-chloropurine riboside (200 mg), and triethylamine (3 ml) in PrOH (60 ml) was heated to 70° C. and reacted for 8 h. After evaporation of the reaction mixture, the residue was separated by column chromatography over silica gel and eluted with $CHCl_3$—$CH_3OH$ (10:1) to yield N[6]-(p-aminobenzyl)-adenosine (195 mg) as a white solid: positive ESIMS m/z 373 [M+H]+ and 395 [M+Na]+; negative ESIMS m/z 371 [M−H]−; $^1$H NMR (300 MHz, DMSO-$d_6$): the adenosine moiety δ 8.34 (1H, s, H-2), 8.19 (2H, s, —NH, H-8), 5.87 (1H, d, 6.0 Hz, H-1'), 5.44-5.41 (2H, m, 2x—OH), 5.20 (1H, brs, —OH), 4.60 (1H, m, H-2'), 4.14 (1H, brs, H-3'), 3.95 (1H, m, H-4'), 3.67 (1H, m, H-5'a), 3.54 (1H, m, H-5'b); the p-aminobenzyl moiety δ 6.99 (2H, d, J=7.6 Hz, H-2", H-6"), 6.46 (2H, d, J=7.6 Hz, H-3", H-5"), 4.90 (2H, brs, —$NH_2$), 4.52 (2H, s, H-7"); $^{13}$C NMR (75 MHz, DMSO-$d_6$): the adenosine moiety δ 154.7 (s, C-6), 152.6 (d, C-2), 148.5 (s, C-4), 140.0 (d, C-8), 119.9 (d, C-5), 88.3 (d, C-1'), 86.2 (d, C-4'), 73.7 (d, C-2'), 70.9 (d, C-3'), 61.9 (t, C-5'); the p-aminobenzyl moiety δ 147.6 (s, C-4"), 128.5 (d, C-2", C-6"), 127.1 (s, C-1"), 114.0 (d, C-3", C-5"), 42.8 (t, C-7").

Example 7: Preparation of N⁶-(m-aminobenzyl)-adenosine

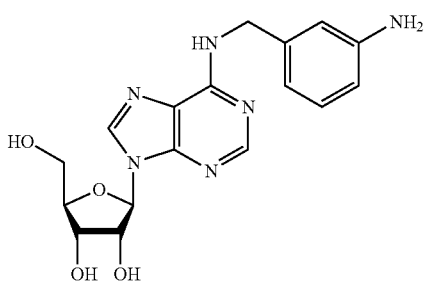

First step, m-aminobenzaldehyde (2.0 g), hydroxyamine hydrochloride (2.02 g), and NaOAc (2.71 g) were dissolved in EtOH (80 ml). The reaction mixture was stirred at room temperature for 6 h. EtOH was removed under reduced pressure. H₂O (40 ml) was added to the residue, and extracted with EtOAc (3×40 ml). The EtOAc of the combined organic layer was removed by rotary evaporation under reduced pressure to yield m-aminobenzaldehyde oxime (1.62 g) as a pale yellowish solid.

Second step, m-aminobenzaldehyde oxime (1.62 g) and concentrated HCl (5 ml) in EtOH (50 ml) was subjected to hydrogenation at atmospheric pressure in the presence of 10% Pd/C (254 mg). The reaction mixture was filtered and the filtrate was concentrated. The residue was suspended in EtOAc, and the suspension was filtered to yield m-aminobenzylamine hydrochloride (1.6 g) as a white solid.

Third step, a mixture of m-aminobenzylamine (222 mg, the hydrochloride), 6-chloropurine riboside (200 mg), and triethylamine (3 ml) in PrOH (60 ml) was heated to 70° C. and reacted for 8 h. After evaporation of the reaction mixture, the residue was separated by column chromatography over silica gel and eluted with CHCl₃—CH₃OH (10:1) to yield N⁶-(p-aminobenzyl)-adenosine (180 mg) as a white solid: positive ESIMS m/z 373 [M+H]⁺ and 395 [M+Na]⁺; negative ESIMS m/z 371 [M−H]⁻; ¹H NMR (300 MHz, DMSO-d₆): the adenosine moiety δ 8.35 (1H, s, H-2), 8.30 (1H, brs, —NH), 8.18 (1H, s, H-8), 5.87 (1H, d, J=6.0 Hz, H-1'), 5.40 (2H, m, 2×—OH), 5.18 (1H, d, J=4.2 Hz, —OH), 4.96 (2H, s, —NH₂), 4.62 (1H, m, H-2'), 4.14 (1H, m, H-3'), 3.95 (1H, m, H-4'), 3.66 (1H, m, H-5'a), 3.56 (1H, m, H-5'b); the m-aminobenzyl moiety δ 6.49 (1H, s, H-4"), 6.45 (1H, d, J=7.8 Hz, H-6"), 6.38 (1H, d, J=7.8 Hz, H-2"), 4.60 (2H, brs, H-7"); ¹³C NMR (75 MHz, DMSO-d₆): the adenosine moiety δ 154.7 (s, C-6), 152.5 (d, C-2), 148.6 (s, C-4), 140.0 (d, C-8), 119.9 (s, C-5), 88.1 (d, C-1'), 86.1 (d, C-4'), 73.6 (d, C-2'), 70.8 (d, C-3'), 61.8 (t, C-5'); the m-aminobenzyl moiety δ 148.6 (s, C-3"), 140.6 (s, C-1"), 128.8 (d, C-5"), 114.7 (d, C-6"), 112.5 (d, C-2", C-4"), 43.0 (t, C-7").

Example 8: Preparation of N⁶-(p-nitrobenzyl)-adenosine

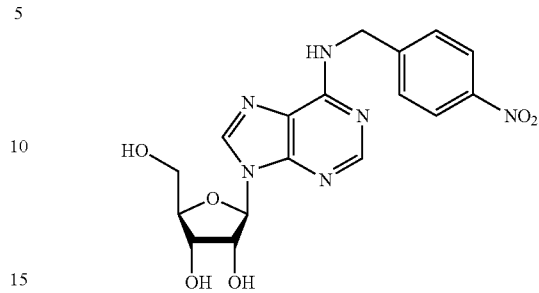

A mixture of p-nitrobenzylamine (158 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with CHCl₃—CH₃OH (10:1) to yield N⁶-(p-aminobenzyl)-adenosine (250 mg) as a white solid: positive ESIMS m/z 403 [M+H]⁺ and 425 [M+Na]⁺; negative ESIMS m/z 401 [M−H]⁻; ¹H NMR (300 MHz, DMSO-d₆): the adenosine moiety δ 8.62 (1H, brs, —NH), 8.41 (1H, s, H-2), 8.19 (1H, s, H-8), 5.89 (1H, d, J=6.3 Hz, H-1'), 5.44 (1H, d, J=6.0 Hz, —OH), 5.33 (1H, m, —OH), 5.18 (1H, d, J=7.2 Hz, —OH), 4.62 (1H, m, H-2'), 4.13 (1H, m, H-3'), 3.95 (1H, m, H-4'), 3.66 (1H, m, H-5'a), 3.54 (1H, m, H-5'b); the p-nitrobenzyl moiety δ 8.16 (1H, d, J=8.4 Hz, H-3", H-5"), 7.56 (1H, d, J=8.4 Hz, H-2", H-6"), 4.81 (2H, brs, H-7"); ¹³C NMR (75 MHz, DMSO-d₆): the adenosine moiety δ 154.4 (s, C-6), 152.4 (d, C-2), 148.7 (s, C-4), 140.3 (d, C-8), 119.9 (s, C-5), 88.0 (d, C-1'), 86.0 (d, C-4'), 73.6 (d, C-2'), 70.7 (d, C-3'), 61.7 (t, C-5'), the p-nitrobenzyl moiety δ 148.3 (s, C-4"), 146.4 (s, C-1"), 128.1 (d, C-2", C-6"), 123.5 (d, C-3", C-5"), 42.7 (t, C-7").

Example 9: Preparation of N⁶-(o-nitrobenzyl)-adenosine

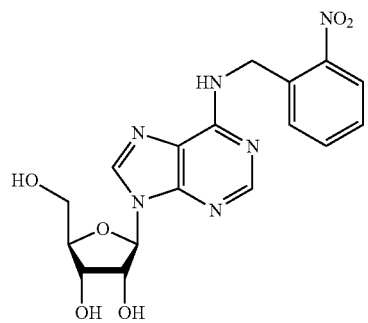

First step, benzotriazole (148 mg) and o-nitrobenzaldehyde (226 mg) were added to a solution of adenosine (251 mg) in anhydrous ethanol (40 ml). The suspension was refluxed in the presence of a few drops of acetic acid as a catalyst for 14 h, using a soxhlet extractor with 4 Å molecular sieves in the thimble. Every 30 min, isobutyraldehyde (1 ml) was added. The reaction mixture was evaporated to give a viscous liquid which was separated by column chromatography over silica gel using chloroform-methanol (30:1~15:1) to yield a product as a pale solid (133 mg).

Second step, the first step product (105 mg) was dissolved in dry tetrahydrofuran (60 ml) and refluxed with sodium borohydride (46 mg) for 8 h. The reaction solution was cooled to room temperature, poured onto ice water, then neutralized with acetic acid, and extract with chloroform. After evaporation of the organic layer, the residue was purified by column chromatography over silica gel using chloroform-methanol (30:1~15:1) to yield $N^6$-(isobutyl)-adenosine as a pale solid (67 mg): positive ESIMS m/z 403[M+H]$^+$; $^1$H NMR (300 MHz, DMSO-d$_6$): the adenosine moiety δ 8.52 (1H, brs, —NH), 8.43 (1H, s, H-8), 8.16 (1H, s, H-2), 5.89 (1H, d, J=5.7 Hz, H-1'), 5.44 (1H, d, J=6.0 Hz, —OH), 5.32 (1H, t, J=6.0 Hz, —OH), 5.19 (1H, d, J=5.1 Hz, —OH), 4.62 (1H, m, H-2'), 4.14 (1H, m, H-3'), 3.96 (1H, m, H-4'), 3.68 (1H, m, H-5a'), 3.55 (1H, m, H-5b'); the o-nitrobenzyl moiety δ 8.04 (1H, dd, J=8.1, 1.2 Hz, H-3"), 7.66 (1H, td, J=8.1, 1.2 Hz, H-5"), 7.46-7.54 (2H, m, H-4", H-6"), 4.98 (2H, m, H-7"); $^{13}$C NMR (125 MHz, DMSO-d$_6$): the adenosine moiety δ 154.4 (C-6), 152.2 (C-2), 148.6 (C-4), 140.7 (C-8), 119.9 (C-5), 87.9 (C-1'), 85.7 (C-4'), 73.5 (C-2'), 70.6 (C-3'), 61.6 (C-5'); the o-nitrobenzyl moiety δ 148.0 (C-2"), 134.8 (C-1"), 133.7 (C-5"), 128.9 (C-3"), 128.0 (C-4"), 124.5 (C-6"), 40.3 (C-7").

Example 10: Preparation of $N^6$-(p-trifluoromethoxybenzyl)-adenosine

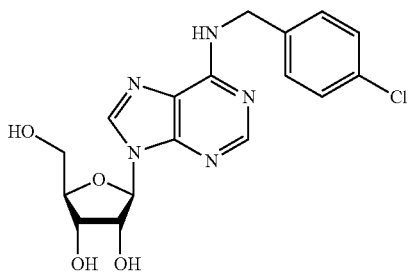

First step, p-chlorobenzylaldehyde (3.0 g), hydroxyamine hydrochloride (2.6 g), and NaOAc (3.5 g) were dissolved in EtOH (80 ml). The reaction mixture was stirred at room temperature for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield p-chlorobenzaldehyde oxime (2.45 g) as a pale yellowish solid.

Second step, p-chlorobenzaldehyde oxime (2.45 g) and zinc dust (6.15 g) in HOAc (25 ml) was stirred at room temperature for 6 h. The reaction solution was filtered to remove the excess zinc dust and ZnOAc residue, and the filtrate was concentrated to yield p-chlorolbenzylamine (1.25 g) as a yellowish oil.

Third step, a mixture of p-chlorobenzylamine (250 mg), 6-chloropurine riboside (200 mg), and triethylamine (3 ml) in PrOH (60 ml) was heated to 70° C. and reacted for 8 h. After evaporation of the reaction mixture, the residue was separated by column chromatography over silica gel and eluted with CHCl$_3$—CH$_3$OH (10:1) to yield $N^6$-(o-hydroxybenzyl)-adenosine (245 mg) as a white solid: positive ESIMS m/z 392 [M+H]$^+$ and 414 [M+Na]$^+$; negative ESIMS m/z 390 [M−H]$^-$; $^1$H NMR (300 MHz, DMSO-d$_6$): the adenosine moiety δ 8.49 (1H, brs, —NH), 8.38 (1H, s, H-2), 8.19 (1H, s, H-8), 5.87 (1H, d, J=6.0 Hz, H-1'), 5.43 (1H, d, J=4.3 Hz, —OH), 5.35 (1H, m, —OH), 5.17 (1H, d, J=4.5 Hz, —OH), 4.60 (1H, m, H-2'), 4.13 (1H, m, H-3'), 3.95 (1H, m, H-4'), 3.66 (1H, m, H-5'a), 3.55 (1H, m, H-5'b); the p-chlorobenzyl moiety δ 7.34 (4H, s, H-2", H-3", H-5", H-6"), 4.67 (2H, brs, H-7"); $^{13}$C NMR (75 MHz, DMSO-d$_6$): the adenosine moiety δ 154.5 (s, C-6), 152.4 (d, C-2), 148.5 (s, C-4), 140.1 (d, C-8), 119.9 (s, C-5), 88.0 (d, C-1'), 86.0 (d, C-4'), 73.6 (d, C-3'), 70.7 (d, C-4'), 61.7 (t, C-5'); the p-chlorobenzyl moiety δ 139.1 (s, C-1"), 131.2 (s, C-4"), 129.0 (d, C-2", C-6"), 128.2 (d, C-3", C-5"), 42.4 (t, C-7").

Example 11: Preparation of $N^6$-(p-fluorobenzyl)-adenosine

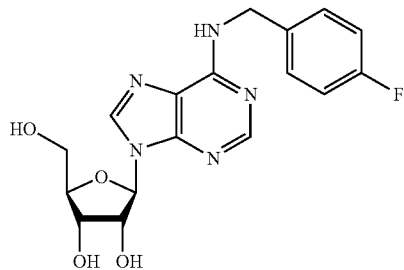

First step, of p-fluorobenzylaldehyde (2 g), hydroxyamine hydrochloride (1.97 g), and NaOAc (2.64 g) were dissolved in EtOH (80 ml). The reaction mixture was stirred at room temperature for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield p-fluorobenzaldehyde oxime (1.8 g) as a pale yellowish solid.

Second step, p-fluorobenzaldehyde oxime (1.8 g) and zinc dust (5.05 g) in HOAc (25 ml) was stirred at room temperature for 6 h. The reaction solution was filtered to remove the excess zinc dust and ZnOAc residue, and the filtrate was concentrated to yield p-fluorobenzylamine (1.25 g) as a yellowish oil.

Third step, a mixture of p-fluorobenzylamine (339 mg), 6-chloropurine riboside (300 mg), and triethylamine (3 ml) in PrOH (60 ml) was heated to 70° C. and reacted for 8 h. After evaporation of the reaction mixture, the residue was separated by column chromatography over silica gel and eluted with CHCl$_3$—CH$_3$OH (20:1) to yield $N^6$-(p-fluoroxybenzyl)-adenosine (335 mg) as a white solid: positive ESIMS m/z 376 [M+H]$^+$ and 398 [M+Na]$^+$; negative ESIMS m/z 374 [M−H]$^-$; $^1$H NMR (300 MHz, DMSO-d$_6$): the adenosine moiety δ 8.48 (1H, brs, —NH), 8.41 (1H, s, H-2), 8.24 (1H, s, H-8), 5.94 (1H, d, J=6.0 Hz, H-1'), 5.52 (2H, m, —OH), 5.29 (1H, m, —OH), 4.67 (1H, m, m, H-2'), 4.21 (1H, m, H-3'), 4.02 (1H, m, H-4'), 3.72 (1H, m, H-5'a), 3.59 (1H, m, H-5'b); the p-fluorobenzyl moiety δ 7.37 (2H, m, H-2", H-6"), 7.09 (2H, m, H-3", H-5"), 4.68 (2H, brs, H-7"); $^{13}$C NMR (75 MHz, DMSO-d$_6$): the adenosine moiety δ 154.6 (s, C-6), 152.5 (d, C-2), 148.6 (s, C-4), 140.2 (d, C-8), 120.0 (s, C-5), 88.3 (d, C-1'), 86.2 (d, C-4'), 73.8 (d, C-2'), 70.9 (d, C-3'), 61.9 (t, C-5'); the p-fluorobenzyl moiety δ 162.9, 159.7 (240.67 Hz, C-4"), 136.3 (s, C-1"), 129.3 (d, J=82.5 Hz, C-2", C-6"), 115.1 (d, J=200.5 Hz, C-3", C-5"), 42.4 (t, C-7").

Example 12: Preparation of N$^6$-(p-trifluoromethoxybenzyl)-adenosine

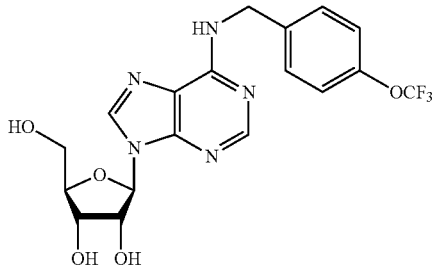

First step, p-trifluoromethoxybenzaldehyde (1.5 g), hydroxyamine hydrochloride (965 mg), and NaOAc (1.30 g) were dissolved in EtOH (80 ml). The reaction mixture was stirred at room temperature for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield p-trifluoromethoxybenzaldehyde oxime (1.3 g) as a pale yellowish solid.

Second step, p-trifluoromethoxybenzaldehyde oxime (1.3 g) and concentrated HCl (2.5 ml) in EtOH (50 ml) was subjected to hydrogenation at atmospheric pressure in the presence of 10% Pd/C (134 mg). The reaction solution was filtered and the filtrate was concentrated. The residue was suspended in EtOAc, and the suspension was filtered to yield p-trifluoromethoxybenzylamine hydrochloride (1.15 g) as a white solid.

Third step, a mixture of p-trifluoromethoxybenzylamine (382 mg, the hydrochloride), 6-chloropurine riboside (300 mg), and triethylamine (3 ml) in PrOH (60 ml) was heated to 70° C. and reacted for 8 h. After evaporation of the reaction mixture, the residue was separated by column chromatography over silica gel eluting with CHCl$_3$—CH$_3$OH (20:1) to yield N$^6$-(p-trifluoromethoxybenzyl)-adenosine (375 mg) as a white solid: positive ESIMS m/z 442 [M+H]$^+$ and 464 [M+Na]$^+$; negative ESIMS m/z 440 [M−H]$^-$; $^1$H NMR (300 MHz, DMSO-d$_6$): the adenosine moiety δ 8.53 (1H, brs, —NH), 8.38 (1H, s, H-2), 8.19 (1H, s, H-8), 5.87 (1H, d, J=6.0 Hz, H-1'), 5.46 (1H, d, J=6.3 Hz, —OH), 5.40 (1H, m, —OH), 5.21 (1H, d, J=4.5 Hz, —OH), 4.57 (1H, m, H-2'), 4.13 (1H, m, H-3'), 3.95 (1H, m, H-4'), 3.65 (1H, m, H-5'a), 3.53 (1H, m, H-5'b); the p-p-trifluoromethoxybenzyl moiety δ 7.43 (2H, d, J=8.1 Hz, H-3", H-5"), 7.28 (2H, d, J=8.1 Hz, H-2", H-6"), 4.71 (2H, brs, H-7"); $^{13}$C NMR (75 MHz, DMSO-d$_6$): the adenosine moiety δ 154.4 (s, C-6), 152.4 (d, C-2), 148.6 (s, C-4), 139.6 (d, C-8), 119.8 (s, C-5), 88.0 (d, C-1'), 85.9 (d, C-4'), 73.5 (d, C-2'), 70.7 (d, C-3'), 61.6 (t, C-5'); the p-trifluoromethoxybenzyl moiety δ 147.1 (s, C-4"), 140.1 (s, C-1"), 128.9 (d, C-3", C-5"), 120.9 (d, C-2", C-6"), 120.7 (m, —OCF$_3$), 40.3 (t, C-7").

Example 13: Preparation of N$^6$-(p-trifluoromethylbenzyl)-adenosine

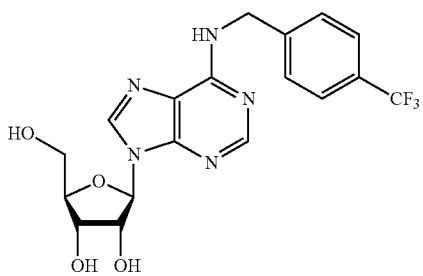

First step, p-trifluoromethylbenzaldehyde (1 g), hydroxyamine hydrochloride (702 mg), and NaOAc (942 mg) were dissolved in EtOH (80 ml). The reaction mixture was stirred at room temperature for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield p-trifluoromethylbenzaldehyde oxime (970 mg) as a pale yellowish solid.

Second step, p-trifluoromethylbenzaldehyde oxime (970 mg) and concentrated HCl (2 ml) in EtOH (50 ml) was subjected to hydrogenation at atmospheric pressure in the presence of 10% Pd/C (109 mg). The reaction solution was filtered and the filtrate was concentrated. The residue was suspended in EtOAc, and the suspension was filtered to yield p-trifluoromethylbenzylamine hydrochloride (863 mg) as a white solid.

Third step, a mixture of p-trifluoromethylbenzylamine (296 mg, the hydrochloride), 6-chloropurine riboside (200 mg), and triethylamine (3 ml) in PrOH (60 ml) was heated to 70° C. and reacted for 8 h. After evaporation of the reaction mixture, the residue was separated by column chromatography over silica gel and eluted with CHCl$_3$—CH$_3$OH (20:1) to yield N$^6$-(p-trifluoromethylbenzyl)-adenosine (268 mg) as a white solid: positive ESIMS m/z 426 [M+H]$^+$ and 448 [M+Na]$^+$; negative ESIMS m/z 424 [M−H]$^-$; $^1$H NMR (300 MHz, DMSO-d$_6$): the adenosine moiety δ 8.57 (1H, brs, —NH), 8.39 (1H, s, H-2), 8.19 (1H, s, H-8), 5.88 (1H, d, 6.3 Hz, H-1'), 5.43 (1H, d, 6.3 Hz, —OH), 5.33 (1H, m, —OH), 5.18 (1H, d, 4.8 Hz, —OH), 4.60 (1H, m, H-2'), 4.13 (1H, m, H-3'), 3.95 (1H, m, H-4'), 3.68-3.64 (1H, m, H-5'a), 3.56-3.54 (1H, m, H-5'b'); the p-trifluoromethylbenzyl moiety δ 7.65 (2H, d, 8.4 Hz, H-3", H-5"), 7.52 (2H, d, 8.4 Hz, H-2", H-6"), 4.78 (1H, brs, H-7"); $^{13}$C NMR (75 MHz, DMSO-d$_6$): the adenosine moiety δ 154.4 (s, C-6), 152.4 (d, C-2), 148.6 (s, C-4), 140.2 (d, C-8), 119.8 (s, C-5), 87.9 (d, C-1'), 85.9 (d, C-4'), 73.5 (d, C-2'), 70.7 (d, C-3'), 61.7 (t, C-5'); the p-trifluoromethylbenzyl moiety δ 145.0 (C-1"), 127.7 (C-2", C-6"), 127.3 (d, J=32 Hz, C-4"), 124.4 (t, J=271 Hz, —CF$_3$), 125.2 (d, J=4.6 Hz, C-3", C-5"), 43.6 (t, C-7").

Example 14: Preparation of N⁶-(isobutyl)-adenosine

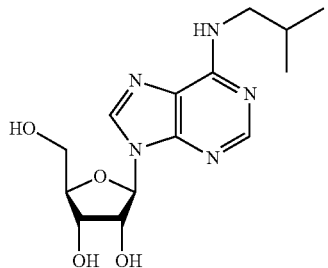

First step, benzotriazole (148 mg) and isobutanol (108 mg) were added to a solution of adenosine (251 mg) in anhydrous ethanol (40 ml). The suspension was refluxed in the presence of a few drops of acetic acid as a catalyst for 14 h, using a soxhlet extractor with 4 Å molecular sieves in the thimble. Every 30 min, isobutyraldehyde (1 ml) was added. The mixture was evaporated to a viscous liquid which was separated by column chromatography over silica gel and eluted with chloroform-methanol (30:1~15:1) to yield a pale solid (368 mg).

Second step, the first step product (368 mg) was dissolved in dry tetrahydrofuran (60 ml) and refluxed with sodium borohydride (191 mg) for 8 h. The reaction solution was cooled to room temperature, poured onto ice water, then neutralized with acetic acid, and extracted with chloroform. After evaporation of the chloroform layer, the residue was purified by column chromatography over silica gel using chloroform-methanol (30:1~15:1) to yield N⁶-(isobutyl)-adenosine as a pale solid (36 mg): positive ESIMS m/z 324 [M+H]⁺; negative ESIMS m/z 322 [M−H]⁻ and 358 [M+Cl]⁻; ¹H NMR (300 MHz, DMSO-d₆): the adenosine moiety δ 8.33 (1H, s, H-2), 8.18 (1H, brs, H-8), 7.92 (1H, brs, —NH), 5.86 (1H, d, J=6.3 Hz, H-1'), 5.42 (2H, d, J=5.1 Hz, —OH×2), 5.17 (1H, m, —OH), 4.61 (1H, m, H-2'), 4.13 (1H, m, H-3'), 3.95 (1H, m, H-4'), 3.68 (1H, m, H-5a'), 3.55 (1H, m, H-5b'); the isobutyl moiety δ 3.29 (2H, m, H-1"), 1.95 (1H, m, H-2"), 0.87 (6H, d, J=6.6 Hz, H-3", H-4"); ¹³C NMR (125 MHz, DMSO-d₆): the adenosine moiety δ 154.8 (C-6), 152.3 (C-2), 148.2 (C-4), 139.6 (C-8), 119.6 (C-5), 87.9 (C-1'), 85.9 (C-4'), 73.4 (C-2'), 70.6 (C-3'), 61.7 (C-5'); the isobutyl moiety δ 47.1 (C-1"), 27.8 (C-2"), 20.1 (C-4", C-3").

Example 15: Preparation of N⁶-(cyclohexylmethyl)-adenosine

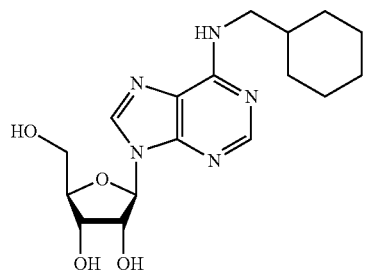

First step, benzotriazole (148 mg) and cyclohexylformaldehyde (168 mg) were added to a solution of adenosine (251 mg) in anhydrous ethanol (40 ml). The suspension was reflux in the presence of a few drops of acetic acid as a catalyst for 14 h, using a soxhlet extractor with 4 Å molecular sieves in the thimble. The reaction mixture was evaporated to a viscous liquid which was separated by column chromatography over silica gel using chloroform-methanol (30:1~15:1) to yield a pale solid (219 mg).

Second step, the first step product (152 mg) was dissolved in dry tetrahydrofuran (60 ml) and refluxed with sodium borohydride (73 mg) for 8 h. The reaction solution was cooled to room temperature, poured onto ice water, then neutralized with acetic acid, and extracted with chloroform. After evaporation of the chloroform, the residue was purified by column chromatography over silica gel using chloroform-methanol (30:1~15:1) to yield N⁶-(cyclohexylmethyl)-adenosine as a pale solid (36 mg): positive ESIMS m/z 364 [M+H]⁺; negative ESIMS m/z 362 [M−H]⁻ and 398 [M+Cl]⁻; ¹H NMR (300 MHz, DMSO-d₆): the adenosine moiety δ 8.32 (1H, s, H-2), 8.18 (1H, s, H-8), 7.88 (1H, brs, —NH), 5.86 (1H, d, J=6.3 Hz, H-1'), 5.42 (2H, d, J=6.0 Hz, —OH×2), 5.17 (1H, d, J=5.1 Hz, —OH), 4.61 (1H, m, H-2'), 4.13 (1H, m, H-3'), 3.95 (1H, m, H-4'), 3.66 (1H, m, H-5a'), 3.51 (1H, m, H-5b'); the cyclohexylmethyl moiety δ 3.32 (2H, m, H-7"), 0.89-1.71 (11H, m, H-1"~H-6"); ¹³C NMR (125 MHz, DMSO-d₆): the adenosine moiety δ 155.5 (C-6), 153.0 (C-2), 148.8 (C-4), 140.3 (C-8), 120.4 (C-5), 88.7 (C-1'), 86.6 (C-4'), 74.1 (C-2'), 71.4 (C-3'), 62.4 (C-5'); the cyclohexylmethyl moiety δ 46.5 (C-7"), 37.9 (C-1"), 31.1 (C-4"), 26.8 (C-3", C-5"), 26.1 (C-2", C-6").

Example 16: Preparation of N⁶-(4-phenylpiperazinyl)-adenosine

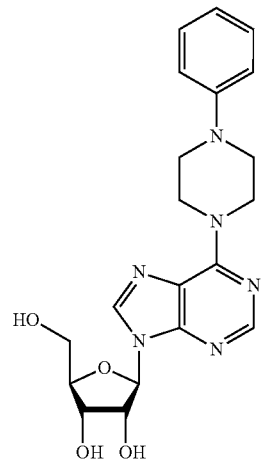

A mixture of N-phenylpiperidine (681 mg), 6-chloropurine riboside (300 mg), and triethylamine (4.5 ml) in PrOH (60 ml) was heated to 70° C. and reacted for 8 h. After evaporation of the reaction mixture, the residue was separated by column chromatography over silica gel and eluted with CHCl₃—CH₃OH (20:1) to yield N⁶-(4-phenylpiperazinyl)-adenosine (230 mg) as a white solid: positive ESIMS m/z 413 [M+H]⁺ and 435[M+Na]⁺; ¹H NMR (300 MHz, DMSO-d₆): the adenosine moiety δ 8.43 (1H, s, H-2), 8.27 (1H, s, H-8), 5.92 (1H, d, 5.7 Hz, H-1'), 5.47 (1H, m, —OH), 5.31 (1H, m, —OH), 5.20 (1H, m, —OH), 4.57 (1H, m, —OH), 4.37 (1H, m, H-2'), 4.14 (1H, m, H-3'), 3.95 (1H, m, H-4'), 3.69-3.65 (1H, m, H-5a'), 3.57-3.55 (1H, m, H-5b');

the 4-phenylpiperazinyl δ 7.23 (2H, t, 7.8 Hz, H-3", H-5"), 7.00 (2H, d, 8.4 Hz, H-2", H-6"), 6.80 (1H, t, 7.2 Hz, H-4"), 4.37 (2H, brs, H-7"), 3.26 (4H, m, H-8", H-9", H-11", H-12").

Example 17: Preparation of N$^6$-(2-furanylmethyl)-adenosine

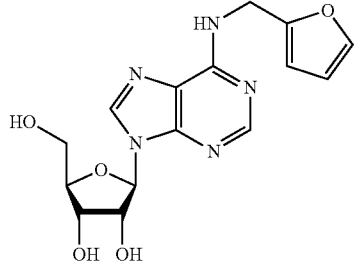

First step, 2-furancarbaldehyde (1.0 g), hydroxyamine hydrochloride (1.27 g), and NaOAc (1.71 g) were dissolved in EtOH (80 ml). The reaction mixture was stirred at room temperature for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield 2-furancarbaldehyde oxime (1.04 g) as a pale yellowish solid.

Second step, 2-furancarbaldehyde oxime (1.04 g) and concentrated HCl (4 ml) in EtOH (50 ml) was subjected to hydrogenation at atmospheric pressure in the presence of 10% Pd/C (200 mg). The reaction solution was filtered and the filtrate was concentrated. The residue was suspended in EtOAc, and the suspension was filtered to yield 2-furanylmethanamine hydrochloride (1.13 g) as a white solid.

Third step, a mixture of 2-furanylmethanamine (281 mg, the hydrochloride), 6-chloropurine riboside (200 mg), and triethylamine (3 ml) in PrOH (60 ml) was heated to 70° C. and reacted for 8 h. After evaporation of the reaction mixture, the residue was separated by column chromatography over silica gel eluting with CHCl$_3$—CH$_3$OH (20:1) to yield N$^6$-(2-furanylmethyl)-adenosine (220 mg) as a white solid: positive ESIMS m/z 348 [M+H]$^+$, 362[M+Na]$^+$ and 370 [M+K]$^+$; negative ESIMS m/z 346 [M−H]$^-$; $^1$H NMR (300 MHz, DMSO-d$_6$): the adenosine moiety δ 8.38 (1H, s, H-2), 8.30 (1H, brs, —NH), 8.23 (1H, s, H-8), 5.88 (1H, d, 6.3 Hz, H-1'), 5.45 (1H, d, 6.0 Hz, —OH), 5.36 (1H, m, —OH), 5.17 (1H, d, 4.5 Hz, —OH), 4.59 (1H, m, H-2'), 4.13 (1H, m, H-3'), 3.95 (1H, m, H-4'), 3.68-3.64 (1H, m, H-5a'), 3.57-3.40 (1H, m, H-5b'); the 2-furanylmethyl moiety δ 7.53 (1H, s, H-5"), 6.34 (1H, m, H-4"), 6.21 (1H, m, H-3"), 4.69 (1H, brs, H-6"); $^{13}$C NMR (75 MHz, DMSO-d$_6$): the adenosine moiety δ 154.4 (s, C-6), 152. (d, C-2), 148.7 (s, C-4), 140.2 (d, C-8), 120.0 (s, C-5), 88.1 (d, C-1'), 86.0 (d, C-4'), 73.6 (d, C-2'), 70.8 (d, C-3'), 61.8 (t, C-6'); the 2-furanylmethyl moiety δ 152.9 (s, C-2"), 142.0 (d, C-5"), 110.6 (d, C-4"), 106.8 (d, C-3"), 36.6 (t, C-6").

Example 18: Preparation of N$^6$-(5-methyl-2-furanylmethyl)-adenosine

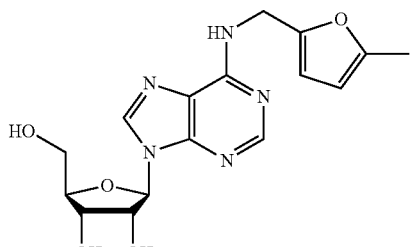

First step, hydroxyamine hydrochloride (1.01 g) and NaOAc (1.33 g) were added to a solution of 5-methyl-2-furancarbaldehyde (890 mg) in EtOH (80 ml). The reaction mixture was stirred at room temperature for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield 5-methyl-2-furancarbaldehyde oxime (950 mg) as a pale yellowish solid.

Second step, 5-methyl-2-furancarbaldehyde oxime (950 mg) and concentrated HCl (3.2 ml) in EtOH (50 ml) was subjected to hydrogenation at atmospheric pressure in the presence of 10% Pd/C (161 mg). The reaction solution was filtered and the filtrate was concentrated. The residue was suspended in EtOAc, and the suspension was filtered to yield 5-methyl-2-furanylmethanamine hydrochloride (897 mg) as a pale yellowish solid.

Third step, a mixture of 5-methyl-2-furanylmethanamine (207 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with CHCl$_3$—CH$_3$OH (20:1) to yield N$^6$-(5-methyl-2-furanylmethyl)-adenosine (227 mg) as a white solid: positive ESIMS m/z 362 [M+H]$^+$, 384 [M+Na]$^+$ and 400 [M+K]$^+$; negative ESIMS m/z 361 [M−H]$^-$; $^1$H NMR (300 MHz, DMSO-d$_6$): the adenosine moiety δ 8.37 (1H, s, H-2), 8.20 (2H, brs, —NH, H-8), 5.88 (1H, d, 6.0 Hz, H-1'), 5.43 (1H, d, 6.3. Hz, —OH), 5.35 (1H, m, —OH), 5.17 (1H, d, 4.8 Hz, —OH), 4.60 (1H, m, H-2'), 4.13 (1H, m, H-3'), 3.95 (1H, m, H-4'), 3.68-3.63 (1H, m, H-5a'), 3.57-3.54 (1H, m, H-5b'); the 5-methyl-2-furanylmethyl moiety δ 6.08 (1H, d, 3.0 Hz, H-3"), 5.93 (1H, d, 3.0 Hz, H-4"), 4.60 (2H, brs, H-7"), 2.19 (3H, s, —CH$_3$); $^{13}$C NMR (75 MHz, DMSO-d$_6$): the adenosine moiety δ 154.5 (s, C-6), 152.4 (d, C-2), 148.7 (s, C-4), 140.2 (d, C-8), 119.9 (s, C-5), 88.1 (d, C-1'), 86.1 (d, C-4'), 73.7 (d, C-2'), 70.8 (d, C-3'), 61.8 (t, C-5'); the 5-methyl-2-furanylmethyl moiety δ 151.1 (s, C-5"), 150.6 (s, C-2"), 107.7 (d, C-3"), 106.5 (d, C-4"), 36.7 (t, C-6"), 13.4 (q, —CH$_3$).

Example 19: Preparation of N⁶-(2-thiopheneylmethyl)-adenosine

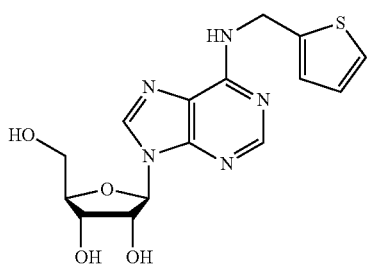

First step, hydroxyamine hydrochloride (3.27 g) and NaOAc (4.39 g) were added to a solution of 2-thiophenecarbaldehyde (3.0 g) in EtOH (80 ml). The reaction mixture was stirred at room temperature for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield 2-thiophenecarbaldehyde oxime (2.75 g) as a pale yellowish solid.

Second step, 2-thiophenecarbaldehyde oxime (2.75 g) and zinc dust (8.63 g) in HOAc (25 ml) was stirred at room temperature for 6 h. The reaction solution was filtered to remove the excess zinc dust and ZnOAc residue, and the filtrate was concentrated to yield 2-thiopheneylmethanamine (1.25 g) as a yellowish oil.

Third step, a mixture of 2-thiopheneylmethanamine (592 mg), 6-chloropurine riboside (500 mg) and triethylamine (7.3 ml) in PrOH (60 ml) was heated to 70° C. and reacted for 8 h. After evaporation of the reaction mixture, the residue was separated by column chromatography over silica gel and eluted with CHCl$_3$—CH$_3$OH (20:1) to yield N⁶-(2-thiopheneylmethyl)-adenosine (490 mg) as a white solid: positive ESIMS m/z 364 [M+H]⁺, 386 [M+Na]⁺ and 402 [M+K]⁺; negative ESIMS m/z 399 [M+Cl]⁻; ¹H NMR (300 MHz, DMSO-d$_6$): the adenosine moiety δ 8.50 (1H, brs, —NH), 8.38 (1H, s, H-2), 8.26 (1H, s, H-8), 5.88 (1H, d, 6.3 Hz, H-1'), 5.43 (1H, brs, —OH), 5.19 (1H, brs, —OH), 4.61 (1H, m, H-2'), 4.14 (1H, m, H-3'), 3.95 (1H, m, H-4'), 3.66 (1H, dd, 12.0 Hz, 3.6 Hz, H-5a'), 3.54 (1H, dd, 12.0 Hz, 3.6 Hz, H-5b'); the 2-thiopheneylmethyl δ 7.32 (1H, m, H-5"), 7.02 (1H, m, H-3"), 6.92 (1H, m, H-4"), 4.85 (2H, brs, H-7"); ¹³C NMR (75 MHz, DMSO-d$_6$): the adenosine moiety δ 154.1 (s, C-6), 152.3 (d, C-2), 148.6 (s, C-4), 140.2 (d, C-8), 119.9 (s, C-5), 88.1 (d, C-1'), 86.1 (d, C-4'), 73.7 (d, C-2'), 70.8 (d, C-3'), 61.8 (t, C-6'); the 2-thiopheneylmethyl moiety δ 143.0 (s, C-2"), 126.7 (d, C-4"), 125.6 (d, C-3"), 124.9 (d, C-5"), 38.3 (t, C-6").

Example 20: Preparation of N⁶-(5-methyl-2-thiopheneylmethyl)-adenosine

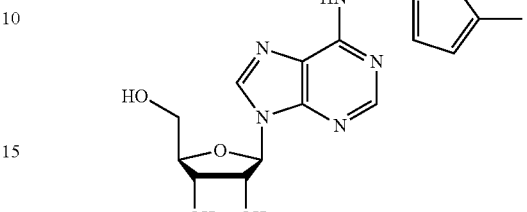

First step, hydroxyamine hydrochloride (2.6 g) and NaOAc (3.4 g) were added to a solution of 5-methyl-2-thiophenecarbaldehyde (2.5 g) in EtOH (80 ml). The reaction mixture was stirred at room temperature for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield 5-methyl-2-thiophenecarbaldehyde oxime (2.1 g) as a pale yellowish solid.

Second step, 5-methyl-2-thiophenecarbaldehyde oxime (2.1 g) and zinc dust (5.89 g) in HOAc (15 ml) was stirred at room temperature for 6 h. The reaction solution was filtered to remove the excess zinc dust and ZnOAc residue, and the filtrate was concentrated to yield 5-methyl-2-thiopheneylmethanamine (960 mg) as a yellowish oil.

Third step, a mixture of 5-methyl-2-thiopheneylmethanamine (262 mg), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with CHCl$_3$—CH$_3$OH (20:1) to yield N⁶-(5-methyl-2-thiopheneylmethyl)-adenosine (160 mg) as a white solid: positive ESIMS m/z 378 [M+H]⁺ and 400 [M+Na]⁺; negative ESIMS m/z 376 [M−H]⁻; ¹H NMR (300 MHz, DMSO-d$_6$): the adenosine moiety δ 8.42 (1H, brs, —NH), 8.37 (1H, s, H-2), 8.25 (1H, s, H-8), 5.88 (1H, d, 6.3 Hz, H-1'), 5.44 (1H, d, 6.0 Hz, —OH), 5.36 (1H, m, —OH), 5.18 (1H, d, 4.8 Hz, —OH), 4.60 (1H, m, H-2'), 4.14 (1H, m, H-3'), 3.95 (1H, m, H-4'), 3.69-3.65 (1H, m, H-5a'), 3.58-3.51 (1H, m, H-5b'); the 5-methyl-2-thiopheneylmethyl moiety δ 6.76 (1H, d, 3.3 Hz, H-4"), 6.57 (1H, d, 3.3 Hz, H-3"), 4.74 (1H, brs, H-7"), 2.33 (1H, s, —CH$_3$); ¹³C NMR (100 MHz, DMSO-d$_6$): the adenosine moiety δ 154.2 (s, C-6), 152.4 (d, C-2), 148.7 (s, C-4), 140.6 (d, C-8), 120.0 (s, C-5), 88.1 (d, C-1'), 86.1 (d, C-4'), 73.7 (d, C-2'), 70.7 (d, C-3'), 61.8 (t, C-5'); the 5-methyl-2-thiopheneylmethyl moiety δ 140.2 (s, C-5"), 138.3 (s, C-2"), 125.5 (d, C-3"), 124.8 (d, C-4"), 38.5 (t, C-6"), 15.1 (q, —CH$_3$).

Example 21: Preparation of N⁶-(3-thiopheneylmethyl)-adenosine

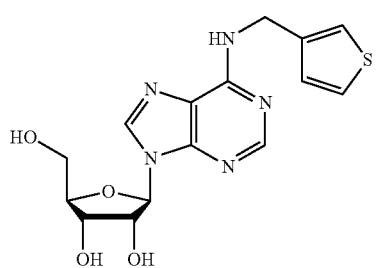

First step, hydroxyamine hydrochloride (874 mg) and NaOAc (1.18 g) were added to a solution of 3-thiophenecarbaldehyde (800 mg) in EtOH (50 ml). The reaction mixture was stirred at room temperature for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield 3-thiophenecarbaldehyde oxime (722 mg) as a pale yellowish solid.

Second step, 3-thiophenecarbaldehyde oxime (722 mg) and zinc dust (2.23 g) in HOAc (5 ml) was stirred at room temperature for 6 h. The reaction solution was filtered to remove the excess zinc dust and ZnOAc residue, and the filtrate was concentrated to yield 3-thiopheneylmethanamine (323 mg) as a yellowish oil.

Third step, a mixture of 3-thiopheneylmethanamine (158 mg), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with CHCl$_3$—CH$_3$OH (20:1) to yield N⁶-(3-thiopheneylmethyl)-adenosine (150 mg) as a white solid: positive ESIMS m/z 364 [M+H]⁺, 386 [M+Na]⁺ and 402 [M+K]⁺; negative ESIMS m/z 362[M−H]⁻; ¹H NMR (300 MHz, DMSO-d$_6$): the adenosine moiety δ 8.36 (2H, s, —NH, H-2), 8.22 (1H, s, H-8), 5.88 (1H, d, 6.0 Hz, H-1'), 5.43 (1H, d, 6.0 Hz, —OH), 5.38 (1H, m, —OH), 5.17 (1H, d, 4.5 Hz, —OH), 4.60 (1H, m, H-2'), 4.13 (1H, m, H-3'), 3.95 (1H, m, H-4'), 3.70-3.64 (1H, m, H-5a'), 3.58 (1H, m, H-5b'); the 3-thiopheneylmethyl moiety δ 7.43 (1H, dd, 4.8 Hz, 3.0 Hz, H-5"), 7.28 (1H, brs, H-2"), 7.08 (1H, dd, 4.8 Hz, 0.9 Hz, H-4"), 4.68 (2H, brs, H-7"); ¹³C NMR (75 MHz, DMSO-d$_6$): the adenosine moiety δ 154.4 (s, C-6), 152.5 (d, C-2), 148.6 (s, C-4), 140.9 (d, C-8), 119.9 (s, C-5), 88.1 (d, C-1'), 86.1 (d, C-4'), 73.7 (d, C-2'), 70.8 (d, C-3'), 61.8 (t, C-5'); the 3-thiopheneylmethyl moiety δ 140.1 (s, C-3"), 127.7 (d, C-4"), 126.2 (d, C-5"), 121.8 (d, C-2"), 39.5 (t, C-6).

Example 22: Preparation of N⁶-(3,4-dihydroxybenzyl)-adenosine

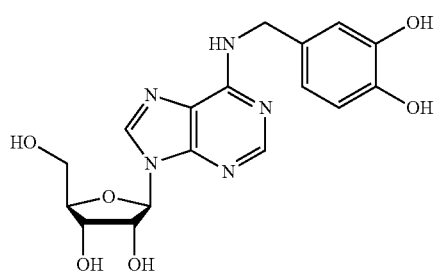

First step, hydroxyamine hydrochloride (2.52 g) and NaOAc (3.26 g) were added to a solution of 3,4-dihydroxybenzaldehyde (2.76 g) in EtOH (80 ml). The reaction mixture was stirred at room temperature for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield 3,4-dihydroxybenzaldehyde oxime (2.72 g) as a pale yellowish solid.

Second step, 3,4-dihydroxybenzaldehyde oxime (2.72 g) and concentrated HCl (8 ml) in EtOH (70 ml) was subjected to hydrogenation at atmospheric pressure in the presence of 10% Pd/C (700 mg). The reaction solution was filtered and the filtrate was concentrated. Then EtOAc was added to the residue and the suspension was filtered to yield 3,4-dihydroxybenzylamine hydrochloride (2.98 g) as a white solid.

Third step, a mixture of 3,4-dihydroxybenzylamine (2.98 g, the hydrochloride), 6-chloropurine riboside (1 g) and N,N-diisopropylethylamine (14 ml) in PrOH (60 ml) was heated to 70° C. and reacted for 8 h. After evaporation of the reaction mixture, the residue was separated by column chromatography over silica gel and eluted with CHCl$_3$—CH$_3$OH (15:1~8:1) to yield N⁶-(3,4-dihydroxybenzyl)-adenosine (0.95 g) as a white solid: positive ESIMS m/z 390 [M+H]⁺; negative ESIMS m/z 388 [M−H]⁻ and 424 [M+Cl]⁻; ¹H NMR (300 MHz, DMSO-d$_6$): the adenosine moiety δ 8.33 (1H, s, H-2), 8.27 (1H, brs, —NH), 8.19 (1H, brs, H-8), 5.87 (1H, d, J=6.3 Hz, H-1'), 5.41 (2H, m, —OH×2), 5.17 (1H, m, —OH), 4.52-4.61 (1H, m, H-2'), 4.13 (1H, m, H-3'), 3.95 (1H, m, H-4'), 3.66 (1H, m, H-5'a), 3.54 (1H, m, H-5'b); the 3,4-dihydroxybenzyl moiety δ 8.75 (1H, s, —OH), 8.64 (1H, s, —OH), 6.71 (1H, brs, H-2"), 6.61 (1H, d, J=7.8 Hz, H-5"), 6.57 (1H, d, J=7.8 Hz, H-6"), 4.52-4.61 (2H, m, H-7"); ¹³C NMR (75 MHz, DMSO-d$_6$): the adenosine moiety δ 154.5 (C-6), 152.3 (C-2), 148.4 (C-4), 139.8 (C-8), 119.7 (C-5), 87.9 (C-1'), 85.9 (C-4'), 73.4 (C-2'), 70.6 (C-3'), 61.6 (C-5'); the 3,4-dihydroxybenzyl moiety δ 144.9 (C-4"), 144.0 (C-3"), 130.8 (C-1"), 115.3 (C-2"), 118.1 (C-6"), 114.7 (C-5"), 42.4 (C-7").

Example 23: Preparation of $N^6$-(3-methoxy-4-hydroxybenzyl)-adenosine

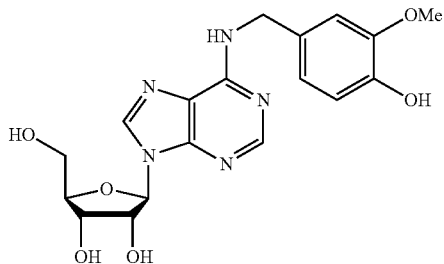

First step, hydroxyamine hydrochloride (2.52 g) and NaOAc (3.26 g) were added to a solution of 3-methoxy-4-hydroxybenzaldehyde (3.04 g) in EtOH (80 ml). The reaction mixture was stirred at room temperature for 6 h. EtOH was removed under reduced pressure. $H_2O$ (40 ml) was added to the residue, and extracted with EtOAc (3×40 ml). The EtOAc of the combined organic layer was removed by rotary evaporation under reduced pressure to yield 3-methoxy-4-dihydroxybenzaldehyde oxime (2.99 g) as a pale yellowish solid.

Second step, 3-methoxy-4-dihydroxybenzaldehyde oxime (2.99 g) and concentrated HCl (8 ml) in EtOH (70 ml) was subjected to hydrogenation at atmospheric pressure in the presence of 10% Pd/C (700 mg). The reaction solution was filtered and the filtrate was concentrated. Then EtOAc was added to the residue and the suspension was filtered to yield 3-methoxy-4-hydroxybenzylamine hydrochloride (3.31 g) as a white solid.

Third step, a mixture of 3-methoxy-4-dihydroxybenzylamine (3.31 g, the hydrochloride), 6-chloropurine riboside (1 g) and N,N-diisopropylethyl amine (14 ml) in PrOH (70 ml) was heated to 70° C. and reacted for 8 h. After evaporation of the reaction mixture, the residue was separated by column chromatography over silica gel and eluted with $CHCl_3$—$CH_3OH$ (15:1) to yield $N^6$-(3-methoxy-4-hydroxybenzyl)-adenosine (1.02 g) as a colorless solid: positive ESIMS m/z 404 $[M+H]^+$; negative ESIMS m/z 402 $[M-H]^-$ and 438 $[M+Cl]^-$; $^1H$ NMR (300 MHz, DMSO): the adenosine moiety δ 8.35 (1H, s, H-2), 8.29 (1H, brs, —NH), 8.20 (1H, brs, H-8), 5.87 (1H, d, J=6.3 Hz, H-1'), 5.37-5.44 (2H, m, —OH×2), 5.18 (1H, J=4.5 Hz, —OH), 4.60 (1H, m, H-2'), 4.11 (1H, m, H-3'), 3.95 (1H, m, H-4'), 3.66 (1H, m, H-5'a), 3.54 (1H, m, 5'b); the 3-methoxy-4-hydroxybenzyl moiety δ 8.77 (1H, s, —OH), 6.96 (1H, d, J=1.5 Hz, H-2"), 6.72 (1H, dd, J=8.1, 1.5 Hz, H-6"), 6.66 (1H, d, J=8.1 Hz, H-5"), 4.60 (2H, m, H-7"), 3.71 (3H, s, —$OCH_3$); $^{13}C$ NMR (125 MHz, DMSO-$d_6$): the adenosine moiety δ 154.4 (C-6), 152.3 (C-2), 147.3 (C-4), 139.8 (C-8), 119.8 (C-5), 87.9 (C-1'), 85.9 (C-4'), 73.4 (C-2'), 70.6 (C-3'), 61.6 (C-5'); the 3-methoxy-4-hydroxybenzyl moiety δ 147.3 (C-4"), 145.3 (C-3"), 130.7 (C-1"), 115.3 (C-2"), 119.8 (C-6"), 112.0 (C-5"), 55.5 (—$OCH_3$), 42.7 (C-7").

Example 24: Preparation of $N^6$-(3-methoxy-4-acetoxybenzyl)-adenosine-5'-acetate

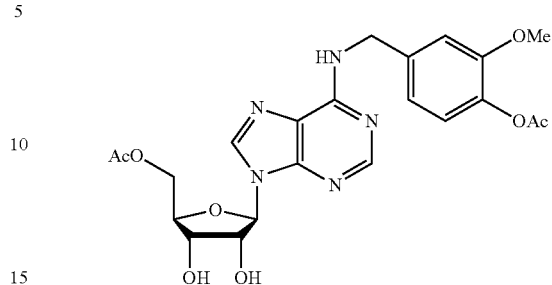

First step, $N^6$-(3-methoxy-4-hydroxybenzyl)-adenosine (1.0 g) prepared in the above example, and 2,2-dimethoxypropane (1.50 g) were added to dry acetone (100 ml), with (1S)-(+)-camphor-10-sulfonic acid (0.60 g) added as a catalyst. The reaction mixture was stirred at room temperature for 5 h. After evaporating the solvent, the oily substance was dissolved in EtOAc, and a $NaHCO_3$ solution was also added. After separation by two-phase extraction, the EtOAc layer was dried by anhydrous sodium sulfate and filtered, and the solvent was evaporated. The resulting product was recrystallized in EtOAc to yield $N^6$-(3-methoxy-4-hydroxybenzyl)-2',3'-O-isopropylidene-adenosine (1.0 g) as a light yellowish solid.

Second step, a mixture of $N^6$-(3-methoxy-4-hydroxybenzyl)-2',3'-O-isopropylidene-adenosine (200 mg), EDCI (172.9 mg), DMAP (138.1 mg), and acetic acid (32.5 mg) in dry $CH_2Cl_2$ (20 ml) was stirred at room temperature for 3 h. After evaporation of the reaction mixture, the residue was separated by column chromatography over silica gel and eluted with $CHCl_3$—$CH_3OH$ (100:1) to yield $N^6$-(3-methoxy-4-hydroxybenzyl)-2',3'-O-isopropylidene-adenosine-5'-acetate (60 mg) as a light yellowish solid.

Third step, $N^6$-(3-methoxy-4-hydroxybenzyl)-2',3'-O-isopropylidene-adenosine-5'-acetate (60 mg) was added in a formic acid solution (20 ml, 50% V/V), and the mixture was stirred at room temperature for 12 h. After evaporation of the reaction mixture, the residue was separated by column chromatography over silica gel and eluted with $CHCl_3$—$CH_3OH$ (50:1) to yield $N^6$-(3-methoxy-4-hydroxybenzyl)-adenosine-5'-acetate (60 mg) as a light yellowish solid: positive ESIMS m/z 488 $[M+H]^+$, 510 $[M+Na]^+$ and 526 $[M+K]^+$; $^1H$ NMR (300 MHz, DMSO-$d_6$): the adenosine moiety δ 8.42 (1H, brs, NH), 8.36 (1H, s, H-8), 8.25 (1H, s, H-2), 5.95 (1H, d, J=4.2 Hz, H-1'), 5.62 (1H, brs, OH), 5.44 (1H, brs, OH), 4.72 (1H, m, H-2'), 4.33 (1H, dd, J=11.7, 3.0 Hz, H-5'a), 4.31 (1H, m, H-3'), 4.18 (1H, dd, J=11.7, 6.0 Hz, H-5'b), 4.11 (1H, m, H-4'); the 3-methoxy-4-substituted-benzyl moiety δ 7.16 (1H, s, H-2"), 6.98 (1H, d, J=7.8 Hz, H-5"), 6.90 (1H, d, J=7.8 Hz, H-6"), 4.72 (2H, brs, H-7"), 3.73 (3H, s, $OCH_3$); the acetyl δ 2.22 (3H, s, $CH_3CO$), 2.00 (3H, s, $CH_3CO$); $^{13}C$ NMR (75 MHz, DMSO-$d_6$): the adenosine moiety δ 154.5 (C-6), 152.7 (C-2), 148.8 (C-4), 139.9 (C-8), 119.7 (C-5), 87.9 (C-1'), 81.6 (C-4'), 73.0 (C-2'), 70.4 (C-3'), 64.0 (C-5'); the 3-methoxy-4-substituted-benzyl moiety δ 150.6 (C-3"), 139.0 (C-1"), 138.0 (C-4"), 122.5 (C-6"), 119.0 (C-5"), 111.8 (C-2"), 55.7 ($OCH_3$), 42.8 (C-7"); the acetyl moiety δ 170.3 (C-1'''), 168.7 (C-1''''), 20.6 (C-2'''), 20.4 (C-2'''').

Example 25: Preparation of N⁶-(3-methoxy-4-lauroyloxybenzyl)-2',3'-O-isopropylidene-adenosine-5'-laurate

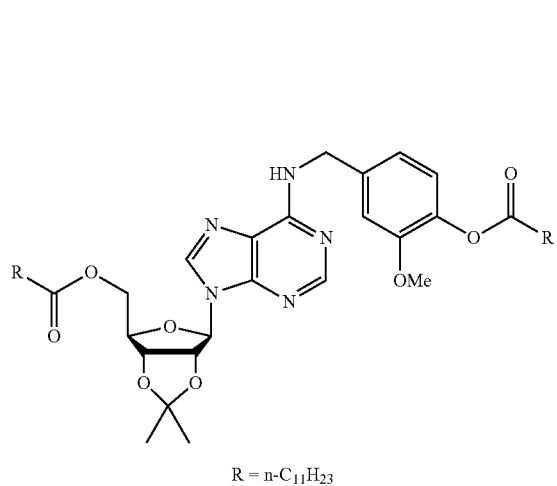

R = n-C$_{11}$H$_{23}$

A mixture of N⁶-(3-methoxy-4-hydroxybenzyl)-2',3'-O-isopropylidene-adenosine (200 mg) prepared in the above example, EDCI (129.8 mg), DMAP (110.2 mg), and lauric acid (99.36 mg) was stirred at room temperature for 3 h in dry CH$_2$Cl$_2$ (20 ml). After evaporation of the reaction mixture, the residue was separated by column chromatography over silica gel and eluted with CHCl$_3$—CH$_3$OH (100:1) to yield N⁶-(3-methoxy-4-lauroyloxybenzyl)-2',3'-O-isopropylidene-adenosine-5'-laurate (210 mg) as a light yellowish solid: positive ESIMS m/z 808 [M+H]⁺, 830 [M+Na]⁺ and 546 [M+K]⁺; ¹H NMR (300 MHz, DMSO-d$_6$): the adenosine moiety δ 8.47 (1H, brs, NH), 8.31 (1H, s, H-8), 8.23 (1H, s, H-2), 6.20 (1H, d, 1.8 Hz, H-1'), 5.48 (1H, dd, J=1.8, 4.5 Hz, H-2'), 5.03 (1H, dd, J=6.0, 3.0 Hz, H-3'), 4.35 (1H, m, H-4'), 4.22 (1H, dd, J=11.4, 4.5 Hz, H-5'a), 4.12 (1H, dd, J=11.4, 6.3 Hz, H-5'b); the 3-methoxy-4-substituted-benzyl moiety δ 7.15 (1H, s, H-2"), 6.93 (1H, d, J=8.1 Hz, H-5"), 6.88 (1H, d, J=8.1 Hz, H-6"), 4.69 (2H, brs, H-7"), 3.70 (3H, s, OMe); the laurate moiety δ 2.49 (2H, t, J=6.9 Hz, H-2'"), 2.17 (2H, t, 6.9 Hz, H-2""), 1.59 (2H, m, H-3'"), 1.40 (2H, m, H-3""), 1.20 (32H, m), 0.85 (6H, t, 6.6 Hz, H-12'", H-12""); the 2',3'-O-isopropylidene moiety δ 1.53 (3H, s), 1.31 (3H, s); ¹³C NMR (75 MHz, DMSO-d$_6$): the adenosine moiety δ 154.4 (C-6), 152.6 (C-2), 148.1 (C-4), 139.9 (C-8), 119.8 (C-5), 89.3 (C-1'), 83.8 (C-4'), 83.3 (C-2'), 81.2 (C-3'), 63.6 (C-5'); the 3-methoxy-4-substituted-benzyl moiety δ 150.5 (C-3"), 138.8 (C-1"), 138.0 (C-4"), 122.3 (C-6"), 119.0 (C-5"), 111.8 (C-2"), 55.6 (OMe), 42.8 (C-7"); the laurate moiety δ 172.5 (C-1'"), 171.1 (C-1""), 33.1, 31.3, 31.3, 29.0, 29.0, 29.0, 29.0, 29.0, 29.0, 28.94, 28.88, 28.74, 28.74, 28.69, 28.4, 28.3, 25.1, 24.3, 22.1, 22.1, 13.9, 13.9; the 2',3'-O-isopropylidene moiety δ 113.3, 26.9, 24.50.

Example 26: Preparation of N⁶-(3-methoxy-4-octanoyloxybenzyl)-adenosine-5'-caprylate

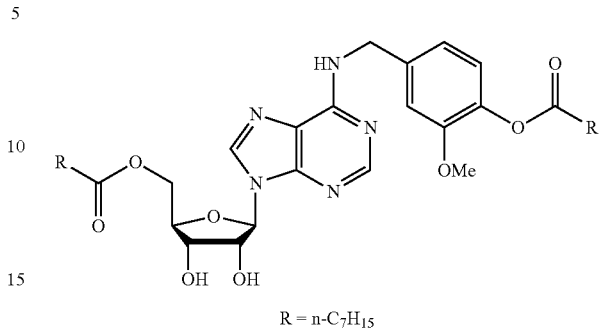

R = n-C$_7$H$_{15}$

First step, a mixture of N⁶-(3-methoxy-4-hydroxybenzyl)-2',3'-O-isopropylidene-adenosine (200 mg), EDCI (192.9 mg), DMAP (138.1 mg), and caprylic acid (288.4 mg) in dry CH$_2$Cl$_2$ (20 ml) was stirred at room temperature for 3 h. After evaporation of the reaction mixture, the residue was separated by column chromatography over silica gel and eluted with CHCl$_3$—CH$_3$OH (100:1) to yield N⁶-(3-methoxy-4-octanoyloxybenzyl)-adenosine-2',3'-O-isopropylidene-5'-caprylate (240 mg) as a light yellowish solid.

Second step, N⁶-(3-methoxy-4-hydroxybenzyl)-2',3'-O-isopropylidene-adenosine-5'-caprylate was added to a formic acid solution (20 ml, 50% V/V), and the mixture was stirred at room temperature for 12 h. After evaporation of the reaction mixture, the residue was separated by column chromatography over silica gel and eluted with CHCl$_3$—CH$_3$OH (50:1) to yield N⁶-(3-methoxy-4-hydroxybenzyl)-adenosine-5'-caprylate (60 mg) as a light yellowish solid: positive ESIMS m/z 656.5 [M+H]⁺, 678.5 [M+Na]⁺ and 696.5 [M+K]⁺; ¹H NMR (300 MHz, DMSO-d$_6$): the adenosine moiety δ 8.44 (1H, brs, NH), 8.35 (1H, s, H-8), 8.24 (1H, s, H-2), 5.94 (1H, d, J=5.4 Hz, H-1'), 5.59 (1H, d, J=5.4 Hz, OH), 5.38 (1H, d, J=5.4 Hz, OH), 4.70 (1H, m, H-2'), 4.34 (1H, dd, J=12.0, 3.3 Hz, H-5'a), 4.28 (1H, m, H-3'), 4.20 (1H, dd, J=12.0, 6.0 Hz, H-5'b), 4.10 (1H, m, H-4'); the 3-methoxy-4-substituted-benzyl moiety δ 7.16 (1H, s, H-2"), 6.95 (H, d, J=7.8 Hz, H-5"), 6.89 (H, d, J=7.8 Hz, H-6"), 4.70 (1H, m, H-7"), 3.73 (3H, s, OMe); the caprylate moiety δ 2.52 (2H, t, J=7.2 Hz, H-2'"), 2.28 (2H, t, J=7.2 Hz, H-2""), 1.62 (2H, m, H-3'"), 1.47 (2H, m, H-3""), 1.20 (16H, m), 0.86 (3H, t, J=6.0 Hz, H-8'"), 0.82 (3H, t, J=6.0 Hz, H-8""); ¹³C NMR (75 MHz, DMSO-d$_6$): the adenosine moiety δ 154.5 (C-6), 152.6 (C-2), 148.2 (C-4), 139.8 (C-8), 119.7 (C-5), 87.9 (C-1'), 81.5 (C-4'), 72.9 (C-2'), 70.3 (C-3'), 63.7 (C-5'); the 3-methoxy-4-substituted-benzyl moiety δ 150.6 (C-3"), 138.9 (C-1"), 138.0 (C-4"), 122.4 (C-2"), 119.0 (C-5"), 111.8 (C-6"), 42.7 (C-7"), 55.6 (OMe); the caprylate moiety δ 172.8 (C-1'"), 171.2 (C-1""), 33.3 (C-2'"), 33.2 (C-2""), 31.2 (C-6'"), 31.1 (C-6""), 28.4 (C-4'"), 28.4 (C-4""), 28.4 (C-5'"), 28.3 (C-5""), 24.5 (C-3'"), 24.4 (C-3""), 22.0 (C-7'"), 22.0 (C-7""), 14.0 (C-8'"), 13.9 (C-8"").

Example 27: Preparation of $N^6$-(3-methoxy-4-octanoyloxybenzyl)-adenosine

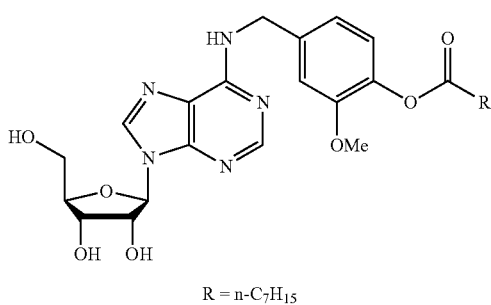

R = n-$C_7H_{15}$

First step, a mixture of $N^6$-(3-methoxy-4-hydroxybenzyl)-2',3'-O-isopropylidene-adenosine (500 mg), EDCI (540.40 mg), DMAP (344.40 mg) and caprylic acid (406.50 mg) was stirred at room temperature for 3 h in dry $CH_2Cl_2$ (20 ml). After evaporation of the reaction mixture, the residue was separated by column chromatography over silica gel and eluted with $CHCl_3$—$CH_3OH$ (100:1) to yield $N^6$-(3-methoxy-4-octanoyloxybenzyl)-adenosine-2',3'-O-isopropylidene-5'-caprylate (165 mg) as a light yellowish solid.

Second step, $N^6$-(3-methoxy-4-hydroxybenzyl)-2',3'-O-isopropylidene-adenosine-5'-caprylate (150 mg) was added to a formic acid solution (20 ml, 50% V/V) and the mixture was stirred at room temperature for 12 h. After evaporation of the reaction mixture, the residue was separated by column chromatography over silica gel and eluted with $CHCl_3$—$CH_3OH$ (50:1) to yield $N^6$-(3-methoxy-4-octanoyloxybenzyl)-adenosine (132 mg) as a light yellowish solid: positive ESIMS m/z 530 [M+H]$^+$, 552 [M+Na]$^+$ and 568 [H+K]$^+$; $^1$H NMR (300 MHz, DMSO-$d_6$): the adenosine moiety δ 8.48 (1H, brs, NH), 8.41 (1H, s, H-8), 8.25 (1H, s, H-2), 5.92 (1H, d, J=6.0 Hz, H-1'), 5.47 (1H, d, J=3.4 Hz, OH), 5.42 (1H, m, OH), 5.22 (1H, d, J=2.7 Hz, OH), 4.64 (1H, m, H-2'), 4.18 (1H, m, H-3'), 4.00 (1H, m, H-4'), 3.70 (1H, dd, J=12.0, 3.3 Hz, H-5'a), 3.58 (1H, dd, J=12.0, 6.0 Hz, H-5'b); the 3-methoxy-4-substituted benzyl moiety δ 7.17 (1H, s, H-2''), 6.96 (H, d, J=7.8 Hz, H-5''), 6.89 (H, d, J=7.8 Hz, H-6''), 4.73 (2H, m, H-7''), 3.73 (3H, s, OMe); the octanoyl moiety δ 2.52 (2H, t, J=7.2 Hz, H-2'''), 1.62 (2H, m, H-3'''), 1.30 (10H, m), 0.84 (3H, t, J=6.0 Hz, H-8'''); $^{13}$C NMR (75 MHz, DMSO-$d_6$): the adenosine moiety δ 154.5 (C-6), 152.4 (C-2), 148.5 (C-4), 140.0 (C-8), 119.8 (C-5), 88.0 (C-1'), 86.0 (C-4'), 73.6 (C-2'), 70.7 (C-3'), 61.7 (C-5'); the 3-methoxy-4-substituted benzyl moiety δ 150.6 (C-3''), 138.9 (C-1''), 138.1 (C-4''), 122.4 (C-2''), 119.0 (C-5''), 111.8 (C-6''), 42.8 (C-7''), 55.7 (OMe); the octanoyl moiety δ 171.3 (C-1'''), 33.2 (C-2'''), 31.2 (C-6'''), 28.4 (C-4'''), 28.3 (C-5'''), 24.5 (C-3'''), 22.1 (C-7'''), 13.9 (C-8''').

Example 28: Preparation of $N^6$-(3-methoxy-4-butanoyloxy-benzyl)-adenosine-5'-butyrate and $N^6$-(3-methoxy-4-butanoyloxy-benzyl)-adenosine

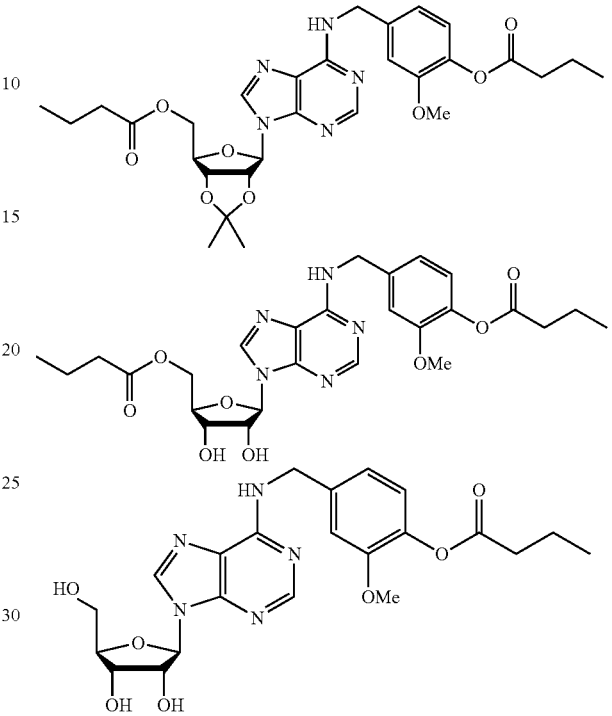

First step, a mixture of $N^6$-(3-methoxy-4-hydroxybenzyl)-2',3'-O-isopropylidene-adenosine (200 mg), EDCI (130 mg), DMAP (110 mg), and n-butanoic acid (43.7 mg) was stirred at room temperature for 3 h in dry $CH_2Cl_2$ (20 ml). After evaporation of the reaction mixture, the residue was separated by column chromatography over silica gel and eluted with $CHCl_3$—$CH_3OH$ (100:1) to yield $N^6$-(3-methoxy-4-butanoyloxy-benzyl)-2',3'-O-isopropylidene-adenosine-5'-butyrate (120 mg) and $N^6$-(3-methoxy-4-butanoyloxy-benzyl)-2',3'-O-isopropylidene-adenosine (80 mg). Among them, $N^6$-(3-methoxy-4-butanoyloxy-benzyl)-2',3'-O-isopropylidene-adenosine-5'-butyrate: positive ESIMS m/z 584.4 [M+H]$^+$, 606.4 [M+Na]$^+$ and 622.4 [M+K]$^+$; $^1$H NMR (300 MHz, acetone-$d_6$): the adenosine moiety δ 8.30 (1H, s, H-8), 8.10 (1H, s, H-2), 7.66 (1H, t, J=6 Hz, NH), 6.22 (1H, d, J=1.8 Hz, H-1'), 5.56 (1H, dd, J=1.8, 3.3 Hz, H-2'), 5.14 (1H, dd, J=3.3, 6.3 Hz, H-3'), 4.42 (1H, m, H-4'), 4.31 (1H, dd, J=11.7, 4.8 Hz, H-5'a), 4.21 (1H, dd, J=11.7, 6.0 Hz, H-5'b); the 3-methoxy-4-substituted benzyl moiety δ 7.19 (1H, s, H-2''), 6.98 (1H, d, J=7.8 Hz, H-6''), 6.94 (1H, d, J=7.8 Hz, H-5''), 4.87 (2H, brs, H-7''), 3.74 (3H, s, OMe); the butyl moiety δ 2.50 (2H, t, J=7.5 Hz, H-2'''), 2.20 (2H, t, J=7.2 Hz, H-2''''), 1.71 (2H, m, H-3'''), 1.53 (2H, m, H-3''''), 1.00 (3H, t, J=7.5 Hz, H-4'''), 0.85 (3H, t, J=7.5 Hz, H-4''''); the 2',3'-O-isopropylidene moiety δ 1.56 (3H, s, Me), 1.36 (3H, s, Me); $^{13}$C NMR (75 MHz, acetone-$d_6$): the adenosine moiety δ 155.2 (C-6), 151.5 (C-2), 148.8 (C-4), 140.1 (C-8), 120.5 (C-5), 90.6 (C-1'), 85.0 (C-2'), 84.3 (C-3'), 82.1 (C-4'), 63.9 (C-5'); the 3-methoxy-4-substituted benzyl moiety δ 153.1 (C-3''), 139.2 (C-1''), 139.0 (C-4''), 122.8 (C-2''), 119.7 (C-5''), 112.3 (C-6''), 55.5 (C—OMe), 43.5 (C-7''); the butyl moiety δ 172.6 (C-1'''), 171.1 (C-1''''), 35.5 (C-2''', C-2''''), 18.5 (C-3'''), 18.3 (C-3''), 13.1 (C-4''', C-4''''); 2',3'-O-isopropylidene δ 114.0, 26.8, 24.9.

Second step, N⁶-(3-methoxy-4-hydroxybenzyl)-2',3'-O-isopropylidene-adenosine-5'-butyrate (80 mg) was added to a formic acid solution (20 ml, 50% V/V), and the mixture was stirred at room temperature for 12 h. After evaporation of the reaction mixture, the residue was separated by column chromatography over silica gel and eluted with CHCl₃—CH₃OH (50:1) to yield N⁶-(3-methoxy-4-hydroxybenzyl)-adenosine-5'-butyrate (80 mg) and N⁶-(3-methoxy-4-hydroxybenzyl)-adenosine (60 mg). Among them, N⁶-(3-methoxy-4-hydroxybenzyl)-adenosine-5'-butyrate: ¹H NMR (300 MHz, DMSO-d₆): the adenosine moiety δ 8.42 (1H, brs, NH), 8.34 (1H, s, H-8), 8.23 (1H, s, H-2), 5.92 (1H, d, J=5.1 Hz, H-1'), 5.57 (1H, d, J=5.4 Hz, OH), 5.36 (1H, d, J=5.4 Hz, OH), 4.68 (1H, m, H-2'), 4.34 (1H, dd, J=12.0, 4.5 Hz, H-5'a), 4.27 (1H, m. H-3'), 4.18 (1H, dd, J=12.0, 6.0 Hz, H-5'b), 4.08 (1H, m, H-4'); the 3-methoxy-4-substituted benzyl moiety δ 7.15 (1H, s, H-2"), 6.95 (1H, d, J=8.1 Hz, H-5"), 6.98 (1H, d, J=8.1 Hz, H-6"), 4.66 (2H, brs, H-7"), 3.71 (3H, s, OMe); the butyl moiety δ 2.49 (2H, t, J=7.2 Hz, H-2'''), 2.25 (2H, t, J=6.9 Hz, H-2''''), 1.62 (2H, m, J=7.2 Hz, H-3'''), 1.48 (2H, m, J=7.2 Hz, H-3''), 0.94 (3H, t, J=7.5 Hz, H-4'''), 0.82 (3H, t, J=7.5 Hz, H-4''''); ¹³C NMR (75 MHz, DMSO-d₆): the adenosine δ 154.4 (C-6), 152.6 (C-2), 148.7 (C-4), 139.8 (C-8), 119.7 (C-5), 87.9 (C-1'), 81.5 (C-4'), 72.9 (C-2'), 70.2 (C-3'), 63.6 (C-5'); the 3-methoxy-4-substituted benzyl moiety δ 150.6 (C-3"), 138.9 (C-1"), 138.0 (C-4"), 122.4 (C-2"), 119.0 (C-5"), 111.8 (C-6"), 55.7 (OMe), 42.7 (C-7"); the butyl moiety δ 172.6 (C-1'''), 171.1 (C-1''), 35.0 (C-2'''), 35.2 (C-2''''), 18.0 (C-3'''), 17.8 (C-3''), 13.3 (C-4''''), 14.3 (C-4''''). N⁶-(3-methoxy-4-hydroxybenzyl)-adenosine: positive ESIMS m/z 474.4 [M+H]⁺, 496.5 [M+Na]⁺ and 512.3 [M+K]⁺; ¹H NMR (300 MHz, DMSO-d₆): the adenosine moiety δ 8.45 (1H, brs, NH), 8.38 (1H, s, H-8), 8.21 (1H, s, H-2), 5.89 (1H, d, J=6.0 Hz, H-1'), 5.42 (1H, d, J=6.0 Hz, OH-2'), 5.37 (1H, m, OH-5'), 5.17 (1H, d, J=4.5 Hz, OH-3'), 4.60 (1H, m, H-2'), 4.14 (1H, m, H-3'), 3.95 (1H, m, H-4'), 3.68 (1H, m, H-5'a), 3.53 (1H, m, H-5'b); the 3-methoxy-4-substituted benzyl moiety δ 7.14 (1H, s, H-2"), 6.94 (1H, d, J=8.1 Hz, H-5"), 6.87 (1H, d, J=8.1 Hz, H-6"), 4.69 (2H, brs, H-7"), 3.71 (3H, s, OMe); the butyl δ 2.49 (2H, t, J=7.2 Hz, H-2'''), 1.62 (2H, hex, J=7.2 Hz, H-3'''), 0.94 (3H, t, J=7.2 Hz, H-4'''); ¹³C NMR (75 MHz, DMSO-d₆): the adenosine moiety δ 154.6 (C-6), 152.4 (C-2), 148.8 (C-4), 140.0 (C-8), 119.8 (C-5), 87.9 (C-1'), 85.9 (C-4'), 73.5 (C-2'), 70.7 (C-3'), 61.6 (C-5'); the 3-methoxy-4-substituted benzyl moiety δ 150.6 (C-3"), 138.9 (C-1"), 138.0 (C-4"), 122.4 (C-2"), 119.0 (C-5"), 111.8 (C-6"), 55.7 (OMe), 42.7 (C-7"); the butyl δ 171.1 (C-1'''), 35.0 (C-2'''), 18.0 (C-3'''), 13.3 (C-4''').

Example 29: Preparation of N⁶-(4-methoxy-3-hydroxybenzyl)-adenosine

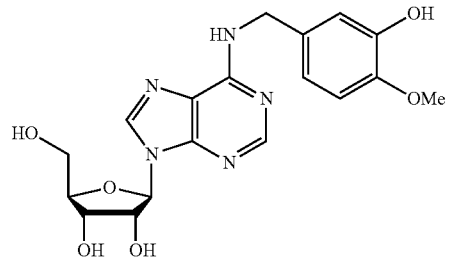

First step, hydroxyamine hydrochloride (1.29 g) and NaOAc (1.67 g) were added to a solution of 4-methoxy-3-hydroxybenzaldehyde (1.55 g) in EtOH (80 ml). The reaction mixture was stirred at room temperature for 6 h. EtOH was removed under reduced pressure. H₂O (40 ml) was added to the residue, and extracted with EtOAc (3×40 ml). The EtOAc of the combined organic layer was removed by rotary evaporation under reduced pressure to yield 4-methoxy-3-hydroxybenzaldehyde oxime (1.45 g) as a pale yellowish solid.

Second step, a solution of 4-methoxy-3-hydroxybenzaldehyde oxime (1.45 g) and concentrated HCl (1 ml) in EtOH (40 ml) was subjected to hydrogenation at atmospheric pressure in the presence of 10% Pd/C (85 mg). The reaction solution was filtered and the filtrate was concentrated to yield 4-methoxy-3-hydroxybenzylamine hydrochloride (1.59 g) as a white solid.

Third step, a mixture of 4-methoxy-3-hydroxybenzylamine (469 mg, the hydrochloride), 6-chloropurine riboside (143 mg) and N,N-diisopropylethylamine (2 ml) in PrOH (40 ml) was heated to 70° C. and reacted for 8 h. After evaporation of the reaction mixture, the residue was separated by column chromatography over silica gel and eluted with CHCl₃—CH₃OH (30:1) to yield N⁶-(4-methoxy-3-hydroxybenzyl)-adenosine (164 mg) as a white solid: positive ESIMS 404 [M+H]⁺; negative ESIMS m/z 402 [M–H]⁻ and 438 [M+Cl]⁻; ¹H NMR (400 MHz, DMSO-d₆): the adenosine moiety δ 8.35 (1H, s, H-2), 8.32 (1H, brs, —NH), 8.19 (1H, brs, H-8), 5.87 (1H, d, J=6.0 Hz, H-1'), 5.41 (1H, d, J=6.4 Hz, —OH), 5.37 (1H, m, —OH), 5.18 (1H, d, J=4.8 Hz, —OH), 4.60 (1H, m, H-2'), 4.13 (1H, m, H-3'), 3.95 (1H, m, H-4'), 3.66 (1H, m, H-5'a), 3.54 (1H, m, H-5'b); the 4-methoxy-3-hydroxybenzyl moiety δ 8.82 (1H, s, —OH), 6.80 (1H, d, J=8.4 Hz, H-5"), 6.76 (1H, brs, H-2"), 6.70 (1H, brd, J=8.4 Hz, H-6"), 4.60 (2H, m, H-7"), 3.71 (3H, s, —OCH₃); ¹³C NMR (125 MHz, DMSO-d₆): the adenosine moiety δ 154.4 (C-6), 152.3 (C-2), 148.4 (C-4), 139.8 (C-8), 119.8 (C-5), 87.9 (C-1'), 85.9 (C-4'), 73.4 (C-2'), 70.6 (C-3'), 61.6 (C-5'); the 4-methoxy-3-hydroxybenzyl moiety δ 146.5 (C-4"), 146.3 (C-3"), 132.6 (C-1"), 117.8 (C-6"), 114.6 (C-2"), 112.1 (C-5"), 55.7 (—OCH₃), 42.4 (C-7").

Example 30: Preparation of N⁶-(3,4-dimethoxybenzyl)-adenosine

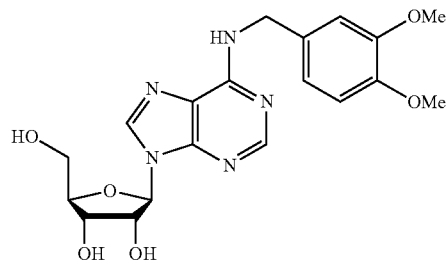

First step, hydroxyamine hydrochloride (1.67 g) and NaOAc (1.67 g) were added to a solution of 3,4-dimethoxybenzaldehyde (1.55 g) in EtOH (40 ml). The reaction mixture was stirred at room temperature for 6 h. EtOH was removed under reduced pressure. H₂O (40 ml) was added to the residue, and extracted with EtOAc (3×40 ml). The EtOAc of the combined organic layer was removed by rotary evaporation under reduced pressure to yield 3,4-dimethoxybenzaldehyde oxime (1.61 g) as a pale yellowish solid.

Second step, a solution of 3,4-dimethoxybenzaldehyde oxime (1.61 g) and concentrated HCl (1 ml) in EtOH (40 ml) was subjected to hydrogenation at atmospheric pressure in the presence of 10% Pd/C (85 mg). The reaction solution was filtered and the filtrate was concentrated to yield 3,4-methoxybenzylamine hydrochloride (1.72 g) as a white solid.

Third step, a mixture of 3,4-dimethoxybenzylamine (504 mg, the hydrochloride), 6-chloropurine riboside (143 mg) and N,N-diisopropylethylamine (2 ml) in PrOH (40 ml) was heated to 70° C. and reacted for 8 h. After evaporation of the reaction mixture, the residue was separated by column chromatography over silica gel and eluted with CHCl$_3$—CH$_3$OH (30:1) to yield N$^6$-(3,4-dimethoxybenzyl)-adenosine (166 mg) as a white solid: positive ESIMS 418 [M+H]$^+$; negative ESIMS m/z 416 [M−H]$^-$ and 452 [M+Cl]$^-$; $^1$H NMR (400 MHz, DMSO-d$_6$): the adenosine moiety δ 8.44 (1H, brs, —NH), 8.41 (1H, s, H-2), 8.22 (1H, brs, H-8), 5.90 (1H, d, J=5.6 Hz, H-1'), 5.41 (1H, d, J=6.0 Hz, —OH), 5.36 (1H, m, —OH), 5.17 (1H, m, —OH), 4.60 (1H, m, H-2'), 4.13 (1H, m, H-3'), 3.95 (1H, m, H-4'), 3.65 (1H, m, H-5'a), 3.54 (1H, m, H-5'b); the 3,4-dimethoxybenzyl moiety δ 7.09 (1H, brd, J=7.6 Hz, H-6"), 7.00 (1H, d, J=7.6 Hz, H-5"), 6.84 (1H, brs, H-2"), 4.60 (2H, m, H-7"), 3.67 (6H, s, 2×—OCH$_3$).

Example 31: Preparation of N$^6$-(3,4-methylenedioxybenzyl)-adenosine

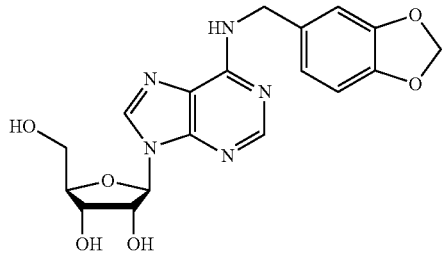

First step, hydroxyamine hydrochloride (921 mg) and NaOAc (1.21 g) were added to a solution of 3,4-methylenedioxybenzaldehyde (1.13 g) in EtOH (80 ml). The reaction mixture was stirred at room temperature for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield 3,4-methylenedioxybenzaldehyde oxime (1.06 g) as a pale yellowish solid.

Second step, a solution of 3,4-methylenedioxybenzaldehyde oxime (1.06 g) and concentrated HCl (2.6 ml) in EtOH (50 ml) was subjected to hydrogenation at atmospheric pressure in the presence of 10% Pd/C (136 mg). The reaction solution was filtered and the filtrate was concentrated to yield 3,4-methylenedioxy benzylamine hydrochloride (900 mg) as a white solid.

Third step, a mixture of 3,4-methylenedioxybenzylamine (900 mg, the hydrochloride), 6-chloropurine riboside (200 mg) and triethylamine (2 ml) in PrOH (60 ml) was heated to 70° C. and reacted for 8 h. After evaporation of the reaction mixture, the residue was separated by column chromatography over silica gel and eluted with CHCl$_3$—CH$_3$OH (20:1) to yield N$^6$-(3,4-methylenedioxybenzyl)-adenosine (225 mg) as a white solid: positive ESIMS m/z 402 [M+H]$^+$ and 424 [M+Na]$^+$; $^1$H NMR (300 MHz, DMSO-d$_6$): the adenosine moiety δ 8.46 (1H, brs, —NH), 8.39 (1H, s, H-2), 8.22 (1H, s, H-8), 5.88 (1H, d, J=6.3 Hz, H-1'), 4.59 (1H, m, H-2'), 4.14 (1H, m, H-3'), 3.95 (1H, m, H-4'), 3.66 (1H, dd, J=12.3, 3.6 Hz, H-5'a), 3.54 (1H, dd, J=12.3, 3.6 Hz, H-5'b); the 3,4-methylenedioxybenzyl moiety δ 6.91 (1H, s, H-2"), 6.81 (2H, m, H-5", H-6"), 4.59 (2H, m, H-7"), 5.94 (2H, s, —OCH$_2$O—); $^{13}$C NMR (75 MHz, DMSO-d$_6$): the adenosine moiety δ 154.0 (s, C-6), 151.9 (d, C-2), 148.4 (s, C-4), 140.1 (d, C-8), 119.8 (s, C-5), 87.9 (d, C-1'), 85.9 (d, C-4'), 73.6 (d, C-2'), 70.6 (d, C-3'), 61.6 (t, C-5'); 3,4-methylenedioxybenzyl moiety δ 147.2 (C-4"), 146.0 (s, C-3"), 133.6 (s, C-1"), 120.5 (d, C-2"), 108.0 (d, C-5"), 107.9 (d, C-6"), 100.8 (—OCH$_2$O—), 42.8 (t, C-7").

Example 32: Preparation of N$^6$-(3,4-methylenedioxybenzyl)-adenosine-5'-caprylate

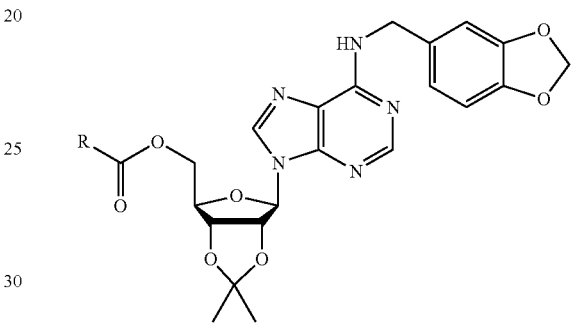

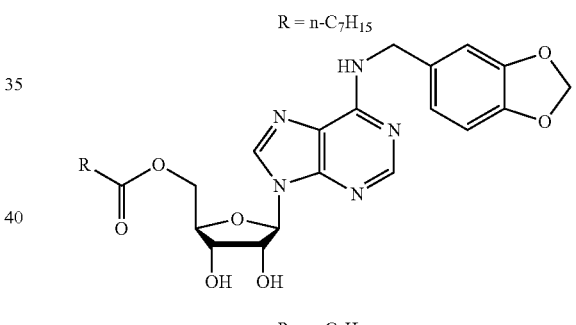

First step, N$^6$-(3,4-methylenedioxybenzyl)-adenosine (200 mg) prepared in the above example, and 2,2-dimethoxypropane (300 mg) were added to dry acetone (50 ml), and (1S)-(+)-camphor-10-sulfonic acid (120 mg) was added as a catalyst. The reaction mixture was stirred at room temperature for 5 h. After evaporation of the reaction mixture, the residue was dissolved in EtOAc, and neutralized with a NaHCO$_3$ solution. After separation by two-phase extraction, EtOAc layer was dried by anhydrous sodium sulfate, filtered, and the filtrate was evaporated to give a residue which was separated by column chromatography over silica gel and eluted with CHCl$_3$—CH$_3$OH (20:1) to yield N$^6$-(3,4-methylenedioxybenzyl)-2',3'-O-isopropylidene-adenosine (1.7 g) as a light yellowish granular crystal.

Second step, a mixture of N$^6$-(3,4-methylenedioxybenzyl)-2',3'-O-isopropylidene-adenosine (220 mg), EDCI (190 mg), DMAP (150 mg), and caprylic acid (85.5 mg) in dry CH$_2$Cl$_2$ (20 ml) was stirred at room temperature for 3 h. After evaporation of the reaction mixture, the residue was separated by column chromatography over silica gel eluting with CHCl₃—CH₃OH (100:1) to yield N⁶-(3,4-methylenedioxybenzyl)-2',3'-O-isopropylidene-adenosine-5'-caprylate (270 mg) as a light yellowish solid: positive ESIMS m/z 568.4 [M+H]⁺, 584.4 [M+Na]⁺ and 606.4[M+K]⁺; ¹H NMR (300 MHz, acetone-d₆): the adenosine moiety δ 8.27 (H, s, H-8), 8.14 (1H, s, H-2), 6.21 (1H, d, J=1.8 Hz, H-1'), 5.56 (1H, dd, J=6.3, 1.8 Hz, H-2'), 5.13 (1H, dd, J=6.3, 3.0 Hz, H-3'), 4.40 (1H, m, H-4'), 4.30 (1H, dd, J=11.7, 4.8 Hz, H-5a'), 4.20 (1H, dd, J=11.7, 6.0 Hz, H-5b'); the 3,4-methylenedioxybenzyl moiety δ 6.97 (1H, d, J=1.2 Hz, H-2"), 6.90 (1H, dd, J=8.1, 1.2 Hz, H-6"), 6.75 (1H, d, J=8.1 Hz, H-5"), 5.58 (2H, s, —OCH₂O—), 4.77 (2H, brs, H-7"); the caprylyl δ 2.22 (2H, dt, J=7.5, 1.5 Hz, H-2'''), 1.51 (2H, m, H-3'''), 1.25 (8H, m, H-4''', H-5''', H-6α" H-7'''), 0.85 (3H, t, J=6.9 Hz, H-8'''); the 2',3'-O-isopropylidene moiety δ 1.56 (3H, s, H-1''''), 1.35 (3H, s, H-3''''); ¹³C NMR (75 MHz, acetone-d₆): the adenosine moiety δ 155.8 (C-6), 153.6 (C-2), 149.8 (C-4), 140.6 (C-8), 120.5 (C-5), 91.2 (C-1'), 85.6 (C-2'), 84.9 (C-3'), 82.7 (C-4'), 64.5 (C-5'); the 3,4-methylenedioxybenzyl moiety δ 148.6 (C-3"), 147.5 (C-4"), 134.8 (C-1"), 121.7 (C-6"), 109.0 (C-2"), 108.7 (C-5"), 101.8 (—OCH₂O—), 44.1 (C-7"), the caprylyl moiety δ 173.3 (C-1'''), 34.2 (C-2'''), 32.4 (C-3'''), 30.2 (C-4'''), 29.6 (C-5'''), 25.5 (C-6'''), 23.2 (C-7'''), 14.2 (C-8'''); the 2',3'-O-isopropylidene δ 114.6 (C-2''''), 25.5 (C-1''''), 27.4 (C-3'''').

Third step, N⁶-(3-methoxy-4-hydroxybenzyl)-2',3'-O-isopropylidene-adenosine-5'-caprylate (220 mg) was added to a formic acid solution (20 ml, 50% V/V), and the mixture was stirred at room temperature for 12 h. After evaporation of the reaction mixture, the residue was separated by column chromatography over silica gel and eluted with CHCl₃—CH₃OH (50:1) to yield N⁶-(3-methoxy-4-hydroxybenzyl)-adenosine-5'-caprylate (162 mg) as a light yellowish solid: positive ESIMS m/z 528.4 [M+H]⁺, 550.4 [M+Na]⁺ and 568.7 [M+K]⁺; ¹H NMR (300 MHz, DMSO-d₆): the adenosine moiety δ 8.27 (2H, s, —NH, H-8), 8.14 (1H, s, H-2), 5.91 (1H, d, J=4.8 Hz, H-1'), 5.40 (1H, d, J=5.4 Hz, —OH), 5.35 (1H, d, J=5.4 Hz, OH), 4.66 (1H, ddd, J=4.8, 4.8, 5.4 Hz, H-2'), 4.35 (2H, brs, H-7"), 4.32 (1H, dd, J=11.6, 3.3 Hz, H-5a'), 4.26 (1H, m, H-3'), 4.18 (1H, dd, J=11.6, 6.6 Hz, H-5b'), 4.06 (1H, m, H-4'); the 3,4-methylenedioxybenzyl moiety δ 6.91 (1H, s, H-2"), 6.83 (2H, m, H-5", H-6"), 5.94 (2H, s, —OCH₂O—); the caprylyl moiety δ 2.25 (2H, t, J=6.6 Hz, H-2'''), 1.45 (2H, t, J=6.6 Hz, H-3'''), 1.17 (8H, m, H-4'''~H-7'''), 0.80 (3H, t, J=6.9 Hz, H-8'''); ¹³C NMR (75 MHz, DMSO-d₆): the adenosine moiety δ 154.7 (C-6), 152.7 (C-2), 148.8 (C-4), 140.1 (C-8), 119.8 (C-5), 88.2 (C-1'), 81.8 (C-4'), 73.2 (C-2'), 70.1 (C-3'), 64.0 (C-5'); the 3,4-methylenedioxybenzyl moiety δ 147.4 (C-3"), 146.2 (C-4"), 134.2 (C-1"), 120.7 (C-6"), 108.2 (C-2"), 108.2 (C-5"), 101.0 (—OCH₂O—), 43.0 (C-7"); the caprylyl moiety δ 173.1 (C-1'''), 33.6 (C-2'''), 31.4 (C-3'''), 31.0 (C-4'''), 28.6 (C-5'''), 24.7 (C-6'''), 22.3 (C-7'''), 14.2 (C-8''').

Example 33: Preparation of N⁶-(3,4-methylenedioxybenzyl)-adenosine-5'-p-methyl-cinnamate

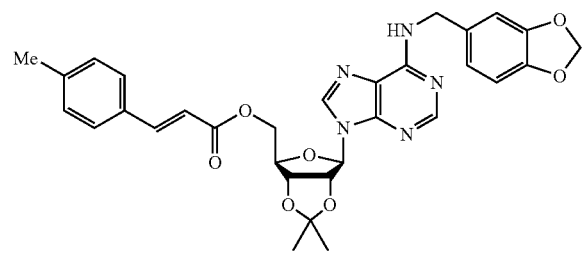

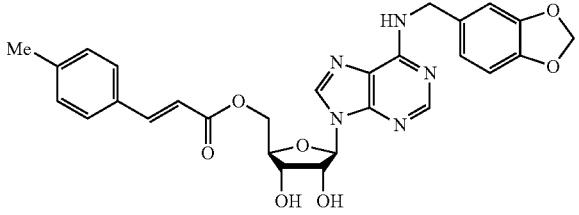

First step, a mixture of N⁶-(3,4-methylenedioxybenzyl)-2',3'-O-isopropylidene-adenosine (441.0 mg), EDCI (383.0 mg), DMAP (305.0 mg), and p-methyl-cinnamic acid (195.0 mg) in dry CH₂Cl₂ (20 ml) was stirred at room temperature for 3 h. After evaporation of the reaction mixture, the residue was separated by column chromatography over silica gel and eluted with CHCl₃—CH₃OH (100:1) to yield N⁶-(3,4-methylenedioxybenzyl)-2',3'-O-isopropylidene-adenosine-5'-p-methyl-cinnamate (562.0 mg) as a light yellowish solid: positive ESIMS m/z 586.4 [M+H]⁺ and 608.3 [M+Na]⁺; 1H NMR (300 MHz, acetone-d₆): the adenosine moiety δ 8.29 (1H, s, H-8), 8.17 (1H, s, H-2), 7.39 (1H, s, NH), 6.24 (1H, d, J=1.8 Hz, H-1'), 5.61 (1H, dd, J=6.0, 2.1 Hz, H-2'), 5.20 (1H, dd, J=6.0, 3.3 Hz, H-3'), 4.50 (1H, m, H-4'), 4.44 (1H, dd, J=15.6, 4.5 Hz, H-5'a), 4.34 (1H, dd, J=15.7, 6.0 Hz, H-5'b); the 3,4-methylenedioxybenzyl moiety δ 6.94 (1H, s, H-2"), 6.98 (1H, d, J=8.1 Hz, H-5"), 6.74 (1H, d, J=8.1 Hz, H-6"), 5.92 (2H, s, —OCH₂O—), 4.74 (2H, brs, H-7"); the p-methyl-cinnamate moiety δ 7.57 (1H, d, J=16.2 Hz, H-7'''), 7.51 (2H, d, J=8.1 Hz, H-2''', H-6'''), 7.22 (2H, d, 8.1 Hz, H-3''', H-5'''), 6.39 (1H, d, J=16.2 Hz, H-8'''), 2.34 (3H, s, Me); the 2',3'-O-isopropylidene moiety δ 1.57 (3H, s, Me), 1.37 (3H, s, Me); ¹³C NMR (75 MHz, DMSO-d₆): the adenosine moiety δ 155.4 (C-6), 153.6 (C-2), 149.5 (C-4), 140.5 (C-8), 120.0 (C-5), 91.3 (C-1'), 85.7 (C-2'), 85.0 (C-3'), 82.7 (C-4'), 64.8 (C-5'); the 3,4-methylenedioxybenzyl moiety δ 147.8 (C-3"), 146.6 (C-4"), 134.8 (C-1"), 121.7 (C-6"), 109.0 (C-2"), 108.7 (C-5"), 101.8 (—OCH₂O—), 44.0 (C-7"); the p-methyl-cinnamate moiety δ 166.8 (C-9'''), 141.6 (C-4'''), 132.5 (C-1'''), 130.4 (C-2''', C-6'''), 129.1 (C-3''', C-5'''), 117.2 (C-8'''), 21.4 (Me); the 2',3'-O-isopropylidene moiety δ 114.6 (C-2''''), 27.4 (C-1''''), 25.5 (C-8'''').

Second step, N⁶-(3-methoxy-4-hydroxybenzyl)-2',3'-O-isopropylidene-adenosine-5'-p-methyl-cinnamate (452.0 mg) was added to a formic acid solution (20 ml, 50% V/V), and the mixture was stirred at room temperature for 12 h, After evaporation of the reaction mixture, the residue was separated by column chromatography over silica gel and eluted with CHCl₃—CH₃OH (50:1) to yield N⁶-(3-methoxy-4-hydroxybenzyl)-adenosine-5'-p-methyl-cinnamate (380.0 mg) as a light yellowish solid: positive ESIMS m/z 546.3 [M+H]⁺, 568.3 [M+Na]⁺ and 586.4 [M+K]⁺; ¹H NMR (300 MHz, DMSO-d₆): the adenosine moiety δ 8.36 (1H, s, H-8), 8.33 (1H, brs, NH), 8.21 (1H, s, H-2), 5.94 (1H, d, J=5.7 Hz, H-1'), 5.57 (1H, d, J=5.7 Hz, OH), 5.40 (1H, d, J=5.1 Hz, OH), 4.73 (1H, m, H-2'), 4.48 (1H, dd, J=11.7, 3.3 Hz, H-5'a), 4.32, (1H, dd, J=11.7, 5.7 Hz, H-5'b), 4.33 (1H, m, H-3'), 4.16 (1H, m, H-4'); the 3,4-methylenedioxybenzyl moiety δ 6.90 (1H, s, H-2"), 6.80 (2H, brs, H-5", H-6"), 5.93 (2H, s, —OCH₂O—), 4.58 (2H, brs, H-7"); the p-methyl-cinnamate δ 7.60 (1H, d, J=16.5 Hz, H-8'''), 7.59 (2H, d, J=8.1 Hz, H-2''', H-6'''), 7.22 (2H, d, J=8.1 Hz, H-3''', H-5'''), 6.57 (1H, d, J=16.5 Hz, H-8'''), 2.31 (3H, s, Me); ¹³C NMR (75 MHz, DMSO-d₆): the adenosine moiety δ 155.3 (C-6), 153.3 (C-2), 149.5 (C-4), 140.4 (C-8), 121.0 (C-5), 88.4 (C-1'), 82.4 (C-4'), 73.6 (C-2'), 71.1 (C-3'), 64.7 (C-5'); the 3,4-methylenedioxybenzyl moiety δ 147.8 (C-3"), 146.6 (C-4"), 134.6 (C-1"), 121.0 (C-6"), 108.6 (C-2"), 108.5 (C-5"), 101.4 (—OCH₂O—), 43.3 (C-7"); the p-methylcinnamate moiety δ 166.8 (C-9'''), 145.6 (C-7'''), 141.3 (C-4'''), 130.2 (C-2''', C-6'''), 129.1 (C-3''', C-5'''), 117.3 (C-8'''), 821.7 (Me).

Example 34: Preparation of $N^6$-(3,4-methylenedioxybenzyl)-$N^6$-propyl-adenosine-2',3',5'-tripropyl ether

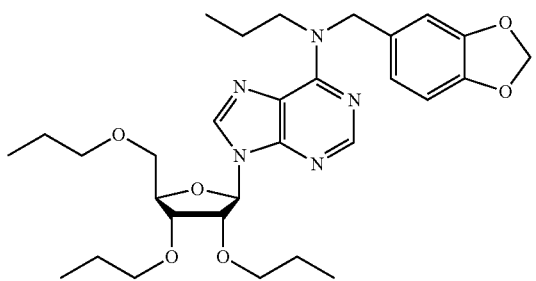

A mixture of $N^6$-(3,4-methylenedioxybenzyl)-adenosine (150 mg) prepared in the above example, 1-iodo-propan (500 mg) and potassium hydroxide (200 mg) in dry THF (20 ml) was refluxed for 24 h. After evaporation of the reaction mixture, the residue was dissolved in distilled water (20 ml), and extracted with EtOAc (3×25 ml). The EtOAc was dried by anhydrous sodium sulfate, and filtered. The filtrate was evaporated and separated by column chromatography over silica gel and eluted with CHCl₃-petroleum ether (1:1) to yield $N^6$-(3,4-methylenedioxybenzyl)-$N^6$-propyl-adenosine-2',3',5'-tripropyl ether: positive ESIMS m/z 570.5 [M+H]⁺, 592.4 [M+Na]⁺ and 608.4 [M+K]⁺; ¹H NMR (300 MHz, acetone-d₆): the adenosine moiety δ 8.29 (1H, s, H-8), 8.27 (1H, s, H-2), 6.20 (1H, d, J=4.2 Hz, H-1'), 4.54 (1H, t, J=4.2 Hz, H-2'), 4.24 (2H, m, H-3', H-4'), 3.79 (1H, dd, J=10.8, 2.7 Hz, H-5'a), 3.64 (1H, dd, J=10.8, 6.0 Hz, H-5'b); the 3,4-methylenedioxybenzyl moiety δ 6.86 (1H, s, H-2"), 6.84 (1H, d, J=8.4 Hz, H-6"), 6.76 (1H, d, J=8.4 Hz, H-5"), 5.93 (2H, s, —OCH₂O—), 5.20 (2H, brs, H-7"); the propyl moiety δ 3.62-3.44 (8H, m, —OCH₂×3, —NCH₂), 1.75-1.50 (8H, m, CH₂×4), 0.96-0.85 (12H, m, Me×4); ¹³C NMR (75 MHz, acetone-d₆): the adenosine moiety δ 155.1 (C-6), 153.1 (C-2), 151.6 (C-4), 138.2 (C-8), 120.5 (C-5), 87.7 (C-1'), 82.7 (C-4'), 81.7 (C-2'), 77.7 (C-3'), 70.7 (C-5'); the 3,4-methylenedioxybenzyl moiety δ 148.7 (C-3"), 147.7 (C-4"), 133.6 (C-1"), 121.9 (C-6"), 109.0 (C-2"), 108.7 (C-5"), 101.8 (—OCH₂O—), 50.2 (br, C-7"); the propyl moiety δ 73.7, 72.8, 72.5, 50.4 (C-1''', C-1'''', C-1''''', C-1''''''), 23.8, 23.7, 23.6, 21.9 (br) (C-2''', C-2'''', C-2''''', C-2''''''), 11.4, 11.0, 10.9, 10.8 (C-3''', C-3'''', C-3''''', C-3'''''').

Example 35: Preparation of $N^6$-(3,4-methylenedioxybenzyl)-adenosine-5'-propyl ether

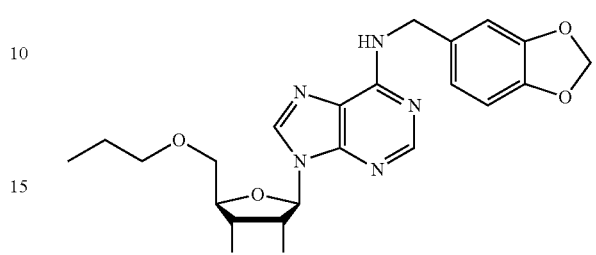

First step, $N^6$-(3,4-methylenedioxybenzyl)-2',3'-O-isopropylidene-adenosine (500 mg) was dissolved in dry THF (25 ml). NaH (500 mg) was added slowly at room temperature and stirred for 2 h. The dry THF (5 ml) solution of 1-iodo-propan (288 mg) was added to the reaction solution and stirred at room temperature for 4 h. The reaction solution was ended by adding proper quantity of distilled water to destroy the excess NaH. After evaporation of the reaction mixture, the residue was dissolved in distilled water (20 ml), and extracted with EtOAc (3×25 ml). The EtOAc was dried by anhydrous sodium sulfate, and filtered. The filtrate evaporated and the residue was separated by column chromatography over silica gel and eluted with petroleum ether-EtOAc (3:2) to yield $N^6$-(3,4-methylenedioxybenzyl)-2',3'-O-isopropylidene-adenosine-5'-propyl ether (268 mg).

Second step, $N^6$-(3,4-methylenedioxybenzyl)-2',3'-O-isopropylidene-adenosine-5'-propyl ether (260 mg) was added to a formic acid solution (20 ml, 50% V/V), and the mixture was stirred at room temperature for 12 h. After evaporation of the reaction mixture, the residue was recrystallised in ethanol to yield $N^6$-(3,4-methylenedioxybenzyl)-adenosine-5'-propyl ether (210 mg) as a white granular crystal: the adenosine moiety δ 8.34 (1H, brs, —NH), 8.34 (1H, s, H-8), 8.22 (1H, s, H-2), 5.92 (1H, d, 6.3 Hz, H-1'), 5.51 (1H, d, J=5.7 Hz, OH), 5.24 (1H, d, J=5.1 Hz, OH), 4.54 (1H, m, H-2'), 4.18 (1H, m, H-3'), 4.02 (1H, m, H-4'), 3.64 (1H, dd, 10.8 Hz, 3.6 Hz, H-5a'), 3.54 (1H, dd, 10.8 Hz, 3.6 Hz, H-5b'); the 3,4-methylenedioxybenzyl moiety δ 6.91 (1H, s, H-2"), 6.81 (2H, s, H-5", H-6"), 5.94 (2H, s, —OCH₂O—), 4.59 (2H, m, H-7"); the propyl δ 3.37 (2H, t, J=7.2 Hz, H-1'''), 1.51 (2H, hex, J=7.2 Hz, H-2'''), 0.85 (2H, t, J=7.2 Hz, H-3'''); ¹³CNMR (75 MHz, DMSO-d₆): the adenosine moiety δ 154.3 (s, C-6), 152.6 (d, C-2), 148.8 (s, C-4), 139.4 (d, C-8), 119.4 (s, C-5), 87.5 (d, C-1'), 83.1 (d, C-4'), 73.6 (d, C-2'), 70.3 (d, C-3'), 70.2 (t, C-5'); the 3,4-methylenedioxybenzyl moiety δ 147.1 (s, C-4"), 145.9 (s, C-3"), 134.0 (s, C-1"), 120.4 (d, C-6"), 107.94 (d, C-2"), 107.88 (d, C-5"), 100.7 (—OCH₂O—), 42.7 (t, C-7"); the propyl δ 72.3 (C-1'''), 22.4 (C-2'''), 10.5 (C-3''').

Example 36: Preparation of N⁶-(4-hydroxy-3,5-dimethxoybenzyl)-adenosine

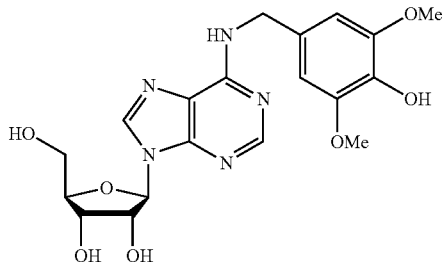

First step, hydroxyamine hydrochloride (1.26 g) and NaOAc (1.65 g) were added to a solution of 4-hydroxy-3,5-dimethxoybenzaldehyde (1.82 g) in EtOH (80 ml). The reaction mixture was stirred at room temperature for 6 h. EtOH was removed under reduced pressure. $H_2O$ (40 ml) was added to the residue, which was then extracted with EtOAc (3×40 ml). The EtOAc of the combined organic layer was removed by rotary evaporation under reduced pressure to yield 4-hydroxy-3,5-dimethxoybenzaldehyde oxime (1.7 g) as a pale yellowish solid.

Second step, a solution of 4-hydroxy-3,5-dimethxoybenzaldehyde oxime (1.7 g) and concentrated HCl (5.2 ml) in EtOH (50 ml) was subjected to hydrogenation at atmospheric pressure in the presence of 10% Pd/C (183 mg). The reaction solution was filtered and the filtrate was concentrated to yield 4-hydroxy-3,5-dimethxoybenzylamine hydrochloride (1.6 g) as a white solid.

Third step, a mixture of 4-hydroxy-3,5-dimethxoybenzylamine (1.58 g, the hydrochloride), 6-chloropurine riboside (526 mg) and triethylamine (7.7 ml) in PrOH (60 ml) was heated to 70° C. and reacted for 8 h. After evaporation of the reaction mixture, the residue was separated by column chromatography over silica gel and eluted with $CHCl_3$—$CH_3OH$ (20:1) to yield N⁶-(4-hydroxy-3,5-dimethxoybenzyl)-adenosine (585 mg) as a white solid: positive ESIMS m/z 434 [M+H]⁺, 456 [M+Na]⁺ and 472 [M+K]⁺; negative ESIMS m/z 432 [M−H]⁻ and 468 [M+Cl]⁻; ¹H NMR (300 MHz, DMSO-$d_6$): the adenosine moiety δ 8.36 (1H, s, H-2), 8.28 (1H, brs, —NH), 8.17 (1H, s, H-8), 5.87 (1H, d, J=6.0 Hz, H-1'), 5.42 (1H, d, J=6.6 Hz, —OH), 5.37 (1H, m, —OH), 4.60 (1H, d, J=5.1 Hz, —OH), 4.60 (H, m, H-2'), 4.13 (1H, m, H-3'), 3.95 (1H, m, H-4'), 3.69-3.64 (1H, m, H-5'a), 3.56-3.50 (1H, m, H-5'b); the 4-hydroxy-3,5-dimethxoybenzyl moiety δ 8.22 (1H, s, —OH), 6.65 (2H, s, H-2", H-6"), 4.60 (2H, m, H-7"), 3.69 (6H, s, 2×—OCH₃); ¹³CNMR (75 MHz, DMSO-$d_6$): the adenosine moiety δ 154.6 (s, C-6), 152.5 (d, C-2), 148.6 (s, C-4), 140.0 (d, C-8), 119.8 (s, C-5), 88.1 (d, C-1'), 86.1 (d, C-4'), 73.6 (d, C-2'), 70.8 (d, C-3'), 61.8 (t, C-5'); the 4-hydroxy-3,5-dimethxoybenzyl moiety δ 147.9 (s, C-3", C-5"), 134.5 (s, C-4"), 130.0 (s, C-1"), 105.3 (d, C-2", C-6"), 43.3 (t, C-7").

Example 37: Preparation of N⁶-(3,4,5-trimethxoybenzyl)-adenosine

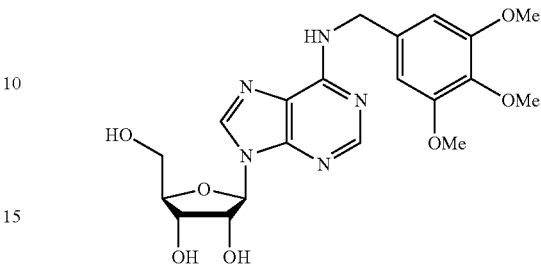

First step, hydroxyamine hydrochloride (748 mg) and NaOAc (1.0 g) were added to a solution of 3,4,5-trimethxoybenzaldehyde (1.16 g) in EtOH (80 ml). The reaction mixture was stirred at room temperature for 6 h. EtOH was removed under reduced pressure. $H_2O$ (40 ml) was added to the residue, which was then extracted with EtOAc (3×40 ml). The EtOAc of the combined organic layer was removed by rotary evaporation under reduced pressure to yield 3,4,5-trimethxoybenzaldehyde oxime (1.16 g) as a pale yellowish solid.

Second step, a solution of 3,4,5-trimethxoybenzaldehyde oxime (1.16 g) and concentrated HCl (5.2 ml) in EtOH (50 ml) was subjected to hydrogenation at atmospheric pressure in the presence of 10% Pd/C (116 mg). The reaction solution was filtered and the filtrate was concentrated to yield 3,4,5-trimethxoybenzylamine hydrochloride (1.1 g) as a white solid.

Third step, a mixture of 3,4,5-trimethxoybenzylamine (327 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with $CHCl_3$—$CH_3OH$ (20:1) to yield N⁶-(3,4,5-trimethxoybenzyl)-adenosine (470 mg) as a white solid: positive ESIMS m/z 448 [M+H]⁺ and 470 [M+Na]⁺; negative ESIMS m/z 446 [M−H]⁻ and 482 [M+Cl]⁻; ¹H NMR (300 MHz, DMSO-$d_6$): the adenosine moiety δ 8.38 (1H, brs, —NH), 8.38 (1H, s, H-2), 8.22 (1H, brs, H-8), 5.88 (1H, d, J=6.1 Hz, H-1'), 5.42 (1H, d, J=6.6 Hz, —OH), 5.37 (1H, m, —OH), 5.18 (1H, d, J=4.5 Hz, —OH), 4.60 (1H, m, H-2'), 4.13 (1H, m, H-3'), 3.95 (1H, m, H-4'), 3.64 (1H, m, H-5'a), 3.54 (1H, m, H-5'b); the 3,4,5-trimethoxybenzyl moiety δ 6.70 (2H, s, H-2", H-6"), 4.60 (2H, m, H-7"), 3.71 (6H, s, —OCH₃×2), 3.60 (3H, s, —OCH₃); ¹³C NMR (75 MHz, DMSO-$d_6$): the adenosine moiety δ 154.6 (s, C-6), 152.5 (d, C-2), 148.6 (s, C-4), 140.2 (d, C-8), 119.9 (s, C-5), 88.2 (d, C-1'), 86.1 (d, C-4'), 73.7 (d, C-2'), 70.9 (d, C-3'), 61.8 (t, C-5'); the 3,4,5-trimethxoybenzyl moiety δ 152.9 (s, C-3", C-5"), 136.5 (s, C-4"), 135.8 (s, C-1"), 104.9 (d, C-2", C-6"), 60.1 (q, —OCH₃), 55.9 (q, —OCH₃), 43.4 (t, C-7").

Example 38: Preparation of N⁶-[(3,4-dimethxoyphenyl)-ethyl]-adenosine

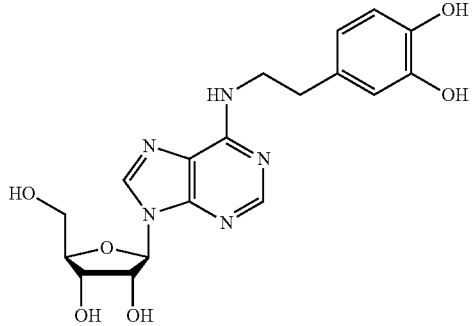

A mixture of dopamine (264 mg, the hydrochloride), 6-chloropurine riboside (200 mg) and triethylamine (5 ml) in PrOH (50 ml) was heated to 70° C. and reacted for 8 h. After evaporation of the reaction mixture, the residue was separated by column chromatography over silica gel and eluted with CHCl₃—CH₃OH (20:1) to yield N⁶-[(3,4-dimethxoyphenyl)-ethyl]-adenosine (230 mg) as a white solid: positive ESIMS m/z 404 [M+H]⁺ and 426 [M+Na]⁺; negative ESIMS m/z 402 [M−H]⁻ and 438 [M+Cl]⁻; ¹H NMR (300 MHz, DMSO-d₆): the adenosine moiety δ 8.34 (1H, s, H-2), 8.23 (1H, s, H-8), 7.78 (1H, brs, —NH), 5.88 (1H, d, J=5.7 Hz, H-1'), 5.44 (2H, m, 2×—OH), 5.19 (1H, m, —OH), 4.61 (1H, m, H-2'), 4.14 (1H, m, H-3'), 3.96 (1H, m, H-4'), 3.66 (1H, m, H-5'a), 3.56 (1H, m, H-517), the dopamine moiety δ 8.76 (1H, brs, —OH), 8.64 (1H, brs, —OH), 6.62 (1H, s, H-2"), 6.63 (1H, d, 7.2 Hz, H-5"), 6.47 (1H, d, J=7.2 Hz, H-6"), 3.65 (2H, m, H-8"), 2.71 (2H, t, J=7.5 Hz, H-7"); ¹³C NMR (75 MHz, DMSO-d₆) δ 154.6 (s, C-6), 152.5 (d, C-2), 148.3 (s, C-4), 139.8 (d, C-8), 119.8 (s, C-5), 88.0 (d, C-1'), 86.0 (d, C-4'), 73.5 (d, C-2'), 70.7 (d, C-3'), 61.8 (t, C-5'); the dopamine moiety δ 145.1 (s, C-3"), 143.6 (s, C-4"), 130.3 (s, C-1"), 119.3 (d, C-2"), 116.1 (d, C-5"), 115.6 (d, C-6"), 41.8 (t, C-8"), 34.5 (t, C-7").

Example 39: Preparation of N⁶-[(3-methoxy-4-hydroxyphenyl)-ethyl]-adenosine

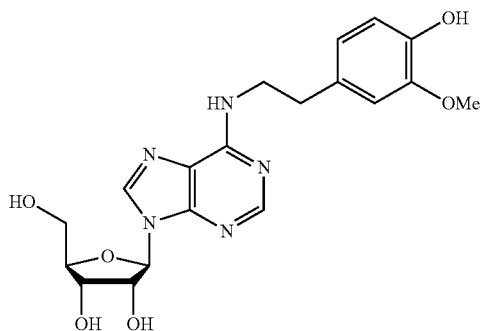

A mixture of 3-methoxy-4-hydroxydopamine (39 mg), 6-chloropurine riboside (50 mg) and triethylamine (0.8 ml) in PrOH (25 ml) was heated to 70° C. and reacted for 8 h. After evaporation of the reaction mixture, the residue was separated by column chromatography over silica gel and eluted with CHCl₃—CH₃OH (20:1~15:1) to yield N⁶-[(3-methoxy-4-hydroxyphenyl)-ethyl]-adenosine (60 mg) as a white solid: positive ESIMS m/z 418 [M+H]⁺; negative ESIMS m/z 416 [M−H]⁻和 452 [M+Cl]⁺; ¹H NMR (300 MHz, DMSO-d₆): the adenosine moiety δ 8.34 (1H, s, H-2), 8.22 (1H, s, H-8), 7.86 (1H, brs, —NH), 5.87 (1H, d, J=6.0 Hz, H-1'), 5.44-5.39 (2H, m, 2×—OH), 5.17 (1H, d, J=4.8 Hz, —OH), 4.60 (1H, m, H-2'), 4.14 (1H, m, H-3'), 3.95 (1H, m, H-4'), 3.66 (1H, m, H-5'a), 3.55 (1H, m, H-5'b); the 3-methoxy-4-hydroxydopamine moiety δ 8.69 (1H, s, —OH), 6.79 (1H, m, H-2"), 6.66 (1H, d, J=7.5 Hz, H-5"), 6.61 (1H, brd, J=7.5 Hz, H-6"), 3.71 (3H, s, —OCH₃), 3.65 (2H, m, H-8"), 2.80 (1H, t, J=7.8 Hz, H-7"); ¹³C NMR (75 MHz, DMSO-d₆): the adenosine moiety δ 154.6 (s, C-6), 152.5 (d, C-2), 148.3 (s, C-4), 139.8 (d, C-8), 119.8 (s, C-5), 87.9 (d, C-1'), 85.9 (d, C-4'), 73.5 (d, C-2'), 70.7 (d, C-3'), 61.7 (t, C-5'); the 3-methoxy-4-hydroxydopamine moiety δ 147.4 (s, C-3"), 144.8 (s, C-4"), 130.2 (s, C-1"), 120.8 (d, C-6"), 115.3 (d, C-5"), 112.8 (d, C-2"), 55.5 (q, —OCH₃), 41.5 (t, C-8"), 34.6 (t, C-7").

Example 40: Preparation of N⁶-[(3-hydroxy-4-methoxyphenyl)-ethyl]-adenosine

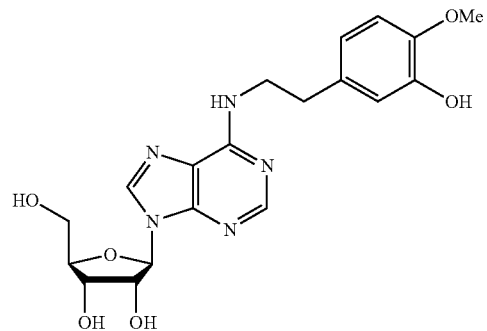

A mixture of 3-hydroxy-4-methoxydopamine (39 mg), 6-chloropurine riboside (50 mg) and triethylamine (0.8 ml) in PrOH (25 ml) was heated to 70° C. and reacted for 8 h. After evaporation of the reaction mixture, the residue was separated by column chromatography over silica gel and eluted with CHCl₃—CH₃OH (20:1~15:1) to yield N⁶-[(3-hydroxy-4-methoxyphenyl)-ethyl]-adenosine (58 mg) as a white solid: positive ESIMS m/z 418 [M+H]⁺ and 440 [M+Na]⁺; negative ESIMS m/z 416 [M−H]⁻ and 452 [M+Cl]⁻; ¹H NMR (300 MHz, DMSO-d₆): the adenosine moiety δ 8.34 (1H, s, H-2), 8.23 (1H, s, H-8), 7.87 (1H, brs, —NH), 5.87 (1H, d, 6.0 Hz, H-1'), 5.46 (2H, m, 2×—OH), 5.17 (1H, d, J=4.8 Hz, —OH), 4.60 (1H, m, H-2'), 4.13 (1H, m, H-3'), 3.95 (1H, m, H-4'), 3.66 (1H, m, H-5'a), 3.55 (1H, m, H-5'b); the 3-hydroxy-4-methoxydopamine moiety δ 8.82 (1H, s, —OH), 6.80 (1H, d, J=7.5 Hz, H-5"), 6.68 (1H, s, H-2"), 6.60 (1H, brd, J=7.5 Hz, H-6"), 3.71 (3H, s, —OCH₃), 3.66 (2H, m, H-8"), 2.76 (1H, t, 7.5 Hz, H-7"); ¹³C NMR (75 MHz, DMSO-d₆): the adenosine moiety δ 154.6 (s, C-6), 152.5 (d, C-2), 148.3 (s, C-4), 139.8 (d, C-8), 119.8 (s, C-5), 88.0 (d, C-1'), 86.0 (d, C-4'), 73.5 (d, C-2'), 70.7 (d, C-3'), 61.8 (t, C-5'); 3-hydroxy-4-methoxydopamine moiety δ 146.4 (s, C-4"), 146.1 (s, C-3"), 132.1 (s, C-1"), 119.2 (d, C-6"), 116.1 (d, C-2"), 112.4 (d, C-5"), 51.7 (q, —OCH₃), 41.6 (t, C-8"), 34.4 (t, C-7").

Example 41: Preparation of N⁶-[(1S,2S)-2-(1,3-dihydroxy-1-phenyl)-propyl]-adenosine

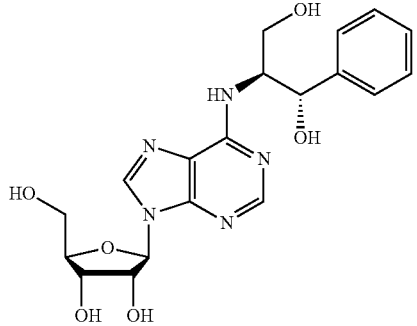

A mixture of (1S,2S)-(+)-2-amino-1-phenyl-1,3-propylene glycol (702 mg), 6-chloropurine riboside (300 mg) in PrOH (50 ml) was heated to 80° C. for 10 h. After evaporation of the reaction mixture, the residue was separated by column chromatography over Sephadex LH-20 gel and eluted with ethanol to yield N⁶-[(1S,2S)-2-(1,3-dihydroxy-1-phenyl)-propyl]-adenosine (350 mg) as a white solid: positive ESIMS m/z 418 [M+H]⁺; negative ESIMS m/z 416 [M−H]⁻; ¹H NMR (300 MHz, DMSO-d₆): the adenosine moiety δ 8.35 (1H, s, H-2), 8.12 (1H, s, H-8), 6.68 (1H, d, J=8.7 Hz, —NH), 5.84 (1H, d, J=6.3 Hz, H-1'), 5.42 (1H, d, J=6.6 Hz, —OH), 5.17 (1H, d, J=4.5 Hz, —OH), 5.34 (1H, m, —OH), 4.57 (1H, m, H-2'), 4.11 (1H, m, H-3'), 3.93 (1H, m, H-4'), 3.66 (1H, m, H-5'a), 3.56 (1H, m, H-5'b); the (1S,2S)-2-(1,3-dihydroxy-1-phenyl)-propyl moiety δ 7.34 (1H, d, J=7.2 Hz, H-2", H-6"), 7.24 (1H, t, J=7.2 Hz, H-3", H-5"), 7.14 (1H, t, J=7.2 Hz, H-4"), 5.78 (1H, d, J=4.2 Hz, —OH) 5.04 (1H, m, H-7"), 4.93 (1H, m, —OH), 4.46 (1H, m, H-8"), 3.65 (1H, m, H-9"a), 3.53 (1H, m, H-9"b), 140.0 (d, C-8), 119.8 (s, C-5); ¹³C NMR (75 MHz, DMSO-d₆): the adenosine moiety δ 154.6 (s, C-6), 152.3 (d, C-2), 148.3 (s, C-4), 88.0 (d, C-1'), 86.0 (d, C-4'), 73.6 (d, C-2'), 70.7 (d, C-3'), 61.7 (t, C-5'); the (1S,2S)-2-(1,3-dihydroxy-1-phenyl)-propyl moiety δ 143.7 (s, C-1"), 127.9 (d, C-2", C-6"), 126.8 (d, C-4"), 126.0 (d, C-3", C-5"), 69.6 (d, C-7"), 60.4 (t, C-9"), 57.2 (d, C-8").

Example 42: Preparation of N⁶-[(1R,2R)-2-(1,3-dihydroxy-1-phenyl)-propyl]-adenosine

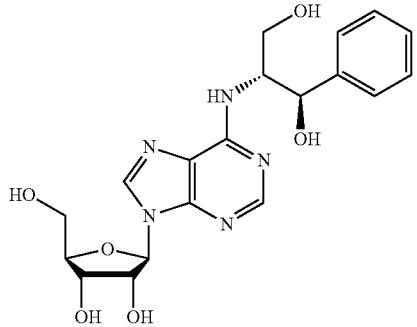

A mixture of (1R,2R)-(−)-2-amino-1-phenyl-1,3-propylene glycol (702 mg), and 6-chloropurine riboside (300 mg) in PrOH (50 ml) was heated to 80° C. for 10 h. After evaporation of the reaction mixture, the residue was separated by column chromatography over Sephadex LH-20 gel and eluted with ethanol to yield N⁶-[(1R,2R)-2-(1,3-dihydroxy-1-phenyl)-propyl]-adenosine (360 mg) as a white solid: positive ESIMS m/z 418 [M+H]⁺; negative ESIMS m/z 416 [M−H]⁻; ¹H NMR (300 MHz, DMSO-d₆): the adenosine moiety δ 8.37 (1H, s, H-2), 8.15 (1H, s, H-8), 6.73 (1H, J=9.0 Hz, —NH), 5.87 (1H, d, J=6.0 Hz, H-1'), 5.46 (1H, d, J=4.5 Hz, —OH), 5.41 (1H, m, —OH), 5.20 (1H, m, —OH), 4.61 (1H, m, H-2'), 4.16 (1H, m, H-3'), 3.97 (1H, m, H-4'), 3.66 (1H, m, H-5'a), 3.55 (1H, m, H-5'b); the (1R,2R)-2-(1,3-dihydroxy-1-phenyl)-propyl moiety δ 7.37 (2H, d, J=7.5 Hz, H-2", H-6"), 7.25 (2H, t, J=7.5 Hz, H-3", H-5"), 7.14 (1H, t, J=7.5 Hz, H-4"), 5.81 (1H, m, OH), 5.07 (1H, m, H-7"), 4.97 (1H, m, —OH), 4.50 (1H, m, H-8"), 3.68 (1H, m, H-9"a), 3.52 (1H, m, H-9"b); ¹³C NMR (75 MHz, DMSO-d₆): the adenosine moiety δ 154.6 (s, C-6), 152.3 (d, C-2), 148.3 (s, C-4), 140.3 (d, C-8), 119.8 (s, C-5), 88.1 (d, C-1'), 86.0 (d, C-4'), 73.5 (d, C-2'), 70.7 (d, C-3'), 61.7 (t, C-5'); the (1R,2R)-2-(1,3-dihydroxy-1-phenyl)-propyl moiety δ 143.7 (s, C-1"), 127.9 (d, C-2", C-6"), 126.8 (d, C-4"), 126.1 (d, C-3", C-5"), 69.6 (d, C-7"), 60.4 (t, C-9"), 57.2 (d, C-8").

Example 43: Preparation of N⁶-[(1H-imidazole-4-yl)-ethyl]-adenosine

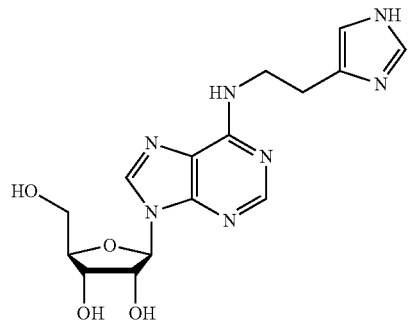

A mixture of histamine (156 mg), 6-chloropurine riboside (200 mg) and triethylamine (3 ml) in PrOH (50 ml) was heated to 80° C. for 10 h. After evaporation of the reaction mixture, the residue was separated by column chromatography over silica gel eluting with CHCl₃—CH₃OH (2:1) to yield N⁶-[(1H-imidazole-4-yl)-ethyl]-adenosine (210 mg) as a white solid: positive ESIMS m/z 362 [M+H]⁺; negative ESIMS m/z 360 [M−H]⁻; ¹H NMR (300 MHz, DMSO-d₆): the adenosine moiety δ 8.34 (1H, s, H-2), 8.22 (1H, s, H-8), 7.93 (1H, brs, —NH) 5.88 (1H, d, J=6.0 Hz, H-1'), 5.44 (3H, m, 3×—OH), 4.60 (1H, m, H-2'), 4.13 (1H, m, H-3'), 3.95 (1H, m, H-4'), 3.65 (1H, m, H-5'a), 3.55 (1H, m, H-5'b); the histamine moiety δ 11.92 (1H, brs, 1"-NH), 7.52 (1H, s, H-2"), 6.82 (1H, s, H-5"), 3.66 (2H, m, H-7"), 2.82 (2H, t, J=7.5 Hz, H-6"); ¹³C NMR (75 MHz, DMSO-d₆): the adenosine moiety δ 154.7 (s, C-6), 152.6 (d, C-2), 148.4 (s, C-4), 140.0 (d, C-8), 119.9 (s, C-5), 88.2 (d, C-1'), 86.1 (d, C-4'), 73.7 (d, C-2'), 70.9 (d, C-3'), 61.8 (t, C-5'); the histamine moiety δ 134.9 (d, C-2"), 134.7 (s, C-4"), 117.0 (d, C-5"), 40.3 (t, C-7"), 26.8 (t, C-6").

Example 44: Preparation of $N^6$-[(1H-Indole-3-yl)-ethyl]-adenosine

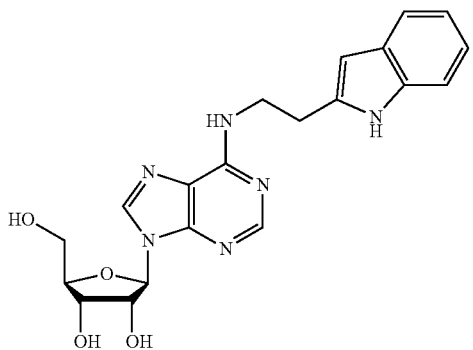

A mixture of tryptamine (224 mg), 6-chloropurine riboside (200 mg) and triethylamine (3 ml) in PrOH (70 ml) was heated to 80° C. After evaporation of the reaction mixture, the residue was separated by column chromatography over silica gel and eluted with $CHCl_3$—$CH_3OH$ (20:1) to yield $N^6$-[(1H-Indole-3-yl)-ethyl]adenosine (230 mg) as a white solid: positive ESIMS m/z 411 [M+H]$^+$, 433 [M+Na]$^+$ and 449 [M+K]$^+$; negative ESIMS m/z 409 [M−H]$^-$ 和 445 [M+Cl]$^-$; $^1$H NMR (300 MHz, DMSO-$d_6$): the adenosine moiety δ 8.35 (1H, s, H-2), 8.26 (1H, s, H-8), 8.00 (1H, brs, —NH), 5.88 (1H, d, J=6.3 Hz, H-1'), 5.43 (2H, m, 2×—OH), 5.17 (1H, d, J=3.9 Hz, —OH), 4.63 (1H, m, H-2'), 4.14 (1H, m, H-3'), 3.95 (1H, m, H-4'), 3.67 (1H, m, H-5'a), 3.55 (1H, m, H-5'b); the tryptamine moiety δ 10.80 (1H, s, —NH), 7.62 (1H, d, J=6.9 Hz, H-4"), 7.32 (1H, d, J=6.9 Hz, H-7"), 7.19 (1H, s, H-2"), 7.06 (1H, t, J=6.9 Hz, H-6"), 6.97 (1H, t, J=6.9 Hz, H-5"), 3.77 (2H, m, H-9"), 3.01 (2H, d, t, J=7.5 Hz, H-8"); $^{13}$C NMR (75 MHz, DMSO-$d_6$): the adenosine moiety δ 154.8 (s, C-6), 152.6 (d, C-2), 148.4 (s, C-4), 139.9 (d, C-8), 120.0 (s, C-5), 88.2 (d, C-1'), 86.1 (d, C-4'), 73.7 (d, C-2'), 70.9 (d, C-3'), 61.9 (t, C-5'); the tryptamine moiety δ 136.4 (s, C-7a"), 127.5 (s, C-3a"), 122.8 (s, C-3"), 121.1 (d, C-2"), 118.6 (d, C-5"), 118.5 (d, C-4"), 112.0 (d, C-6"), 111.5 (d, C-7"), 40.7 (t, C-9"), 25.2 (t, C-8").

Example 45: Preparation of $N^6$-[(±)-1-(phenyl)-ethyl]-adenosine

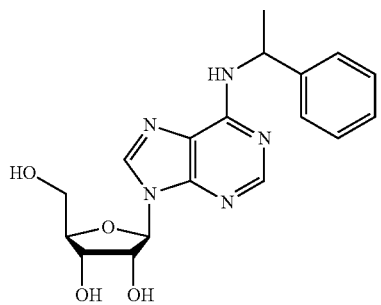

First step, hydroxyamine hydrochloride (2.60 g) and NaOAc (3.40 g) were added to a solution of acetophenone (2.40 g) in EtOH (80 ml). The reaction mixture was stirred at room temperature for 6 h. EtOH was removed under reduced pressure. $H_2O$ (40 ml) was added to the residue, and extracted with EtOAc (3×40 ml). The EtOAc of the combined organic layer was removed by rotary evaporation under reduced pressure to yield acetophenone oxime (2.68 g) as a pale yellowish solid.

Second step, a solution of acetophenone oxime (2.68 g) and concentrated HCl (8 ml) in EtOH (50 ml) was subjected to hydrogenation at atmospheric pressure in the presence of 10% Pd/C (420 mg). The reaction solution was filtered and the filtrate was concentrated to yield phenylethylamine hydrochloride (2.17 g) as a white solid.

Third step, a mixture of phenylethylamine (2.17 g, the hydrochloride), 6-chloropurine riboside (660 mg) and triethylamine (9 ml) in PrOH (60 ml) was heated to 70° C. for 8 h. After evaporation of the reaction mixture, the residue was separated by column chromatography over silica gel and eluted with $CHCl_3$—$CH_3OH$ (20:1) to yield $N^6$-[(±)-1-(phenyl)-ethyl]-adenosine (468 mg) as a white solid: positive ESIMS m/z 372 [M+H]$^+$, 394 [M+Na]$^+$ and 410 [M+K]$^+$; $^1$H NMR (300 MHz, DMSO-$d_6$): the adenosine moiety δ 8.37 (1H, s, H-2), 8.31 (1H, brs, —NH), 8.16 (1H, s, H-8), 5.86 (1H, d, J=6.0 Hz, H-1'), 5.43 (1H, dd, J=6.3, 1.2 Hz, —OH), 5.37 (1H, m, —OH), 5.16 (1H, d, J=4.8 Hz, —OH), 4.57 (1H, m, H-2'), 4.14 (1H, m, H-3'), 3.95 (1H, m, H-4'), 3.66 (1H, m, H-5'a), 3.54 (1H, m, H-5'b); the (±)-1-(phenyl)-ethyl moiety δ 7.42 (2H, brd, J=7.2 Hz, H-2", H-6"), 7.27 (2H, t, J=7.2 Hz, H-3", H-5"), 7.17 (1H, t, J=7.2 Hz, H-4"), 5.51 (1H, m, H-7"), 1.53 (3H, d, J=6.9 Hz, H-8"); $^{13}$C NMR (75 MHz, DMSO-$d_6$): the adenosine moiety δ 153.9 (s, C-6), 152.4 (d, C-2), 148.6 (s, C-4), 139.9 (d, C-8), 119.8 (s, C-5), 88.0 (d, C-1'), 86.0 (d, C-4'), 73.6 (d, C-2'), 70.7 (d, C-3'), 61.7 (t, C-5'); the (±)-1-(phenyl)-ethyl moiety δ 145.2 (s, C-1"), 128.3 (d, C-2", C-6"), 126.6 (d, C-4"), 126.2 (d, C-3", C-5"), 48.9 (d, C-7"), 22.6 (q, C-8").

Example 46: Preparation of $N^6$-[(±)-1-(4-methoxy-phenyl)-ethyl]-adenosine

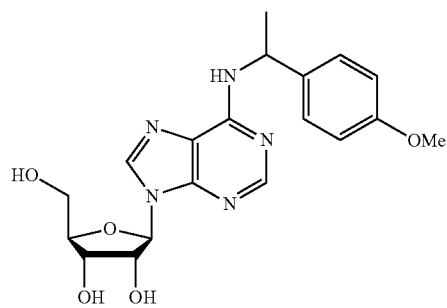

First step, hydroxyamine hydrochloride (4.60 g) and NaOAc (10.92 g) were added to a solution of 4-methoxyacetophenone (5 g) in EtOH (80 ml). The reaction mixture was stirred at 60° C. for 6 h. EtOH was removed under reduced pressure. $H_2O$ (40 ml) was added to the residue, and extracted with EtOAc (3×40 ml). The EtOAc of the combined organic layer was removed by rotary evaporation under reduced pressure to yield 4-methoxyacetophenone oxime (5.03 g) as a pale yellowish solid.

Second step, a solution of 4-methoxyacetophenone oxime (5.03 g) and concentrated HCl (13.3 ml) in EtOH (50 ml) was subjected to hydrogenation at atmospheric pressure in the presence of 10% Pd/C (510 mg). The reaction solution was filtered and the filtrate was concentrated to yield 1-(4-methoxyphenyl)-ethylamine hydrochloride (5.6 g) as a white solid.

Third step, a mixture of 1-(4-methoxyphenyl)-ethylamine (314 mg, the hydrochloride), 6-chloropurine riboside (200 mg) and triethylamine (3 ml) in PrOH (50 ml) was heated to 70° C. for 8 h. After evaporation of the reaction mixture, the residue was separated by column chromatography over silica gel and eluted with CHCl$_3$—CH$_3$OH (20:1) to yield N$^6$-[(±)-1-(4-methoxyphenyl)-ethyl]-adenosine (225 mg) as a white solid: positive ESIMS m/z 402 [M+H]$^+$和 424 [M+Na]$^+$; negative ESIMS m/z 400 [M−H]$^-$; $^1$H NMR (300 MHz, DMSO-d$_6$): the adenosine moiety δ 8.39 (1H, s, H-2), 8.22 (1H, brs, —NH), 8.20 (1H, s, H-8), 5.92 (1H, d, J=6.0 Hz, H-1'), 5.49 (2H, m, 2×—OH), 5.24 (1H, d, J=4.5 Hz, —OH), 4.64 (1H, m, H-2'), 4.18 (1H, m, H-3'), 4.01 (1H, m, H-4'), 3.66 (1H, m, H-5'a), 3.55 (1H, m, H-511); the (±)-1-(4-methoxyphenyl)-ethyl moiety δ 7.36 (1H, d, J=8.1 Hz, H-2", H-6"), 6.83 (1H, d, J=8.1 Hz, H-3", H-5"), 5.49 (1H, m, H-7"), 3.68 (3H, s, —OCH$_3$), 1.52 (1H, d, J=6.9 Hz, H-8"); $^{13}$C NMR (75 MHz, DMSO-d$_6$): the adenosine moiety δ 153.9 (s, C-6), 152.4 (d, C-2), 148.6 (s, C-4), 139.9 (d, C-8), 119.8 (s, C-5), 88.1 (d, C-1'), 86.1 (d, C-4'), 73.7 (d, C-2'), 70.8 (d, C-3'), 61.8 (t, C-5'); the (±)-1-(4-methoxyphenyl)-ethyl moiety δ 158.1 (s, C-4"), 137.1 (s, C-1"), 127.4 (d, C-2", C-6"), 113.7 (d, C-3", C-5"), 55.1 (q, —OCH$_3$), 48.3 (d, C-7"), 22.5 (q, C-8").

Example 47: Preparation of N$^6$-[(±)-1-(4-hydroxyphenyl)-ethyl]-adenosine

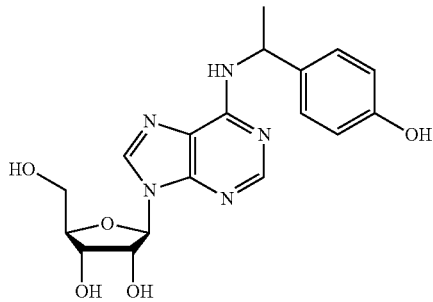

First step, hydroxyamine hydrochloride (5.07 g) and NaOAc (12.05 g) were added to a solution of 4-hydroxyacetophenone (5 g) in EtOH (80 ml). The reaction mixture was stirred at 60° C. for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield 4-hydroxyacetophenone oxime (4.53 g) as a pale yellowish solid.

Second step, a solution of 4-hydroxyacetophenone oxime (4.53 g) in EtOH (50 ml) was subjected to hydrogenation at atmospheric pressure in the presence of 10% Pd/C (502 mg). The reaction solution was filtered and the filtrate was concentrated to yield the 1-(4-hydroxyphenyl)-ethylamine (5.2 g) as a white solid.

Third step, a mixture of 1-(4-hydroxyphenyl)-ethylamine (288 mg), 6-chloropurine riboside (200 mg) and triethylamine (3 ml) in PrOH (60 ml) was heated to 70° C. for 8 h. After evaporation of the reaction mixture, the residue was separated by column chromatography over silica gel and eluted with CHCl$_3$—CH$_3$OH (20:1) to yield N$^6$-[(±)-1-(4-hydroxyphenyl)-ethyl]-adenosine (220 mg) as a white solid: positive ESIMS m/z 388 [M+H]$^+$和 410 [M+Na]$^+$; negative ESIMS m/z 386 [M−H]$^-$; $^1$H NMR (300 MHz, DMSO-d$_6$): the adenosine moiety δ 8.36 (1H, s, H-2), 8.17 (1H, s, H-8), 8.12 (1H, d, J=8.4 Hz, —NH), 5.88 (1H, d, J=5.7 Hz, H-1'), 5.45 (2H, m, 2×—OH), 5.19 (1H, d, J=4.5 Hz, —OH), 4.60 (1H, m, H-2'), 4.15 (1H, m, H-3'), 3.97 (1H, m, H-4'), 3.66 (1H, m, H-5a'), 3.55 (1H, m, H-5'b); the (±)-1-(4-hydroxyphenyl)-ethyl moiety δ 9.27 (1H, s, —OH), 7.23 (1H, d, J=8.1 Hz, H-2", H-6"), 6.67 (1H, d, J=8.1 Hz, H-3", H-5"), 5.42 (1H, m, H-7"), 1.49 (1H, d, J=6.9 Hz, H-8"); $^{13}$C NMR (75 MHz, DMSO-d$_6$): the adenosine moiety δ 153.8 (s, C-6), 152.3 (d, C-2), 148.5 (s, C-4), 139.8 (d, C-8), 119.7 (s, C-5), 88.0 (d, C-1'), 86.0 (d, C-4'), 73.6 (d, C-2'), 70.7 (d, C-3'), 61.8 (t, C-5'); the (±)-1-(4-hydroxyphenyl)-ethyl moiety δ 156.1 (s, C-4"), 135.3 (s, C-1"), 127.3 (d, C-2", C-6"), 114.9 (d, C-3", C-5"), 48.3 (d, C-7"), 22.5 (q, C-8").

Example 48: Preparation of N$^6$-[(±)-1-(4-aminophenyl)-ethyl]-adenosine

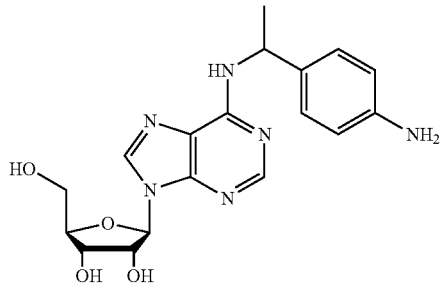

First step, hydroxyamine hydrochloride (4.18 g) and NaOAc (9.93 g) were added to a solution of p-aminoacetophenone (5 g) in EtOH (80 ml). The reaction mixture was stirred at 60° C. for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield p-aminoacetophenone oxime (5.56 g) as a pale yellowish solid.

Second step, a solution of p-aminoacetophenone oxime (5.56 g) and concentrated HCl (20 ml) in EtOH (50 ml) was subjected to hydrogenation at atmospheric pressure in the presence of 10% Pd/C (784 mg). The reaction solution was filtered and the filtrate was concentrated to yield 1-(p-aminophenyl)-ethylamine hydrochloride (7.5 g) as a white solid.

Third step, a mixture of 1-(p-aminophenyl)-ethylamine (363 mg, the hydrochloride), 6-chloropurine riboside (200 mg) and triethylamine (3 ml) in PrOH (60 ml) was heated to 70° C. for 8 h. After evaporation of the reaction mixture, the residue was separated by column chromatography over silica gel and eluted with CHCl$_3$—CH$_3$OH (20:1) to yield N$^6$-[(±)-1-(4-aminophenyl)-ethyl]-adenosine (220 mg) as a white solid: positive ESIMS m/z 387 [M+H]$^+$ and 409 [M+Na]$^+$; negative ESIMS m/z 385 [M−H]$^-$ and 421 [M+Cl]$^-$; $^1$H NMR (300 MHz, DMSO-d$_6$): the adenosine moiety δ 8.34 (1H, s, H-2), 8.15 (1H, s, H-8), 8.00 (1H, d, J=8.4 Hz, —NH), 5.86 (1H, d, J=5.7 Hz, H-1'), 5.40 (2H, m, 2×—OH), 5.15 (1H, d, J=4.5 Hz, —OH), 4.58 (1H, m, H-2'), 4.12 (1H, m, H-3'), 3.94 (1H, m, H-4'), 3.66 (1H, m, H-5'a), 353 (1H, m, H-5'b); the (±)-1-(4-aminophenyl)-ethyl moiety δ 7.08 (2H, d, J=8.4 Hz, H-2", H-6"), 6.46 (1H, d, J=8.4 Hz, H-3", H-5"), 5.43 (1H, m, H-7"), 4.88 (1H, brs, —NH$_2$), 1.46 (1H, d, J=6.9 Hz, H-8"); $^{13}$CNMR (75 MHz, DMSO-d$_6$): the adenosine moiety δ 153.9 (s, C-6), 152.4 (d, C-2), 148.5 (s, C-4), 139.7 (d, C-8), 119.8 (s, C-5), 88.0 (d, C-1'), 86.0 (d, C-4'), 73.6 (d, C-2'), 70.8 (d, C-3'), 61.8 (t, C-5'); the (±)-1-(4-aminophenyl)-ethyl moiety δ 147.4 (s, C-4"), 132.1 (s, C-1"), 127.0 (d, C-2", C-6"), 113.7 (d, C-3", C-5"), 48.2 (d, C-7"), 22.4 (q, C-8").

Example 49: Preparation of N$^6$-{(±)-1-[4-(2-methyl-propyl)-phenyl]-ethyl}-adenosine

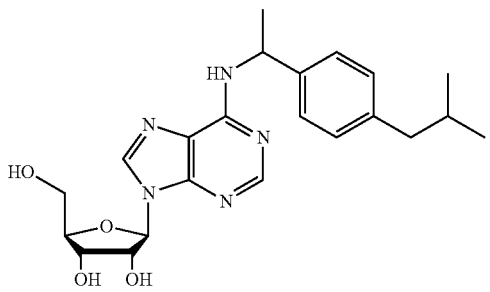

First step, hydroxyamine hydrochloride (3.34 g) and NaOAc (7.95 g) were added to a solution of 4-(2-methyl-propyl)-acetophenone (5 g) in EtOH (80 ml). The reaction mixture was stirred at 60° C. for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield 4-(2-methyl-propyl)-acetophenone oxime (5.43 g) as a pale yellowish solid.

Second step, a solution of 4-(2-methyl-propyl)-acetophenone oxime (5.43 g) and concentrated HCl (15 ml) in EtOH (50 ml) was subjected to hydrogenation at atmospheric pressure in the presence of 10% Pd/C (601 mg). The reaction solution was filtered and the filtrate was concentrated to yield 1-[4-(2-methyl-propyl)-phenyl]-ethylamine hydrochloride (6.0 g) as a white solid.

Third step, a mixture of 1-[4-(2-methyl-propyl)-phenyl]-ethylamine (449 mg, the hydrochloride), 6-chloropurine riboside (200 mg) and triethylamine (3 ml) in PrOH (60 ml) was heated to 70° C. for 8 h. After evaporation of the reaction mixture, the residue was separated by column chromatography over silica gel and eluted with CHCl$_3$—CH$_3$OH (20:1) to yield N$^6$-{(±)-1-[4-(2-methyl-propyl)-phenyl]-ethyl}-adenosine (240 mg) as a white solid: positive ESIMS m/z 428 [M+H]$^+$, 450 [M+Na]$^+$ and 466 [M+K]$^+$; negative ESIMS m/z 426 [M−H]$^+$; $^1$H NMR (300 MHz, DMSO-d$_6$): the adenosine moiety δ 8.36 (1H, s, H-2), 8.25 (1H, brs, —NH), 8.15 (1H, s, H-8), 5.86 (1H, d, J=4.8 Hz, H-1'), 5.41 (1H, m, —OH), 5.37 (1H, m, —OH), 5.16 (1H, d, J=4.8 Hz, —OH), 4.58 (1H, m, H-2'), 4.12 (1H, m, H-3'), 3.94 (1H, m, H-4'), 3.65 (1H, m, H-5'a), 3.55 (1H, m, H-5'b); the (±)-1-[4-(2-methyl-propyl)-phenyl]-ethyl moiety δ 7.32 (2H, d, J=7.8 Hz, H-2", H-6"), 7.05 (2H, d, J=7.8 Hz, H-3", H-5"), 5.49 (1H, m, H-7"), 2.37 (2H, d, J=7.2 Hz, H-1'''), 1.77 (1H, m, H-2'''), 1.51 (3H, d, J=7.2 Hz, H-3''', H-4'''), 0.82 (6H, d, J=6.3 Hz, H-8"); $^{13}$C NMR (75 MHz, DMSO-d$_6$): the adenosine moiety δ 153.9 (s, C-6), 152.3 (d, C-2), 148.5 (s, C-4), 139.8 (d, C-8), 119.7 (s, C-5), 88.0 (d, C-1'), 85.9 (d, C-4'), 73.6 (d, C-2'), 70.7 (d, C-3'), 61.7 (t, C-5'); the (±)-1-[4-(2-methyl-propyl)-phenyl]-ethyl moiety δ 142.3 (s, C-1"), 139.4 (s, C-4"), 128.8 (d, C-2", C-6"), 126.0 (d, C-3", C-5"), 48.4 (d, C-7"), 44.3 (t, C-1'''), 29.6 (d, C-2'''), 22.4 (q, C-8"), 22.2 (q, C-3''', C-4''').

Example 50: Preparation of N$^6$-[(±)-1-(3-methoxy-4-hydroxy-phenyl)-ethyl]-adenosine

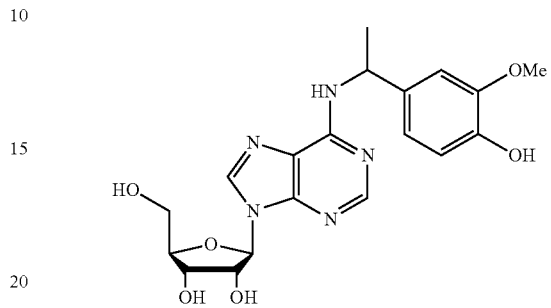

First step, hydroxyamine hydrochloride (4.15 g) and NaOAc (9.84 g) were added to a solution of 3-methoxy-4-hydroxy-acetophenone (5 g) in EtOH (80 ml). The reaction mixture was stirred at 60° C. for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield 3-methoxy-4-hydroxy-acetophenone oxime (5.43 g) as a pale yellowish solid.

Second step, a solution of 3-methoxy-4-hydroxy-acetophenone oxime (5.43 g) and concentrated HCl (12.5 ml) in EtOH (50 ml) was subjected to hydrogenation at atmospheric pressure in the presence of 10% Pd/C (681 mg). The reaction solution was filtered and the filtrate was concentrated to yield 1-(3-methoxy-4-hydroxy-phenyl)-ethylamine hydrochloride (6.0 g) as a white solid.

Third step, a mixture of 1-(3-methoxy-4-hydroxy-phenyl)-ethylamine (3.97 g, the hydrochloride), 6-chloropurine riboside (2 g) and triethylamine (30 ml) in PrOH (60 ml) was heated to 70° C. for 8 h. After evaporation of the reaction mixture, the residue was separated by column chromatography over silica gel and eluted with CHCl$_3$—CH$_3$OH (20:1) to yield N$^6$-[(±)-1-(3-methoxy-4-hydroxy-phenyl)-ethyl]-adenosine (2.30 g) as a white solid: positive ESIMS m/z 418 [M+H]$^+$ and 440 [M+Na]$^+$; negative ESIMS m/z 416 [M−H]$^−$ and 452 [M+Cl]$^−$; $^1$H NMR (300 MHz, DMSO-d$_6$): the adenosine moiety δ 8.39 (1H, s, H-2), 8.30 (1H, s, H-8), 8.14 (1H, d, J=8.7 Hz, —NH), 5.90 (1H, d, 6.0 Hz, H-1'), 5.46 (2H, m, 2×—OH), 4.62 (1H, m, H-2'), 4.17 (1H, m, H-3'), 3.98 (1H, m, H-4'), 3.66 (1H, m, H-5'a), 3.55 (1H, m, H-5'6); the (±)-1-(3-methoxy-4-hydroxy-phenyl)-ethyl moiety δ 8.79 (1H, brs, —OH), 7.09 (1H, s, H-2"), 6.84 (1H, d, J=8.1 Hz, H-6"), 6.68 (1H, d, J=8.1 Hz, H-5"), 5.23 (1H, m, H-7"), 3.75 (3H, s, —OCH$_3$), 1.50 (3H, d, J=6.9 Hz, H-8"); $^{13}$C NMR (75 MHz, DMSO-d$_6$): the adenosine moiety δ 153.8 (s, C-6), 152.3 (d, C-2), 148.6 (s, C-4), 139.9 (d, C-8), 119.8 (s, C-5), 88.1 (d, C-1'), 86.0 (d, C-4'), 73.6 (d, C-2'), 70.8 (d, C-3'), 61.8 (t, C-5'); the (±)-1-(3-methoxy-4-hydroxy-phenyl)-ethyl moiety δ 147.5 (s, C-3"), 145.3 (s, C-4"), 136.0 (s, C-1"), 118.7 (d, C-2"), 115.1 (d, C-6"), 110.8 (d, C-5"), 48.7 (d, C-7"), 22.7 (q, C-8").

Example 51: Preparation of N⁶-[(±)-1-(3,4-dimethoxyphenyl)-ethyl]adenosine

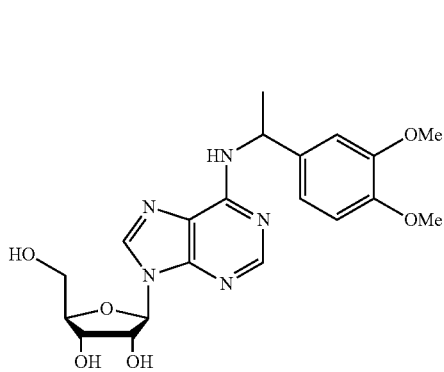

First step, hydroxyamine hydrochloride (3.83 g) and NaOAc (9.11 g) were added to a solution of 3,4-dimethoxy-acetophenone (5 g) in EtOH (80 ml). The reaction mixture was stirred at 60° C. for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield 3,4-dimethoxy-acetophenone oxime (5.16 g) as a pale yellowish solid.

Second step, 3,4-dimethoxy-acetophenone oxime (5 g) and zinc dust (6.70 g) in HOAc (25 ml) was stirred at room temperature for 6 h. The reaction solution was filtered to remove the excess zinc dust and ZnOAc residue, and the filtrate was concentrated to yield 3,4-dimethoxyphenyl-ethylamine (1.2 g) as a yellowish oil.

Third step, a mixture of 3,4-dimethoxyphenyl-ethylamine (381 mg), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with CHCl$_3$—CH$_3$OH (20:1) to yield N⁶-[(±)-1-(3,4-dimethoxyphenyl)-ethyl]adenosine (240 mg) as a white solid: positive ESIMS m/z 432 [M+H]⁺, 454 [M+Na]⁺ and 470 [M+K]⁺: negative ESIMS m/z 430 [M–H]⁻; ¹H NMR (300 MHz, DMSO-d$_6$): the adenosine moiety δ 8.36 (1H, s, H-2), 8.19 (1H, brs, —NH), 8.16 (1H, s, H-8), 5.86 (1H, d, J=6.0 Hz, H-1'), 5.45 (2H, m, 2×—OH), 5.16 (1H, d, J=3.9 Hz, —OH), 4.58 (1H, m, H-2'), 4.13 (1H, m, H-3'), 3.95 (1H, m, H-4'), 3.66 (1H, m, H-5'a), 3.56 (1H, m, H-5'6); the (±)-1-(3,4-dimethoxyphenyl)-ethyl moiety δ 7.12 (1H, brs, H-2"), 6.92 (1H, brd, J=7.8 Hz, H-6"), 6.83 (1H, d, J=7.8 Hz, H-5"), 5.45 (1H, m, H-7"), 3.72 (3H, s, —OCH$_3$), 3.68 (3H, s, —OCH$_3$), 1.50 (3H, d, J=6.9 Hz, H-8"); ¹³C NMR (75 MHz, DMSO-d$_6$): the adenosine moiety δ 153.9 (s, C-6), 152.3 (d, C-2), 148.7 (s, C-4), 139.8 (d, C-8), 119.8 (s, C-5), 88.0 (d, C-1'), 86.0 (d, C-4'), 73.6 (d, C-2'), 70.7 (d, C-3'), 61.7 (t, C-5'); the (±)-1-(3,4-dimethoxyphenyl)-ethyl moiety δ 148.6 (s, C-3"), 147.6 (s, C-4"), 137.7 (s, C-1"), 118.2 (d, C-2"), 111.6 (d, C-6"), 110.5 (d, C-5"), 55.5 (q, —OCH$_3$), 55.3 (q, —OCH$_3$), 48.7 (d, C-7"), 22.7 (q, C-8").

Example 52: Preparation of N⁶-[(±)-1-(3,4,5-trimethoxyphenyl)-ethyl]-adenosine

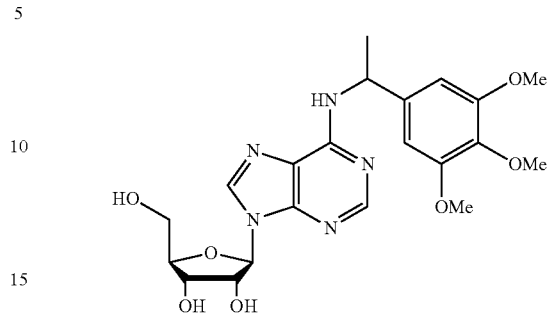

First step, hydroxyamine hydrochloride (2.87 g) and NaOAc (6.82 g) were added to a solution of 3,4,5-trimethoxy-acetophenone (5 g) in EtOH (80 ml). The reaction mixture was stirred at 60° C. for 6 h. EtOH was removed under reduced pressure. H$_2$O (40 ml) was added to the residue, and extracted with EtOAc (3×40 ml). The EtOAc of the combined organic layer was removed by rotary evaporation under reduced pressure to yield 3,4,5-trimethoxy-acetophenone oxime (5.36 g) as a pale yellowish solid.

Second step, a solution of 3,4,5-trimethoxy-acetophenone oxime (5.36 g) and concentrated HCl (13 ml) in EtOH (50 ml) was subjected to hydrogenation at atmospheric pressure in the presence of 10% Pd/C (505 mg). The reaction solution was filtered and the filtrate was concentrated to yield 1-(3,4,5-trimethoxyphenyl)-ethylamine hydrochloride (5.85 g) as a white solid.

Third step, a mixture of 1-(3,4,5-trimethoxyphenyl)-ethylamine (520 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with CHCl$_3$—CH$_3$OH (20:1) to yield N⁶-[(±)-1-(3,4,5-trimethoxyphenyl)-ethyl]-adenosine (260 mg) as a white solid: positive ESIMS m/z 462 [M+H]⁺; negative ESIMS m/z 460 [M–H]⁻ 和 496 [M+Cl]⁻; ¹H NMR (300 MHz, DMSO-d$_6$): the adenosine moiety δ 8.38 (1H, s, H-2), 8.23 (1H, d, J=7.5 Hz, —NH), 8.18 (1H, s, H-8), 5.87 (1H, d, J=6.0 Hz, H-1'), 5.42 (1H, d, J=6.3 Hz, —OH), 5.36 (1H, m, —OH), 5.17 (1H, d, J=4.8 Hz, —OH), 4.59 (1H, m, H-2'), 4.13 (1H, m, H-3'), 3.94 (1H, m, H-4'), 3.66 (1H, m, H-5'a), 3.55 (1H, m, H-5'b); the (±)-1-(3,4,5-trimethoxyphenyl)-ethyl moiety δ 6.81 (2H, s, H-2", H-6"), 5.48 (1H, m, H-7"), 3.74 (6H, s, 2×—OCH$_3$), 3.59 (3H, s, —OCH$_3$), 1.50 (3H, d, J=6.9 Hz, H-8"); ¹³C NMR (75 MHz, DMSO-d$_6$): the adenosine moiety δ 153.9 (s, C-6), 152.4 (d, C-2), 148.6 (s, C-4), 139.9 (d, C-8), 119.8 (s, C-5), 88.1 (d, C-1'), 86.0 (d, C-4'), 73.6 (d, C-2'), 70.7 (d, C-3'), 61.7 (t, C-5'); the (±)-1-(3,4,5-trimethoxyphenyl)-ethyl moiety δ 152.8 (s, C-3", C-5"), 140.9 (s, C-1"), 136.3 (s, C-4"), 103.8 (d, C-2", C-6"), 60.0 (q, —OCH$_3$), 55.9 (q, 2×—OCH$_3$), 49.2 (d, C-7"), 22.8 (q, C-8").

Example 53: Preparation of $N^6$-[(±)-1-(3,4,5-trimethoxyphenyl)-ethyl]-adenosine-5'-caprylate

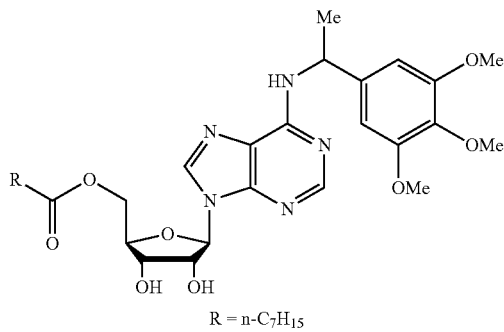

R = n-$C_7H_{15}$

First step, 6-chloropurine riboside (2.0 g) and 2,2-dimethoxypropane (5.80 g) in dry acetone (100 ml), (1S)-(+)-camphor-10-sulfonic acid (1.60 g) was added as a catalyst. The reaction mixture was stirred at room temperature for 11 h. After evaporating the solvent, the mixture was dissolved in chloroform (200 ml), and a $NaHCO_3$ solution (3×30 ml) was added. The water layer was extracted with chloroform (30 ml), then the chloroform layer was dried by anhydrous sodium sulfate and filtered. After evaporation of the solvent, the mixture was separated by column chromatography over silica gel eluting with $CHCl_3$—$CH_3OH$ (100:1) to yield 2',3'-O-isopropylidene-6-chloropurine riboside (2.24 g) as a white solid.

Second step, a mixture of hydrochloric salt of 1-(3,4,5-trimethoxyphenyl)-ethylamine (2.0 g) prepared in the above example, 2',3'-O-isopropylidene-6-chloropurine riboside (1.60 g) and triethylamine (1.20 g) in EtOH (70 ml) was refluxed for 10 h. After evaporation of the reaction mixture, the residue was separated by column chromatography over silica gel and eluted with $CHCl_3$—$CH_3OH$ (100:1) to yield 2',3'-O-isopropylidene-$N^6$-(3,4,5-trimethoxybenzyl)-adenosine (1.4 g) as a white solid.

Third step, a mixture of $N^6$-(3,4,5-trimethoxybenzyl)-adenosine (700 mg), caprylic acid (241 mg), EDCI (537 mg), and DMAP (427.6 mg) in dry $CH_2Cl_2$ (60 ml) was stirred at room temperature for 3 h. After evaporation of the reaction mixture, the residue was separated by column chromatography over silica gel and eluted with $CHCl_3$—$CH_3OH$ (100:1) to yield $N^6$-[(±)-1-(3,4,5-trimethoxyphenyl)-ethyl]-2',3'-O-isopropylidene-adenosine-5'-caprylate (450 mg).

Fourth step, $N^6$-[(±)-1-(3,4,5-trimethoxyphenyl)-ethyl]-2',3'-O-isopropylidene-adenosine-5'-caprylate (450 mg) was added to a formic acid solution (20 ml, 50% V/V), and the mixture was stirred at room temperature for 12 h, After evaporation of the reaction mixture, the residue was separated by column chromatography over silica gel and eluted with $CHCl_3$—$CH_3OH$ (50:1) to yield $N^6$-[(±)-1-(3,4,5-trimethoxyphenyl)-ethyl]-adenosine-5'-caprylate (360 mg) as a white solid: positive ESIMS m/z 588 [M+H]$^+$, 610 [M+Na]$^+$ and 626 [M+K]$^+$; $^1$H NMR (300 MHz, DMSO-$d_6$): positive δ 8.35 (1H, s, H-8), 8.23 (1H, s, H-2), 8.18 (1H, brd, J=8.1 Hz, NH), 5.97 (1H, d, J=4.2 Hz, H-1'), 5.61 (1H, brs, —OH), 5.41 (1H, brs, —OH), 4.70 (1H, m, H-2'), 4.34 (1H, dd, J=11.7, 1.8 Hz, H-3'), 4.32 (1H, m, H-3'), 4.22 (1H, dd, J=11.7, 5.7 Hz, H-5'b), 4.15 (1H, m, H-4'); the 1-(3,4,5-trimethoxyphenyl)-ethyl moiety δ 6.83 (2H, s, H-2", H-6"), 5.50 (1H, m, H-7"), 3.75 (6H, s, —OMe), 3.62 (3H, s, —OMe), 1.52 (3H, d, J=6.6 Hz, H-8"); the capryl moiety δ 2.25 (2H, t, H-2'''), 1.45 (2H, m, H-3'''), 1.14 (8H, m, H-4"'-H-7'''), 0.77 (3H, t, H-8'''). $^{13}$C NMR (75 MHz, DMSO-$d_6$): the adenosine moiety δ 153.8 (C-6), 152.6 (C-4), 148.5 (C-2), 140.9 (C-8), 119.8 (C-5) 88.1 (C-1'), 81.6 (C-4'), 73.1 (C-3'), 70.4 (C-2'), 63.8 (C-5'); the 1-(3,4,5-trimethoxyphenyl)-ethyl moiety δ 152.8 (C-3", C-5"), 139.6 (C-1"), 136.3 (C-4"), 103.8 (C-2", C-6"), 59.9 (MeO-4"), 55.9 (MeO-3", 5"'), 49.2 (C-7"), 22.8 (C-8"); the capryl moiety δ 172.8 (C-1'''), 33.4 (C-2'''), 31.2 (C-3'''), 28.4 (C-4'''), 28.4 (C-5'''), 24.5 (C-6'''), 22.1 (C-7'''), 13.9 (C-8''').

Example 54: Preparation of $N^6$-[(±)-1-(3,4,5-trimethoxyphenyl)-ethyl]-adenosine-5'-p-methoxyphenyl propionate

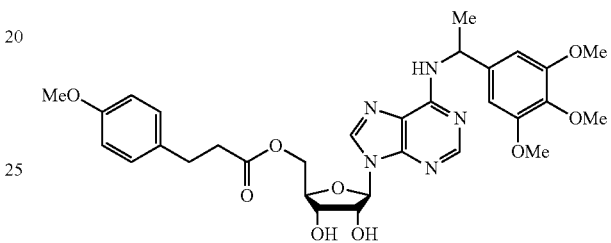

First step, a mixture of $N^6$-[(±)-1-(3,4,5-trimethoxyphenyl)-ethyl]-2',3'-O-isopropylidene-adenosine (250.7 mg), p-methoxy-phenylpropionic acid (108.1 mg), EDCI (191.7 mg) and DMAP (152.7 mg) in dry $CH_2Cl_2$ (20 ml) was stirred at room temperature for 2 h. After evaporation of the reaction mixture, the residue was separated by column chromatography over silica gel and eluted with $CHCl_3$—$CH_3OH$ (50:1) to yield $N^6$-[(±)-1-(3,4,5-trimethoxyphenyl)-ethyl]-2',3'-O-isopropylidene-adenosine-5'-p-methoxy-phenyl propionate (302 mg).

Second step, $N^6$-[(±)-1-(3,4,5-trimethoxyphenyl)-ethyl]-2',3'-O-isopropylidene-adenosine-5'-p-methoxy-phenyl propionate (120 mg) was added to a formic acid solution (20 ml, 50% V/V), and the mixture was stirred at room temperature for 12 h. After evaporation of the reaction mixture, the residue was separated by column chromatography over silica gel and eluted with $CHCl_3$—$CH_3OH$ (50:1) to yield $N^6$-[(±)-1-(3,4,5-trimethoxyphenyl)-ethyl]-adenosine-5'-p-methoxy-phenyl propionate (120 mg) as a pale yellowish solid: positive ESIMS m/z 624.4 [M+H]$^+$, 546.4 [M+Na]$^+$ and 662.3 [M+K]$^+$; $^1$H NMR (300 MHz, DMSO-$d_6$): the adenosine moiety δ 8.37 (1H, s, H-8), 8.24 (2H, brs, H-2, NH), 5.96 (1H, d, J=4.5 Hz, H-1'), 5.63 (1H, d, J=5.4 Hz, OH), 5.41 (1H, d, J=5.4 Hz, OH), 4.68 (1H, m, H-2'), 4.34 (1H, dd, J=12.0, 3.6 Hz, H-5'a), 4.27 (1H, m, H-3'), 4.22 (1H, dd, J=12.0, 5.7 Hz, H-5'b), 4.10 (1H, m, H-4'); the 1-(3,4,5-trimethoxyphenyl)-ethyl moiety δ 6.83 (2H, s, H-2", H-6"), 5.50 (1H, m, H-7"), 3.74 (6H, s, MeO-3", MeO-5"), 3.60 (3H, s, MeO-4"), 1.52 (3H, d, J=6.6 Hz, H-8"); the p-methoxy-hydrocinnamoyl δ 7.09-7.06 (2H, d, J=8.1 Hz, H-2''', H-6'''), 6.75 (2H, d, J=8.1 Hz, H-3''', H-5'''), 3.66 (3H, s, MeO-4'''), 2.74 (2H, t, J=7.2 Hz, H-8'''), 2.57 (2H, t, J=7.2 Hz, H-7'''); $^{13}$C NMR (75 MHz, DMSO-$d_6$): the adenosine moiety δ 153.8 (C-6), 152.7 (C-2), 148.9 (C-4), 141.0 (C-8), 119.6 (C-5), 88.0 (C-1'), 81.6 (C-4'), 79.3 (C-3'), 73.1 (C-2'), 70.3 (C-5'); the 1-(3,4,5-trimethoxyphenyl)-ethyl moiety δ 152.8 (C-3", C-5"), 139.7 (C-1"), 136.3 (C-4"), 103.8 (C-2", C-6"), 60.0 (MeO-4"), 55.9 (MeO-3", MeO-5"), 49.2 (C-7"), 22.9 (C-8"); the p-methoxy-hydrocinnamoyl moiety δ 172.2 (C-9'''), 157.7 (C-4'''), 132.3 (C-1'''), 129.3 (C-2''', C-6'''), 113.8 (C-3''', C-5'''), 55.0 (MeO-4'''), 35.4 (C-8'''), 29.5 (C-7''').

Example 55: Preparation of $N^6$-[(±)-1-(3,4,5-trimethoxyphenyl)-ethyl]-adenosine-5'-propyl ether

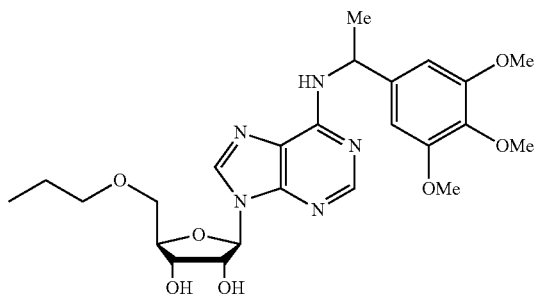

First step, 6-chloropurine riboside (10.0 g) and 2,2-dimethoxypropane (29.0 g) were added to dry acetone (200 ml), and (1S)-(+)-camphor-10-sulfonic acid (4.05 g) was added as a catalyst. The reaction mixture was stirred at room temperature for 3 h. After evaporating the solvent, the mixture was dissolved in distilled water (60 ml), and extracted with EtOAc (3×60 ml), then the EtOAc layer was dried by anhydrous sodium sulfate, and filtered. After evaporation of the solvent, the mixture was separated by column chromatography over silica gel and eluted with $CHCl_3$ to yield 2',3'-O-isopropylidene-6-chloropurine riboside (10.0 g) as a pale yellowish solid.

Second step, a mixture of 1-(3,4,5-trimethoxyphenyl)-ethylamine (0.730 g), 2',3'-O-isopropylidene-6-chloropurine riboside (0.80 g) and triethylamine (1.20 g) in 95% EtOH (50 ml) was refluxed for 8 h. After evaporation of the reaction mixture, the residue was suspended in EtOAc (150 ml), and filtered. The filtrate was evaporated. The residue was separated by column chromatography over silica gel and eluted with $CHCl_3$—$CH_3OH$ (100:1) to yield $N^6$-[(±)-1-(3,4,5-trimethoxyphenyl)-ethyl]-2',3'-O-isopropylidene-adenosine (1.24 g) as a pale yellowish solid.

Third step, $N^6$-[(±)-1-(3,4,5-trimethoxyphenyl)-ethyl]-2',3'-O-isopropylidene-adenosine (240 mg) was dissolved in dry THF (10 ml). NaH (240 mg) was added slowly at room temperature and stirred for 2 h. The dry THF (5 ml) solution of 1-iodo-propan (137.5 mg) was added to the reaction solution and stirred at room temperature for 4 h. The reaction solution was ended by adding proper quantity of distilled water to destroy the excess NaH. After evaporation of the reaction mixture, the residue was dissolved in distilled water (20 ml), and extracted with EtOAc (3×25 ml). The EtOAc was dried by anhydrous sodium sulfate, and filtered. The filtrate was evaporated and the residue was separated by column chromatography over silica gel and eluted with petroleum ether-EtOAc (3:2) to yield $N^6$-[(±)-1-(3,4,5-trimethoxyphenyl)-ethyl]-2',3'-O-isopropylidene-adenosine-5'-propyl ether (205 mg).

Fourth step, $N^6$-[(±)-1-(3,4,5-trimethoxyphenyl)-ethyl]-2',3'-O-isopropylidene-adenosine-5'-propyl ether (200 mg) was added to a formic acid solution (20 ml, 50% V/V), and the mixture was stirred at room temperature for 12 h. After evaporation of the reaction mixture, the residue was separated by column chromatography over silica gel and eluted with $CHCl_3$—$CH_3OH$ (50:1) to yield $N^6$-[(±)-1-(3,4,5-trimethoxyphenyl)-ethyl]-adenosine-5'-propyl ether (120 mg) as a white solid: positive ESIMS m/z 504[M+H]$^+$, 526[M+Na]$^+$ and 542[M+K]$^+$; $^1H$ NMR (300 MHz, DMSO-$d_6$): the adenosine moiety δ 8.37 (1H, s, H-8), 8.22 (1H, brs, H-2), 8.14 (1H, brs, NH), 5.94 (1H, d, J=4.5 Hz, H-1'), 5.53 (1H, brs, OH), 5.26 (1H, brs, OH), 4.54 (1H, m, H-2'), 4.20 (1H, m, H-3'), 4.03 (1H, m, H-4'), 3.64 (1H, dd, J=12.0, 3.6 Hz, H-5'a), 3.54 (1H, dd, J=12.0, 5.7 Hz, H-5'b); the (±)-1-(3,4,5-trimethoxyphenyl)-ethyl moiety δ 6.82 (2H, s, H-2", H-6"), 5.52 (1H, m, H-7"), 3.75 (6H, s, MeO-3", MeO-5"), 3.61 (3H, s, MeO-4"), 1.51 (3H, d, 6.6 Hz, H-8"); the propyl moiety δ 3.37 (2H, t, J=6.0 Hz, H-1'''), 1.52 (2H, m, H-2'''), 0.85 (3H, t, J=7.2 Hz, H-3'''); $^{13}C$ NMR (75 MHz, DMSO-$d_6$): the adenosine moiety δ 153.7 (C-6), 152.6 (C-2), 148.9 (C-4), 139.0 (C-8), 119.3 (C-5), 87.6 (C-1'), 83.2 (C-4'), 73.8 (C-3'), 70.4 (C-2'), 70.2 (C-5'); the (±)-1-(3,4,5-trimethoxyphenyl)-ethyl moiety δ 152.7 (C-3", C-5"), 141.0 (C-1"), 136.2 (C-4"), 103.8 (C-2", C-6"), 59.9.4 (MeO-4"), 55.8 (MeO-3", MeO-5"), 49.2 (C-7"), 22.8 (C-8"); the propyl moiety δ 72.4 (C-1'''), 22.5 (C-2'''), 10.6 (C-3''').

Example 56: Preparation of $N^6$-[(±)-1-(3,4,5-trimethoxyphenyl)-ethyl]-adenosine-5'-decanoic ether

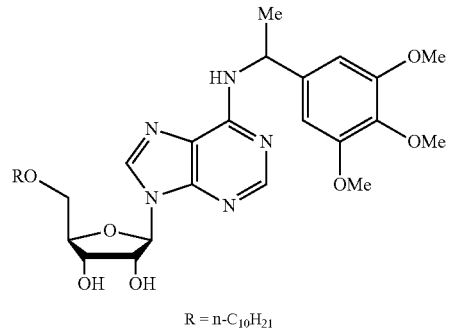

R = n-$C_{10}H_{21}$

First step, $N^6$-[(±)-1-(3,4,5-trimethoxyphenyl)-ethyl]-2',3'-O-isopropylidene-adenosine (240 mg) was dissolved in dry THF (10 ml). NaH (240 mg) was added slowly at room temperature and stirred for 2 h. The dry THF (5 ml) solution of 1-iodo-decane (167.0 mg) was added to the reaction solution and stirred at room temperature for 4 h. The reaction solution was ended by adding proper quantity of distilled water to destroy the excess NaH. After evaporation of the reaction mixture, the residue was dissolved in distilled water (20 ml), and extracted with EtOAc (3×25 ml). The EtOAc was dried by anhydrous sodium sulfate, and filtered. The filtrate was evaporated and the residue was separated by column chromatography over silica gel eluting with petroleum ether-EtOAc (3:2) to yield preparation of $N^6$-[(±)-1-(3,4,5-trimethoxyphenyl)-ethyl]-2',3'-O-isopropylidene-adenosine-5'-decanoic ether (150 mg).

Second step, $N^6$-[(±)-1-(3,4,5-trimethoxyphenyl)-ethyl]-2',3'-O-isopropylidene-adenosine-5'-decanoic ether (150 mg) was added to a formic acid solution (20 ml, 50% V/V), and the mixture was stirred at room temperature for 12 h, After evaporation of the reaction mixture, the residue was separated by column chromatography over silica gel and eluted with $CHCl_3$—$CH_3OH$ (50:1) to yield $N^6$-[(±)-1-(3, 4,5-trimethoxyphenyl)-ethyl]-adenosine-5'-decanoic ether (98 mg) as a white solid: positive ESIMS m/z 602 [M+H]+, 624 [M+Na]+ and 640 [M+K]+; 1H NMR (300 MHz, acetone-d6): the adenosine δ 8.27 (1H, s, H-8), 8.22 (1H, brs, H-2), 7.17 (1H, brd, J=4.8 Hz, NH), 6.09 (1H, d, J=4.8 Hz, H-1'), 4.68 (1H, m, H-2'), 4.45 (1H, m, H-3'), 4.18 (1H, m, H-4'), 3.74 (1H, dd, J=12.0, 3.6 Hz, H-5'a), 3.63 (1H, dd, J=12.0, 5.7 Hz, H-5'b); the 1-(3,4,5-trimethoxyphenyl)-ethyl moiety δ 6.86 (2H, s, H-2", H-6"), 5.58 (1H, m, H-7"), 3.78 (6H, s, MeO-3", MeO-5"), 3.67 (3H, s, MeO-4"), 1.62, 1.63 (3H, d, 6.9 Hz, H-8"); the decyl moiety δ 3.48 (2H, t, J=6.3 Hz, H-1'''), 1.55 (2H, m, H-2'''), 1.23 (14H, m), 0.85 (3H, t, J=6.6 Hz, H-10'''); 13C NMR (75 MHz, acetone-d6): the adenosine moiety δ 154.9 (C-6), 153.5 (C-2), 150.0 (C-4), 141.4 (C-8), 120.5 (C-5), 89.3 (C-1'), 84.8 (C-4'), 76.0 (C-3'), 71.9 (C-2'), 71.1 (C-5'); the 1-(3,4,5-trimethoxyphenyl)-ethyl moiety δ 154.9 (C-3", C-5"), 139.5 (C-1"), 138.0 (C-4"), 104.73, 104.67 (C-2", C-6"), 60.4 (MeO-4"), 56.3 (MeO-3", MeO-5"), 50.6 (C-7"), 23.1 (C-8"); the decyl moiety δ 72.1 (C-1'''), 32.6 (C-2'''), 30.6-29.0 (CH2×6), 26.9 (C-9'''), 23.3 (C-10''').

Example 57: Preparation of N6-[(R)-1-(phenyl)-ethyl]-adenosine

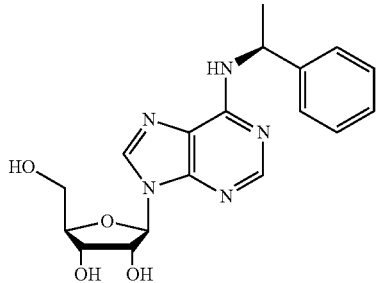

A mixture of (R)-1-(phenyl)-ethylamine (509 mg), 6-chloropurine riboside (300 mg) in EtOH (50 ml) was refluxed for 8 h. After evaporation of the reaction mixture, the residue was separated by column chromatography over Sephadex LH-20 gel and eluted with ethanol to yield N6-[(R)-1-(phenyl)-ethyl]adenosine (320 mg) as a white solid: positive ESIMS m/z 372 [M+H]+; 1H NMR (300 MHz, DMSO-d6): the adenosine moiety δ 8.38 (1H, s, H-2), 8.31 (1H, d, J=6.9 Hz, —NH), 8.17 (1H, s, H-8), 5.89 (1H, d, J=6.0 Hz, H-1'), 5.45 (2H, m, 2×—OH), 5.21 (1H, d, J=4.5 Hz, —OH), 4.62 (1H, m, H-2'), 4.61 (1H, m, H-3'), 3.97 (1H, m, H-4'), 3.68 (1H, m, H-5'a), 3.56 (1H, m, H-5'b); the (R)-1-(phenyl)-ethyl moiety δ 7.43 (2H, d, J=7.2 Hz, H-2", H-6"), 7.27 (2H, t, J=7.2 Hz, H-3", H-5"), 7.16 (1H, t, J=7.2 Hz, H-4"), 5.48 (1H, m, H-7"), 1.53 (3H, d, J=6.9 Hz, H-8"); 13C NMR (75 MHz, DMSO-d6): the adenosine moiety δ 153.9 (s, C-6), 152.3 (d, C-2), 148.5 (s, C-4), 139.9 (d, C-8), 119.8 (s, C-5), 88.1 (d, C-1'), 86.0 (d, C-4'), 73.5 (d, C-2'), 70.7 (d, C-3'), 61.7 (t, C-5'); the (R)-1-(phenyl)-ethyl moiety δ 145.2 (s, C-1"), 128.2 (d, C-2", C-6"), 126.5 (d, C-4"), 126.2 (d, C-3", C-5"), 48.8 (d, C-7"), 22.5 (q, C-8").

Example 58: Preparation of N6-[(S)-1-(phenyl)-ethyl]-adenosine

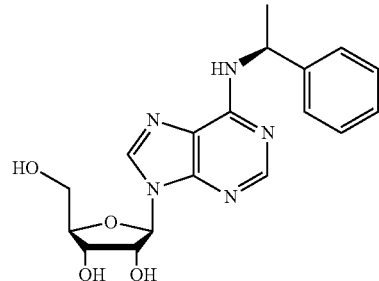

A mixture of (S)-1-(phenyl)-ethylamine (509 mg) and 6-chloropurine riboside (300 mg) in EtOH (50 ml) was refluxed for 8 h. After evaporation of the reaction mixture, the residue was separated by column chromatography over Sephadex LH-20 gel and eluted with ethanol to yield N6-[(S)-1-(phenyl)-ethyl]-adenosine (315 mg): positive ESIMS m/z 372 [M+H]+ and 394 [M+Na]+; 1H NMR (300 MHz, DMSO-d6): the adenosine moiety δ 8.38 (1H, s, H-2), 8.31 (1H, d, J=7.5 Hz, —NH), 8.16 (1H, s, H-8), 5.89 (1H, d, J=6.0 Hz, H-1'), 5.44 (1H, J=6.0 Hz, —OH), 5.37 (1H, m, —OH), 5.18 (1H, d, J=4.5 Hz, —OH), 4.59 (1H, m, H-2'), 4.15 (1H, m, H-3'), 3.96 (1H, m, H-4'), 3.67 (1H, m, H-5'a), 3.55 (1H, m, H-5'b); the (S)-1-(phenyl)-ethyl moiety δ 7.43 (2H, d, J=7.2 Hz, H-2", H-6"), 7.27 (2H, t, J=7.2 Hz, H-3", H-5"), 7.16 (1H, t, J=7.2 Hz, H-4"), 5.51 (1H, m, C-7"), 1.53 (3H, d, J=6.9 Hz, H-8"); 13C NMR (75 MHz, DMSO-d6): the adenosine moiety δ 153.9 (s, C-6), 152.3 (d, C-2), 148.6 (s, C-4), 139.9 (d, C-8), 119.7 (s, C-5), 87.9 (d, C-1'), 85.9 (d, C-4'), 73.6 (d, C-2'), 70.6 (d, C-3'), 61.6 (t, C-5'); the (S)-1-(phenyl)-ethyl moiety δ 145.2 (s, C-1"), 128.2 (d, C-2", C-6"), 126.5 (d, C-4"), 126.2 (d, C-3", C-5"), 48.8 (d, C-7"), 22.5 (q, C-8").

Example 59: Preparation of N6-[(R)-1-(4-methylphenyl)-ethyl]-adenosine

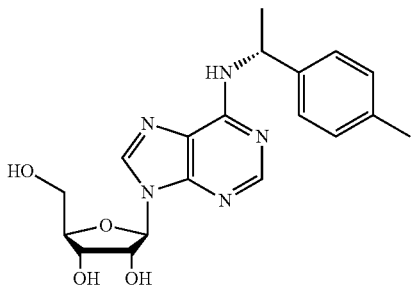

A mixture of (R)-1-(4-methylphenyl)-ethylamine (568 mg) and 6-chloropurine riboside (300 mg) in PrOH (50 ml) was heated to 80° C. for 7 h. After evaporation of the reaction mixture, the residue was separated by column chromatography over Sephadex LH-20 gel and eluted with ethanol to yield N6-[(R)-1-(4-methylphenyl)-ethyl]adenosine (325 mg) as a white solid: positive ESIMS m/z 386

[M+H]⁺ and 408 [M+Na]⁺; negative ESIMS m/z 384 [M−H]⁻; ¹H NMR (300 MHz, DMSO-d₆): the adenosine moiety δ 8.36 (1H, s, H-2), 8.27 (1H, brs, —NH), 8.14 (1H, s, H-8), 5.85 (1H, d, J=6.3 Hz, H-1'), 5.42 (1H, d, J=6.3 Hz, —OH), 5.38 (1H, m, —OH), 5.17 (1H, d, J=4.8 Hz, —OH), 4.58 (1H, m, H-2'), 4.12 (1H, m, H-3'), 3.94 (1H, m, H-4'), 3.63 (1H, m, H-5'a), 3.52 (1H, m, H-5'b); the (R)-1-(4-methylphenyl)-ethyl moiety δ 7.30 (2H, s, H-2", H-6"), 7.07 (2H, s, H-3", H-5"), 5.49 (1H, m, H-7"), 2.22 (3H, s, —CH₃), 1.50 (3H, s, H-8"); ¹³C NMR (75 MHz, DMSO-d₆): the adenosine moiety δ 153.9 (s, C-6), 152.3 (d, C-2), 148.6 (s, C-4), 139.9 (d, C-8), 119.8 (s, C-5), 88.1 (d, C-1'), 86.0 (d, C-4'), 73.5 (d, C-2'), 70.8 (d, C-3'), 61.8 (t, C-5'); the (R)-1-(4-methylphenyl)-ethyl moiety δ 142.2 (s, C-1"), 135.6 (s, C-4"), 128.8 (d, C-2", C-6"), 126.1 (d, C-3", C-5"), 48.6 (d, C-7"), 22.5 (q, C-8"), 20.7 (q, —CH₃).

Example 60: Preparation of N⁶-[(S)-1-(4-methyl-phenyl)-ethyl]adenosine

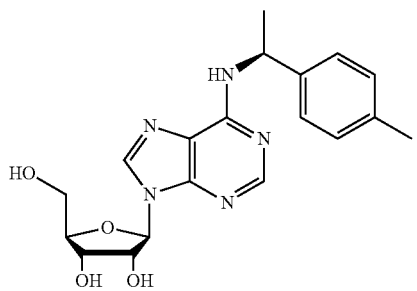

A mixture of (S)-1-(4-methylphenyl)-ethylamine (568 mg) and 6-chloropurine riboside (300 mg) in PrOH (50 ml) was heated to 80° C. for 7 h. After evaporation of the reaction mixture, the residue was separated by column chromatography over Sephadex LH-20 gel and eluted with ethanol to yield N⁶-[(S)-1-(4-methylphenyl)-ethyl]adenosine (320 mg) as a white solid: positive ESIMS m/z 386 [M+H]⁺ and 408 [M+Na]⁺; negative ESIMS m/z 384 [M−H]⁻; ¹H NMR (300 MHz, DMSO-d₆): the adenosine moiety δ 8.36 (1H, s, H-2), 8.26 (1H, brs, —NH), 8.14 (1H, s, H-8), 5.86 (1H, d, J=6.0 Hz, H-1'), 5.42 (1H, d, J=6.3 Hz, —OH), 5.36 (1H, m, —OH), 5.17 (1H, d, J=4.8 Hz, —OH), 4.57 (1H, m, H-2'), 4.12 (1H, m, H-3'), 3.94 (1H, m, H-4'), 3.64 (1H, m, H-5'a), 3.54 (1H, m, H-5'b); the (S)-1-(4-methylphenyl)-ethyl moiety δ 7.30 (2H, s, H-2", H-6"), 7.07 (2H, s, H-3", H-5"), 5.48 (1H, m, H-7"), 2.22 (3H, s, —CH₃), 1.50 (3H, s, H-8"); ¹³C NMR (75 MHz, DMSO-d₆): the adenosine moiety δ 153.9 (s, C-6), 152.3 (d, C-2), 148.6 (s, C-4), 139.8 (d, C-8), 119.7 (s, C-5), 87.9 (d, C-1'), 85.9 (d, C-4'), 73.6 (d, C-2'), 70.7 (d, C-3'), 61.7 (t, C-5'); part for (S)-1-(4-methylphenyl)-ethyl moiety δ 142.2 (s, C-1"), 135.6 (s, C-4"), 128.7 (d, C-2", C-6"), 126.1 (d, C-3", C-5"), 48.6 (d, C-7"), 22.5 (q, C-8"), 20.7 (q, —CH₃).

Example 61: Preparation of N⁶-[(S)-1-(4-methoxyphenyl)-ethyl]adenosine

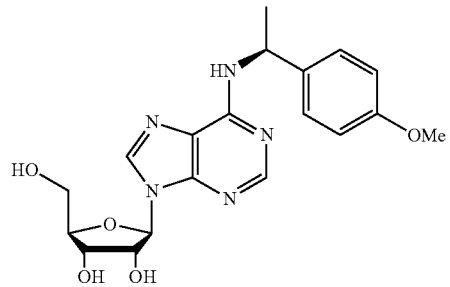

A mixture of (S)-1-(4-methoxyphenyl)-ethylamine (475 mg) and 6-chloropurine riboside (300 mg) in PrOH (70 ml) was heated to 70° C. and reacted for 8 h. After evaporation of the reaction mixture, the residue was separated by column chromatography over Sephadex LH-20 gel and eluted with ethanol to yield N⁶-[(S)-1-(4-methoxyphenyl)-ethyl]adenosine (345 mg) as a white solid: positive ESIMS m/z 402 [M+H]⁺ and 424 [M+Na]⁺; ¹H NMR (300 MHz, DMSO-d₆): the adenosine moiety δ 8.38 (1H, s, H-2), 8.23 (1H, brs, —NH), 8.18 (1H, s, H-8), 5.90 (1H, d, J=6.3 Hz, H-1'), 5.46 (1H, d, J=6.3 Hz, —OH), 5.42 (1H, m, —OH), 5.20 (1H, d, J=4.5 Hz, —OH), 4.61 (1H, m, H-2'), 4.16 (1H, m, H-3'), 3.98 (1H, m, H-4'), 3.66 (1H, m, H-5'a), 3.54 (1H, m, H-5'b); the (S)-1-(4-methoxyphenyl)-ethyl moiety δ 7.35 (1H, d, J=8.4 Hz, H-2", H-6"), 6.84 (1H, d, J=8.4 Hz, H-3", H-5"), 5.48 (1H, m, H-7"), 3.71 (3H, s, —OCH₃), 1.51 (3H, d, 7.2 Hz, H-8"); ¹³C NMR (75 MHz, DMSO-d₆): the adenosine moiety δ153.9 (s, C-6), 152.3 (d, C-2), 148.6 (s, C-4), 139.8 (d, C-8), 119.7 (s, C-5), 88.0 (d, C-1'), 85.9 (d, C-4'), 73.6 (d, C-2'), 70.7 (d, C-3'), 61.7 (t, C-5'); the (S)-1-(4-methoxyphenyl)-ethyl moiety δ 158.0 (s, C-4"), 137.1 (s, C-1"), 127.3 (d, C-2", C-6"), 113.6 (d, C-3", C-5"), 55.0 (q, —OCH₃), 48.2 (d, C-7"), 22.5 (q, C-8").

Example 62: Preparation of N⁶-[(R)-1-(4-methoxyphenyl)-ethyl]-adenosine

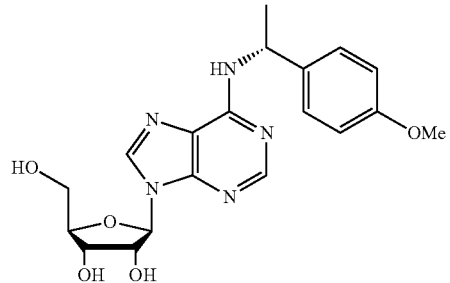

A mixture of (R)-1-(4-methoxyphenyl)-ethylamine (475 mg) and 6-chloropurine riboside (300 mg) in PrOH (70 ml) was heated to 70° C. and reacted for 8 h. After evaporation of the reaction mixture, the residue was separated by column chromatography over Sephadex LH-20 gel and eluted with ethanol to yield N⁶-[(R)-1-(4-methoxyphenyl)-ethyl]-adenosine (350 mg) as a white solid: positive ESIMS m/z 402 [M+H]⁺ and 424 [M+Na]⁺; ¹H NMR (300 MHz, DMSO-d₆): the adenosine moiety δ 8.36 (1H, s, H-2), 8.24 (1H, brs, —NH), 8.15 (1H, s, H-8), 5.86 (1H, d, J=6.3 Hz, H-1'), 5.42 (1H, d, J=6.3 Hz, —OH), 5.37 (1H, m, —OH), 5.17 (1H, d, J=4.5 Hz, —OH), 4.49 (1H, m, H-2'), 4.12 (1H, m, H-3'), 3.94 (1H, m, H-4'), 3.66 (1H, m, H-5'a), 3.55 (1H, m, H-5'b); the (R)-1-(4-methoxyphenyl)-ethyl moiety δ 7.35 (1H, d, J=8.4 Hz, H-2", H-6"), 6.83 (1H, d, J=8.4 Hz, H-3", H-5"), 5.46 (1H, m, H-7"), 3.78 (3H, s, —OCH₃), 1.50 (3H, d, J=7.2 Hz, H-8"); ¹³C NMR (75 MHz, DMSO-d₆): the adenosine moiety δ 153.9 (s, C-6), 152.4 (d, C-2), 148.6 (s, C-4), 139.9 (d, C-8), 119.8 (s, C-5), 88.2 (d, C-1'), 86.1 (d, C-4'), 73.6 (d, C-2'), 70.8 (d, C-3'), 61.8 (t, C-5'); the (R)-1-(4-methoxyphenyl)-ethyl moiety δ 158.1 (s, C-4"), 137.1 (s, C-1"), 127.4 (d, C-2", C-6"), 113.6 (d, C-3", C-5"), 55.1 (q, —OCH₃), 48.3 (d, C-7"), 22.5 (q, C-8").

Example 63: Preparation of N⁶-[(D)-2-(hydroxy)-1-(phenyl)-ethyl]-adenosine

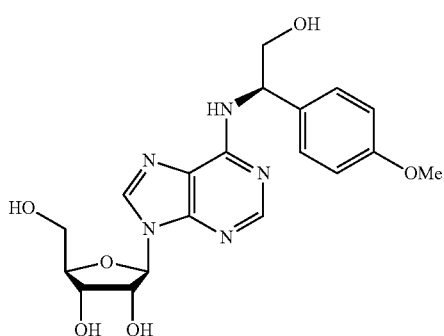

A mixture of (D)-phenylglycinol (425 mg) and 6-chloropurine riboside (300 mg) in PrOH (50 ml) was heated to 80° C. for 10 h. After evaporation of the reaction mixture, the residue was separated by column chromatography over silica gel and eluted with CHCl₃—CH₃OH (20:1~15:1) to yield N⁶-[(R)-1-(4-methoxyphenyl)-ethyl]adenosine (330 mg) as a white solid: positive ESIMS m/z 388 [M+H]⁺ and 410 [M+Na]⁺; negative ESIMS m/z 386 [M–H]⁻; ¹H NMR (300 MHz, DMSO-d₆): the adenosine moiety δ 8.39 (1H, s, H-2), 8.14 (1H, s, H-8), 8.11 (1H, d, J=8.4 Hz, —NH), 5.86 (1H, d, J=6.0 Hz, H-1'), 5.43 (1H, d, J=6.0 Hz, —OH), 5.35 (1H, m, —OH), 5.17 (1H, d, J=4.5 Hz, —OH), 4.95 (1H, m —OH), 4.57 (1H, m, H-2'), 4.13 (1H, m, H-3'), 3.94 (1H, m, H-4'), 3.66 (1H, m, H-5'a), 3.55 (1H, m, H-5'b); the (D)-2-(hydroxy)-1-(phenyl)-ethyl moiety δ 7.41 (2H, d, J=7.5 Hz, H-2", H-6"), 7.27 (2H, t, J=7.5 Hz, H-3", H-5"), 7.18 (1H, t, J=7.5 Hz, H-4"), 5.35 (1H, m, H-7"), 3.68 (2H, m, H-8"); ¹³C NMR (75 MHz, DMSO-d₆): the adenosine moiety δ 154.5 (s, C-6), 152.4 (d, C-2), 148.6 (s, C-4), 140.0 (d, C-8), 119.9 (s, C-5), 88.0 (d, C-1'), 86.0 (d, C-4'), 73.7 (d, C-2'), 70.7 (d, C-3'), 61.7 (t, C-5'); the (D)-2-(hydroxy)-1-(phenyl)-ethyl moiety δ 141.6 (s, C-1"), 128.2 (d, C-3", C-5"), 127.1 (d, C-2", C-6"), 126.9 (d, C-4"), 64.8 (t, C-8"), 56.2 (d, C-7").

Example 64: Preparation of N⁶-[(L)-2-(hydroxy)-1-(phenyl)-ethyl]-adenosine

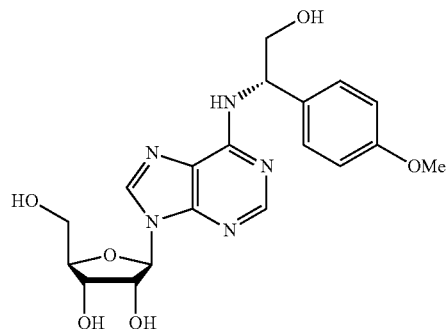

A mixture of (L)-phenylglycinol (425 mg) and 6-chloropurine riboside (300 mg) in PrOH (50 ml) was heated to 80° C. for 10 h. After evaporation of the reaction mixture, the residue was separated by column chromatography over silica gel and eluted with CHCl₃—CH₃OH (20:1~15:1) to yield N⁶-[(L)-2-(hydroxy)-1-(phenyl)-ethyl]-adenosine (325 mg) as a white solid: positive ESIMS m/z 388 [M+H]⁺ and 410[M+Na]⁺; negative ESIMS m/z 386 [M–H]⁻; ¹H NMR (300 MHz, DMSO-d₆): the adenosine moiety δ 8.38 (1H, s, H-2), 8.14 (1H, s, H-8), 8.10 (1H, d, J=8.7 Hz, —NH), 5.86 (1H, d, J=6.0 Hz, H-1'), 5.42 (1H, d, J=6.3 Hz, —OH), 5.38 (1H, m, —OH), 5.17 (1H, d, J=4.8 Hz, —OH), 4.95 (1H, t, J=5.7 Hz, —OH), 4.59 (1H, m, H-2'), 4.12 (1H, m, H-3'), 3.94 (1H, m, H-4'), 3.66 (3H, m, H-5'a), 3.55 (1H, m, H-5'b); the (L)-2-(hydroxy)-1-(phenyl)-ethyl moiety δ 7.41 (2H, d, J=7.5 Hz, H-2", H-6"), 7.28 (2H, t, J=7.5 Hz, H-3", H-5"), 7.18 (1H, t, J=7.5 Hz, H-4"), 5.40 (1H, m, H-7"), 3.69 (2H, m H-8"); ¹³C NMR (75 MHz, DMSO-d₆): the adenosine moiety δ 154.4 (s, C-6), 152.3 (d, C-2), 148.5 (s, C-4), 140.0 (d, C-8), 120.0 (s, C-5), 88.1 (d, C-1'), 86.0 (d, C-4'), 73.5 (d, C-2'), 70.7 (d, C-3'), 61.7 (t, C-5'); the (L)-2-(hydroxy)-1-(phenyl)-ethyl moiety δ 141.6 (s, C-1"), 128.1 (d, C-2", C-6"), 127.1 (d, C-3", C-5"), 126.8 (d, C-4"), 64.7 (t, C-8"), 56.1 (d, C-7").

Example 65: Preparation of N⁶-[(R)-1-(3-methoxyphenyl)-ethyl]-adenosine

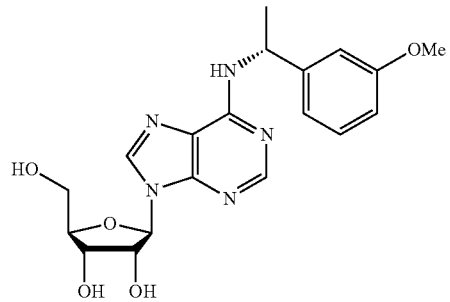

A mixture of (R)-1-(3-methoxyphenyl)-ethylamine (635 mg) and 6-chloropurine riboside (300 mg) in PrOH (50 ml) was heated to 80° C. for 6 h. After evaporation of the reaction mixture, the residue was separated by column chromatography over Sephadex LH-20 gel and eluted with ethanol to yield N⁶-[(R)-1-(3-methoxyphenyl)-ethyl]-adenosine (335 mg) as a white solid: positive ESIMS m/z 402 [M+H]⁺; negative ESIMS m/z 400 [M−H]⁻; ¹H NMR (300 MHz, DMSO-$d_6$): the adenosine moiety δ 8.39 (1H, s, H-2), 8.30 (1H, brd, J=4.8 Hz, —NH), 8.18 (1H, s, H-8), 5.90 (1H, d, J=6.3 Hz, H-1'), 5.46 (2H, m, 2×—OH), 5.21 (1H, m, —OH), 4.63 (1H, m, H-2'), 4.17 (1H, m, H-3'), 3.98 (1H, m, H-4'), 3.68 (1H, m, H-5'a), 3.58 (1H, m, H-5'b); the (R)-1-(3-methoxyphenyl)-ethyl moiety δ 7.19 (1H, t, J=7.5 Hz, H-5"), 7.03 (1H, brs, H-2"), 7.00 (1H, brd, J=7.5 Hz, H-6"), 6.74 (1H, dd, J=7.5, 1.5 Hz, H-4"), 5.49 (1H, m, H-7"), 3.70 (3H, s, —OCH₃), 1.52 (1H, d, J=6.6 Hz, H-8"); ¹³CNMR (75 MHz, DMSO-$d_6$): the adenosine moiety δ 153.9 (s, C-6), 152.3 (d, C-2), 148.6 (s, C-4), 139.9 (d, C-8), 119.8 (s, C-5), 88.1 (d, C-1'), 86.0 (d, C-4'), 73.5 (d, C-2'), 70.8 (d, C-3'), 61.8 (t, C-5'); the (R)-1-(3-methoxyphenyl)-ethyl moiety δ 159.3 (s, C-3"), 146.9 (s, C-1"), 129.3 (d, C-5"), 118.5 (d, C-6"), 112.2 (d, C-2"), 111.7 (d, C-4"), 55.0 (q, —OCH₃), 48.9 (d, C-7"), 22.6 (q, C-8").

Example 66: Preparation of N⁶-[(S)-1-(3-methoxyphenyl)-ethyl]-adenosine

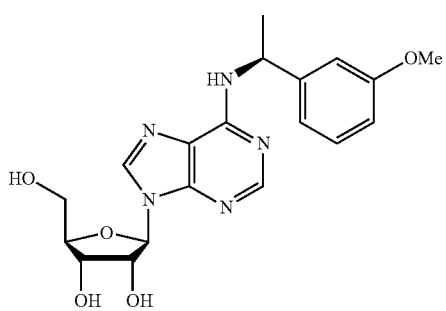

A mixture of (S)-1-(3-methoxyphenyl)-ethylamine (635 mg) and 6-chloropurine riboside (300 mg) in PrOH (50 ml) was heated to 80° C. for 6 h. After evaporation of the reaction mixture, the residue was separated by column chromatography over Sephadex LH-20 gel and eluted with ethanol to yield N⁶-[(S)-1-(3-methoxyphenyl)-ethyl]-adenosine (340 mg) as a white solid: positive ESIMS m/z 402 [M+H]⁺; negative ESIMS m/z 400 [M−H]⁻; ¹H NMR (300 MHz, DMSO-$d_6$): the adenosine moiety δ 8.40 (1H, s, H-2), 8.28 (1H, brs, —NH), 8.18 (1H, s, H-8), 5.91 (1H, d, J=6.0 Hz, H-1'), 5.47 (1H, m, —OH), 5.42 (1H, m, —OH), 5.21 (1H, d, J=3.9 Hz, —OH), 4.62 (1H, m, H-2'), 4.17 (1H, m, H-3'), 3.98 (1H, m, H-4'), 3.66 (1H, m, H-5'a), 3.56 (1H, m, H-5'b); the (S)-1-(3-methoxyphenyl)-ethyl moiety δ 7.19 (1H, t, J=7.5 Hz, H-5"), 7.02 (1H, brs, H-2"), 7.00 (1H, brd, J=7.5 Hz, H-6"), 6.74 (1H, d, J=7.5 Hz, H-4"), 5.49 (1H, m, H-7"), 3.70 (4H, m, H-5a', —OCH₃), 1.52 (3H, d, J=6.9 Hz, H-8"); ¹³C NMR (75 MHz, DMSO-$d_6$): the adenosine moiety δ 153.9 (s, C-6), 152.4 (d, C-2), 148.6 (s, C-4), 139.9 (d, C-8), 119.7 (s, C-5), 88.0 (d, C-1'), 86.0 (d, C-4'), 73.7 (d, C-2'), 70.7 (d, C-3'), 61.7 (t, C-5'); the (S)-1-(3-methoxyphenyl)-ethyl moiety δ 159.3 (s, C-3"), 146.9 (s, C-1"), 129.3 (d, C-5"), 118.5 (d, C-6"), 112.2 (d, C-2"), 111.7 (d, C-4"), 55.0 (q, —OCH₃), 48.9 (d, C-7"), 22.6 (q, C-8").

Example 67: Preparation of N⁶-[(S)-1-(4-nitrophenyl)-ethyl]-adenosine

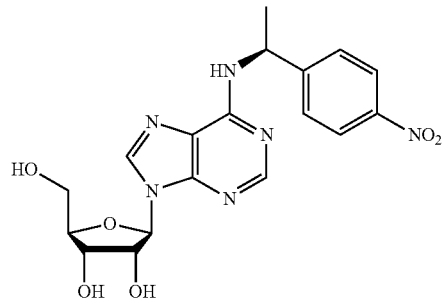

A mixture of (S)-1-(4-nitrophenyl)-ethylamine (638 mg) and 6-chloropurine riboside (300 mg) in PrOH (50 ml) was heated to 80° C. for 10 h. After evaporation of the reaction mixture, the residue was separated by column chromatography over Sephadex LH-20 gel and eluted with ethanol to yield N⁶-[(S)-1-(4-nitrophenyl)-ethyl]-adenosine (350 mg) as a white solid: positive ESIMS m/z 417 [M+H]⁺ and 439 [M+Na]⁺; negative ESIMS m/z 415 [M−H]⁻ and 451 [M+Cl]⁻; ¹H NMR (300 MHz, DMSO-$d_6$): the adenosine moiety δ 8.53 (1H, brs, —NH), 8.40 (1H, s, H-2), 8.14 (1H, m, H-8), 5.87 (1H, d, J=6.0 Hz, H-1'), 5.41 (1H, d, J=6.3 Hz, —OH), 5.29 (1H, m, —OH), 5.16 (1H, d, J=4.8 Hz, —OH), 4.56 (1H, m, H-2'), 4.13 (1H, m, H-3'), 3.94 (1H, m, H-4'), 3.66 (1H, m, H-5'a), 3.54 (1H, m, H-5'b); the (S)-1-(4-nitrophenyl)-ethyl moiety δ 8.16 (2H, d, J=8.4 Hz, H-3", H-5"), 7.68 (2H, d, J=8.4 Hz, H-2", H-6"), 5.56 (1H, m, H-7"), 1.56 (3H, d, J=7.2 Hz, H-8"); ¹³C NMR (75 MHz, DMSO-$d_6$): the adenosine moiety δ 153.7 (s, C-6), 152.3 (d, C-2), 148.7 (s, C-4), 140.1 (s, C-8), 119.8 (s, C-5), 87.9 (d, C-1'), 85.9 (d, C-4'), 73.6 (d, C-2'), 70.6 (d, C-3'), 61.6 (t, C-5'); the (S)-1-(4-nitrophenyl)-ethyl moiety δ 153.4 (s, C-4"), 146.3 (s, C-1"), 127.4 (d, C-2", C-6"), 123.6 (d, C-3", C-5"), 48.8 (d, C-7"), 22.1 (t, C-8").

Example 68: Preparation of N⁶-[(R)-1-(4-chlorophenyl)-ethyl]-adenosine

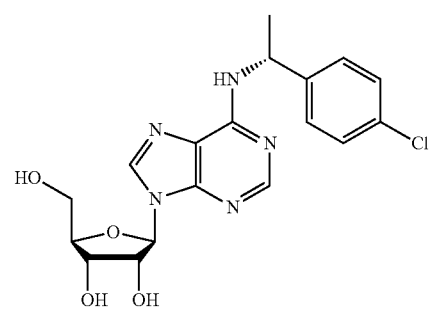

A mixture of (R)-1-(4-chlorophenyl)-ethylamine (490 mg) and 6-chloropurine riboside (300 mg) in EtOH (50 ml) was refluxed for 12 h. After evaporation of the reaction mixture, the residue was separated by column chromatography over Sephadex LH-20 gel and eluted with ethanol to yield N⁶-[(R)-1-(4-chlorophenyl)-ethyl]-adenosine (345 mg) as a white solid: negative ESIMS m/z 406 [M+H]⁺ and 428 [M+Na]⁺; ¹H NMR (300 MHz, DMSO-$d_6$): the adenosine moiety δ 8.38 (2H, m, H-2, —NH), 8.16 (1H, s, H-8), 5.88 (1H, d, J=6.0 Hz, H-1'), 5.43 (1H, d, J=6.0 Hz, —OH), 5.38 (1H, m, —OH), 5.19 (1H, d, J=4.2 Hz, —OH), 4.60 (1H, m, H-2'), 4.14 (1H, m, H-3'), 3.96 (1H, m, H-4'), 3.66 (1H, m, H-5'a), 3.54 (1H, m, H-5'b); the (R)-1-(4-chlorophenyl)-ethyl moiety δ 7.44 (1H, d, J=8.4 Hz, H-2", H-6"), 7.33 (1H, d, J=8.4 Hz, H-3", H-5"), 5.45 (1H, m, H-7"), 1.51 (3H, d, J=7.2 Hz, H-8"); ¹³C NMR (75 MHz, DMSO-$d_6$): the adenosine moiety 153.8 (s, C-6), 152.3 (d, C-2), 148.6 (s, C-4), 140.0 (d, C-8), 119.8 (s, C-5), 88.0 (d, C-1'), 85.9 (d, C-4'), 73.5 (d, C-2'), 70.7 (d, C-3'), 61.7 (t, C-5'); the RR)-1-(4-chlorophenyl)-ethyl moiety δ 144.2 (s, C-1"), 131.1 (s, C-4"), 128.2 (d, C-2", C-6"), 128.1 (d, C-3", C-5"), 48.4 (d, C-7"), 22.3 (q, C-8").

Example 69: Preparation of N⁶-[(S)-1-(4-chlorophenyl)-ethyl]-adenosine

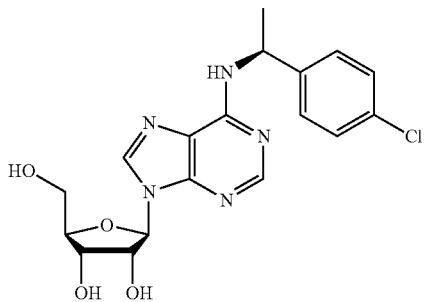

A mixture of (S)-1-(4-chlorophenyl)-ethylamine (490 mg) and 6-chloropurine riboside (300 mg) in EtOH (50 ml) was refluxed for 12 h. After evaporation of the reaction mixture, the residue was separated by column chromatography over Sephadex LH-20 gel and eluted with ethanol to yield N⁶-[(S)-1-(4-chlorophenyl)-ethyl]adenosine (340 mg) as a white solid: positive ESIMS m/z 406 [M+H]⁺ and 428 [M+Na]⁺; ¹H NMR (300 MHz, DMSO-$d_6$): the adenosine moiety δ 8.41 (1H, s, H-2), 8.38 (1H, brs, —NH), 8.18 (1H, s, H-8), 5.92 (1H, d, J=5.4 Hz, H-1'), 5.47 (1H, d, J=5.7 Hz, —OH), 5.40 (1H, m, —OH), 5.22 (1H, d, J=3.6 Hz, —OH), 4.62 (1H, m, H-2'), 4.18 (1H, m, H-3'), 3.99 (1H, m, H-4'), 3.68 (1H, m, H-5'a), 3.56 (1H, m, H-5'b); the (S)-1-(4-chlorophenyl)-ethyl moiety δ 7.45 (1H, d, J=7.8 Hz, H-2", H-6"), 7.33 (1H, d, J=7.8 Hz, H-3", H-5"), 5.47 (1H, m, H-7"), 1.53 (3H, d, J=6.3 Hz, H-8"); ¹³C NMR (75 MHz, DMSO-$d_6$): the adenosine moiety δ 153.8 (s, C-6), 152.3 (d, C-2), 148.7 (s, C-4), 139.9 (d, C-8), 119.7 (s, C-5), 88.0 (d, C-1'), 85.9 (d, C-4'), 73.7 (d, C-2'), 70.7 (d, C-3'), 61.7 (t, C-5'); the (S)-1-(4-chlorophenyl)-ethyl moiety δ 144.3 (s, C-1"), 131.1 (s, C-4"), 128.2 (d, C-2", C-6"), 128.1 (d, C-3", C-5"), 48.4 (d, C-7"), 22.3 (q, C-8").

Example 70: Preparation of N⁶-[(R)-1-(4-fluorophenyl)-ethyl]-adenosine

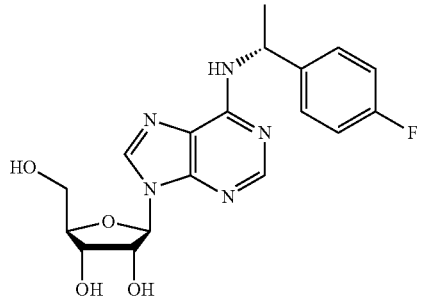

A mixture of (R)-1-(4-fluorophenyl)-ethylamine (438 mg) and 6-chloropurine riboside (300 mg) in EtOH (50 ml) was refluxed for 12 h. After evaporation of the reaction mixture, the residue was separated by column chromatography over Sephadex LH-20 gel and eluted with ethanol to yield N⁶-[(R)-1-(4-fluorophenyl)-ethyl]-adenosine (325 mg) as a white solid: positive ESIMS m/z 390 [M+H]⁺ and 412 [M+Na]⁺; ¹H NMR (300 MHz, DMSO-$d_6$): the adenosine moiety δ 8.38 (1H, s, H-2), 8.35 (1H, brs, —NH), 8.17 (1H, s, H-8), 5.89 (1H, d, J=6.0 Hz, H-1'), 5.42 (2H, m, 2×—OH), 5.18 (1H, m, —OH), 4.61 (1H, m, H-2'), 4.15 (1H, m, H-3'), 3.97 (1H, m, H-4'), 3.68 (1H, m, H-5'a), 3.55 (1H, m, H-5'b); the (R)-1-(4-fluorophenyl)-ethyl moiety δ 7.48 (2H, m, H-2", H-6"), 7.10 (2H, m, H-3", H-5"), 5.55 (1H, brs, H-7"), 1.52 (1H, d, J=6.6 Hz, H-8"); ¹³C NMR (75 MHz, DMSO-$d_6$): the adenosine moiety δ 153.8 (s, C-6), 152.3 (d, C-2), 148.5 (s, C-4), 141.4 (d, C-8), 119.8 (s, C-5), 88.0 (d, C-1'), 85.9 (d, C-4'), 73.5 (d, C-2'), 70.7 (d, C-3'), 61.7 (t, C-5'); the (R)-1-(4-fluorophenyl)-ethyl moiety δ 161.0 (d, J=240.5 Hz, C-4"), 139.9 (s, C-1"), 128.1 (d, J=8.3 Hz, C-2", C-6"), 114.9 (d, J=20.5 Hz, C-3", C-5"), 48.2 (d, C-7"), 22.5 (q, C-8").

Example 71: Preparation of N⁶-[(S)-1-(4-fluorophenyl)-ethyl]-adenosine

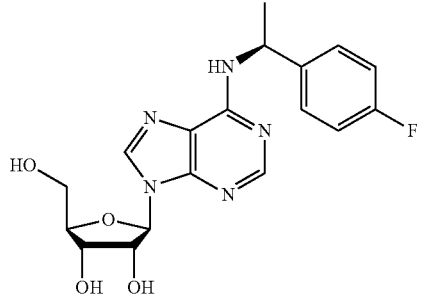

A mixture of (S)-1-(4-fluorophenyl)-ethylamine (438 mg) and 6-chloropurine riboside (300 mg) in EtOH (50 ml) was refluxed for 12 h. After evaporation of the reaction mixture, the residue was separated by column chromatography over Sephadex LH-20 gel and eluted with ethanol to yield N⁶-[(S)-1-(4-fluorophenyl)-ethyl]-adenosine (330 mg) as a white solid: positive ESIMS m/z 390 [M+H]⁺; ¹H NMR (300 MHz, DMSO-$d_6$): the adenosine moiety δ 8.38 (1H, s, H-2), 8.35 (1H, brs, —NH), 8.16 (1H, s, H-8), 5.88 (1H, d, J=5.7 Hz, H-1'), 5.43 (1H, d, J=4.8 Hz, —OH), 5.35 (1H, m, —OH), 5.18 (1H, m, —OH), 4.58 (1H, m, H-2'), 4.15 (1H, m, H-3'), 3.96 (1H, m, H-4'), 3.66 (1H, m, H-5'a), 3.55 (1H, m, H-5'b); the (S)-1-(4-fluorophenyl)-ethyl moiety δ 7.48 (2H, m, H-2", H-6"), 7.10 (2H, t, J=8.4 Hz, H-3", H-5"), 5.47 (1H, m, H-7"), 1.52 (1H, d, J=6.6 Hz, H-8"); $^{13}$C NMR (75 MHz, DMSO-$d_6$): the adenosine moiety δ 153.8 (s, C-6), 152.3 (d, C-2), 148.6 (s, C-4), 141.4 (s, C-8), 119.7 (s, C-5), 87.9 (d, C-1'), 85.9 (d, C-4'), 73.6 (d, C-2'), 70.6 (d, C-3'), 61.6 (t, C-5'); the (S)-1-(4-fluorophenyl)-ethyl moiety δ 160.9 (s, J=240.4 Hz, C-4"), 139.8 (d, C-1"), 128.1 (d, J=8.0 Hz, C-2", C-6"), 114.8 (d, J=21.6 Hz, C-3", C-5"), 48.2 (d, C-7"), 22.5 (q, C-8").

Example 72: Preparation of N$^6$-[(±)-1-(phenyl)-propyl]-adenosine

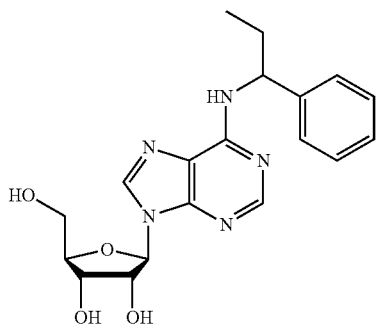

First step, hydroxyamine hydrochloride (5.15 g) and NaOAc (12.23 g) were added to a solution of 1-propiophenone (5 g) in EtOH (80 ml). The reaction mixture was stirred at 60° C. for 6 h. EtOH was removed under reduced pressure. H$_2$O (40 ml) was added to the residue, and the resulting solution was extracted with EtOAc (3×40 ml). The EtOAc of the combined organic layer was removed by rotary evaporation under reduced pressure to yield 1-propiophenone oxime (4.75 g) as a pale yellowish solid.

Second step, a solution of 1-propiophenone oxime (4.75 g) and concentrated HCl (16.8 ml) in EtOH (50 ml) was subjected to hydrogenation at atmospheric pressure in the presence of 10% Pd/C (674 mg). The reaction solution was filtered and the filtrate was concentrated to yield 1-(phenyl)-propylamine hydrochloride (5.40 g) as a white solid.

Third step, a mixture of 1-(phenyl)-propylamine (359 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with CHCl$_3$—CH$_3$OH (20:1) to yield N$^6$-[(±)-1-(phenyl)-propyl]-adenosine (215 mg) as a white solid: positive ESIMS m/z 386 [M+H]$^+$; negative ESIMS m/z 420 [M+Cl]$^-$; $^1$H NMR (300 MHz, DMSO-$d_6$): the adenosine moiety δ 8.36 (1H, s, H-2), 8.31 (1H, brs, —NH), 8.14 (1H, s, H-8), 5.86 (1H, d, J=6.0 Hz, H-1'), 5.40 (1H, m, —OH), 5.36 (1H, m, —OH), 5.15 (1H, d, J=4.5 Hz, —OH), 4.58 (1H, m, H-2'), 4.12 (1H, m, H-3'), 3.94 (1H, m, H-4'), 3.66 (1H, m, H-5'a), 3.56 (1H, m, H-5'b); the (±)-1-(phenyl)-propyl moiety δ 7.44 (2H, d, J=7.2 Hz, H-2", H-6"), 7.27 (2H, t, J=7.4 Hz, H-3", H-5"), 7.18 (1H, t, J=7.4 Hz, H-4"), 5.25 (1H, m, H-7"), 1.95 (1H, m, H-8"a), 1.83 (1H, m, H-8"b), 0.89 (3H, t, J=6.6 Hz, H-9"); $^{13}$C NMR (75 MHz, DMSO-$d_6$): the adenosine moiety δ 154.3 (s, C-6), 152.2 (d, C-2), 148.4 (s, C-4), 139.7 (d, C-8), 119.7 (s, C-5), 87.9 (d, C-1'), 85.9 (d, C-4'), 73.4 (d, C-2'), 70.6 (d, C-3'), 61.6 (t, C-5'); the (±)-1-(phenyl)-propyl moiety δ 144.2 (s, C-1"), 128.1 (d, C-2", C-6"), 126.7 (d, C-3", C-5"), 126.6 (d, C-4"), 55.2 (d, C-7"), 29.0 (t, C-8"), 11.5 (q, C-9").

Example 73: Preparation of N$^6$-[(±)-1-(4-hydroxyphenyl)-propyl]-adenosine

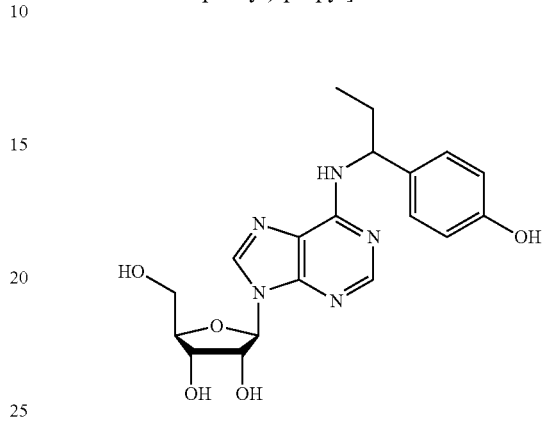

First step, hydroxyamine hydrochloride (4.60 g) and NaOAc (10.9 g) were added to a solution of 1-(4-hydroxy)-propiophenone (5 g) in EtOH (80 ml). The reaction mixture was stirred at 60° C. for 6 h. EtOH was removed under reduced pressure. H$_2$O (40 ml) was added to the residue, and the resulting solution was extracted with EtOAc (3×40 ml). The EtOAc of the combined organic layer was removed by rotary evaporation under reduced pressure to yield 1-(4-hydroxy)-propiophenone oxime (2.72 g) as a pale yellowish solid.

Second step, a solution of 1-(4-hydroxy)-propiophenone oxime (2.72 g) and concentrated HCl (7.25 ml) in EtOH (50 ml) was subjected to hydrogenation at atmospheric pressure in the presence of 10% Pd/C (350 mg). The reaction solution was filtered and the filtrate was concentrated to yield 1-(4-hydroxyphenyl)-propylamine hydrochloride (3.1 g) as a white solid.

Third step, a mixture of 1-(4-hydroxyphenyl)-propylamine (392 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with CHCl$_3$—CH$_3$OH (20:1) to yield N$^6$-[(±)-1-(4-hydroxyphenyl)-propyl]-adenosine (225 mg) as a white solid: positive ESIMS m/z 402 [M+H]$^+$ and 424 [M+Na]$^+$; negative ESIMS m/z 400 [M−H]$^-$ 和 436 [M+Cl]$^-$; $^1$H NMR (300 MHz, DMSO-$d_6$): the adenosine moiety δ 8.34 (1H, s, H-2), 8.14 (2H, s, H-8, —NH), 5.85 (1H, d, J=5.7 Hz, H-1'), 5.40 (1H, m, —OH), 5.15 (2H, m, 2×—OH), 4.58 (1H, m, H-2'), 4.12 (1H, m, H-3'), 3.93 (1H, m, H-4'), 3.67 (1H, m, H-5'a), 3.56 (1H, m, H-5'b); the (±)-1-(4-hydroxyphenyl)-propyl moiety δ 9.19 (1H, s, —OH), 7.23 (1H, d, J=8.1 Hz, H-2", H-6"), 6.65 (1H, d, J=8.1 Hz, H-3", H-5"), 5.40 (1H, m, H-7"), 1.90 (1H, m, H-8"a), 1.78 (1H, m, H-8"b), 0.85 (3H, t, J=6.6 Hz, H-9"); $^{13}$C NMR (75 MHz, DMSO-$d_6$): the adenosine moiety δ 154.3 (s, C-6), 152.4 (d, C-2), 148.5 (s, C-4), 139.8 (d, C-8), 119.8 (s, C-5), 88.2 (d, C-1'), 86.0 (d, C-4'), 73.6 (d, C-2'), 70.8 (d, C-3'), 61.8 (t, C-5'); the (±)-1-(4-hydroxyphenyl)-propyl moiety δ 156.1 (s, C-4"), 134.4 (s, C-1"), 127.9 (d, C-2", C-6"), 115.0 (d, C-3", C-5"), 54.7 (d, C-7"), 29.1 (t, C-8"), 11.5 (q, C-9").

Example 74: Preparation of $N^6$-[(±)-1-(4-methoxyphenyl)-propyl]-adenosine

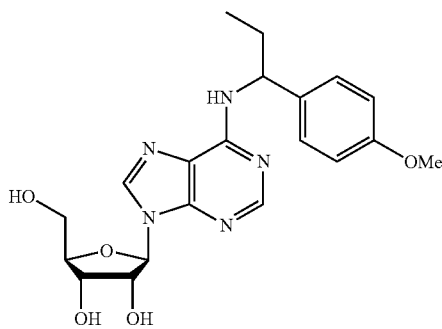

First step, hydroxyamine hydrochloride (3.55 g) and NaOAc (8.44 g) were added to a solution of 1-(4-methoxy)-propiophenone (5 g) in EtOH (80 ml). The reaction mixture was stirred at 60° C. for 6 h. EtOH was removed under reduced pressure. $H_2O$ (40 ml) was added to the residue, and the solution was extracted with EtOAc (3×40 ml). The EtOAc of the combined organic layer was removed by rotary evaporation under reduced pressure to yield 1-(4-methoxy)-propiophenone oxime (4.60 g) as a pale yellowish solid.

Second step, a solution of 1-(4-methoxy)-propiophenone oxime (4.60 g) and concentrated HCl (13.6 ml) in EtOH (50 ml) was subjected to hydrogenation at atmospheric pressure in the presence of 10% Pd/C (350 mg). The reaction solution was filtered and the filtrate was concentrated to yield 1-(4-methoxyphenyl)-propylamine hydrochloride (5.0 g) as a white solid.

Third step, a mixture of 1-(4-methoxyphenyl)-propylamine (424 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with $CHCl_3$—$CH_3OH$ (20:1) to yield $N^6$-[(±)-1-(4-methoxyphenyl)-propyl]-adenosine (230 mg) as a white solid: positive ESIMS m/z 416 [M+H]$^+$ and 438 [M+Na]$^+$; negative ESIMS m/z 414 [M−H]$^-$ $^1$H NMR (300 MHz, DMSO-$d_6$): the adenosine moiety δ 8.35 (1H, s, H-2), 8.22 (1H, d, J=8.1 Hz, —NH), 8.14 (1H, s, H-8), 5.86 (1H, d, J=6.3 Hz, H-1'), 5.40 (2H, m, 2×—OH), 5.15 (1H, d, J=4.2 Hz, —OH), 4.58 (1H, m, H-2'), 4.12 (1H, m, H-3'), 3.93 (1H, m, H-4'), 3.66 (1H, m, H-5'a), 3.54 (1H, m, H-5'b); the (±)-1-(4-methoxyphenyl)-propyl moiety δ 7.35 (2H, d, J=8.4 Hz, H-2", H-6"), 6.83 (2H, d, J=8.4 Hz, H-3", H-5"), 5.17 (1H, m, H-7"), 3.69 (3H, s, —$OCH_3$), 1.93 (1H, m, H-8"a), 1.80 (1H, m, H-8"b), 0.86 (3H, t, J=6.9 Hz, H-9"); $^{13}$C NMR (75 MHz, DMSO-$d_6$): the adenosine moiety δ 154.3 (s, C-6), 152.3 (d, C-2), 148.4 (s, C-4), 139.8 (d, C-8), 119.8 (s, C-5), 88.1 (d, C-1'), 85.9 (d, C-4'), 73.5 (d, C-2'), 70.7 (d, C-3'), 61.7 (t, C-5'); the (±)-1-(4-methoxyphenyl)-propyl moiety δ 158.0 (s, C-4"), 136.1 (s, C-1"), 127.9 (d, C-2", C-6"), 113.5 (d, C-3", C-5"), 55.0 (q, —$OCH_3$), 54.6 (d, C-7"), 29.0 (t, C-8"), 11.5 (q, C-9").

Example 75: Preparation of $N^6$-[(R)-1-(phenyl)-propyl]-adenosine

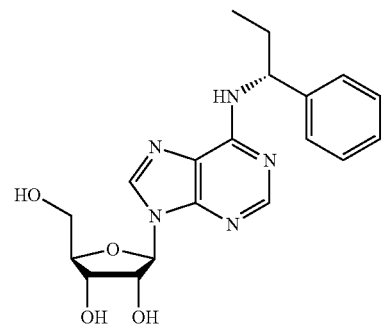

A mixture of (R)-1-(phenyl)-propylamine (1.41 g), 6-chloropurine riboside (1 g) and triethylamine (15 ml) in PrOH (70 ml) was heated to 70° C. and reacted for 8 h. After evaporation of the reaction mixture, the residue was separated by column chromatography over silica gel and eluted with $CHCl_3$:MeOH (20:1) to yield $N^6$-[(R)-1-(phenyl)-propyl]-adenosine (1.15 g) as a white solid: positive ESIMS m/z 386 [M+H]$^+$ and 408 [M+Na]$^+$; $^1$H NMR (300 MHz, DMSO-$d_6$): the adenosine moiety δ 8.36 (1H, s, H-2), 8.32 (1H, d, J=8.4 Hz, —NH), 8.14 (1H, s, H-8), 5.85 (1H, d, J=6.3 Hz, H-1'), 5.40 (1H, d, J=6.0 Hz, —OH), 5.37 (1H, m, —OH), 5.15 (1H, d, J=4.2 Hz, —OH), 4.58 (1H, m, H-2'), 4.12 (1H, m, H-3'), 3.94 (1H, m, H-4'), 3.66 (1H, m, H-5'a), 3.55 (1H, m, H-5'b); the (R)-1-(phenyl)-propyl moiety δ 7.44 (2H, d, J=7.2 Hz, H-2", H-6"), 7.28 (2H, t, J=7.2 Hz, H-3", H-5"), 7.17 (1H, t, J=7.2 Hz, H-4"), 5.26 (1H, m, H-7"), 1.94 (1H, m, H-8"a), 1.84 (1H, m, H-8"b), 0.89 (3H, t, J=6.9 Hz, H-9"); $^{13}$C NMR (75 MHz, DMSO-$d_6$): the adenosine moiety δ 154.4 (s, C-6), 152.4 (d, C-2), 148.5 (s, C-4), 139.9 (d, C-8), 119.9 (s, C-5), 88.2 (d, C-1'), 86.1 (d, C-4'), 73.6 (d, C-2'), 70.8 (d, C-3'), 61.8 (t, C-5'); the (R)-1-(phenyl)-propyl moiety δ 144.2 (s, C-1"), 128.2 (d, C-2", C-6"), 126.8 (d, C-3", C-5"), 126.7 (d, C-4"), 55.3 (d, C-7"), 29.1 (t, C-8"), 11.6 (q, C-9").

Example 76: Preparation of $N^6$-[(R)-1-(phenyl)-propyl]-adenosine-2',3',5'-triacetate

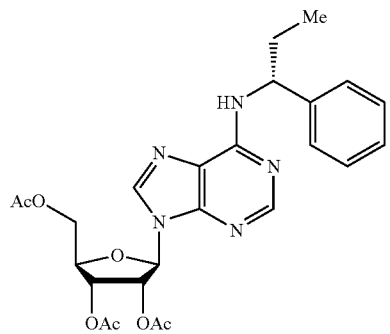

$N^6$-[(R)-1-(phenyl)-propyl]-adenosine (220 mg) was dissolved in dry pyridine (6.0 ml). A proper quantity of molecular sieve and acetic anhydride (1.0 ml) were added. The reaction solution was stirred at room temperature for 12 h. After evaporation, EtOAc and copper sulfate solution were added to extract. The EtOAc layer was dried by anhydrous sodium sulfate, and filtered. The filtrate was evaporated and the residue was purified by column chromatography over silica gel and eluted with CHCl₃:MeOH (200:1) to yield N⁶-[(R)-1-(phenyl)-propyl]-adenosine-2',3',5'-triacetate (218 mg) as a pale yellowish solid: positive ESIMS m/z 512[M+H]⁺, 534[M+Na]⁺ and 550[M+K]⁺; $^1$H NMR (300 MHz, DMSO-d₆): the adenosine moiety δ 8.38 (2H, brs, NH, H-8), 8.19 (1H, s, H-2), 6.20 (1H, d, J=5.1 Hz, H-1'), 6.04 (1H, t, J=5.4 Hz, H-2'), 5.61 (1H, t, J=5.4 Hz, H-3'), 4.36 (1H, dd, J=11.4, 3.6 Hz, H-5'a), 4.35 (1H, m, H-4'), 4.22 (1H, dd, J=11.4, 6.3 Hz, H-5'b); the (R)-1-(phenyl)-propyl moiety δ 7.44 (2H, d, J=7.2 Hz, H-2", H-6"), 7.27 (2H, t, J=7.2 Hz, H-3", H-5"), 7.17 (1H, t, J=7.2 Hz, H-4"), 5.23 (1H, m, H-7"), 1.85 (2H, m, H-8"), 0.89 (3H, t, J=7.2 Hz, H-9"); the acetyl 452.10 (3H, s, CH₃CO), 2.01 (3H, s, CH₃CO), 2.00 (3H, s, CH₃CO); $^{13}$C NMR (75 MHz, DMSO-d₆): the adenosine moiety δ 154.3 (C-6), 152.7 (C-2), 148.5 (C-4), 140.0 (C-8), 119.6 (C-5), 85.6 (C-1'), 79.5 (C-4'), 71.8 (C-3'), 70.1 (C-2'), 62.9 (C-5'); the (R)-1-(phenyl)-propyl moiety δ 144.1 (C-1"), 128.2 (C-2", C-6"), 126.7 (C-3"), 126.6 (C-5"), 124.1 (C-4"), 55.2 (C-7"), 29.0 (C-8"), 11.5 (C-9"); the acetyl δ 170.1 (C=O), 169.5 (C=O), 169.3 (C=O), 20.5, 20.4, 20.20.

Example 77: Preparation of N⁶-[(R)-1-(phenyl)-propyl]-adenosine-5'-acetate

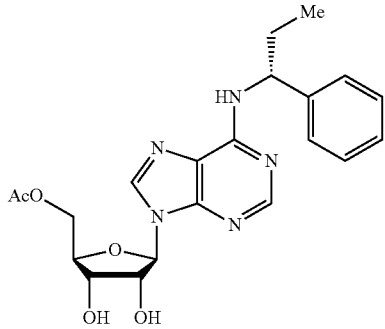

First step, a mixture of N⁶-[(R)-1-(phenyl)-propyl]-2',3'-O-isopropylidene-adenosine (300 mg), EDCI (298 mg), DMAP (237 mg) and acetic acid (56 mg) in dry CH₂Cl₂ (25 ml) was stirred at room temperature for 4 h. Distilled water (30 ml) was added and extracted with CH₂Cl₂ (3×30 ml), the CH₂Cl₂ layer was dried with anhydrous sodium sulfate, filtered and concentrated. The mixture was separated by column chromatography over silica gel eluting with CHCl₃—CH₃OH (200:1) to yield a pale yellowish N⁶-[(R)-1-(phenyl)-propyl]-2',3'-O-isopropylidene-adenosine-5'-acetate (305 mg) as a pale yellowish solid, the productive rate is 84.0%.

Second step, N⁶-[(R)-1-(phenyl)-propyl]-2',3'-O-isopropylidene-adenosine-5'-acetate (300 mg) was added to a formic acid solution (20 ml, 50% V/V), and the mixture was stirred at room temperature for 12 h. After evaporation of the reaction mixture, the residue was separated by column chromatography over silica gel and eluted with CHCl₃—CH₃OH (50:1) to yield N⁶-[(R)-1-(phenyl)-propyl]-adenosine-5'-acetate (248 mg) as a white solid, the productive rate is 90.5%: positive ESIMS m/z 428 [M+H]⁺, 450 [M+Na]⁺;

$^1$H NMR (300 MHz, DMSO-d₆): the adenosine moiety δ 8.34 (1H, s, H-2), 8.28 (1H, brd, J=8.1 Hz, NH), 8.17 (1H, brs H-8), 5.89 (1H, d, J=4.8 Hz, H-1'), 5.55 (1H, d, J=5.7 Hz, OH), 5.35 (1H, d, J=5.1 Hz, OH), 4.64 (1H, m, H-2'), 4.29 (1H, dd, J=11.7, 3.3 Hz, H-5'a), 4.14 (1H, dd, J=11.7, 6.0 Hz, H-5'b), 4.23 (1H, m, H-3'), 4.06 (1H, m, H-4'); the (R)-1-(phenyl)-propyl moiety δ 7.43 (2H, d, J=7.2 Hz, H-2", H-6"), 7.27 (2H, t, J=7.2 Hz, H-3", H-5"), 7.17 (1H, t, J=7.8 Hz, H-4"), 5.25 (1H, m, H-7"), 1.98 (1H, m, H-8"a), 1.82 (1H, m, H-8"b 0.89 (3H, t, J=6.0 Hz, H-9"); the acetyl 451.98 (3H, s); $^{13}$C NMR (75 MHz, DMSO-d₆): the adenosine moiety δ 154.3 (s, C-6), 152.6 (d, C-2), 148.8 (s, C-4), 139.6 (d, C-8), 119.6 (s, C-5), 87.9 (d, C-1'), 81.6 (d, C-4'), 73.0 (d, C-3'), 70.4 (d, C-2'), 64.0 (t, C-5'); the (R)-1-(phenyl)-propyl moiety δ 144.3 (s, C-1"), 128.2 (d, C-2", C-6"), 126.7 (d, C-3", C-5"), 126.6 (d, C-4"), 55.3 (d, C-7"), 29.1 (t, C-8"), 11.5 (q, C-9"); the acetyl δ 170.3, 20.60.

Example 78: Preparation of N⁶-[(S)-1-(phenyl)-propyl]-adenosine

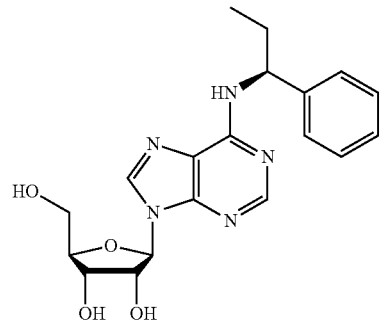

A mixture of (S)-1-(phenyl)-propylamine (1.41 g), 6-chloropurine riboside (1 g) and triethylamine (15 ml) in PrOH (70 ml) was heated to 70° C. and reacted for 8 h. After evaporation of the reaction mixture, the residue was separated by column chromatography over silica gel and eluted with CHCl₃:MeOH (20:1) to yield N⁶-[(S)-1-(phenyl)-propyl]-adenosine (1.1 g) as a white solid: positive ESIMS m/z 386 [M+H]⁺; $^1$H NMR (300 MHz, DMSO-d₆): the adenosine moiety δ 8.37 (1H, s, H-2), 8.32 (1H, d, J=7.5 Hz, —NH), 8.14 (1H, s, H-8), 5.86 (1H, d, J=6.0 Hz, H-1'), 5.42 (1H, d, J=6.0 Hz, —OH), 5.36 (1H, m, —OH), 5.16 (1H, d, J=3.9 Hz, —OH), 4.58 (1H, m, H-2'), 4.12 (1H, m, H-3'), 3.94 (1H, m, H-4'), 3.65 (1H, m, H-5'a), 3.54 (1H, m, H-5'b); the (S)-1-(phenyl)-propyl moiety δ 7.44 (2H, d, J=7.2 Hz, H-2", H-6"), 7.28 (2H, t, J=7.2 Hz, H-3", H-5"), 7.17 (1H, t, J=7.2 Hz, H-4"), 5.24 (1H, m, H-7"), 1.95 (1H, m, H-8"a), 1.83 (1H, m, H-8"b), 0.89 (3H, t, J=6.9 Hz, H-9"); $^{13}$C NMR (75 MHz, DMSO-d₆): the adenosine moiety δ 154.4 (s, C-6), 152.4 (d, C-2), 148.5 (s, C-4), 139.9 (d, C-8), 119.8 (s, C-5), 88.1 (d, C-1'), 86.1 (d, C-4'), 73.7 (d, C-2'), 70.8 (d, C-3'), 61.8 (t, C-5'); the (S)-1-(phenyl)-propyl moiety δ 144.3 (s, C-1"), 128.3 (d, C-2", C-6"), 126.8 (d, C-3", C-5"), 126.7 (d, C-4"), 55.3 (d, C-7"), 29.1 (t, C-8"), 11.6 (q, C-9").

Example 79: Preparation of $N^6$-[(S)-1-(phenyl)-propyl]-adenosine-2',3',5'-triacetate

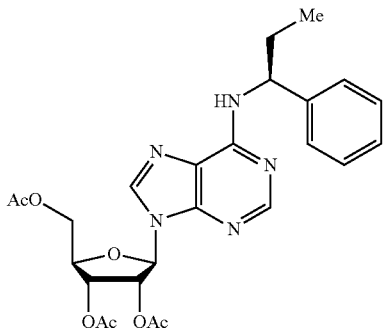

A mixture of $N^6$-[(S)-1-(phenyl)-propyl]-adenosine (200 mg), EDCI (197 mg), DMAP (158.5 mg) and acetic acid (140.2 mg) in dry $CH_2Cl_2$ (15 ml) was stirred at room temperature for 3 h. Distilled water (40 ml) was added and the resulting solution was extracted with $CH_2Cl_2$ (3×30 ml). The $CH_2Cl_2$ layer was dried with anhydrous sodium sulfate, filtered and evaporated. The resulting mixture was separated by column chromatography over silica gel and eluted with $CHCl_3$—$CH_3OH$ (200:1) to yield $N^6$-[(S)-1-(phenyl)-propyl]-adenosine-2',3',5'-triacetate (260 mg) as a pale yellowish solid, the productive rate is 98.1%: positive ESIMS m/z 512 [M+H]$^+$, 534 [M+Na]$^+$ and 550 [M+K]$^+$; $^1H$ NMR (300 MHz, acetone-d$_6$): the adenosine moiety δ 8.27 (2H, s, H-8, H-2), 7.56 (1H, brs, NH), 6.27 (1H, d, J=5.1 Hz, H-1'), 6.12 (1H, dd, J=5.1, 5.4, H-2'), 5.76 (1H, dd, J=4.8, 4.8 Hz, H-3'), 4.44 (1H, m, H-4'), 4.46 (1H, dd, J=12.6, 3.3 Hz, H-5'a), 4.34 (1H, dd, J=12.6, 6.3 Hz, H-5'b); the (S)-1-(phenyl)-propyl moiety δ 7.49 (2H, d, J=7.8 Hz, H-2", H-6"), 7.27 (2H, t, J=7.8 Hz, H-3", H-5"), 7.17 (1H, t, J=7.8 Hz, H-4"), 5.39 (1H, m, H-7"), 1.97 (2H, m, H-8"), 0.97 (3H, t, J=7.2 Hz, H-9"); the acetyl 452.10 (3H, s), 2.00 (3H, s), 1.98 (3H, s); $^{13}C$ NMR (75 MHz, acetone-d$_6$): the adenosine moiety δ 155.2 (s, C-6), 153.8 (d, C-2), 149.6 (s, C-4), 140.2 (d, C-8), 120.5 (s, C-5), 87.1 (d, C-1'), 80.9 (d, C-4'), 73.5 (d, C-3'), 71.3 (d, C-2'), 63.7 (t, C-5'); the (S)-1-(phenyl)-propyl moiety δ 144.5 (s, C-1"), 129.0 (d, C-2", C-6"), 127.50 (d, C-3", C-5"), 127.46 (d, C-4"), 56.4 (d, C-7"), 30.3 (t, C-8"), 11.5 (q, C-9"); the acetyl δ 170.7, 170.1, 170.0, 20.6, 20.4, 20.30.

Example 80: Preparation of $N^6$-[(S)-1-(phenyl)-propyl]-adenosine-5'-acetate

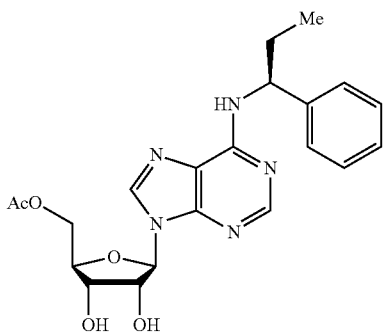

First step, a mixture of $N^6$-[(S)-1-(phenyl)-propyl]-2',3'-O-isopropylidene-adenosine (330 mg), EDCI (297.4 mg), DMAP (236.9 mg) and acetic acid (55.9 mg) in dry $CH_2Cl_2$ (15 ml) was stirred at room temperature for 4 h. Distilled water (30 ml) was added and the resulting solution was extracted with $CH_2Cl_2$ (3×30 ml). The $CH_2Cl_2$ layer was dried with anhydrous sodium sulfate, and filtered. The filtrate was evaporated and the residue was separated by column chromatography over silica gel and eluted with $CHCl_3$—$CH_3OH$ (200:1) to yield $N^6$-[(S)-1-(phenyl)-propyl]-2',3'-O-isopropylidene-adenosine-5'-acetate (320 mg) as a pale yellowish solid, the productive rate is 88.2%:

Second step, $N^6$-[(S)-1-(phenyl)-propyl]-2',3'-O-isopropylidene-adenosine-5'-acetate (240 mg) was added to a formic acid solution (20 ml, 50% V/V), and the mixture was stirred at room temperature for 12 h, After evaporation of the reaction mixture, the residue was separated by column chromatography over silica gel and eluted with $CHCl_3$—$CH_3OH$ (50:1) to yield $N^6$-[(S)-1-(phenyl)-propyl]-adenosine-5'-acetate (180 mg) as a white solid, the productive rate is 82.2%: positive ESIMS m/z 428 [M+H]$^+$, 450 [M+Na]$^+$; $^1H$ NMR (300 MHz, DMSO-d$_6$): the adenosine moiety δ 8.34 (1H, s, H-2), 8.28 (1H, brd, J=8.1 Hz, NH), 8.17 (1H, brs H-8), 5.89 (1H, d, J=4.8 Hz, H-1'), 5.55 (1H, d, J=5.7 Hz, OH), 5.35 (1H, d, J=5.1 Hz, OH), 4.64 (1H, m, H-2'), 4.29 (1H, dd, J=11.7, 3.3 Hz, H-5'a), 4.14 (1H, dd, J=11.7, 6.0 Hz, H-5'b), 4.23 (1H, m, H-3'), 4.06 (1H, m, H-4'); the (S)-1-(phenyl)-propyl δ 7.43 (2H, d, J=7.2 Hz, H-2", H-6"), 7.27 (2H, t, J=7.2 Hz, H-3", H-5"), 7.17 (1H, t, J=7.8 Hz, H-4"), 5.25 (1H, m, H-7"), 1.98 (1H, m, H-8"a), 1.82 (1H, m, H-8"b), 0.89 (3H, t, J=6.0 Hz, H-9"); the adenosine moiety δ 1.98 (3H, s); $^{13}C$ NMR (75 MHz, DMSO-d$_6$): the adenosine moiety δ 154.3 (s, C-6), 152.6 (d, C-2), 148.8 (s, C-4), 139.6 (d, C-8), 119.6 (s, C-5), 87.9 (d, C-1'), 81.6 (d, C-4'), 73.0 (d, C-3'), 70.4 (d, C-2'), 64.0 (t, C-5'); the (S)-1-(phenyl)-propyl δ 144.3 (s, C-1"), 128.2 (d, C-2", C-6"), 126.7 (d, C-3", C-5"), 126.6 (d, C-4"), 55.3 (d, C-7"), 29.1 (t, C-8"), 11.5 (q, C-9"); the acetyl δ 170.3, 20.60.

Example 81: Preparation of $N^6$-[(S)-1-(phenyl)-propyl]-adenosine-5'-p-methyl-phenylpropionate

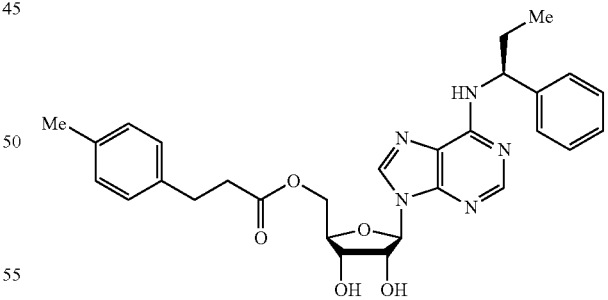

First step, $N^6$-[(S)-1-(phenyl)-propyl]-adenosine (2.50 g) prepared in the above example, and 2,2-dimethoxypropane (5.40 g) were added to dry acetone (100 ml), and (1S)-(+)-camphor-10-sulfonic acid (1 g) was added as a catalyst. The reaction solution was stirred at room temperature for 3 h. After evaporation of the reaction mixture, the residue was dissolved in water (40 ml), extracted with chloroform (3×30 ml), and the chloroform layer was dried by anhydrous sodium sulfate, filtered and evaporated to remove the solvent. The product was separated by column chromatography over silica gel and eluted with CHCl$_3$—CH$_3$OH (200:1) to yield N$^6$-[(S)-1-(phenyl)-propyl]-2',3'-O-isopropylidene-adenosine (2.4 g).

Second step, a mixture of N$^6$-[(S)-1-(phenyl)-propyl]-2', 3'-O-isopropylidene-adenosine (300 mg), EDCI (297.40 mg), DMAP (236.90 mg) and p-methyl phenylpropionic acid (152.80 mg) in dry CH$_2$Cl$_2$ (20 ml) was stirred at room temperature for 4 h. Distilled water (30 ml) was added and the resulting solution was extracted with CH$_2$Cl$_2$ (3×30 ml), and the CH$_2$Cl$_2$ layer was dried by anhydrous sodium sulfate, and filtered. The filtrate was evaporated, and the residue was separated by column chromatography over silica gel and eluted with CHCl$_3$—CH$_3$OH (200:1) to yield N$^6$-[(S)-1-(phenyl)-propyl]-2',3'-O-isopropylidene-adenosine-5'-p-methyl-phenylpropionate (369.0 mg).

Third step, N$^6$-[(S)-1-(phenyl)-propyl]-2',3'-O-isopropylidene-adenosine-5'-p-methyl-phenylpropionate (369.0 mg) was added to a formic acid solution (20 ml, 50% V/V), and the mixture was stirred at room temperature for 12 h. After evaporation of the reaction mixture, the residue was separated by column chromatography over silica gel and eluted with CHCl$_3$—CH$_3$OH (50:1) to yield N$^6$-[(S)-1-(phenyl)-propyl]-adenosine-5'-p-methyl-phenylpropionate (174 mg) as a light yellowish solid: positive ESIMS m/z 532 [M+H]$^+$, 554[M+Na]$^+$; $^1$H NMR (300 MHz, acetone-d$_6$): the adenosine moiety δ 8.19 (1H, s, H-2), 8.17 (1H, brs H-8), 7.19 (1H, brs, NH), 6.03 (1H, d, J=4.2 Hz, H-1'), 4.81 (1H, dd, J=4.2, 4.8, H-2'), 4.46 (1H, dd, J=5.4, 4.8 Hz, H-3'), 4.37 (1H, dd, J=11.7, 3.3 Hz, H-5'a), 4.28 (1H, dd, J=11.7, 4.8 Hz, H-5'b), 4.23 (1H, m, H-4'); the (S)-1-(phenyl)-propyl moiety δ 7.50 (2H, d, J=7.2 Hz, H-2", H-6"), 7.28 (2H, t, J=7.2 Hz, H-3", H-5"), 7.18 (1H, t, J=7.8 Hz, H-4"), 5.39 (1H, m, H-7"), 1.98 (2H, m, H-8"), 0.98 (3H, t, J=7.2 Hz, H-9"); the p-methyl-phenylpropionyl moiety δ 7.07 (2H, d, J=8.1 Hz, H-3''', H-5'''), 7.01 (2H, d, J=8.1 Hz, H-2''', H-6'''), 2.82 (2H, t, J=7.5 Hz, H-7'''), 2.60 (2H, t, J=7.5 Hz, H-8'''), 2.23 (3H, s, Me); $^{13}$C NMR (75 MHz, acetone-d$_6$): the adenosine moiety δ 155.5 (s, C-6), 153.5 (d, C-2), 149.7 (s, C-4), 140.0 (d, C-8), 120.8 (s, C-5), 89.8 (d, C-1'), 82.9 (d, C-4'), 74.8 (d, C-3'), 71.7 (d, C-2'), 64.4 (t, C-5'); the (S)-1-(phenyl)-propyl moiety δ 144.9 (s, C-1"), 129.0 (d, C-2", C-6"), 127.6 (d, C-3", C-5"), 127.6 (d, C-4"), 56.4 (d, C-7"), 30.2 (t, C-8"), 11.6 (q, C-9"); the p-methyl-phenylpropionyl moiety δ 172.8 (C-9'''), 138.4 (C-4'''), 138.6 (C-1'''), 129.8 (C-2''', C-6'''), 129.0 (C-3''', C-5'''), 36.3 (C-7'''), 31.0 (C-8'''), 20.9 (Me).

Example 82: Preparation of N$^6$-[(S)-1-(phenyl)-propyl]-adenosine-5'-p-methyl-cinnamate

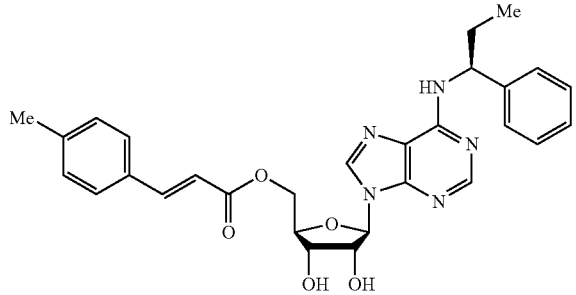

First step, a mixture of N$^6$-[(S)-1-(phenyl)-propyl]-2',3'-O-isopropylidene-adenosine (300 mg), EDCI (297.40 mg), DMAP (236.90 mg) and p-methyl-cinnamic acid (150 mg) in dry CH$_2$Cl$_2$ (15 ml) was stirred at room temperature for 4 h. Distilled water (30 ml) was added and the resulting solution was extracted with CH$_2$Cl$_2$ (3×30 ml), and the CH$_2$Cl$_2$ layer was dried by anhydrous sodium sulfate, and filtered. The filtrate was evaporated, and the residue was separated by column chromatography over silica gel and eluted with CHCl$_3$—CH$_3$OH (200:1) to yield N$^6$-[(S)-1-(phenyl)-propyl]-2',3'-O-isopropylidene-adenosine-5'-p-methyl-cinnamate (235 mg).

Second step, N$^6$-[(S)-1-(phenyl)-propyl]-2',3'-O-isopropylidene-adenosine-5'-p-methyl-cinnamate (230 mg) was added to a formic acid solution (20 ml, 50% V/V), and the mixture was stirred at room temperature for 12 h. After evaporation of the reaction mixture, the residue was separated by column chromatography over silica gel and eluted with CHCl$_3$—CH$_3$OH (50:1) to yield N$^6$-[(S)-1-(phenyl)-propyl]-adenosine-5'-p-methyl-cinnamate (185 mg) as a yellowish solid: positive ESIMS m/z 530 [M+H]$^+$, 552 [M+Na]$^+$ and 568 [M+K]$^+$; $^1$H NMR (300 MHz, DMSO-d$_6$): the adenosine moiety δ 8.36 (1H, s, H-2), 8.25 (1H, brd, J=7.5 Hz, NH), 8.14 (1H, brs, H-8), 5.91 (1H, d, J=4.2 Hz, H-1'), 5.54 (1H, d, J=6.0 Hz, OH), 5.38 (1H, d, J=5.4 Hz, OH), 4.70 (1H, dd, J=4.2, 4.8, H-2'), 4.30 (1H, dd, J=5.4, 4.8 Hz, H-3'), 4.45 (1H, dd, J=11.7, 3.3 Hz, H-5'a), 4.30 (1H, dd, J=11.7, 4.8 Hz, H-5'b), 4.15 (1H, m, H-4'); the (S)-1-(phenyl)-propyl moiety δ 7.42 (2H, d, J=7.2 Hz, H-2", H-6"), 7.23 (2H, t, J=7.2 Hz, H-3", H-5"), 7.14 (1H, t, J=7.8 Hz, H-4"), 5.25 (1H, m, H-7"), 1.98 (2H, m, H-8"), 0.88 (3H, t, J=7.2 Hz, H-9"); the p-methyl-cinnamyl moiety δ 7.59 (2H, d, J=8.1 Hz, H-3''', H-5'''), 7.23 (2H, d, J=8.1 Hz, H-2''', H-6'''), 7.60 (1H, d, J=16.2 Hz, H-7'''), 6.59 (1H, d, J=16.2 Hz, H-8'''), 2.32 (3H, s, Me); $^{13}$C NMR (75 MHz, acetone-d$_6$): the adenosine moiety δ 155.3 (s, C-6), 153.5 (d, C-2), 149.6 (s, C-4), 139.9 (d, C-8), 120.6 (s, C-5), 89.7 (d, C-1'), 83.0 (d, C-4'), 75.0 (d, C-3'), 71.8 (d, C-2'), 64.5 (t, C-5'); the (S)-1-(phenyl)-propyl moiety δ 144.5 (s, C-1"), 129.0 (d, C-2", C-6"), 127.5 (d, C-3", C-5"), 127.5 (d, C-4"), 56.3 (d, C-7"), 30.2 (t, C-8"), 11.5 (q, C-9"); the p-methyl-cinnamyl moiety δ 167.0 (C-9'''), 145.8 (C-7'''), 141.5 (C-4'''), 132.3 (C-1'''), 130.3 (C-2''', C-6'''), 129.0 (C-3''', C-5'''), 117.2 (C-8'''), 21.4 (Me).

Example 83: Preparation of N$^6$-[(S)-1-(phenyl)-propyl]-adenosine-5'-propyl ether

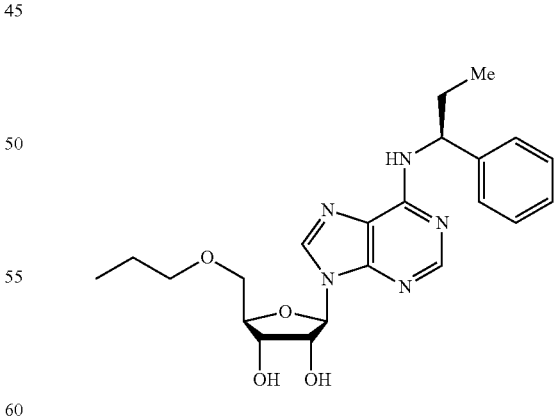

First step, N$^6$-[(S)-1-(phenyl)-propyl]-adenosine (4.0 g) prepared in the above example, and 2,2-dimethoxypropane (8.67 g) were added to dry acetone (60 ml), and (1S)-(+)-camphor-10-sulfonic acid (2.42 g) was added as a catalyst. The reaction solution was stirred at room temperature for 12 h. After evaporation of the reaction mixture, the residue was dissolved in saturated NaHCO$_3$ solution (60 ml), and extracted with EtOAC (3×40 ml). The EtOAc layer was dried by anhydrous sodium sulfate, and filtered. The filtrate was evaporated the solvent and the residue was separated by column chromatography over silica gel and eluted with CHCl$_3$—CH$_3$OH 100:1) to yield N$^6$-[(S)-1-(phenyl)-propyl]-2',3'-O-isopropylidene-adenosine (3.2 g).

Second step, N$^6$-[(S)-1-(phenyl)-propyl]-2',3'-O-isopropylidene-adenosine (425.5 mg) was dissolved in dry THF (15 ml). NaH (425.0 mg) was added slowly at room temperature and stirred for 2 h. The dry THF (5 ml) solution of 1-iodo-propan (220.0 mg) was added to the reaction solution and stirred at room temperature for 4 h. The reaction solution was ended by adding proper quantity of distilled water to destroy the excess NaH. After evaporation of the reaction mixture, the residue was dissolved in distilled water (20 ml), and extracted with EtOAc (3×25 ml). The EtOAc was dried by anhydrous sodium sulfate, and filtered. The filtrate was evaporated and the residue was separated by column chromatography over silica gel and eluted with petroleum ether-EtOAc (3:2) to yield N$^6$-[(S)-1-(phenyl)-propyl]-2',3'-O-isopropylidene-adenosine-5'-propyl ether (205 mg).

Third step, N$^6$-[(S)-1-(phenyl)-propyl]-2',3'-O-isopropylidene-adenosine-5'-propyl ether (200 mg) was added to a formic acid solution (20 ml, 50% V/V), and the mixture was stirred at room temperature for 12 h, After evaporation of the reaction mixture, the residue was separated by column chromatography over silica gel and eluted with CHCl$_3$—CH$_3$OH (50:1) to yield N$^6$-[(S)-1-(phenyl)-propyl]-adenosine-5'-propyl ether (80 mg) as a white solid: $^1$H NMR (300 MHz, DMSO-d$_6$): the adenosine moiety δ 8.31 (1H, s, H-2), 8.19 (1H, brs H-8), 5.91 (1H, d, J=4.2 Hz, H-1'), 5.51 (1H, d, J=5.4 Hz, OH), 5.24 (1H, J=4.8 Hz, OH), 4.51 (1H, m, H-2'), 4.18 (1H, m, H-3'), 4.02 (1H, m, H-4'), 3.65 (1H, m, H-5'a), 3.53 (1H, m, H-5'b); the (S)-1-(phenyl)-propyl moiety δ 7.45 (2H, d, J=6.9 Hz, H-2'', H-6''), 7.27 (2H, t, J=7.2 Hz, H-3'', H-5''), 7.16 (1H, t, J=7.2 Hz, H-4''), 5.24 (1H, s, H-7''), 1.95-1.80 (2H, m, H-8''a, H-8''b), 0.85 (3H, m, H-9''); the propyl moiety δ 3.37 (2H, m, H-1'''), 1.52 (2H, m, H-2'''), 0.90 (3H, m, H-3'''); $^{13}$C NMR (75 MHz, DMSO-d$_6$): the adenosine moiety δ 154.2 (s, C-6), 152.5 (d, C-2), 148.8 (s, C-4), 138.9 (d, C-8), 119.3 (s, C-5), 87.5 (d, C-1'), 83.1 (d, C-4'), 73.7 (d, C-3'), 70.3 (d, C-2'), 70.2 (t, C-5'); the (S)-1-(phenyl)-propyl moiety δ 144.3 (s, C-1''), 128.1 (d, C-2'', C-6''), 126.7 (d, C-3'', C-5''), 126.5 (d, C-4''), 55.2 (d, C-7''), 29.0 (t, C-8''), 10.9 (q, C-9''); the propyl moiety δ 71.7, 23.5, 11.50.

Example 84: Preparation of N$^6$-[(S)-1-(phenyl)-propyl]-adenosine-5'-decanoic ether was dissolved in dry THF (15 ml). NaH (356.0 mg) was added slowly at room temperature and stirred for 2 h. The dry THF (5 ml) solution of 1-iodo-decane (340.0 mg) was added to the reaction solution and stirred at room temperature for 4 h. The reaction solution was ended by adding proper quantity of distilled water to destroy the excess NaH. After evaporation of the reaction mixture, the residue was dissolved in distilled water (20 ml), and extracted with EtOAc (3×25 ml). The EtOAc was dried by anhydrous sodium sulfate, and filtered. The filtrate was evaporated, and the residue was separated by column chromatography over silica gel and eluted with petroleum ether-EtOAc (3:2) to yield N$^6$-[(S)-1-(phenyl)-propyl]-2',3'-O-isopropylidene-adenosine-5'-decanoic ether (245 mg) as a pale yellowish solid.

Second step, N$^6$-[(S)-1-(phenyl)-propyl]-2',3'-O-isopropylidene-adenosine-5'-decanoic ether (240 mg) was added to a formic acid solution (20 ml, 50% V/V), and the mixture was stirred at room temperature for 12 h. After evaporation of the reaction mixture, the residue was separated by column chromatography over silica gel and eluted with CHCl$_3$—CH$_3$OH (50:1) to yield N$^6$-[(S)-1-(phenyl)-propyl]-adenosine-5'-decanoic ether (124 mg) as a white solid: positive ESIMS m/z 526 [M+H]$^+$, 548 [M+Na]$^+$ and 554 [M+K]$^+$; $^1$H NMR (300 MHz, acetone-d$_6$): the adenosine moiety δ 8.24 (1H, s, H-8), 8.18 (1H, d, J=7.5 Hz, H-2), 7.12 (1H, brd, J=8.7 Hz, NH), 6.05 (1H, d, J=4.2 Hz, H-1'), 4.98 (1H, m, —OH), 4.65 (1H, dd, J=4.8, 4.2 Hz, H-2'), 4.51 (1H, m, —OH), 4.22 (1H, dd, J=4.5, 4.5 Hz, H-3'), 4.16 (1H, dt, J=3.3, 3.6, H-4'), 3.73 (1H, dd, J=10.8, 3.3 Hz, H-5'a), 3.63 (1H, dd, J=10.8, 3.6 Hz, H-5'b); the (S)-1-(phenyl)-propyl moiety δ 7.51 (2H, d, J=7.2 Hz, H-2'', H-6''), 7.29 (2H, t, J=7.2 Hz, H-3'', H-5''), 7.19 (1H, t, J=7.2 Hz, H-4''), 5.39 (1H, m, H-7''), 2.07 (1H, m, H-8''a), 1.97 (1H, m, H-8''b), 0.98 (3H, t, J=7.2 Hz, H-9''); the decyl moiety δ 3.49 (2H, brt, J=6.3 Hz, H-1'''), 1.58 (2H, hex, H-2'''), 1.30 (14H, m), 0.85 (3H, t, J=6.9 Hz, H-9'''). $^{13}$CNMR (75 MHz, DMSO-d$_6$): the adenosine moiety δ 155.5 (s, C-6), 153.5 (d, C-2), 150.0 (s, C-4), 139.5 (d, C-8), 120.6 (s, C-5), 89.3 (d, C-1'), 84.7 (d, C-4'), 75.9 (d, C-5'), 72.1 (d, C-2'), 71.1 (t, C-3'); the (S)-1-(phenyl)-propyl moiety δ 145.0 (s, C-1''), 129.0 (d, C-2'', C-6''), 127.64 (d, C-3'', C-5''), 127.56 (d, C-4''), 56.5 (d, C-7''), 30.8 (t, C-8''), 11.4 (q, C-9''); the decyl moiety δ 71.9 (t, C-1'''), 32.6, 30.4, 30.3, 30.2, 30.2, 30.1, 26.9, 23.3, 14.3 (q, C-3''').

Example 85: Preparation of N$^6$-[(R)-1-(phenyl)-propyl]-adenosine-5'-o-nitrophenyl ether

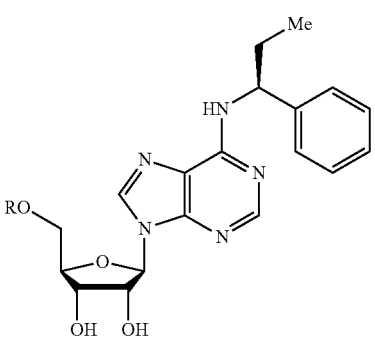

R = n-C$_{10}$H$_{21}$

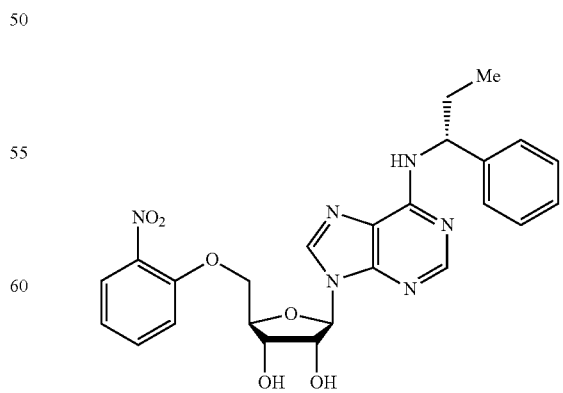

First step, N$^6$-[(S)-1-(phenyl)-propyl]-2',3'-O-isopropylidene-adenosine (400.0 mg) prepared in the above example First step, N$^6$-[(R)-1-(phenyl)-propyl]-2',3'-O-isopropylidene-adenosine (500.0 mg) prepared in the above example was dissolved in dry THF (40 ml). NaH (550.0 mg) was added slowly at room temperature and stirred for 2 h. The dry THF (5 ml) solution of o-fluoronitrobenzene (414.5 mg) was added to the reaction solution and stirred at room temperature for 4 h. The reaction solution was ended by adding proper quantity of distilled water to destroy the excess NaH. After evaporation of the reaction mixture, the residue was dissolved in distilled water (20 ml), and extracted with EtOAc (3×25 ml). The EtOAc was dried by anhydrous sodium sulfate, and filtered, The filtrate was evaporated and the residue was separated by column chromatography over silica gel and eluted with petroleum ether-EtOAc (3:2) to yield $N^6$-[(R)-1-(phenyl)-propyl]-2',3'-O-isopropylidene-adenosine-5'-o-nitrophenyl ether (246 mg) as a pale yellowish solid.

Second step, $N^6$-[(R)-1-(phenyl)-propyl]-2',3'-O-isopropylidene-adenosine-5'-o-nitrophenyl ether (246 mg) was added to a formic acid solution (20 ml, 50% V/V), and the mixture was stirred at room temperature for 12 h. After evaporation of the reaction mixture, the residue was separated by column chromatography over silica gel and eluted with $CHCl_3$—$CH_3OH$ (50:1) to yield $N^6$-[(R)-1-(phenyl)-propyl]-adenosine-5'-o-nitrophenyl ether (80 mg) as a white solid: positive ESIMS m/z 428 [M+H]$^+$, 450 [M+Na]$^+$ and 466 [M+K]$^+$; $^1$H NMR (300 MHz, DMSO-d$_6$): the adenosine moiety δ 8.30 (1H, s, NH), 8.23 (1H, s, H-8), 8.16 (1H, s, H-2), 5.96 (1H, d, J=5.7 Hz, H-1'), 5.62 (1H, d, J=5.7 Hz, —OH), 5.41 (1H, d, J=4.8 Hz, —OH), 4.65 (1H, m, H-2'), 4.45 (1H, m, H-3'), 4.45-4.36 (2H, m, H-5'), 4.26 (1H, m, H-4'); the (R)-1-(phenyl)-propyl moiety δ 7.44 (2H, d, J=7.2 Hz, H-2", H-6"), 7.27 (2H, t, J=7.2 Hz, H-3", H-5"), 7.10 (1H, t, J=7.2 Hz, H-4"), 5.26 (1H, m, H-7"), 1.84 (2H, m, H-8"), 0.89 (3H, t, J=7.2 Hz, H-9"); the o-nitrophenyl moiety δ 7.88 (1H, dd, J=8.4, 1.2 Hz, H-3'''), 7.62 (1H, t, J=7.8 Hz, H-5'''), 7.38 (1H, d, J=8.4 Hz, H-4'''), 7.18 (1H, d, J=7.8 Hz, H-6'''); $^{13}$CNMR (75 MHz, DMSO-d$_6$): the adenosine moiety δ 154.2 (s, C-6), 152.6 (d, C-2), 148.9 (s, C-4), 138.7 (d, C-8), 119.3 (s, C-5), 87.2 (d, C-1'), 82.1 (d, C-4'), 73.2 (d, C-5'), 70.2 (d, C-2'), 69.2 (t, C-3'); the (R)-1-(phenyl)-propyl moiety δ 144.2 (s, C-1"), 128.1 (d, C-2", C-6"), 126.7 (d, C-3", C-5"), 126.5 (d, C-4"), 55.1 (d, C-7"), 29.0 (t, C-8"), 11.4 (q, C-9"); the o-nitrophenyl moiety δ 151.1 (s, C-1'''), 139.4 (d, C-5'''), 134.6 (s, C-2'''), 125.1 (d, C-3'''), 120.9 (d, C-4'''), 115.2 (d, C-6''').

Example 86: Preparation of $N^6$-[(R)-1-(phenyl)-propyl]-adenosine-5'-propyl ether

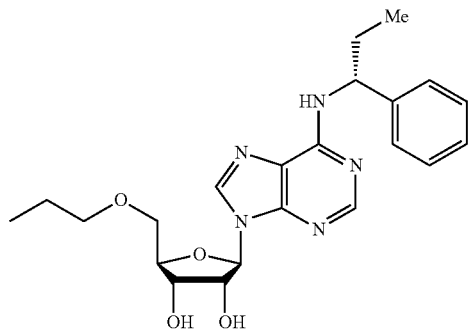

First step, $N^6$-[(R)-1-(phenyl)-propyl]-2',3'-O-isopropylidene-adenosine (500.0 mg) prepared in the above example was dissolved in dry THF (40 ml). NaH (550.0 mg) was added slowly at room temperature and stirred for 2 h. The dry THF (10 ml) solution of 1-iodo-propan (699.1 mg) was added to the reaction solution and stirred at room temperature for 4 h. The reaction solution was ended by adding proper quantity of distilled water to destroy the excess NaH. After evaporation of the reaction mixture, the residue was dissolved in distilled water (20 ml), and extracted with EtOAc (3×25 ml). The EtOAc was dried by anhydrous sodium sulfate, and filtered. The filtrate was evaporated and the residue was separated by column chromatography over silica gel and eluted with petroleum ether-EtOAc (3:2) to yield $N^6$-[(R)-1-(phenyl)-propyl]-2',3'-O-isopropylidene-adenosine-5'-propyl ether (268 mg) as a yellowish solid.

Second step, $N^6$-[(R)-1-(phenyl)-propyl]-2',3'-O-isopropylidene-adenosine-5'-propyl ether (240 mg) was added to a formic acid solution (20 ml, 50% V/V), and the mixture was stirred at room temperature for 12 h. After evaporation of the reaction mixture, the residue was separated by column chromatography over silica gel and eluted with $CHCl_3$—$CH_3OH$ (50:1) to yield $N^6$-[(R)-1-(phenyl)-propyl]-adenosine-5'-propyl ether (160 mg) as a white solid: $^1$H NMR (300 MHz, acetone-d$_6$): the adenosine moiety δ 8.31 (1H, s, H-8), 8.19 (1H, brs, H-2), 7.33 (1H, brs, NH), 6.11 (1H, d, J=3.6 Hz, H-1'), 5.52 (1H, m, —OH), 5.34 (1H, m, —OH), 4.67 (1H, m, H-2'), 4.45 (1H, m, H-3'), 4.19 (1H, m, H-4'), 3.71 (1H, dd, J=10.8, 3.6 Hz, H-5'a), 3.60 (1H, dd, J=10.8, 3.0 Hz, H-5'b); the (R)-1-(phenyl)-propyl moiety δ 7.45 (2H, d, J=7.2 Hz, H-2", H-6"), 7.24 (2H, t, J=7.2 Hz, H-3", H-5"), 7.14 (1H, t, J=7.2 Hz, H-4"), 5.52 (1H, m, H-7"), 1.93 (2H, m, H-8"), 0.85 (3H, t, J=6.9 Hz, H-9"); the propyl moiety δ 3.39 (2H, brt, J=6.3 Hz, H-1'''), 1.55 (2H, hex, H-2'''), 0.94 (3H, t, J=7.2 Hz, H-3'''); $^{13}$CNMR (75 MHz, DMSO-d$_6$): the adenosine moiety δ 155.2 (s, C-6), 153.5 (d, C-2), 149.7 (s, C-4), 139.5 (d, C-8), 120.2 (s, C-5), 89.3 (d, C-1'), 84.7 (d, C-4'), 76.0 (d, C-5'), 71.7 (d, C-2'), 70.9 (t, C-3'); the (R)-1-(phenyl)-propyl moiety δ 144.6 (s, C-1"), 129.0 (d, C-2", C-6"), 127.5 (d, C-3", C-5"), 127.5 (d, C-4"), 56.5 (d, C-7"), 30.9 (t, C-8"), 10.9 (q, C-9"); the propyl moiety δ 73.6 (t, C-1'''), 23.5 (t, C-2'''), 11.5 (q, C-3''').

Example 87: Preparation of $N^6$-[(±)-1-(phenyl)-butyl]-adenosine

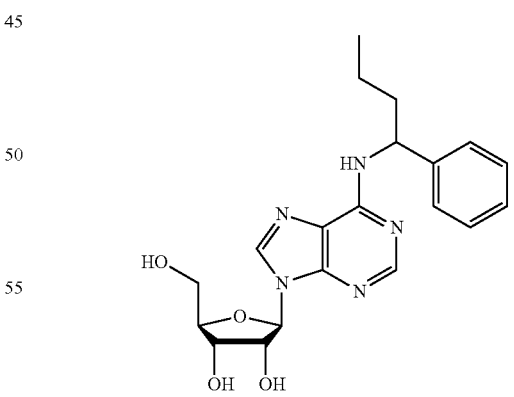

First step, hydroxyamine hydrochloride (4.66 g) and NaOAc (11.07 g) were added to a solution of 1-(phenyl)-butanone (5 g) in EtOH (80 ml). The reaction mixture was stirred at 60° C. for 6 h. EtOH was removed under reduced pressure. H$_2$O (40 ml) was added to the residue, and the resulting solution was extracted with EtOAc (3×40 ml). The EtOAc of the combined organic layer was removed by rotary evaporation under reduced pressure to yield 1-(phenyl)-butanone oxime (5.5 g) as a pale yellowish solid.

Second step, 1-(phenyl)-butanone oxime (5.5 g) and concentrated HCl (17.8 ml) in EtOH (50 ml) was subjected to hydrogenation at atmospheric pressure in the presence of 10% Pd/C (714 mg). The reaction solution was filtered and the filtrate was concentrated. The residue was suspended in EtOAc, and the suspension was filtered to yield 1-(phenyl)-butylamine hydrochloride (6.0 g) as a white solid.

Third step, a mixture of 1-(phenyl)-butylamine (390 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with CHCl₃—CH₃OH (20:1) to yield $N^6$-[(±)-1-(phenyl)-butyl]-adenosine (225 mg) as a white solid: positive ESIMS m/z 400 [M+H]⁺ and 422 [M+Na]⁺; negative ESIMS m/z 398 [M−H]⁻ and 434 [M+Cl]⁻; ¹H NMR (300 MHz, DMSO-$d_6$): the adenosine moiety δ 8.36 (1H, s, H-2), 8.31 (1H, brs, —NH), 8.14 (1H, s, H-8), 5.85 (1H, d, J=6.0 Hz, H-1'), 5.40 (1H, m, —OH), 5.36 (1H, m, —OH), 5.15 (1H, J=4.2 Hz, —OH), 4.58 (1H, m, H-2'), 4.12 (1H, m, H-3'), 3.94 (1H, m, H-4'), 3.66 (1H, m, H-5'a), 3.56 (1H, m, H-5'b); the (±)-1-(phenyl)-butyl moiety δ 7.44 (2H, d, J=8.4 Hz, H-2", H-6"), 7.27 (2H, t, J=8.4 Hz, H-3", H-5"), 7.16 (1H, t, J=8.4 Hz, H-4"), 5.40 (1H, m, H-7"), 1.96 (1H, m, H-8"a), 1.75 (1H, m, H-8"b), 1.33 (2H, m, H-9"), 0.88 (3H, t, J=7.2 Hz, H-10"); ¹³C NMR (75 MHz, DMSO-$d_6$): the adenosine moiety δ 154.3 (s, C-6), 152.4 (d, C-2), 148.5 (s, C-4), 139.9 (d, C-8), 119.8 (s, C-5), 88.1 (d, C-1'), 86.0 (d, C-4'), 73.6 (d, C-3'), 70.8 (d, C-2'), 61.8 (t, C-5'); the (±)-1-(phenyl)-butyl moiety δ 144.5 (s, C-1"), 128.2 (d, C-2", C-6"), 126.7 (d, C-3", C-4", C-5"), 53.1 (d, C-7"), 38.1 (t, C-8"), 19.6 (t, C-9"), 13.7 (q, C-10").

Example 88: Preparation of $N^6$-[(±)-1-(4-methoxyphenyl)-butyl]-adenosine

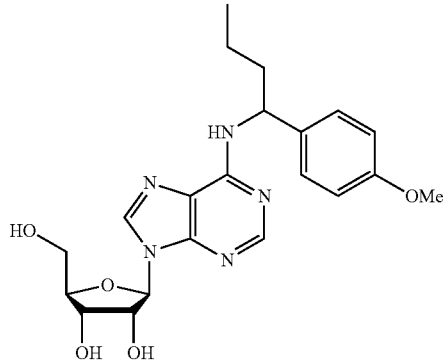

First step, hydroxyamine hydrochloride (619 mg) and NaOAc (1.47 g) were added to a solution of 1-(4-methoxyphenyl)-butanone (800 mg) in EtOH (80 ml). The reaction mixture was stirred at 60° C. for 6 h. EtOH was removed under reduced pressure. H₂O (40 ml) was added to the residue, and the resulting solution was extracted with EtOAc (3×40 ml). The EtOAc of the combined organic layer was removed by rotary evaporation under reduced pressure to yield 1-(4-methoxyphenyl)-butanone oxime (870 mg) as a pale yellowish solid.

Second step, a mixture of 1-(4-methoxyphenyl)-butanone oxime (870 mg) and concentrated HCl (2.38 ml) in EtOH (50 ml) was subjected to hydrogenation at atmospheric pressure in the presence of 10% Pd/C (90 mg). The reaction solution was filtered and the filtrate was concentrated. The residue was suspended in EtOAc, and the suspension was filtered to yield 1-(4-methoxyphenyl)-butylamine hydrochloride (965 mg) as a white solid.

Third step, a mixture of 1-(4-methoxyphenyl)-butylamine (453 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with CHCl₃—CH₃OH (20:1) to yield $N^6$-[(±)-1-(4-methoxyphenyl)-butyl]-adenosine (240 mg) as a white solid: positive ESIMS m/z 430 [M+H]⁺ and 352 [M+Na]⁺; ¹H NMR (300 MHz, DMSO-$d_6$): the adenosine moiety δ 8.37 (1H, s, H-2), 8.21 (1H, m, —NH), 8.17 (1H, brs, H-8), 5.89 (1H, d, J=6.3 Hz, H-1'), 5.48 (2H, m, 2×—OH), 5.22 (1H, d, J=4.8 Hz, —OH), 4.61 (1H, m, H-2'), 4.16 (1H, m, H-3'), 3.98 (1H, m, H-4'), 3.66 (1H, m, H-5'a), 3.56 (1H, m, H-5'b); the (±)-1-(4-methoxyphenyl)-butyl moiety δ 7.36 (2H, d, J=8.4 Hz, C-2", C-6"), 6.83 (2H, d, J=8.4 Hz, C-3", C-5"), 5.32 (1H, m, H-7"), 3.76 (3H, s, —OH₃), 1.91 (1H, m, H-8"a), 1.72 (1H, m, H-8"b), 1.24 (2H, m, H-9"), 0.86 (3H, t, J=7.5 Hz, H-10"); ¹³C NMR (75 MHz, DMSO-$d_6$): the adenosine moiety δ 154.3 (s, C-6), 152.4 (d, C-2), 148.5 (s, C-4), 140.0 (d, C-8), 119.8 (s, C-5), 88.2 (d, C-1'), 86.1 (d, C-4'), 73.6 (d, C-2'), 70.8 (d, C-3'), 61.8 (t, C-5'); the (±)-1-(4-methoxyphenyl)-butyl moiety δ 158.1 (s, C-4"), 136.3 (s, C-1"), 127.9 (d, C-2", C-6"), 113.7 (d, C-3", C-5"), 55.1 (q, —OCH₃), 52.6 (d, C-7"), 38.2 (t, C-8"), 19.6 (t, C-9"), 13.7 (q, C-10").

Example 89: Preparation of $N^6$-[(R)-(phenyl)-butyl]-adenosine

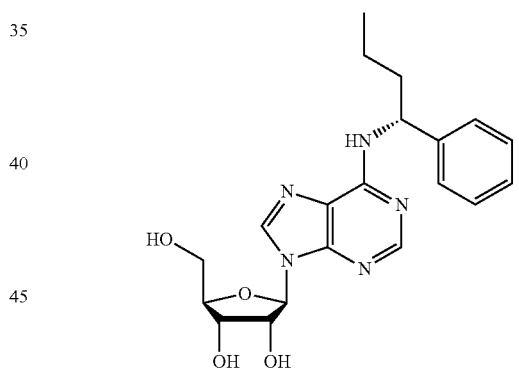

A mixture of (R)-1-(phenyl)-butylamine (470 mg) and 6-chloropurine riboside (300 mg) in EtOH (50 ml) was refluxed for 10 h. After evaporation of the reaction mixture, the residue was separated by column chromatography over Sephadex LH-20 gel and eluted with ethanol to yield $N^6$-[(R)-1-(phenyl)-butyl]-adenosine (340 mg) as a white solid: positive ESIMS m/z 400 [M+H]⁺ and 422 [M+Na]⁺; ¹H NMR (300 MHz, DMSO-$d_6$): the adenosine moiety δ 8.38 (1H, s, H-2), 8.32 (1H, d, J=7.8 Hz, —NH), 8.16 (1H, s, H-8), 5.88 (1H, d, J=6.0 Hz, H-1'), 5.39 (2H, brs, 3×—OH), 4.61 (1H, m, H-2'), 4.15 (1H, m, H-3'), 3.97 (1H, m, H-4'), 3.67 (1H, m, H-5'a), 3.55 (1H, m, H-5'b); the (R)-1-(phenyl)-butyl moiety δ 7.45 (2H, d, J=7.2 Hz, H-2", H-6"), 7.37 (2H, t, J=7.2 Hz, H-3", H-5"), 7.16 (1H, t, J=7.2 Hz, H-4"), 5.40 (1H, brm, H-7"), 1.97 (1H, m, H-8"a), 1.75 (1H, m, H-8"b), 1.34 (2H, m, H-9"), 0.88 (3H, t, J=6.6 Hz, H-10"); ¹³C NMR (75 MHz, DMSO-$d_6$): the adenosine moiety δ 154.3 (s, C-6), 152.3 (d, C-2), 148.5 (s, C-4), 139.8 (d, C-8), 119.7 (s, C-5), 88.0 (d, C-1'), 85.9 (d, C-4'), 73.5 (d, C-2'), 70.7 (d, C-3'), 61.7 (t, C-5'); the (R)-1-(phenyl)-butyl moiety δ 144.4 (s, C-1"), 128.2 (d, C-2", C-6"), 126.7 (d, C-3", C-5"), 126.6 (d, C-4"), 53.0 (d, C-7"), 38.0 (t, C-8"), 19.5 (t, C-9"), 13.6 (q, C-10").

Example 90: Preparation of $N^6$-[(S)-(phenyl)-butyl]-adenosine

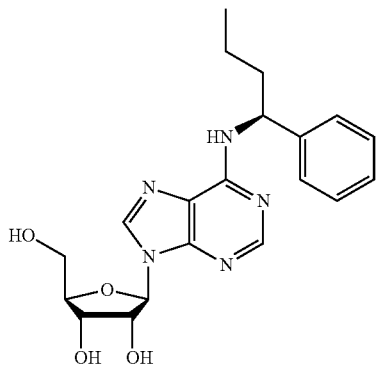

A mixture of (S)-1-(phenyl)-butylamine (470 mg) and 6-chloropurine riboside (300 mg) in EtOH (50 ml) was refluxed for 10 h. After evaporation of the reaction mixture, the residue was separated by column chromatography over Sephadex LH-20 gel and eluted with ethanol to yield $N^6$-[(S)-1-(phenyl)-butyl]-adenosine (350 mg) as a white solid: positive ESIMS ink 400 [M+H]$^+$ and 422 [M+Na]$^+$; $^1$H NMR (300 MHz, DMSO-d$_6$): the adenosine moiety δ 8.38 (1H, s, H-2), 8.32 (1H, d, J=7.8 Hz, —NH), 8.16 (1H, s, H-8), 5.88 (1H, d, J=6.3 Hz, H-1'), 5.39 (2H, brs, 3×—OH), 4.60 (1H, m, H-2'), 4.14 (1H, m, H-3'), 3.96 (1H, m, H-4'), 3.67 (1H, m, H-5'a), 3.55 (1H, m, H-5'b); the (S)-1-(phenyl)-butyl moiety δ 7.45 (2H, d, J=7.5 Hz, H-2", H-6"), 7.27 (2H, t, J=7.5 Hz, H-3", H-5"), 7.16 (1H, t, J=7.5 Hz, H-4"), 5.39 (1H, brs, H-7"), 1.97 (1H, m, H-8"a), 1.75 (1H, m, H-8"b), 1.31 (2H, m, H-9"), 0.88 (3H, t, J=7.2 Hz, H-10"); $^{13}$C NMR (75 MHz, DMSO-d$_6$): the adenosine moiety δ 154.3 (s, C-6), 152.3 (d, C-2), 148.5 (s, C-4), 139.8 (d, C-8), 119.8 (s, C-5), 88.0 (d, C-1'), 85.9 (d, C-4'), 73.5 (d, C-2'), 70.7 (d, C-3'), 61.7 (t, C-5'), the (S)-1-(phenyl)-butyl moiety δ 144.4 (s, C-1"), 128.2 (d, C-2", C-6"), 126.7 (d, C-3", C-5"), 126.6 (d, C-4"), 53.0 (d, C-7"), 38.0 (t, C-8"), 19.5 (t, C-9"), 13.6 (q, C-10").

Example 91: Preparation of $N^6$-[(±)-1-(naphthalene-2-yl)-ethyl]-adenosine

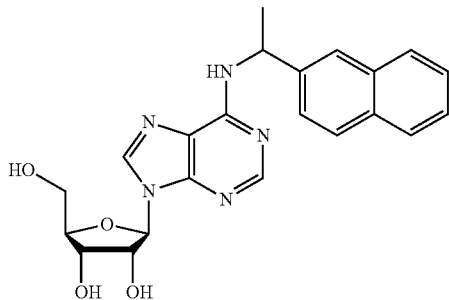

First step, hydroxyamine hydrochloride (4.1 g) and NaOAc (9.6 g) were added to a solution of 2-acetonaphthone (5 g) in EtOH (80 ml). The reaction mixture was stirred at 60° C. for 6 h. EtOH was removed under reduced pressure. H$_2$O (40 ml) was added to the residue, and the resulting solution was extracted with EtOAc (3×40 ml). The EtOAc of the combined organic layer was removed by rotary evaporation under reduced pressure to yield 2-acetonaphthone oxime (5.45 g) as a pale yellowish solid.

Second step, 2-acetonaphthone oxime (5.45 g) and concentrated HCl (15.53 ml) in EtOH (50 ml) was subjected to hydrogenation at atmospheric pressure in the presence of 10% Pd/C (623 mg). The reaction solution was filtered and the filtrate was concentrated. The residue was suspended in EtOAc, and the suspension was filtered to yield 1-(naphthalene-2-yl)-ethylamine hydrochloride (6.0 g) as a white solid.

Third step, a mixture of 1-(naphthalene-2-yl)-ethylamine (436 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with CHCl$_3$—CH$_3$OH (20:1) to yield $N^6$-[(±)-1-(naphthalene-2-yl)-ethyl]-adenosine (240 mg) as a white solid: positive ESIMS m/z 422 [M+H]$^+$, 444 [M+Na]$^+$ and 460 [M+K]$^+$; $^1$H NMR (300 MHz, DMSO-d$_6$): the adenosine moiety δ 8.43 (1H, m, —NH), 8.41 (1H, m, H-2), 8.19 (1H, s, H-8), 5.91 (1H, d, J=6.0 Hz, H-1'), 5.46 (2H, m, 2×—OH), 5.23 (1H, d, J=4.2 Hz, —OH), 4.63 (1H, m, H-2'), 4.17 (1H, m, H-3'), 4.00 (1H, m, H-4'), 3.69 (1H, m, H-5'a), 3.56 (1H, m, H-5'b); the (±)-1-(naphthalene-2-yl)-ethyl moiety δ 7.90 (1H, brs, H-1"), 7.84 (3H, m, H-4", H-5", H-8"), 7.64 (1H, d, J=8.4 Hz, H-3"), 7.43 (2H, m, H-6", H-7"), 5.68 (1H, m, H-9"), 1.63 (3H, d, J=7.2 Hz, H-10"); $^{13}$C NMR (75 MHz, DMSO-d$_6$): the adenosine moiety δ 154.0 (s, C-6), 152.4 (d, C-2), 148.7 (s, C-4), 139.9 (d, C-8), 119.9 (s, C-5), 88.1 (d, C-1'), 86.0 (d, C-4'), 73.6 (d, C-2'), 70.7 (d, C-3'), 61.7 (d, C-5'); the (±)-1-(naphthalene-2-yl)-ethyl moiety δ 142.8 (s, C-2"), 132.9 (s, C-4"a), 132.1 (s, C-8"a), 127.9 (d, C-4"), 127.7 (s, C-7"), 127.5 (d, C-6"), 126.2 (d, C-5"), 125.6 (d, C-8"), 125.2 (d, C-3"), 124.2 (d, C-1"), 49.1 (d, C-9"), 22.5 (q, C-10").

Example 92: Preparation of $N^6$-{(±)-1-[1-(phenyl)-2-(methyl)]-propyl}-adenosine First step, hydroxyamine hydrochloride (3.87 g) and NaOAc (9.20 g) were added to a solution of 1-[1-(phenyl)-2-(methyl)]-acetone (5 g) in EtOH (80 ml). The reaction mixture was stirred at 60° C. for 6 h. EtOH was removed under reduced pressure. H$_2$O (40 ml) was added to the residue, and the resulting solution was extracted with EtOAc (3×40 ml). The EtOAc of the combined organic layer was removed by rotary evaporation under reduced pressure to yield 1-[1-(phenyl)-2-(methyl)]-acetone oxime (5.5 g) as a pale yellowish solid.

Second step, 1-[1-(phenyl)-2-(methyl)]-acetone oxime (5.5 g) and concentrated HCl (18 ml) in EtOH (50 ml) was subjected to hydrogenation at atmospheric pressure in the presence of 10% Pd/C (715 mg). The reaction solution was filtered and the filtrate was concentrated. The residue was suspended in EtOAc, and the suspension was filtered to yield 1-[1-(phenyl)-2-(methyl)]-propylamine hydrochloride (6.0 g) as a white solid.

Third step, a mixture of 1-[1-(phenyl)-2-(methyl)]-propylamine (390 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with $CHCl_3$—$CH_3OH$ (20:1) to yield $N^6$-{(±)-1-[1-(phenyl)-2-(methyl)]-propyl}-adenosine (220 mg) as a white solid: positive ESIMS m/z 400 [M+H]$^+$ and 422 [M+Na]$^+$; negative ESIMS m/z 398 [M−H]$^−$; $^1$H NMR (300 MHz, DMSO-$d_6$): the adenosine moiety δ 8.35 (1H, s, H-2), 8.31 (1H, brs, —NH), 8.15 (1H, s, H-8), 5.84 (1H, d, J=6.3 Hz, H-1'), 5.39 (2H, m, 2×—OH), 5.15 (1H, d, J=4.5 Hz, —OH), 4.57 (1H, m, H-2'), 4.12 (1H, m, H-3'), 3.93 (1H, m, H-4'), 3.66 (1H, m, H-5'a), 3.55 (1H, m, H-5'b); the (±)-1-[1-(phenyl)-2-(methyl)]-propyl moiety δ 7.47 (2H, d, J=7.5 Hz, H-2'', H-6''), 7.28 (2H, t, J=7.5 Hz, H-3'', H-5''), 7.17 (1H, t, J=7.5 Hz, H-4''), 5.00 (1H, m, H-7''), 2.27 (1H, m, H-8''), 1.01 (3H, d, J=6.6 Hz, H-9''), 0.70 (3H, d, J=6.6 Hz, H-10''); $^{13}$CNMR (75 MHz, DMSO-$d_6$): the adenosine moiety δ 154.4 (s, C-6), 152.3 (d, C-2), 148.5 (s, C-4), 139.8 (d, C-8), 119.7 (s, C-5), 88.1 (d, C-1'), 86.0 (d, C-4'), 73.6 (d, C-2'), 70.7 (d, C-3'), 61.7 (t, C-5'); the (±)-1-[1-(phenyl)-2-(methyl)]-propyl moiety δ 143.3 (s, C-1''), 128.1 (d, C-2'', C-6''), 127.6 (d, C-3'', C-5''), 126.7 (d, C-4''), 60.3 (d, C-7''), 32.5 (t, C-8''), 20.1 (q, C-9'', C-10'').

Example 93: Preparation of $N^6$-[(±)-1-(cyclohexylphenyl)-methyl]-adenosine

EtOAc of the combined organic layer was removed by rotary evaporation under reduced pressure to yield benzoylcyclohexane oxime (3.25 g) as a pale yellowish solid.

Second step, benzoylcyclohexane oxime (3.25 g) and concentrated HCl (8.45 ml) in EtOH (50 ml) was subjected to hydrogenation at atmospheric pressure in the presence of 10% Pd/C (339 mg). The reaction solution was filtered and the filtrate was concentrated. The residue was suspended in EtOAc, and the suspension was filtered to yield 1-(cyclohexylphenyl)-methylamine hydrochloride (3.5 g) as a white solid.

Third step, a mixture of 1-(cyclohexylphenyl)-methylamine (474 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with $CHCl_3$—$CH_3OH$ (20:1) to yield $N^6$-[(±)-1-(cyclohexylphenyl)-methyl]-adenosine (245 mg) as a white solid: positive ESIMS m/z 440 [M+H]$^+$, 462 [M+Na]$^+$ and 478 [M+K]$^+$; negative ESIMS m/z 438 [M−H]$^−$ and 474 [M+Cl]$^−$; $^1$H NMR (300 MHz, DMSO-$d_6$): the adenosine moiety δ 8.35 (1H, s, H-2), 8.28 (1H, brd, J=7.5 Hz, —NH), 8.16 (1H, s, H-8), 5.87 (1H, d, J=6.0 Hz, H-1'), 5.43 (2H, m, 2×—OH), 5.18 (1H, d, J=4.2 Hz, —OH), 4.59 (1H, m, H-2'), 4.14 (1H, m, H-3'), 3.95 (1H, m, H-4'), 3.66 (1H, m, H-5'a), 3.55 (1H, m, H-5'b); the (±)-1-(cyclohexylphenyl)-methyl moiety δ 7.45 (2H, d, 7.8 Hz, H-2'', H-6''), 7.27 (2H, t, J=7.8 Hz, H-3'', H-5''), 7.17 (1H, t, J=7.8 Hz, H-4''), 5.10 (1H, m, H-7''), 1.99-0.85 (11H, m, H-1'''~H-6'''); $^{13}$C NMR (75 MHz, DMSO-$d_6$): the adenosine moiety δ 154.4 (s, H-6), 152.3 (d, C-2), 148.4 (s, C-4), 139.8 (d, C-8), 119.7 (s, C-5), 88.1 (d, C-1'), 85.9 (d, C-4'), 73.5 (d, C-2'), 70.7 (d, C-3'), 61.7 (t, C-5'); the (±)-1-(cyclohexylphenyl)-methyl moiety δ 142.9 (s, C-1''), 128.1 (d, C-2'', C-6''), 127.7 (d, C-3'', C-5''), 126.7 (d, C-4''), 58.8 (d, C-7''), 41.5 (d, C-1'''), 30.0 (t, C-2''', C-6'''), 26.0 (t, C-4'''), 25.4 (t, C-3''', C-5''').

Example 94: Preparation of $N^6$-[(±)-1-(1,2-diphenyl)-ethyl]-adenosine

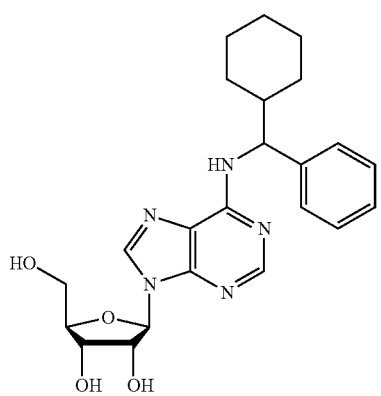

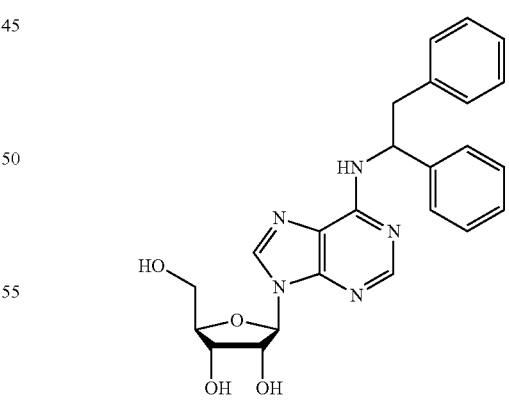

First step, hydroxyamine hydrochloride (2.20 g) and NaOAc (5.23 g) were added to a solution of benzoylcyclohexane (3 g) in EtOH (80 ml). The reaction mixture was stirred at 60° C. for 6 h. EtOH was removed under reduced pressure. H$_2$O (40 ml) was added to the residue, and the resulting solution was extracted with EtOAc (3×40 ml). The First step, hydroxyamine hydrochloride (3.52 g) and NaOAc (8.36 g) were added to a solution of 2-phenylacetophenone (5 g) in EtOH (80 ml). The reaction mixture was stirred at 60° C. for 6 h. EtOH was removed under reduced pressure. H$_2$O (40 ml) was added to the residue, and the resulting solution was extracted with EtOAc (3×40 ml). The EtOAc of the combined organic layer was removed by rotary evaporation under reduced pressure to yield 2-phenylacetophenone oxime (5.39 g) as a pale yellowish solid.

Second step, 2-phenylacetophenone oxime (5.39 g) and concentrated HCl (13.47 ml) in EtOH (50 ml) was subjected to hydrogenation at atmospheric pressure in the presence of 10% Pd/C (541 mg). The reaction solution was filtered and the filtrate was concentrated. The residue was suspended in EtOAc, and the suspension was filtered to yield 1-(1,2-diphenyl)-ethylamine hydrochloride (5.9 g) as a white solid.

Third step, a mixture of 1-(1,2-diphenyl)-ethylamine (490 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with $CHCl_3$—$CH_3OH$ (20:1) to yield $N^6$-[(±)-1-(1,2-diphenyl)-ethyl]adenosine (250 mg) as a white solid: positive ESIMS m/z 448 [M+H]$^+$, 470 [M+Na]$^+$ and 486 [M+K]$^+$; negative ESIMS m/z 446 [M−H]$^-$ and 482 [M+Cl]$^-$; $^1$H NMR (300 MHz, DMSO-d$_6$): the adenosine moiety δ 8.48 (1H, d, J=8.7 Hz, —NH), 8.34 (1H, s, H-2), 8.08 (1H, brs, H-8), 5.82 (1H, d, J=5.7 Hz, H-1'), 5.39 (1H, m, —OH), 5.32 (1H, m, —OH), 5.14 (1H, d, J=4.5 Hz, —OH), 4.55 (1H, m, H-2'), 4.11 (1H, m, H-3'), 3.92 (1H, m, H-4'), 3.65 (1H, m, H-5'a), 3.52 (1H, m, H-5'b); the (±)-1-(1,2-diphenyl)-ethyl moiety δ 7.51 (2H, d, J=7.8 Hz, H-2", H-6"), 7.32 (2H, d, J=7.8 Hz, H-2''', H-6'''), 7.29 (2H, t, J=7.8 Hz, H-3", H-5"), 7.26 (1H, t J=7.8 Hz, H-4"), 7.21 (2H, J=7.8 Hz, H-3''', H-5'''), 7.10 (1H, J=7.8 Hz, H-4'''), 5.64 (1H, m, H-7"), 3.09 (1H, m, H-7'''a), 3.05 (1H, m, H-7'''b); $^{13}$C NMR (75 MHz, DMSO-d$_6$): the adenosine moiety δ 154.2 (s, C-6), 152.4 (d, C-2), 148.5 (s, C-4), 140.0 (d, C-8), 119.9 (s, C-5), 88.2 (d, C-1'), 86.1 (d, C-4'), 73.7 (d, C-2'), 70.8 (d, C-3'), 61.8 (t, C-5'); the (±)-1-(1,2-diphenyl)-ethyl moiety δ 144.0 (s, C-1"), 139.3 (s, C-1'''), 129.3 (d, C-2''', C-6'''), 128.4 (d, C-2", C-6"), 128.3 (d, C-3''', C-5''', C-4'''), 126.9 (d, C-3", C-5"), 126.3 (d, C-4"), 55.2 (d, C-7"), 42.1 (d, C-7''').

Example 95: Preparation of $N^6$-(diphenylmethyl)-adenosine

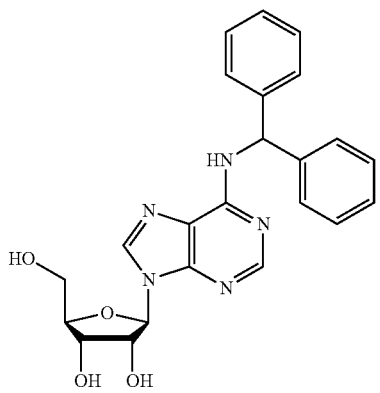

First step, hydroxyamine hydrochloride (670 mg) and NaOAc (900 mg) were added to a solution of benzophenone (1.0 g) in EtOH (80 ml). The reaction mixture was stirred at 60° C. for 6 h. EtOH was removed under reduced pressure. H$_2$O (40 ml) was added to the residue, and the resulting solution was extracted with EtOAc (3×40 ml). The EtOAc of the combined organic layer was removed by rotary evaporation under reduced pressure to yield benzophenone oxime (900 mg) as a pale yellowish solid.

Second step, benzophenone oxime (900 mg) and concentrated HCl (1.84 ml) in EtOH (50 ml) was subjected to hydrogenation at atmospheric pressure in the presence of 10% Pd/C (100 mg). The reaction solution was filtered and the filtrate was concentrated. The residue was suspended in EtOAc, and the suspension was filtered to yield diphenylmethylamine hydrochloride (2.17 g) as a white solid.

Third step, a mixture of diphenylmethylamine (583 mg, the hydrochloride), 6-chloropurine riboside (200 mg) and triethylamine (9 ml) in PrOH (60 ml) was heated to 70° C. and reacted for 8 h. After evaporation of the reaction mixture, the residue was separated by column chromatography over silica gel and eluted with $CHCl_3$—$CH_3OH$ (20:1) to yield $N^6$-(diphenylmethyl)-adenosine (240 mg) as a white solid: positive ESIMS m/z 434 [M+H]$^+$ and 456 [M+Na]$^+$; negative ESIMS m/z 432 [M−H]$^-$; $^1$H NMR (300 MHz, DMSO-d$_6$): the adenosine moiety δ 8.72 (1H, d, J=9.3 Hz, —NH), 8.42 (1H, s, H-2), 8.23 (1H, s, H-8), 5.89 (1H, d, J=6.0 Hz, H-1'), 5.44 (1H, d, J=5.7 Hz, —OH), 5.33 (1H, m, —OH), 5.17 (1H, d, J=4.2 Hz, —OH), 4.60 (1H, m, H-2'), 4.15 (1H, m, H-3'), 3.95 (1H, m, H-4'), 3.67 (1H, m, H-5'a), 3.54 (1H, m, H-5'b); the diphenylmethyl moiety δ 7.43 (4H, d, J=7.5 Hz, H-2", H-2''', H-6", H-6'''), 7.31 (4H, t, J=7.5 Hz, H-3", H-3''', H-5", H-5'''), 7.23 (2H, t, J=7.5 Hz, H-4", H-4'''), 6.82 (1H, brs, H-7"); $^{13}$C NMR (75 MHz, DMSO-d$_6$): the adenosine moiety δ 153.9 (s, C-6), 152.5 (d, C-2), 149.0 (s, C-4), 140.3 (d, C-8), 119.9 (s, C-5), 88.2 (d, C-1'), 86.1 (d, C-4'), 73.8 (d, C-2'), 70.8 (d, C-3'), 61.8 (t, C-5'); the diphenylmethyl moiety δ 142.6 (s, C-1", C-1'''), 128.6 (d, C-2", C-6", C-2''', C-6'''), 127.8 (d, C-3", C-5", C-3''', C-5'''), 127.2 (d, C-4", C-4'''), 57.0 (d, C-7").

Example 96: Preparation of $N^6$-[(±)-(6-methoxy-1,2,3,4-tetrahydro-naphthalene-1-yl)]-adenosine

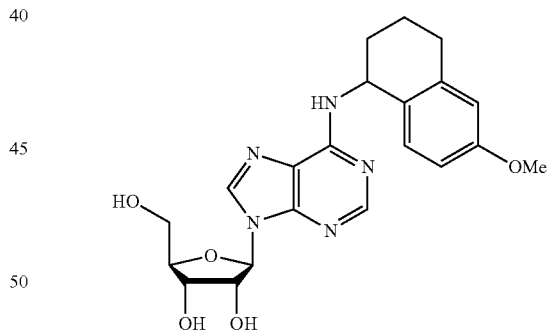

First step, hydroxyamine hydrochloride (2.60 g) and NaOAc (3.40 g) were added to a solution of 6-methoxy-1,2,3,4-tetrahydro-1-tetralone (3.52 g) in EtOH (80 ml). The reaction mixture was stirred at room temperature for 6 h. EtOH was removed under reduced pressure. H$_2$O (40 ml) was added to the residue, and the resulting solution was extracted with EtOAc (3×40 ml). The EtOAc of the combined organic layer was removed by rotary evaporation under reduced pressure to yield 6-methoxy-1,2,3,4-tetrahydro-1-tetralone oxime (3.74 g) as a pale yellowish solid.

Second step, 6-methoxy-1,2,3,4-tetrahydro-1-tetralone oxime (1.87 g) and concentrated HCl (4 ml) in EtOH (50 ml) was subjected to hydrogenation at atmospheric pressure in the presence of 10% Pd/C (150 mg). The reaction solution was filtered and the filtrate was concentrated. The residue was suspended in EtOAc, and the suspension was filtered to yield (±)-6-methoxy-1,2,3,4-tetrahydro-naphthalene-1-ylamine hydrochloride (2.13 g) as a white solid.

Third step, a mixture of (±)-6-methoxy-1,2,3,4-tetrahydro-naphthalene-1-ylamine (298 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with $CHCl_3$—$CH_3OH$ (20:1) to yield $N^6$-[(±)-(6-methoxy-1,2,3,4-tetrahydro-naphthalene-1-yl)]-adenosine (240 mg) as a white solid: positive ESIMS m/z 428 [M+H]$^+$ and 450 [M+Na]$^+$; negative ESIMS m/z 462 [M+Cl]$^-$; $^1$H NMR (300 MHz, DMSO-$d_6$): the adenosine moiety δ 8.35 (1H, s, H-2), 8.24 (1H, brs, H-8), 7.96 (1H, d, J=8.7 Hz, —NH), 5.89 (1H, d, J=6.3 Hz, H-1'), 5.44 (1H, d, J=6.9 Hz, —OH), 5.40 (1H, m, —OH), 5.18 (1H, d, J=4.8 Hz, —OH), 4.62 (1H, m, H-2'), 4.14 (1H, m, H-3'), 3.96 (1H, m, H-4'), 3.66 (1H, m, H-5'a), 3.55 (1H, m, H-5'b); the (±)-(6-methoxy-1,2,3,4-tetrahydro-naphthalene-1-yl) moiety δ 7.04 (1H, d, J=9.0 Hz, H-8''), 6.65 (2H, m, H-5'', H-7''), 5.58 (1H, m, H-1''), 3.69 (3H, m, —OCH$_3$), 2.73 (2H, m, H-4''), 1.96 (2H, m, H-3''), 1.94, 1.72 (1H, m, each, H-2''); $^{13}$C NMR (75 MHz, DMSO-$d_6$): the adenosine moiety δ 154.4 (s, C-6), 152.6 (d, C-2), 148.6 (s, C-4), 139.9 (d, C-8), 119.6 (s, C-5), 88.2 (d, C-1'), 86.1 (d, C-4'), 73.6 (d, C-2'), 70.9 (d, C-3'), 61.8 (t, C-5'); the (±)-(6-methoxy-1,2,3,4-tetrahydro-naphthalene-1-yl) moiety δ 158.0 (s, C-6''), 138.7 (s, C-4''a), 130.1 (d, C-8''), 129.1 (d, C-8''a), 113.1 (d, C-5''), 112.4 (d, C-7''), 56.1 (q, —OCH$_3$), 47.2 (d, C-1''), 29.9 (t, C-2''), 29.4 (t, C-3''), 20.6 (t, C-4'').

Example 97: Preparation of $N^6$-[(±)-(5-hydroxy-1,2,3,4-tetrahydro-naphthalene-1-yl)]-adenosine was suspended in EtOAc, and the suspension was filtered to yield (±)-5-hydroxy-1,2,3,4-tetrahydro-naphthalene-1-ylamine hydrochloride (590 mg) as a white solid.

Third step, a mixture of (±)-5-hydroxy-1,2,3,4-tetrahydro-naphthalene-1-ylamine (279 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with $CHCl_3$—$CH_3OH$ (20:1) to yield $N^6$-[(±)-(5-hydroxy-1,2,3,4-tetrahydro-naphthalene-1-yl)]-adenosine (230 mg) as a white solid: positive ESIMS m/z 414 [M+H]$^+$ and 436 [M+Na]$^+$; negative ESIMS m/z 412 [M–H]$^-$ and 448 [M+Cl]$^-$; $^1$H NMR (300 MHz, DMSO-$d_6$): the adenosine moiety δ 8.34 (1H, s, H-2), 8.24 (1H, s, H-8), 7.96 (1H, d, J=8.1 Hz, —NH), 5.89 (1H, d, J=6.0 Hz, H-1'), 5.45 (1H, d, J=5.7 Hz, OH), 5.43 (1H, m, —OH), 5.18 (1H, d, J=4.5 Hz, —OH), 4.63 (1H, m, H-2'), 4.14 (1H, m, H-3'), 3.96 (1H, m, H-4'), 3.67 (1H, m, H-5'a), 3.55 (1H, m, H-5'b); the (±)-5-hydroxy-1,2,3,4-tetrahydro-naphthalene-1-yl moiety δ 9.24 (1H, s, —OH), 6.87 (1H, t, J=7.8 Hz, H-7''), 6.64 (1H, d, J=7.8 Hz, H-8''), 6.61 (1H, d, J=7.8 Hz, H-6''), 5.58 (1H, m, H-1''), 2.57 (2H, m, H-4''), 1.94 (2H, m, H-3''), 1.94, 1.70 (1H, m, each; H-2''); $^{13}$C NMR (75 MHz, DMSO-$d_6$): the adenosine moiety δ 154.4 (s, C-6), 152.6 (d, C-2), 148.6 (s, C-4), 140.0 (d, C-8), 119.6 (s, C-5), 88.2 (d, C-1'), 86.1 (d, C-4'), 73.6 (d, C-2'), 70.9 (d, C-3'), 61.8 (t, C-5'); the (±)-5-hydroxy-1,2,3,4-tetrahydro-naphthalene-1-yl moiety δ 154.8 (s, C-5''), 139.3 (d, C-7''), 125.9 (d, C-8''), 124.3 (s, C-8''a), 118.2 (s, C-4''a), 112.6 (d, C-6''), 47.9 (d, C-1''), 29.4 (t, C-2''), 23.1 (t, C-3''), 20.2 (t, C-4'').

Example 98: Preparation of $N^6$-(fluorene-9-yl)-adenosine

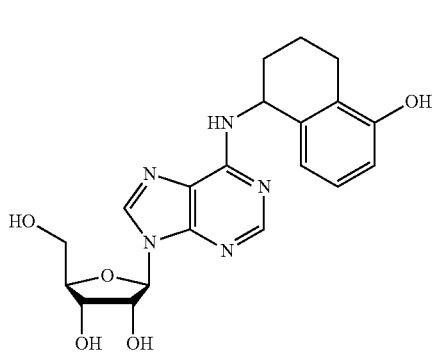

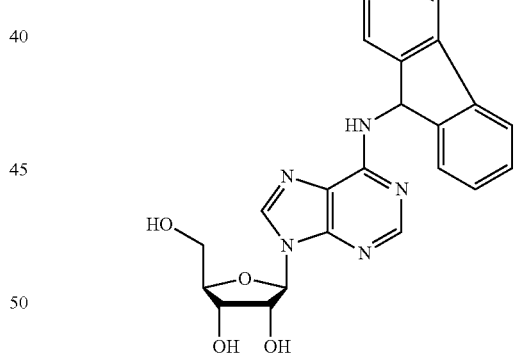

First step, hydroxyamine hydrochloride (337 mg) and NaOAc (507 mg) were added to a solution of 5-hydroxy-1,2,3,4-tetrahydro-1-tetralone (500 mg) in EtOH (80 ml). The reaction mixture was stirred at room temperature for 6 h. EtOH was removed under reduced pressure. H$_2$O (40 ml) was added to the residue, and the resulting solution was extracted with EtOAc (3×40 ml). The EtOAc of the combined organic layer was removed by rotary evaporation under reduced pressure to yield 5-hydroxy-1,2,3,4-tetrahydro-1-tetralone oxime (531 mg) as a pale yellowish solid.

Second step, 5-hydroxy-1,2,3,4-tetrahydro-1-tetralone oxime (531 mg) and concentrated HCl (4 ml) in EtOH (50 ml) was subjected to hydrogenation at atmospheric pressure in the presence of 10% Pd/C (50 mg). The reaction solution was filtered and the filtrate was concentrated. The residue First step, 9-fluorenone oxime (400 mg) and concentrated HCl (0.86 ml) in EtOH (50 ml) was subjected to hydrogenation at atmospheric pressure in the presence of 10% Pd/C (33 mg). The reaction solution was filtered and the filtrate was concentrated. The residue was suspended in EtOAc, and the suspension was filtered to yield fluorenamine hydrochloride (240 mg) as a white solid.

Second step, a mixture of fluorenamine (304 mg, the hydrochloride), 6-chloropurine riboside (200 mg) and triethylamine (3 ml) in PrOH (60 ml) was heated to 70° C. and reacted for 8 h. After evaporation of the reaction mixture, the residue was separated by column chromatography over silica gel and eluted with $CHCl_3$—$CH_3OH$ (20:1) to yield $N^6$-(fluorene-9-yl)-adenosine (208 mg) as a white solid:

positive ESIMS m/z 432 [M+H]+ and 454 [M+Na]+; negative ESIMS m/z 430 [M−H]− and 466 [M+Cl]−; $^1$H NMR (300 MHz, DMSO-$d_6$): the adenosine moiety δ 8.46 (1H, d, J=8.1 Hz, —NH), 8.38 (2H, s, H-2, H-8), 5.94 (1H, d, J=5.4 Hz, H-1'), 5.52 (1H, d, J=5.7 Hz, —OH), 5.44 (1H, m, —OH), 5.25 (1H, d, J=4.8 Hz, —OH), 4.66 (1H, m, H-2'), 4.19 (1H, m, H-3'), 4.01 (1H, m, H-4'), 3.67 (1H, m, H-5'a), 3.56 (1H, m, H-5'b); the 9-fluorene moiety δ 7.86 (2H, d, J=7.5 Hz, H-4", H-5"), 7.46 (2H, d, J=7.5 Hz, H-1", H-8'"), 7.40 (2H, t, J=7.5 Hz, H-2", H-7"), 7.26 (2H, t, J=7.5 Hz, H-3", H-6'"), 6.69 (1H, d, J=8.1 Hz, H-9"); $^{13}$C NMR (75 MHz, DMSO-$d_6$): the adenosine moiety δ 155.1 (s, C-6), 152.4 (d, C-2), 148.8 (s, C-4), 140.3 (d, C-8), 120.2 (s, C-5), 88.1 (d, C-1'), 86.0 (d, C-4'), 73.6 (d, C-2'), 70.7 (d, C-3'), 61.7 (t, C-5'); the 9-fluorene moiety δ 145.0 (s, C-8"a, C-9"a), 140.3 (s, C-4"a, C-5"a), 128.3 (d, C-1", C-8"), 127.5 (d, C-3", C-6"), 124.8 (d, C-2", C-7"), 120.2 (d, C-4", C-5"), 54.9 (d, C-9").

Example 99: Preparation of N$^6$-{(1S,2R)-[2-hydroxy-(1,2-diphenyl)]-ethyl}-adenosine

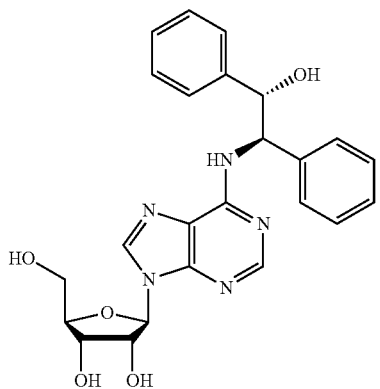

A mixture of (1S,2R)-2-amino-1,2-diphenylethanol (896 mg, the hydrochloride), 6-chloropurine riboside (300 mg) in EtOH (50 ml) was refluxed for 18 h. After evaporation of the reaction mixture, the residue was separated by column chromatography over Sephadex LH-20 gel and eluted with ethanol to yield N$^6$-{(1S,2R)-[2-hydroxy-(1,2-diphenyl)]-ethyl}-adenosine (400 mg) as a white solid: positive ESIMS m/z 464 [M+H]+, 486 [M+Na]+ and 502 [M+K]+; negative ESIMS m/z 462 [M−H]− and 498 [M+Cl]−; $^1$H NMR (300 MHz, DMSO-$d_6$): the adenosine moiety δ 8.33 (1H, s, H-2), 8.11 (1H, s, H-8), 8.06 (1H, brs, —NH), 5.82 (1H, d, J=6.0 Hz, H-1'), 5.40 (1H, d, J=6.0 Hz, —OH), 5.31 (1H, m, —OH), 5.14 (1H, d, J=4.5 Hz, —OH), 4.53 (1H, m, H-2'), 4.08 (1H, m, H-3'), 3.91 (1H, m, H-4'), 3.62 (1H, m, H-5'a), 3.51 (1H, m, H-5'b); the (1S,2R)-[2-hydroxy-(1,2-diphenyl)]-ethyl moiety δ 7.40 (4H, m, H-2", H-6", H-2'", H-6'"), 7.22 (4H, m, H-3", H-5", H-3'", H-5'"), 7.15 (2H, t, J=7.5 Hz, H-4", H-4'"), 5.53 (1H, m, —OH), 5.51 (1H, m, H-7"), 5.08 (1H, m, H-7'"); $^{13}$C NMR (75 MHz, DMSO-$d_6$): the adenosine moiety δ 153.6 (s, C-6), 152.2 (d, C-2), 148.4 (s, C-4), 140.0 (d, C-8), 119.7 (s, C-5), 88.0 (d, C-1'), 85.9 (d, C-4'), 73.6 (d, C-2'), 70.7 (d, C-3'), 61.6 (t, C-5'); the (1S,2R)-[2-hydroxy-(1,2-diphenyl)]-ethyl moiety δ 143.4 (s, C-1'"), 141.2 (s, C-1"), 128.4 (C-2'", C-6'"), 127.6 (d, C-2", C-6"), 127.6 (d, C-3'", C-5'"), 127.0 (d, C-3", C-5", C-4'"), 126.7 (d, C-4"), 74.4 (d, C-7'"), 59.2 (d, C-7").

Example 100: Preparation of N$^6$-{(1R,2S)-[2-hydroxy-(1,2-diphenyl)]-ethyl}-adenosine

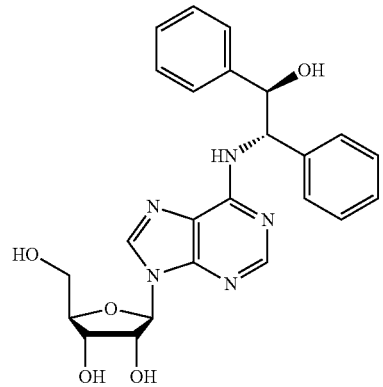

A mixture of (1R,2S)-2-amino-1,2-diphenylethanol (896 mg, the hydrochloride), 6-chloropurine riboside (300 mg) in EtOH (50 ml) was refluxed for 18 h. After evaporation of the reaction mixture, the residue was separated by column chromatography over Sephadex LH-20 gel and eluted with ethanol to yield N$^6$-{(1R,2S)-[2-hydroxy-(1,2-diphenyl)]-ethyl}-adenosine (390 mg) as a white solid: positive ESIMS m/z 464 [M+H]+; negative ESIMS m/z 462 [M−H]− and 498 [M+Cl]−; $^1$H NMR (300 MHz, DMSO-$d_6$): the adenosine moiety δ 8.33 (1H, s, H-2), 8.10 (1H, s, H-8), 8.07 (1H, brs, —NH), 5.81 (1H, d, J=6.0 Hz, H-1'), 5.38 (1H, d, J=6.0 Hz, —OH), 5.31 (1H, m, —OH), 5.14 (1H, d, J=4.5 Hz, —OH), 4.54 (1H, m, H-2'), 4.09 (1H, m, H-3'), 3.91 (1H, m, H-4'), 3.64 (1H, m, H-5'a), 3.53 (1H, m, H-5'b); the (1R,2S)-[2-hydroxy-(1,2-diphenyl)]-ethyl moiety δ 7.39 (4H, m, H-2", H-6", H-2'", H-6'"), 7.22 (4H, m, H-3", H-5", H-3'", H-5'"), 7.16 (2H, t, J=7.5 Hz, H-4", H-4'"), 5.52 (1H, m, —OH), 5.48 (1H, m, H-7"), 5.08 (1H, m, H-7'"); $^{13}$C NMR (75 MHz, DMSO-$d_6$): the adenosine moiety δ 153.6 (s, C-6), 152.2 (d, C-2), 148.4 (s, C-4), 140.1 (d, C-8), 119.8 (s, C-5), 88.1 (d, C-1'), 86.0 (d, C-4'), 73.5 (d, C-2'), 70.7 (d, C-3'), 61.7 (t, C-5'); the (1R,2S)-[2-hydroxy-(1,2-diphenyl)]-ethyl moiety δ 143.4 (s, C-1'"), 141.2 (s, C-1"), 128.4 (C-2'", C-6'"), 127.7 (d, C-2", C-6"), 127.6 (d, C-3'", C-5'"), 127.0 (d, C-3", C-5", C-4'"), 126.7 (d, C-4"), 74.4 (d, C-7'"), 59.2 (d, C-7").

Example 101: Preparation of N$^6$-{(1R,2S)-2-[1-hydroxy-1-(3-hydroxyphenyl)]-propyl}-adenosine

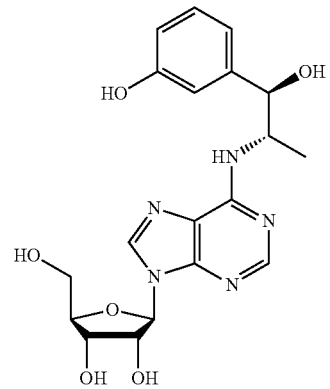

A mixture of Metaraminol bitartrate [(−)-α-(1-amino-ethyl)-3-hydroxy-phenylmethanol](400 mg, as the bitartrate), 6-chloropurine riboside (241 mg) and triethylamine (3.6 ml) in EtOH (50 ml) was refluxed for 18 h. After evaporation of the reaction mixture, the residue was separated by column chromatography over silica gel and eluted with CHCl$_3$—CH$_3$OH (4:1) to yield N$^6$-{(1R,2S)-2-[1-hydroxy-1-(3-hydroxyphenyl)]-propyl}-adenosine (350 mg) as a pale yellowish solid: positive ESIMS m/z 418 [M+H]$^+$ and 440 [M+Na]$^+$; negative ESIMS m/z 416 [M−H]$^-$ and 452[M+Cl]$^-$; $^1$H NMR (300 MHz, DMSO-d$_6$): the adenosine moiety δ 8.35 (1H, s, H-2), 8.22 (1H, s, H-8), 7.33 (1H, brd, J=8.7 Hz, —NH), 5.87 (1H, d, J=5.7 Hz, H-1'), 5.43 (1H, d, J=6.3 Hz, —OH), 5.39 (1H, m, —OH), 5.17 (1H, d, J=4.5 Hz, —OH), 4.74 (1H, t, J=4.5 Hz, —OH), 4.59 (1H, m, H-2'), 4.13 (1H, m, H-3'), 3.95 (1H, m, H-4'), 3.66 (1H, m, H-5'a), 3.55 (1H, m, H-5'7), the (1R,2S)-2-[1-hydroxy-1-(3-hydroxyphenyl)]-propyl moiety δ 9.25 (1H, s, —OH), 7.07 (1H, t, J=7.5 Hz, H-5"), 6.84 (2H, m, H-2", H-6"), 6.56 (1H, dd, J=7.5 Hz, 1.5 Hz, H-4"), 5.42 (m, 1H, H-7"), 4.90 (1H, m, H-8"), 1.05 (1H, d, J=6.6 Hz, H-9"); $^{13}$C NMR (75 MHz, DMSO-d$_6$): the adenosine moiety δ 154.0 (s, C-6), 152.5 (d, C-2), 148.4 (s, C-4), 139.9 (d, C-8), 119.9 (s, C-5), 88.1 (d, C-1'), 86.0 (d, C-4'), 73.6 (d, C-2'), 70.8 (d, C-3'), 61.8 (t, C-5'); the (1R,2S)-2-[1-hydroxy-1-(3-hydroxyphenyl)]-propyl moiety δ 157.1 (s, C-3"), 145.1 (s, C-1"), 128.9 (d, C-5"), 117.0 (d, C-6"), 113.7 (d, C-2"), 113.2 (d, C-4"), 73.9 (d, C-7"), 51.3 (d, C-8"), 14.4 (q, C-9").

Example 102: Preparation of N-(6-adenosine)-(L)-phenylalanine

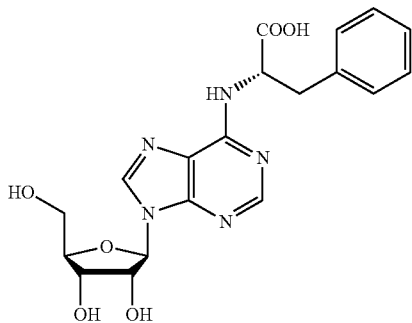

A mixture of L-phenylalanine (231 mg), 6-chloropurine riboside (200 mg) and K$_2$CO$_3$ (192 mg) in a mixed solvent of 1,4-dioxane and H$_2$O (1:1, 6 ml) was refluxed for 8 h. HOAc was added to neutralized the excess K$_2$CO$_3$. After evaporation of the reaction mixture, the residue was separated by column chromatography over reverse phase ODS gel and eluted with CH$_3$OH/H$_2$O (0%, 15%, 45%) to yield N-(6-adenosine)-(L)-phenylalanine (240 mg) as a pale yellowish solid: positive ESIMS m/z 416 [M+H]$^+$, 438 [M+Na]$^+$ and 454 [M+K]$^+$, negative ESIMS m/z 414 [M−H]$^-$ and 450 [M+Cl]$^-$; $^1$H NMR (300 MHz, DMSO-d$_6$): the adenosine moiety δ 8.36 (1H, s, H-2), 8.18 (1H, s, H-8), 7.80 (1H, brs, —NH), 5.86 (1H, d, J=6.0 Hz, H-1'), 5.45 (1H, m, —OH), 5.33 (1H, m, —OH), 5.17 (1H, m, —OH), 4.59 (1H, m, H-2'), 4.13 (1H, m, H-3'), 3.94 (1H, m, H-4'), 3.65 (1H, m, H-5'a), 3.52 (1H, m, H-5'b); the L-phenylalanine moiety δ 7.26 (2H, d, J=6.9 Hz, H-2", H-6"), 7.22 (2H, t, J=6.9 Hz, H-3", H-5"), 7.12 (1H, t, J=6.9 Hz, H-4"), 4.87 (1H, m, H-7"), 3.23 (2H, m, H-7"); $^{13}$C NMR (75 MHz, DMSO-d$_6$): the adenosine moiety δ 154.4 (s, C-6), 152.3 (d, C-2), 148.7 (s, C-4), 140.3 (d, C-8), 119.9 (s, C-5), 88.2 (d, C-1'), 86.1 (d, C-4'), 73.7 (d, C-2'), 70.8 (d, C-3'), 61.8 (t, C-5'); the (L)-phenylalanine moiety δ 173.7 (s, C-9"), 138.4 (s, C-1"), 129.2 (d, C-2", C-6"), 128.3 (d, C-3", C-5"), 126.5 (d, C-4"), 54.8 (d, C-8"), 36.4 (t, C-7").

Example 103: Preparation of N-(6-adenosine)-(D)-phenylalanine

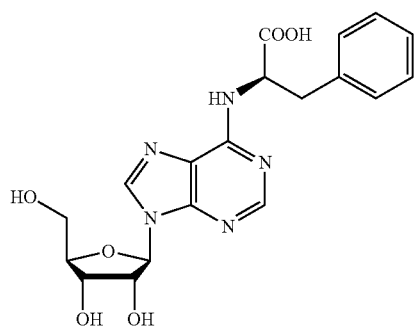

A mixture of D-phenylalanine (231 mg), 6-chloropurine riboside (200 mg) and K$_2$CO$_3$ (192 mg) in a mixed solvent of 1,4-dioxane and H$_2$O (1:1, 6 ml) was refluxed for 8 h. HOAc was added to neutralize the excess K$_2$CO$_3$. After evaporation of the reaction mixture, the residue was separated by column chromatography over reverse phase ODS gel and eluted with CH$_3$OH/H$_2$O (0%, 15%, 45%) to yield N-(6-adenosine)-(D)-phenylalanine (235 mg) as a pale yellowish solid: negative ESIMS m/z 414 [M−H]$^-$; $^1$H NMR (300 MHz, DMSO-d$_6$): the adenosine moiety δ 8.27 (1H, s, H-2), 8.21 (1H, s, H-8), 5.85 (1H, d, J=6.3 Hz, H-1'), 5.63 (1H, m, —OH), 5.46 (1H, m, —OH), 5.34 (1H, m, —OH), 4.60 (1H, m, H-2'), 4.26 (1H, m, H-3'), 3.94 (1H, m, H-4'), 3.66 (1H, m, H-5'a), 3.53 (1H, m, H-5'b); the (D)-phenylalanine moiety δ 7.04 (5H, m, H-2"~H-6"), 4.13 (1H, m, H-8"), 3.22 (1H, m, H-7"a), 3.18 (1H, m, H-7"b); $^{13}$C NMR (75 MHz, DMSO-d$_6$): the adenosine moiety δ 153.7 (s, C-6), 152.6 (d, C-2), 148.1 (s, C-4), 139.7 (d, C-8), 119.8 (s, C-5), 88.2 (d, C-1'), 86.0 (d, C-4'), 73.8 (d, C-2'), 70.6 (d, C-3'), 61.8 (t, C-5'); the (D)-phenylalanine moiety δ 173.4 (s, C-9"), 139.0 (s, C-1"), 129.7 (d, C-2", C-6"), 127.7 (d, C-3", C-5"), 125.7 (d, C-4"), 55.9 (d, C-8"), 37.0 (t, C-7").

Example 104: Preparation of N-(6-adenosine)-(L)-phenylalanine ethyl ester

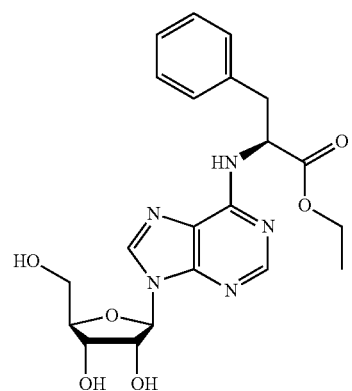

A mixture of L-phenylalanine (322 mg, as the hydrochloride), 6-chloropurine riboside (200 mg) and triethylamine (3 ml) in PrOH (50 ml) was heated to 80° C. for 10 h. After evaporation of the reaction mixture, the residue was separated by column chromatography over silica gel and eluted with $CHCl_3$—$CH_3OH$ (20:1~15:1) to yield N-(6-adenosine)-(L)-phenylalanine ethyl ester (160 mg) as white solid: positive ESIMS m/z 444 [M+H]+, 466 [M+Na]+ and 482 [M+K]+; negative ESIMS m/z 442 [M−H]−; $^1$H NMR (300 MHz, DMSO-$d_6$): the adenosine moiety δ 8.39 (1H, s, H-2), 8.17 (1H, s, H-8), 8.13 (1H, brs, —NH), 5.87 (1H, d, J=5.7 Hz, H-1'), 5.44 (1H, brd, J=5.7 Hz, —OH), 5.29 (1H, m, —OH), 5.17 (1H, brd, J=4.2 Hz, —OH), 4.96 (1H, m, H-2'), 4.14 (1H, m, H-3'), 3.95 (1H, m, H-4'), 3.65 (1H, brs, J=12.0 Hz, H-5'a), 3.52 (1H, m, H-5'b'); the (L)-phenylalanine ethyl ester moiety δ 7.29 (2H, d, J=7.2 Hz, H-2", H-6"), 7.24 (2H, t, J=7.2 Hz, H-3", H-5"), 7.17 (1H, t, J=7.2 Hz, H-4"), 6.48 (1H, d, J=8.1 Hz, H-6"), 4.58 (1H, m, H-8"), 4.07 (2H, q, J=7.2 Hz, —OCH$_2$CH$_3$), 3.26 (2H, m, H-7"), 1.07 (3H, t, J=7.2 Hz, —OCH$_2$CH$_3$); $^{13}$C NMR (75 MHz, DMSO-$d_6$): the adenosine moiety δ 154.0 (s, C-6), 152.0 (d, C-2), 148.7 (s, C-4), 140.2 (d, C-8), 119.7 (s, C-5), 88.1 (d, C-1'), 86.1 (d, C-4'), 73.7 (d, C-2'), 70.7 (d, C-3'), 61.8 (t, C-5'); the (L)-phenylalanine ethyl ester moiety δ 171.9 (s, C-9"), 137.8 (s, C-1"), 129.0 (s, C-2", C-6"), 128.2 (s, C-3", C-5"), 126.4 (d, C-4"), 60.5 (t, —OCH$_2$CH$_3$), 54.6 (d, C-8"), 36.2 (d, C-7"), 14.0 (q, —OCH$_2$CH$_3$).

Example 105: Preparation of N-(6-adenosine)-(D)-phenylalanine methyl ester

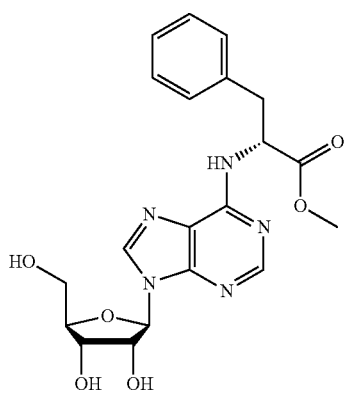

A mixture of D-phenylalanine methyl ester (302 mg, the hydrochloride), 6-chloropurine riboside (200 mg) and triethylamine (3 ml) in PrOH (50 ml) was heated to 80° C. for 10 h. After evaporation of the reaction mixture, the residue was separated by column chromatography over silica gel and eluted with $CHCl_3$—$CH_3OH$ (15:1~10:1) to yield N-(6-adenosine)-(D)-phenylalanine methyl ester (155 mg) as white solid: positive ESIMS m/z 430 [M+H]+ and 452 [M+Na]+; $^1$H NMR (300 MHz, DMSO-$d_6$): the adenosine moiety δ 8.39 (1H, s, H-2), 8.18 (2H, —NH, H-8), 5.88 (1H, d, J=5.7 Hz, H-1'), 5.46 (1H, m, —OH), 5.29 (1H, m, —OH), 5.19 (1H, m, —OH), 4.59 (1H, m, H-2'), 4.14 (1H, m, H-3'), 3.94 (1H, m, H-4'), 3.65 (1H, m, H-5'a), 3.55 (1H, m, H-5'b); the D-phenylalanine methyl ester moiety δ 7.29 (2H, d, J=7.2 Hz, H-2", H-6"), 7.24 (2H, t, J=7.2 Hz, H-3", H-5"), 7.15 (1H, t, J=7.2 Hz, H-4"), 5.00 (1H, m, H-8"), 3.62 (3H, s, —OCH$_3$), 3.24 (2H, m, H-7"); $^{13}$C NMR (75 MHz, DMSO-$d_6$): the adenosine moiety δ 154.1 (s, C-6), 152.0 (d, C-2), 148.7 (s, C-4), 140.2 (d, C-8), 119.8 (s, C-5), 87.9 (d, C-1'), 85.8 (d, C-4'), 73.5 (d, C-2'), 70.6 (d, C-3'), 61.6 (t, C-5'); the D-phenylalanine methyl ester moiety δ 172.5 (s, C-9"), 137.9 (s, C-1"), 128.0 (d, C-2", C-6"), 128.2 (d, C-3", C-5"), 126.4 (d, C-4"), 54.5 (d, C-8"), 52.0 (q, —OCH$_3$), 36.1 (t, C-7").

Example 106: Preparation of N-(6-adenosine)-(D)-tyrosine

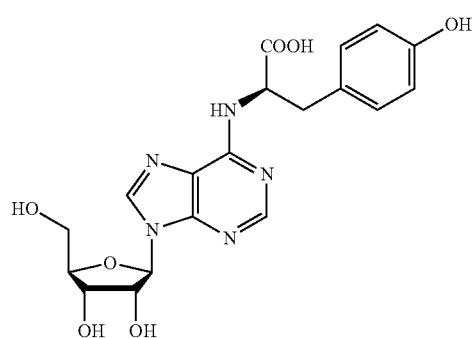

A mixture of (D)-tyrosine (254 mg), 6-chloropurine riboside (200 mg) and $K_2CO_3$ (192 mg) in a mixed solvent of 1,4-dioxane and $H_2O$ (1:1, 6 ml) was refluxed for 8 h. HOAc was added to neutralize the excess $K_2CO_3$. After evaporation of the reaction mixture, the residue was separated by column chromatography over reverse phase ODS gel and eluted with $CH_3OH/H_2O$ (0%, 15%, 45%) to yield N-(6-adenosine)-(D)-tyrosine (240 mg) as a pale yellowish solid: negative ESIMS m/z 430 [M−H]− and 466 [M+Cl]−; $^1$H NMR (300 MHz, DMSO-$d_6$): the adenosine moiety δ 8.27 (1H, s, H-2), 8.20 (1H, s, H-8), 7.07 (1H, d, J=5.7 Hz, —NH), 5.84 (1H, d, J=6.3 Hz, H-1'), 5.56 (1H, m, —OH), 5.47 (1H, m, —OH), 5.27 (1H, m, —OH), 4.61 (1H, m, H-2'), 4.13 (1H, m, H-3'), 3.94 (1H, m, H-4'), 3.65 (1H, m, H-5'a), 3.53 (1H, m, H-5'b); the D-tyrosine moiety δ 9.06 (1H, s, —OH), 6.80 (2H, d, J=8.1 Hz, H-2", H-6"), 6.48 (2H, d, J=8.1 Hz, H-3", H-5"), 4.21 (1H, m, H-8"), 3.23 (1H, m, H-7"a), 3.07 (1H, m, H-7"b); $^{13}$CNMR (75 MHz, DMSO-$d_6$): the adenosine moiety δ 153.7 (s, C-6), 152.6 (d, C-2), 148.0 (s, C-4), 139.8 (d, C-8), 119.9 (s, C-5), 88.2 (d, C-1'), 86.1 (d, C-4'), 73.8 (d, C-2'), 70.8 (d, C-3'), 61.8 (t, C-5'); the D-tyrosine moiety δ 173.8 (s, C-9"), 155.7 (s, C-4"), 130.5 (d, C-2", C-6"), 128.7 (s, C-1"), 114.7 (d, C-3", C-5"), 56.1 (d, C-8"), 36.1 (t, C-7").

Example 107: Preparation of N-(6-adenosine)-(L)-tyrosine

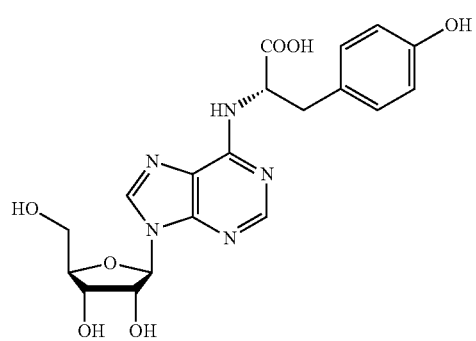

A mixture of (L)-tyrosine (254 mg), 6-chloropurine riboside (200 mg) and K$_2$CO$_3$ (192 mg) in a mixed solvent of 1,4-dioxane and H$_2$O (1:1, 6 ml) was refluxed for 8 h. HOAc was added to neutralize the excess K$_2$CO$_3$. After evaporation of the reaction mixture, the residue was separated by column chromatography over reverse phase ODS gel and eluted with CH$_3$OH/H$_2$O (0%, 15%, 45%) to yield N-(6-adenosine)-(D)-tyrosine (250 mg) as a pale yellowish solid: negative ESIMS m/z 430 [M–H]$^-$; $^1$H NMR (300 MHz, DMSO-d$_6$): the adenosine moiety δ 8.27 (1H, s, H-2), 8.20 (1H, s, H-8), 7.04 (1H, bs, —NH), 5.85 (1H, d, J=6.3 Hz, H-1'), 5.65 (1H, m, —OH), 5.47 (1H, m, —OH), 5.37 (1H, m, —OH), 4.60 (1H, m, H-2'), 4.13 (1H, m, H-3'), 3.94 (1H, m, H-4'), 3.64 (1H, m, H-5'a), 3.54 (1H, m, H-5'b); the L-tyrosine moiety δ 9.14 (1H, s, —OH), 6.79 (2H, d, J=8.4 Hz, H-2", H-6"), 6.48 (2H, d, J=8.4 Hz, H-3", H-5"), 4.20 (1H, m, H-8"), 3.24 (1H, dd, J=13.5, 6.0 Hz, H-7"a), 3.12 (1H, dd, J=13.5, 3.6 Hz, H-7"b); $^{13}$C NMR (75 MHz, DMSO-d$_6$): the adenosine moiety δ 153.8 (s, C-6), 152.7 (d, C-2), 148.1 (s, C-4), 139.8 (d, C-8), 119.9 (s, C-5), 88.2 (d, C-1'), 86.1 (d, C-4'), 73.8 (d, C-2'), 70.8 (d, C-3'), 61.9 (t, C-5'); the L-tyrosine moiety δ 174.0 (s, C-9"), 155.7 (s, C-4"), 130.5 (d, C-2", C-6"), 128.9 (s, C-1"), 114.9 (d, C-3", C-5"), 56.3 (d, C-8"), 36.3 (t, C-7").

Example 108: Preparation of N-(6-adenosine)-(D)-tyrosine ethyl ester

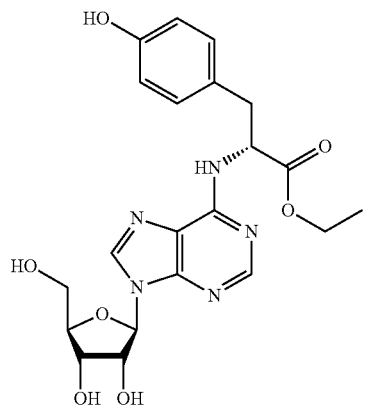

A mixture of D-tyrosine ethyl ester (686 mg, the hydrochloride), 6-chloropurine riboside (200 mg) and triethylamine (3 ml) in PrOH (50 ml) was heated to 80° C. for 10 h. After evaporation of the reaction mixture, the residue was separated by column chromatography over silica gel and eluted with CHCl$_3$—CH$_3$OH (8:1) to yield preparation of N-(6-adenosine)-(D)-tyrosine ethyl ester (250 mg) as white solid: positive ESIMS m/z 460 [M+H]$^+$; negative ESIMS m/z 458 [M–H]$^-$ and 494 [M+Cl]$^-$; $^1$H NMR (300 MHz, DMSO-d$_6$): the adenosine moiety δ 8.39 (1H, s, H-2), 8.17 (1H, H-8), 8.00 (1H, d, 7.5 Hz, —NH), 5.87 (1H, d, J=5.7 Hz, H-1'), 5.43 (1H, d, J=6.3 Hz, —OH), 5.30 (1H, m, —OH), 5.16 (1H, d, J=4.8 Hz, —OH), 4.57 (1H, m, H-2'), 4.12 (1H, m, H-3'), 3.94 (1H, m, H-4'), 3.66 (1H, m, H-5'a), 3.53 (1H, m, H-5'b); the (D)-tyrosine ethyl ester moiety δ 9.17 (1H, s, —OH), 7.07 (2H, d, J=7.8 Hz, H-2", H-6"), 6.62 (2H, d, J=7.8 Hz, H-3", H-5"), 4.86 (1H, m, H-8"), 4.05 (2H, q, J=7.5 Hz, —OCH$_2$CH$_3$), 3.10 (2H, m, H-7"), 1.11 (3H, t, J=7.5 Hz, —OCH$_2$CH$_3$); $^{13}$C NMR (75 MHz, DMSO-d$_6$): the adenosine moiety δ 153.8 (s, C-6), 151.7 (d, C-2), 148.6 (s, C-4), 140.0 (d, C-8), 119.5 (s, C-5), 87.6 (d, C-1'), 85.6 (d, C-4'), 73.2 (d, C-2'), 70.3 (d, C-3'), 61.3 (t, C-5'); the (D)-tyrosine ethyl ester moiety δ 171.9 (s, C-9"), 155.6 (s, C-4"), 129.7 (d, C-2", C-6"), 127.5 (s, C-1"), 114.7 (d, C-3", C-5"), 60.2 (t, —OCH$_2$CH$_3$), 54.7 (d, C-8"), 35.2 (t, C-7"), 13.8 (q, —OCH$_2$CH$_3$).

Example 109: Preparation of N-(6-adenosine)-(L)-tyrosine ethyl ester

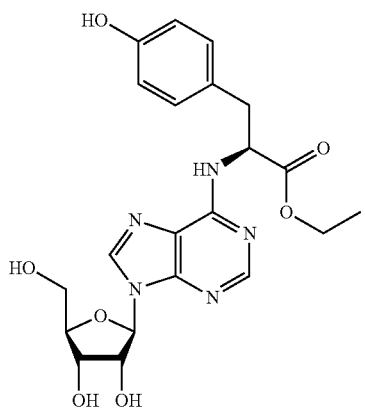

A mixture of L-tyrosine ethyl ester (686 mg, the hydrochloride), 6-chloropurine riboside (200 mg) and triethylamine (3 ml) in PrOH (50 ml) was heated to 80° C. for 10 h. After evaporation of the reaction mixture, the residue was separated by column chromatography over silica gel and eluted with CHCl$_3$—CH$_3$OH (8:1) to yield preparation of N-(6-adenosine)-(L)-tyrosine ethyl ester (260 mg) as white solid: positive ESIMS m/z 460 [M+H]$^+$; negative ESIMS m/z 458 [M–H]$^-$ and 494 [M+Cl]$^+$; $^1$H NMR (300 MHz, DMSO-d$_6$): the adenosine moiety δ 8.39 (1H, s, H-2), 8.17 (1H, s, H-8), 8.01 (1H, brd, J=6.9 Hz, —NH), 5.87 (1H, d, J=6.0 Hz, H-1'), 5.43 (1H, d, J=6.0 Hz, —OH), 5.29 (1H, m, —OH), 5.16 (1H, d, J=4.5 Hz, —OH), 4.58 (1H, H-2'), 4.12 (1H, m, H-3'), 3.93 (1H, m, H-4'), 3.65 (1H, m, H-5'a), 3.54 (1H, m, H-5'b); the (L)-tyrosine ethyl ester moiety δ 9.17 (1H, s, —OH), 7.07 (2H, d, J=8.1 Hz, H-2", H-6"), 6.62 (2H, d, J=8.1 Hz, H-3", H-5"), 4.84 (1H, m, H-8"), 4.06 (2H, q, J=7.2 Hz, —OCH$_2$CH$_3$)), 3.10 (2H, m, H-7"), 1.11 (3H, t, J=7.2 Hz, —OCH$_2$CH$_3$); $^{13}$C NMR (75 MHz, DMSO-d$_6$): the adenosine moiety δ 154.2 (d, C-6), 152.2 (d, C-2), 148.8 (s, C-4), 140.4 (d, C-8), 119.9 (s, C-5), 88.1 (d, C-1'), 86.0 (d, C-4'), 73.7 (d, C-2'), 70.8 (d, C-3'), 61.8 (t, C-5'); the (L)-tyrosine ethyl ester moiety δ 172.3 (s, C-9"), 156.1 (s, C-4"), 130.2 (d, C-2", C-6"), 127.9 (s, C-1"), 115.2 (d, C-3", C-5"), 60.7 (t, —OCH$_2$CH$_3$), 55.1 (d, C-8"), 35.7 (t, C-7"), 14.2 (q, —OCH$_2$CH$_3$).

Example 110: Preparation of N-(6-adenosine)-(L)-3-hydroxy-tyrosine

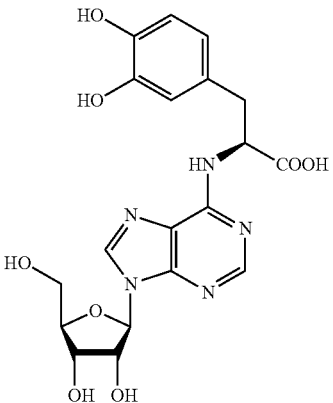

A mixture of levodopa (3-hydroxy-L-tyrosine, 276 mg), 6-chloropurine riboside (200 mg) and K$_2$CO$_3$ (192 mg) in a mixed solvent of 1,4-dioxane and H$_2$O (1:1, 6 ml) was refluxed for 8 h. HOAc was added to neutralized the excess K$_2$CO$_3$. After evaporation of the reaction mixture, the residue was separated by column chromatography over reverse phase ODS gel and eluted with CH$_3$OH/H$_2$O (0%, 15%, 45%) to yield N-(6-adenosine)-(L)-3-hydroxy-tyrosine (200 mg) as a pale yellowish solid: positive ESIMS m/z 448 [M+H]$^+$, 470 [M+Na]$^+$ and 486 [M+K]$^+$; negative ESIMS m/z 446 [M–H]$^-$ and 482 [M+Cl]$^-$; $^1$H NMR (300 MHz, DMSO-d$_6$): the adenosine moiety δ 8.36 (1H, s, H-2), 8.19 (1H, s, H-8), 7.62 (1H, d, 6.3 Hz, —NH), 5.87 (1H, d, J=6.0 Hz, H-1'), 5.44 (1H, brs, —OH), 5.34 (1H, brs, —OH), 5.16 (1H, brs, —OH), 4.59 (1H, m, H-2'), 4.13 (1H, m, H-3'), 3.94 (1H, m, H-4'), 3.66 (1H, d, J=12.0 Hz, H-5'a), 3.53 (1H, d, J=12.0 Hz, H-5'b); the levodopa moiety δ 8.70 (2H, brs, 2×OH), 6.65 (1H, s, H-2"), 6.57 (1H, d, J=8.1 Hz, H-5"), 6.48 (1H, d, J=8.1 Hz, H-6"), 4.78 (1H, m, H-8"), 3.05 (2H, m, H-7"); $^{13}$C NMR (75 MHz, DMSO-d$_6$): the adenosine moiety δ 154.3 (s, C-6), 152.2 (d, C-2), 148.6 (s, C-4), 140.2 (d, C-8), 119.9 (s, C-5), 88.1 (d, C-1'), 86.0 (d, C-4'), 73.5 (d, C-2'), 70.7 (d, C-3'), 61.7 (t, C-5'); the levodopa moiety δ 173.7 (s, C-9"), 144.9 (s, C-3"), 143.7 (s, C-4"), 129.0 (s, C-1"), 119.9 (d, C-2"), 116.6 (d, C-5"), 115.4 (d, C-6"), 54.9 (d, C-8"), 35.9 (t, C-7").

Example 111: Preparation of N-(6-adenosine)-(L)-tryptophan

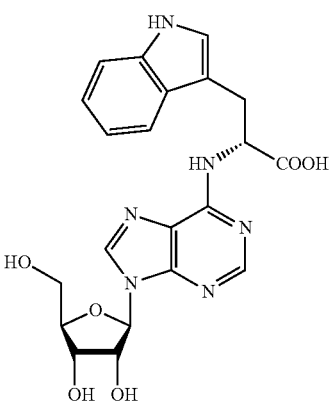

A mixture of L-tryptophan (858 mg), 6-chloropurine riboside (300 mg) and K$_2$CO$_3$ (290 mg) in a mixed solvent of 1,4-dioxane and H$_2$O (1:1, 6 ml) was refluxed for 8 h. HOAc was added to neutralize the excess K$_2$CO$_3$. After evaporation of the reaction mixture, the residue was separated by column chromatography over reverse phase ODS gel and eluted with CH$_3$OH/H$_2$O (0%, 15%, 45%) to yield N-(6-adenosine)-(L)-tryptophan (260 mg) as a pale yellowish solid: positive ESIMS m/z 454 [M+H]$^+$; negative ESIMS m/z 453 [M–H]$^-$; $^1$H NMR (300 MHz, DMSO-d$_6$): the adenosine moiety δ 8.29 (1H, s, H-2), 8.25 (1H, s, H-8), 6.17 (2H, m, 2×—OH), 5.90 (1H, d, J=6.0 Hz, H-1'), 5.67 (1H, m, —OH), 4.57 (H, m, H-2'), 4.19 (1H, m, H-3'), 4.00 (1H, m, H-4'), 3.68 (1H, m, H-5'a), 3.57 (1H, m, H-5'b); the (L)-tryptophan moiety δ 10.79 (1H, s, —NH), 7.37 (1H, d, J=7.8 Hz, H-4"), 7.25 (1H, d, J=7.8 Hz, H-7"), 7.05 (1H, d, J=6.0 Hz, —NH), 7.02 (1H, s, H-2"), 6.94 (1H, t, J=7.5 Hz, H-6"), 6.78 (1H, t, J=7.5 Hz, H-5"), 4.57 (1H, m, H-9"), 3.55 (1H, m, H-8"a), 3.30 (1H, m, H-8"b); $^{13}$C NMR (75 MHz, DMSO-d$_6$): the adenosine δ 154.0 (s, C-6), 152.7 (d, C-2), 148.1 (s, C-4), 139.7 (d, C-8), 120.0 (s, C-5), 88.3 (d, C-1'), 86.1 (d, C-4'), 74.0 (d, C-2'), 70.7 (d, C-3'), 61.8 (t, C-5'); the (L)-tryptophan moiety δ 174.4 (s, C-10"), 136.0 (s, C-7a"), 128.4 (C-3a"), 123.5 (C-2"), 120.5 (d, C-6"), 118.7 (d, C-5"), 118.0 (d, C-4"), 111.3 (d, C-7"), 111.2 (s, C-3"), 55.8 (d, C-9"), 27.2 (t, C-8").

Example 112: Preparation of N-(6-adenosine)-(D)-tryptophan

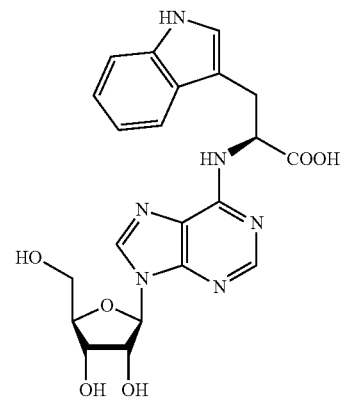

A mixture of D-tryptophan (285 mg), 6-chloropurine riboside (200 mg) and K$_2$CO$_3$ (192 mg) in a mixed solvent of 1,4-dioxane and H$_2$O (1:1, 6 ml) was refluxed for 8 h. HOAc was added to neutralize the excess K$_2$CO$_3$. After evaporation of the reaction mixture, the residue was separated by column chromatography over reverse phase ODS gel and eluted with CH$_3$OH/H$_2$O (0%, 15%, 45%) to yield N-(6-adenosine)-(D)-tryptophan (255 mg) as a pale yellowish solid: positive ESIMS m/z 454 [M+H]$^+$; negative ESIMS m/z 453 [M–H]$^-$; $^1$H NMR (300 MHz, DMSO-d$_6$): the adenosine moiety δ 8.28 (1H, s, H-2), 8.24 (1H, s, H-8), 5.89 (1H, d, J=6.0 Hz, H-1'), 4.60 (H, m, H-2'), 4.17 (1H, m, H-3'), 3.99 (1H, m, H-4'), 3.68 (1H, m, H-5'a), 3.57 (1H, m, H-5'b); the (D)-tryptophan moiety δ 10.75 (1H, s, —NH), 7.38 (1H, d, J=7.8 Hz, H-4"), 7.25 (1H, d, J=7.8 Hz, H-7"), 7.06 (1H, d, J=6.0 Hz, —NH), 7.04 (1H, s, H-2"), 6.95 (1H, t, J=7.5 Hz, H-6"), 6.82 (1H, t, J=7.5 Hz, H-5"), 4.57 (1H, m, H-9"), 3.53 (1H, m, H-8"a), 3.28 (1H, m, H-8"b); $^{13}$C NMR (75 MHz, DMSO-$d_6$): the adenosine moiety δ 154.5 (s, C-6), 153.2 (d, C-2), 148.6 (s, C-4), 140.3 (d, C-8), 120.5 (s, C-5), 88.8 (d, C-1'), 86.6 (d, C-4'), 74.3 (d, C-2'), 71.3 (d, C-3'), 62.4 (t, C-5'); the (D)-tryptophan moiety δ 175.0 (s, C-10"), 136.5 (s, C-7"a), 128.8 (C-3"a), 124.0 (C-2"), 121.1 (d, C-6"), 119.2 (d, C-5"), 118.6 (d, C-4"), 111.7 (d, C-7"), 111.7 (s, C-3"), 56.2 (d, C-9"), 27.8 (t, C-8").

Example 113: Preparation of N-(6-adenosine)-(L)-tryptophan ethyl ester

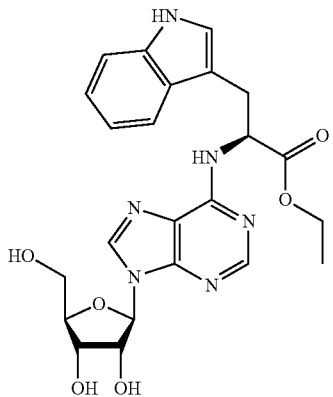

A mixture of L-tryptophan ethyl ester (752 mg, the hydrochloride), 6-chloropurine riboside (200 mg) and triethylamine (3 ml) in PrOH (50 ml) was heated to 80° C. for 10 h. After evaporation of the reaction mixture, the residue was separated by column chromatography over silica gel and eluted with CHCl$_3$—CH$_3$OH (8:1) to yield preparation of N-(6-adenosine)-(L)-tryptophan ethyl ester (260 mg) as white solid: positive ESIMS m/z 483 [M+H]$^+$ and 521 [M+K]$^+$: negative ESIMS m/z 481 [M–H]$^-$; $^1$H NMR (300 MHz, DMSO-$d_6$): the adenosine moiety δ 8.38 (1H, s, H-2), 8.17 (1H, s, H-8), 7.97 (1H, d, J=8.1 Hz, —NH), 5.87 (1H, d, J=5.7 Hz, H-1'), 5.44 (1H, d, J=5.7 Hz, —OH), 5.29 (1H, m, —OH), 5.18 (1H, d, J=4.8 Hz, —OH), 4.57 (1H, m, H-2'), 4.11 (1H, m, H-3'), 4.94 (1H, m, H-4'), 3.65 (1H, m, H-5'a), 3.54 (1H, m, H-5'b); the L-tryptophan ethyl ester moiety δ 10.81 (1H, s, —NH), 7.54 (1H, d, J=7.5 Hz, H-7"), 7.31 (1H, d, J=7.5 Hz, H-4"), 7.20 (1H, s, H-2"), 7.05 (1H, t, J=7.5 Hz, H-5"), 6.97 (1H, t, J=7.5 Hz, H-6"), 4.96 (1H, m, H-9"), 4.06 (2H, q, J=7.5 Hz, —OCH$_2$CH$_3$), 3.35 (2H, m, H-8"), 1.10 (3H, t, J=7.5 Hz, —OCH$_2$CH$_3$); $^{13}$C NMR (75 MHz, DMSO-$d_6$): the adenosine moiety δ 154.2 (s, C-6), 152.2 (d, C-2), 148.8 (s, C-4), 140.4 (d, C-8), 119.9 (s, C-5), 88.1 (d, C-1'), 86.0 (d, C-4'), 73.7 (d, C-2'), 70.7 (d, C-3'), 61.7 (t, C-5'); the L-tryptophan ethyl ester moiety δ 172.5 (s, C-10"), 136.3 (d, C-2"), 127.2 (s, C-7"a), 124.0 (d, C-3"a), 121.1 (d, C-4"), 118.6 (d, C-5"), 118.2 (d, C-7"), 111.6 (s, C-3"), 110.0 (d, C-6"), 60.7 (t, —OCH$_2$CH$_3$), 54.2 (d, C-9"), 26.8 (t, C-8"), 14.1 (q, —OCH$_2$CH$_3$).

Example 114: Preparation of N-(6-adenosine)-(D)-tryptophan ethyl ester

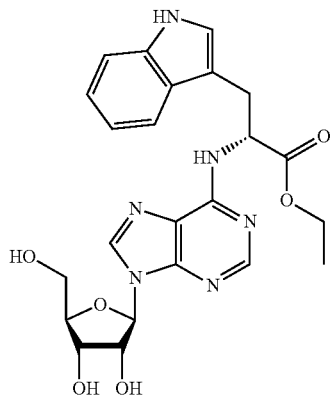

A mixture of D-tryptophan ethyl ester (752 mg, the hydrochloride), 6-chloropurine riboside (200 mg) and triethylamine (3 ml) in PrOH (50 ml) was heated to 80° C. for 10 h. After evaporation of the reaction mixture, the residue was separated by column chromatography over silica gel and eluted with CHCl$_3$—CH$_3$OH (8:1) to yield preparation of N-(6-adenosine)-(D)-tryptophan ethyl ester (265 mg) as white solid: positive ESIMS m/z 483 [M+H]$^+$ and 505 [M+Na]$^+$; negative ESIMS m/z 481 [M–H]$^-$ and 517 [M+Cl]$^-$; $^1$H NMR (300 MHz, DMSO-$d_6$): the adenosine moiety δ 8.40 (1H, s, H-2), 8.19 (1H, s, H-8), 7.97 (1H, d, J=7.2 Hz, —NH), 5.89 (1H, d, J=5.7 Hz, H-1'), 5.48 (1H, d, J=5.7 Hz, —OH), 5.34 (1H, m, —OH), 5.21 (1H, d, J=4.8 Hz, —OH), 4.59 (1H, m, H-2'), 4.13 (1H, m, H-3'), 3.67 (1H, m, H-5'a), 3.55 (1H, m, H-5'b); the D-tryptophan ethyl ester moiety δ 10.83 (1H, s, —NH), 7.55 (1H, d, 7.5 Hz, H-7"), 7.32 (1H, d, J=7.5 Hz, H-4"), 7.22 (1H, s, H-2"), 7.06 (1H, t, J=7.5 Hz, H-5"), 6.98 (1H, t, J=7.5 Hz, H-6"), 5.00 (1H, m, H-9"), 4.08 (2H, q, J=7.2 Hz, —OCH$_2$CH$_3$), 3.39 (2H, m, H-8"), 1.11 (3H, t, J=7.2 Hz, —OCH$_2$CH$_3$); $^{13}$C NMR (75 MHz, DMSO-$d_6$): the adenosine moiety δ 154.1 (s, C-6), 152.1 (d, C-2), 148.7 (s, C-4), 140.2 (d, C-8), 119.8 (s, C-5), 88.0 (d, C-1'), 85.9 (d, C-4'), 73.6 (d, C-2'), 70.6 (d, C-3'), 61.6 (t, C-5'); the D-tryptophan ethyl ester moiety δ 172.4 (s, C-10"), 136.2 (d, C-2"), 127.1 (s, C-7"a), 123.9 (d, C-3"a), 121.0 (d, C-4"), 118.5 (d, C-5"), 118.1 (d, C-7"), 111.5 (s, C-3"), 110.0 (d, C-6"), 60.6 (t, —OCH$_2$CH$_3$), 54.1 (d, C-9"), 26.8 (t, C-8"), 14.0 (q, —OCH$_2$CH$_3$).

Example 115: Preparation of N-(6-adenosine)-5-hydroxy tryptophan

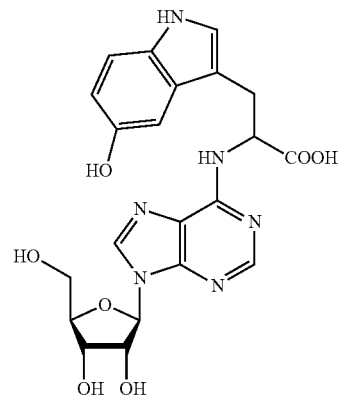

A mixture of 5-hydroxy tryptophan (308 mg), 6-chloropurine riboside (200 mg) and $K_2CO_3$ (192 mg) in a mixed solvent of 1,4-dioxane and $H_2O$ (1:1, 6 ml) was refluxed for 8 h. HOAc was added to neutralize the excess $K_2CO_3$. After evaporation of the reaction mixture, the residue was separated by column chromatography over reverse phase ODS gel and eluted with $CH_3OH/H_2O$ (0%, 15%, 45%) to yield N-(6-adenosine)-5-hydroxy tryptophan (265 mg) as a pale yellowish solid: negative ESIMS m/z 469 [M−H]−; ¹H NMR (300 MHz, DMSO-$d_6$): the adenosine moiety δ 8.24 (1H, s, H-2), 8.20 (1H, s, H-8), 7.16 (1H, d, J=6.0 Hz, —NH), 5.83 (1H, d, J=6.3 Hz, H-1'), 4.33 (1H, m, H-2'), 4.11 (1H, m, H-3'), 3.94 (1H, m, H-4'), 3.65 (1H, m, H-5'a), 3.52 (1H, m, H-5'b); the 5-hydroxy tryptophan moiety δ 10.26 (1H, brs, —OH), 7.00 (1H, d, J=9.0 Hz, H-7"), 6.87 (1H, d, J=1.5 Hz, H-2"), 6.75 (1H, d, J=2.0 Hz, H-4"), 6.45 (1H, dd, J=9.0 Hz, 2.0 Hz, H-6"), 5.51 (2H, brs, 2×OH), 4.57 (1H, t, J=5.4 Hz, H-9"), 3.43 (1H, m, H-8"a), 3.16 (1H, m, H-0); ¹³C NMR (75 MHz, DMSO-$d_6$): the adenosine moiety δ 153.9 (s, C-6), 152.6 (d, C-2), 148.0 (s, C-4), 139.7 (d, C-8), 119.9 (s, C-5), 88.2 (d, C-1'), 86.0 (d, C-4'), 73.8 (d, C-2'), 70.7 (d, C-3'), 61.8 (t, C-5'); the 5-hydroxy tryptophan moiety δ 174.6 (s, C-10"), 150.2 (s, C-5"), 130.5 (s, C-7a"), 129.1 (s, C-3a"), 123.9 (d, C-2"), 111.3 (d, C-6"), 111.0 (d, C-7"), 110.3 (d, C-4"), 102.8 (s, C-3"), 55.5 (d, C-8"), 27.4 (t, C-9").

Example 116: Preparation of N-(6-adenosine)-(D)-histidine

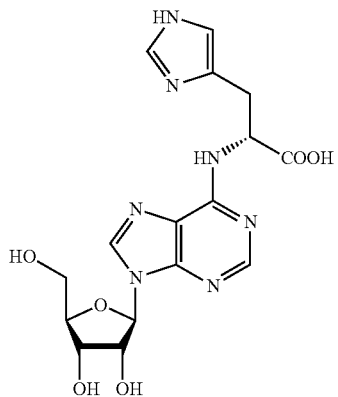

A mixture of D-histidine (217 mg), 6-chloropurine riboside (200 mg) and $K_2CO_3$ (192 mg) in a mixed solvent of 1,4-dioxane and $H_2O$ (1:1, 6 ml) was refluxed for 8 h. HOAc was added to neutralize the excess $K_2CO_3$. After evaporation of the reaction mixture, the residue was separated by column chromatography over reverse phase ODS gel and eluted with $CH_3OH/H_2O$ (0%, 15%, 45%) to yield N-(6-adenosine)-(D)-histidine (230 mg) as a pale yellowish solid: positive ESIMS m/z 406 [M+H]+, 428 [M+Na]+ and 444 [M+K]+; negative ESIMS m/z 404 [M−H]− and 440 [M+Cl]−; ¹H NMR (300 MHz, DMSO-$d_6$): the adenosine moiety δ 8.38 (1H, s, H-2), 8.21 (1H, s, H-8), 7.85 (1H, d, J=6.9 Hz, —NH), 5.89 (1H, d, J=6.3 Hz, H-1'), 5.75 (3H, m, 3×—OH), 4.61 (1H, m, H-2'), 4.15 (1H, m, H-3'), 3.96 (1H, m, H-4'), 3.67 (1H, m, H-5'a), 3.55 (1H, m, H-5'b); the D-histidine moiety δ 7.71 (1H, s, H-2"), 6.89 (1H, s, H-5"), 4.89 (1H, m, H-7"), 3.17 (2H, m, H-6"); ¹³C NMR (75 MHz, DMSO-$d_6$): the adenosine moiety δ 154.2 (s, C-6), 152.2 (d, C-2), 148.6 (s, C-4), 140.3 (d, C-8), 119.9 (s, C-5), 88.1 (d, C-1'), 86.0 (d, C-4'), 73.8 (d, C-2'), 70.7 (d, C-3'), 61.7 (t, C-5'); the D-histidine moiety δ 173.5 (s, C-8"), 134.8 (d, C-2"), 133.6 (s, C-4"), 116.7 (d, C-5"), 53.4 (d, C-7"), 28.4 (t, C-6").

Example 117: Preparation of N-(6-adenosine)-(L)-histidine

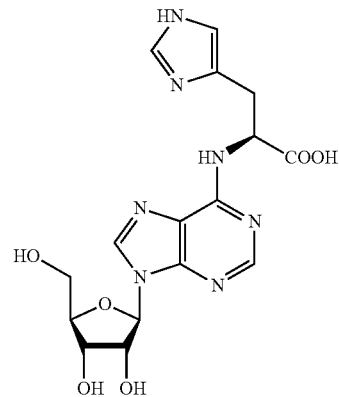

A mixture of L-histidine (217 mg), 6-chloropurine riboside (200 mg) and $K_2CO_3$ (192 mg) in a mixed solvent of 1,4-dioxane and $H_2O$ (1:1, 6 ml) was refluxed for 8 h. HOAc was added to neutralize the excess $K_2CO_3$. After evaporation of the reaction mixture, the residue was separated by column chromatography over reverse phase ODS gel and eluted with $CH_3OH/H_2O$ (0%, 15%, 45%) to yield N-(6-adenosine)-(L)-histidine (230 mg) as a pale yellowish solid: positive ESIMS m/z 406 [M+H]+ and 444 [M+K]+; negative ESIMS m/z 404 [M−H]− and 440 [M+Cl]−; ¹H NMR (300 MHz, DMSO-$d_6$): the adenosine moiety δ 8.37 (1H, s, H-2), 8.21 (1H, s, H-8), 7.88 (1H, brd, J=7.5 Hz, —NH), 5.90 (1H, d, J=6.3 Hz, H-1'), 4.61 (1H, m, H-2'), 4.15 (1H, m, H-3'), 3.96 (1H, m, H-4'), 3.67 (1H, dd, J=12.0, 3.3 Hz, H-5'a), 3.55 (1H, dd, J=12.0, 3.3 Hz, H-5'b); the L-histidine moiety δ 7.70 (1H, m, H-2"), 6.89 (1H, s, H-5"), 4.90 (1H, m, H-7"), 3.17 (2H, m, H-6"); ¹³C NMR (75 MHz, DMSO-$d_6$): the adenosine moiety δ 154.2 (s, C-6), 152.2 (d, C-2), 148.6 (s, C-4), 140.2 (d, C-8), 119.9 (s, C-5), 88.1 (d, C-1'), 85.9 (d, C-4'), 73.6 (d, C-2'), 70.7 (d, C-3'), 61.7 (t, C-5'); the L-histidine moiety δ 173.3 (s, C-8"), 134.8 (d, C-2"), 133.7 (s, C-4"), 116.6 (d, C-5"), 53.3 (t, C-7"), 28.3 (t, C-6").

Example 118: Preparation of N-(6-adenosine)-(L)-proline

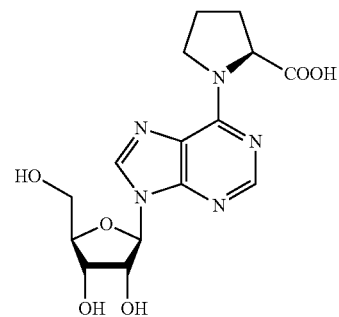

A mixture of L-proline (161 mg), 6-chloropurine riboside (200 mg) and $K_2CO_3$ (192 mg) in a mixed solvent of 1,4-dioxane and $H_2O$ (1:1, 6 ml) was refluxed for 8 h. HOAc was added to neutralize the excess $K_2CO_3$. After evaporation of the reaction mixture, the residue was separated by column chromatography over reverse phase ODS gel and eluted with $CH_3OH/H_2O$ (0%, 15%, 45%) to yield N-(6-adenosine)-(DL)-proline (205 mg) as a pale yellowish solid: positive ESIMS m/z 366 [M+H]$^+$, 388 [M+Na]$^+$ and 404 [M+K]$^+$; negative ESIMS m/z 364 [M−H]$^-$; $^1$H NMR (300 MHz, DMSO-$d_6$): the adenosine moiety δ 8.38, 8.31 (1H, s, H-2), 8.24, 8.16 (1H, s, H-8), 5.90, 5.88 (1H, d, J=6.6 Hz, H-1'), 4.60, 4.61 (1H, m, H-2'), 4.16, 4.13 (1H, m, H-3'), 3.94 (1H, m, H-4'), 3.78, 3.68 (1H, m, H-5'a), 3.58, 3.54 (1H, m, H-5'b); the (DL)-proline moiety δ 5.53, 4.60 (1H, m, H-2''), 4.15 (2H, m, H-5''), 2.32, 2.28 (2H, m, H-3''), 2.00, 1.80 (2H, m, H-4''); $^{13}$C NMR (75 MHz, DMSO-$d_6$): the adenosine moiety δ 153.1, 152.5 (s, C-6), 152.3, 152.0 (d, C-2), 150.0, 149.5 (s, C-4), 139.8, 139.6 (d, C-8), 120.5, 120.2 (s, C-5), 88.1, 88.1 (d, C-1'), 86.1, 86.0 (d, C-4'), 73.9, 73.7 (d, C-2'), 70.9, 70.8 (d, C-3'), 61.9, 61.8 (t, C-5'); the (DL)-proline moiety δ 174.4, 174.2 (s, C-1''), 61.0, 60.2 (C-2''), 49.3, 47.8 (C-5''), 31.0, 29.0 (C-3''), 24.6, 22.2 (C-4'').

Example 119: Preparation of N-(6-adenosine)-(D)-proline

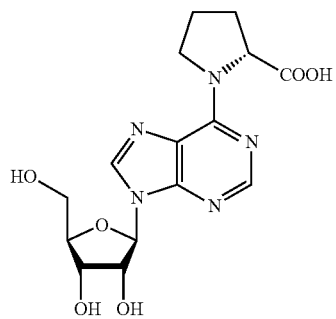

A mixture of D-proline (161 mg), 6-chloropurine riboside (200 mg) and $K_2CO_3$ (192 mg) in a mixed solvent of 1,4-dioxane and $H_2O$ (1:1, 6 ml) was refluxed for 8 h. HOAc was added to neutralize the excess $K_2CO_3$. After evaporation of the reaction mixture, the residue was separated by column chromatography over reverse phase ODS gel and eluted with $CH_3OH/H_2O$ (0%, 15%, 45%) to yield N-(6-adenosine)-(DL)-proline (205 mg) as white solid: positive ESIMS m/z 366 [M+H]$^+$ and 388 [M+Na]$^+$; negative ESIMS m/z 364 [M−H]$^-$; $^1$H NMR (300 MHz, DMSO-$d_6$): the adenosine moiety δ 8.38, 8.31 (1H, s, H-2), 8.24, 8.16 (1H, s, H-8), 5.90, 5.88 (1H, d, J=6.6 Hz, H-1'), 4.60, 4.61 (1H, m, H-2'), 4.16, 4.13 (1H, m, H-3'), 3.94 (1H, m, H-4'), 3.78, 3.68 (1H, m, H-5'a), 3.58, 3.54 (1H, m, H-5'b); the (DL)-proline moiety δ 5.53, 4.60 (1H, m, H-2''), 4.15 (2H, m, H-5''), 2.32, 2.28 (2H, m, H-3''), 2.00, 1.80 (2H, m, H-4''); $^{13}$C NMR (75 MHz, DMSO-$d_6$): the adenosine moiety δ 153.1, 152.5 (s, C-6), 152.3, 152.0 (d, C-2), 150.0, 149.5 (s, C-4), 139.8, 139.6 (d, C-8), 120.5, 120.2 (s, C-5), 88.1, 88.1 (d, C-1'), 86.1, 86.0 (d, C-4'), 73.9, 73.7 (d, C-2'), 70.9, 70.8 (d, C-3'), 61.9, 61.8 (t, C-5'); the (DL)-proline moiety δ 174.4, 174.2 (s, C-1''), 61.0, 60.2 (C-2''), 49.3, 47.8 (C-5''), 31.0, 29.0 (C-3''), 24.6, 22.2 (C-4'').

Example 120: Preparation of N-(6-adenosine)-(L)-valine

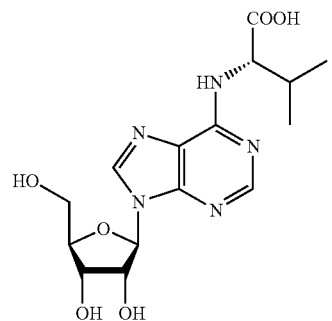

A mixture of L-valine (164 mg), 6-chloropurine riboside (200 mg) and $K_2CO_3$ (192 mg) in a mixed solvent of 1,4-dioxane and $H_2O$ (1:1, 6 ml) was refluxed for 8 h. HOAc was added to neutralize the excess $K_2CO_3$. After evaporation of the reaction mixture, the residue was separated by column chromatography over reverse phase ODS gel and eluted with $CH_3OH/H_2O$ (0%, 15%, 45%) to yield N-(6-adenosine)-(L)-valine (325 mg) as white solid: positive ESIMS m/z 368 [M+H]$^+$; negative ESIMS m/z 366 [M−H]$^-$; $^1$H NMR (300 MHz, DMSO-$d_6$): the adenosine moiety δ 8.42 (1H, s, H-2), 8.23 (1H, s, H-8), 7.45 (1H, d, J=8.4 Hz, —NH), 5.90 (1H, d, J=5.7 Hz, H-1'), 5.53 (3H, m, 3×—OH), 4.62 (1H, m, H-2'), 4.16 (1H, m, H-3'), 3.97 (1H, m, H-4'), 3.68 (1H, dd, J=12.0, 3.0 Hz, H-5'a), 3.55 (1H, dd, J=12.0, 3.3 Hz, H-5'b); the L-valine moiety δ 4.62 (2H, m, H-2''), 2.25 (1H, m, H-3''), 0.98 (6H, d, J=6.0 Hz, H-4'', H-5''); $^{13}$C NMR (75 MHz, DMSO-$d_6$): the adenosine moiety δ 154.5 (s, C-6), 152.2 (d, C-2), 148.7 (s, C-4), 140.3 (d, C-8), 119.8 (s, C-5), 88.1 (d, C-1'), 86.0 (d, C-4'), 73.6 (d, C-2'), 70.7 (d, C-3'), 61.7 (t, C-5'); the L-valine moiety δ 173.5 (s, C-1''), 58.7 (d, C-2''), 29.7 (d, C-3''), 19.2 (t, C-4''), 18.9 (t, C-5'').

Example 121: Preparation of N-(6-adenosine)-(D)-valine

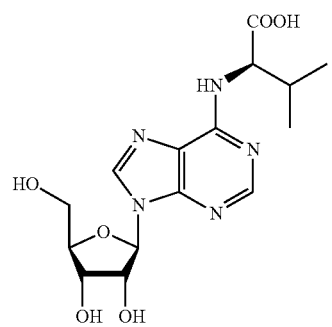

A mixture of D-valine (164 mg), 6-chloropurine riboside (200 mg) and $K_2CO_3$ (192 mg) in a mixed solvent of 1,4-dioxane and $H_2O$ (1:1, 6 ml) was refluxed for 8 h. HOAc was added to neutralize the excess $K_2CO_3$. After evaporation of the reaction mixture, the residue was separated by column chromatography over reverse phase ODS gel and eluted with CH$_3$OH/H$_2$O (0%, 15%, 45%) to yield N-(6-adenosine)-(D)-valine (205 mg) as a pale yellowish solid: positive ESIMS m/z 368 [M+H]$^+$ and 390 [M+Na]$^+$; negative ESIMS m/z 366 [M−H]$^-$ and 402 [M+Cl]$^-$; $^1$H NMR (300 MHz, DMSO-d$_6$): the adenosine moiety δ 8.42 (1H, s, H-2), 8.23 (1H, s, H-8), 7.48 (1H, brd, J=8.1 Hz, —NH), 5.90 (1H, d, J=6.3 Hz, H-1'), 5.43 (3H, m, 3×—OH), 4.61 (1H, m, H-2'), 4.16 (1H, m, H-3'), 3.97 (1H, m, H-4'), 3.66 (1H, dd, J=12.0, 3.3 Hz, H-5'a), 3.55 (1H, dd, J=12.0, 3.3 Hz, H-5'b); the D-valine moiety 455.28 (1H, brs, H-2"), 2.26 (1H, m, H-3"), 0.98 (6H, t, J=6.6 Hz, H-4", H-5"); $^{13}$C NMR (75 MHz, DMSO-d$_6$): the adenosine moiety δ 154.4 (s, C-6), 152.1 (d, C-2), 148.7 (s, C-4), 140.3 (d, C-8), 119.8 (s, C-5), 88.0 (d, C-1'), 85.9 (d, C-4'), 73.6 (d, C-2'), 70.7 (d, C-3'), 61.7 (t, C-5'); the D-valine moiety δ 173.4 (s, C-1"), 58.7 (t, C-2"), 29.7 (t, C-3"), 19.2 (t, C-4", C-5").

Example 122: Preparation of N-(6-adenosine)-(D)-threonine

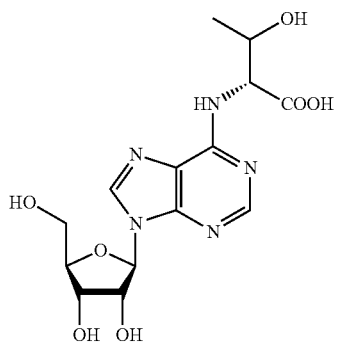

A mixture of D-threonine (167 mg), 6-chloropurine riboside (200 mg) and K$_2$CO$_3$ (192 mg) in a mixed solvent of 1,4-dioxane and H$_2$O (1:1, 6 ml) was refluxed for 8 h. HOAc was added to neutralize the excess K$_2$CO$_3$. After evaporation of the reaction mixture, the residue was separated by column chromatography over reverse phase ODS gel and eluted with CH$_3$OH/H$_2$O (0%, 15%, 45%) to yield N-(6-adenosine)-(D)-threonine (215 mg) as a pale yellowish solid: positive ESIMS m/z 370 [M+H]$^+$; negative ESIMS m/z 368 [M−H]$^-$; $^1$H NMR (300 MHz, DMSO-d$_6$): the adenosine moiety δ 8.45 (1H, s, H-2), 8.23 (1H, s, H-8), 7.02 (1H, d, J=7.8 Hz, —NH), 5.89 (1H, d, J=6.3 Hz, H-1'), 5.46 (1H, d, J=6.3 Hz, —OH), 5.31 (1H, m, —OH), 5.18 (1H, d, J=4.2 Hz, —OH), 4.61 (1H, m, H-2'), 4.14 (1H, m, H-3'), 3.96 (1H, m, H-4'), 3.65 (1H, m, H-5'a), 3.56 (1H, m, H-5'b); the D-threonine moiety δ 4.69 (1H, m, H-2"), 4.29 (1H, m, H-3"), 1.17 (3H, d, J=6.6 Hz, H-4"); $^{13}$CNMR (75 MHz, DMSO-d$_6$): the adenosine moiety δ 154.9 (s, C-6), 152.5 (d, C-2), 148.8 (s, C-4), 140.8 (d, C-8), 120.2 (s, C-5), 88.4 (d, C-1'), 86.2 (d, C-4'), 73.8 (d, C-2'), 70.9 (d, C-3'), 61.9 (t, C-5'); the D-threonine moiety δ 172.8 (s, C-1"), 66.9 (d, C-3"), 58.9 (d, C-2"), 21.0 (q, C-4").

Example 123: Preparation of N-(6-adenosine)-(L)-threonine

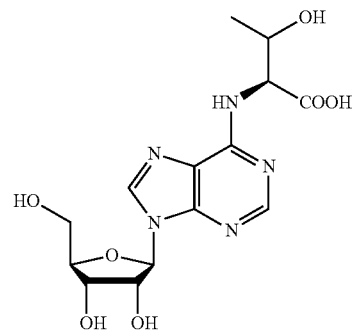

A mixture of L-threonine (167 mg), 6-chloropurine riboside (200 mg) and K$_2$CO$_3$ (192 mg) in a mixed solvent of 1,4-dioxane and H$_2$O (1:1, 6 ml) was refluxed for 8 h. HOAc was added to neutralize the excess K$_2$CO$_3$. After evaporation of the reaction mixture, the residue was separated by column chromatography over reverse phase ODS gel and eluted with CH$_3$OH/H$_2$O (0%, 15%, 45%) to yield N-(6-adenosine)-(L)-threonine (210 mg) as a pale yellowish solid: positive ESIMS m/z 370 [M+H]$^+$; negative ESIMS m/z 368 [M−H]$^-$; $^1$H NMR (300 MHz, DMSO-d$_6$): the adenosine moiety δ 8.45 (1H, s, H-2), 8.24 (1H, s, H-8), 7.03 (1H, d, J=8.4 Hz, —NH), 5.92 (1H, d, J=5.7 Hz, H-1'), 5.48 (3H, m, 3×—OH), 4.62 (1H, m, H-2'), 4.17 (1H, m, H-3'), 3.97 (1H, m, H-4'), 3.68 (1H, m, H-5'a), 3.56 (1H, m, H-5'b); the L-threonine moiety δ 4.69 (1H, d, J=7.5 Hz, H-2"), 4.31 (1H, m, H-3"), 1.17 (3H, d, J=6.6 Hz, H-4"); $^{13}$C NMR (75 MHz, DMSO-d$_6$): the adenosine moiety δ 154.8 (s, C-6), 152.3 (d, C-2), 148.7 (s, C-4), 140.6 (d, C-8), 120.0 (s, C-5), 88.1 (d, C-1'), 86.0 (d, C-4'), 73.7 (d, C-2'), 70.7 (d, C-3'), 61.7 (t, C-5'); the L-threonine moiety δ 172.6 (s, C-1"), 66.7 (d, C-3"), 58.7 (d, C-2"), 20.8 (q, C-4").

Example 124: Preparation of N-(6-adenosine)-(L)-serine

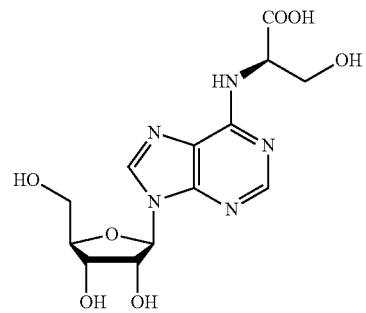

A mixture of L-serine (147 mg), 6-chloropurine riboside (200 mg) and K$_2$CO$_3$ (192 mg) in a mixed solvent of 1,4-dioxane and H$_2$O (1:1, 6 ml) was refluxed for 8 h. HOAc was added to neutralize the excess K$_2$CO$_3$. After evaporation of the reaction mixture, the residue was separated by column chromatography over reverse phase ODS gel and eluted with CH$_3$OH/H$_2$O (0%, 15%, 45%) to yield N-(6-adenosine)-(L)-serine (210 mg) as a pale yellowish solid: positive ESIMS m/z 356 [M+H]$^+$; negative ESIMS m/z 354 [M−H]$^-$; $^1$H NMR (300 MHz, DMSO-d$_6$): the adenosine moiety δ 8.43 (1H, s, H-2), 8.24 (1H, s, H-8), 7.43 (1H, d, 7.2 Hz, —NH), 5.91 (1H, d, J=5.7 Hz, H-1'), 5.43 (3H, m, 3×—OH), 4.61 (1H, m, H-2'), 4.16 (1H, m, H-3'), 3.96 (1H, m, H-4'), 3.68 (1H, m, H-5'a), 3.55 (1H, m, H-5'b); the L-serine moiety δ 4.71 (1H, m, H-2''), 3.88 (2H, m, H-3''); $^{13}$C NMR (75 MHz, DMSO-d$_6$): the adenosine moiety δ 154.3 (s, C-6), 152.3 (d, C-2), 148.7 (s, C-4), 140.4 (d, C-8), 120.0 (s, C-5), 88.0 (d, C-1'), 86.0 (d, C-4'), 73.7 (d, C-2'), 70.7 (d, C-3'), 61.7 (t, C-5'); the L-serine moiety δ 172.4 (s, C-1''), 61.5 (t, C-3''), 55.9 (d, C-2'').

Example 125: Preparation of N-(6-adenosine)-(D)-serine

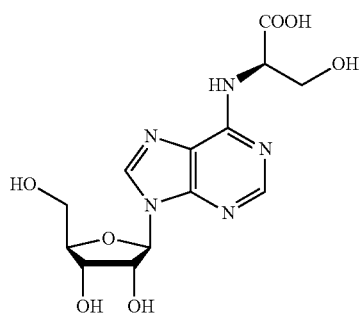

A mixture of D-serine (147 mg), 6-chloropurine riboside (200 mg) and K$_2$CO$_3$ (192 mg) in a mixed solvent of 1,4-dioxane and H$_2$O (1:1, 6 ml) was refluxed for 8 h. HOAc was added to neutralize the excess K$_2$CO$_3$. After evaporation of the reaction mixture, the residue was separated by column chromatography over reverse phase ODS gel and eluted with CH$_3$OH/H$_2$O (0%, 15%, 45%) to yield N-(6-adenosine)-(D)-serine (200 mg) as a pale yellowish solid: positive ESIMS m/z 356 [M+H]$^+$; negative ESIMS m/z 354 [M–H]$^-$; $^1$H NMR (300 MHz, DMSO-d$_6$): the adenosine moiety δ 8.42 (1H, s, H-2), 8.22 (1H, s, H-8), 7.42 (1H, d, J=7.8 Hz, —NH), 5.89 (1H, d, J=6.3 Hz, H-1'), 5.46 (1H, m, —OH), 5.34 (1H, m, —OH), 5.20 (1H, m, —OH), 4.61 (1H, m, H-2'), 4.14 (1H, m, H-3'), 3.96 (1H, m, H-4'), 3.67 6 (1H, m, H-5'a), 3.54 (1H, m, H-5'b); the D-serine moiety δ 4.71 (1H, m, H-2''), 3.87 (2H, m, H-3''); $^{13}$C NMR (75 MHz, DMSO-d$_6$): the adenosine moiety δ 154.3 (s, C-6), 152.2 (d, C-2), 148.7 (s, C-4), 140.5 (d, C-8), 120.0 (s, C-5), 88.1 (d, C-1'), 86.0 (d, C-4'), 73.6 (d, C-2'), 70.7 (d, C-3'), 61.7 (t, C-5'); the D-serine moiety δ 172.3 (s, C-1''), 61.4 (t, C-3''), 55.8 (d, C-2'').

Example 126: Preparation of N-(6-adenosine)-glycine

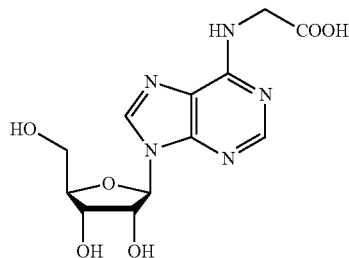

A mixture of glycine (105 mg), 6-chloropurine riboside (200 mg) and K$_2$CO$_3$ (192 mg) in a mixed solvent of 1,4-dioxane and H$_2$O (1:1, 6 ml) was refluxed for 8 h. HOAc was added to neutralize the excess K$_2$CO$_3$. After evaporation of the reaction mixture, the residue was separated by column chromatography over reverse phase ODS gel and eluted with CH$_3$OH/H$_2$O (0%, 15%, 45%) to yield N-(6-adenosine)-glycine (180 mg) as a white solid: positive ESIMS m/z 326 [M+H]$^+$; negative ESIMS m/z 324 [M–H]$^-$; $^1$H NMR (300 MHz, DMSO-d$_6$): the adenosine moiety δ 8.39 (1H, s, H-2), 8.22 (1H, s, H-8), 8.00 (1H, brs, —NH), 5.89 (1H, d, J=6.3 Hz, H-1'), 5.43 (3H, m, 3×—OH), 4.61 (1H, m, H-2'), 4.14 (1H, m, H-3'), 3.96 (1H, m, H-4'), 3.66 (1H, dd, J=12.0, 3.3 Hz, H-5'a), 3.55 (1H, dd, J=12.0, 3.3 Hz, H-5'b); the glycine moiety δ 4.10 (2H, m, H-2''); $^{13}$C NMR (75 MHz, DMSO-d$_6$): the adenosine moiety δ 154.5 (s, C-6), 152.2 (d, C-2), 148.6 (s, C-4), 140.2 (d, C-8), 119.9 (s, C-5), 88.0 (d, C-1'), 85.9 (d, C-4'), 73.5 (d, C-2'), 70.7 (d, C-3'), 61.7 (t, C-5'); the glycine moiety δ 171.7 (s, C-1''), 41.8 (t, C-2'').

Example 127: Preparation of N-(6-adenosine)-(D)-prolinol

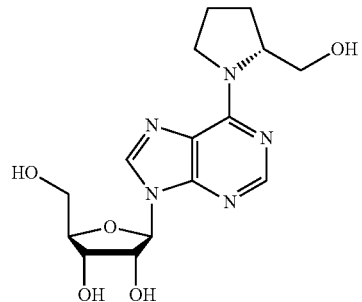

A mixture of D-prolinol (425 mg) and 6-chloropurine riboside (300 mg) in PrOH (50 ml) was heated to 80° C. for 6 h. The solution was cooled to room temperature, separated out a white solid, filtered to yield N-(6-adenosine)-(D)-prolinol (300 mg): positive ESIMS m/z 352 [M+H]$^+$ and 374 [M+Na]$^+$; negative ESIMS m/z 350 [M–H]$^-$; $^1$H NMR (300 MHz, DMSO-d$_6$): the adenosine moiety δ 8.35 (1H, s, H-2), 8.20 (1H, s, H-8), 5.89 (1H, d, J=6.3 Hz, H-1'), 5.43 (1H, d, J=5.7 Hz, —OH), 5.40 (1H, m, —OH), 5.18 (1H, d, J=4.8 Hz, —OH), 4.58 (1H, m, H-2'), 4.13 (1H, m, H-3'), 3.95 (1H, m, H-4'), 3.66 (1H, m, H-5'a), 3.55 (1H, m, H-5'b); the D-prolinol moiety δ 4.90 (1H, m, —OH), 4.85 (1H, brs, H-2''), 4.38 (1H, m, H-5''a), 3.97 (1H, m, H-5''b), 3.65 (1H, m, H-1''a), 3.43 (1H, m, H-1''b), 2.10-1.90 (4H, m, H-3'', H-4'').

Example 128: Preparation of N-(6-adenosine)-(L)-prolinol

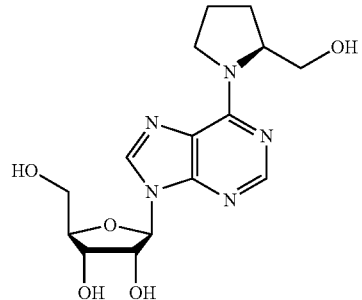

A mixture of L-prolinol (425 mg) and 6-chloropurine riboside (300 mg) in PrOH (50 ml) was heated to 80° C. for 6 h. The solution was cooled to room temperature, separated out a white solid, filtered to yield N-(6-adenosine)-(L)-prolinol (300 mg): positive ESIMS m/z 352 [M+H]+ and 374 [M+Na]+; negative ESIMS m/z 350 [M−H]−; 1H NMR (300 MHz, DMSO-d6): the adenosine moiety δ 8.36 (1H, s, H-2), 8.20 (1H, s, H-8), 5.89 (1H, d, J=6.0 Hz, H-1'), 5.44 (1H, d, J=6.0 Hz, —OH), 5.30 (1H, m, —OH), 5.18 (1H, d, J=4.5 Hz, —OH), 4.57 (1H, m, H-2'), 4.13 (1H, m, H-3'), 3.95 (1H, m, H-4'), 3.66 (1H, m, H-5'a), 3.54 (1H, m, H-5'b); the L-prolinol moiety δ 4.90 (1H, m, —OH), 4.84 (1H, m, H-2"), 4.39 (1H, m, H-5"a), 4.00 (1H, m, H-5"b), 3.64 (1H, m, H-1"a), 3.43 (1H, m, H-1"b), 2.10-1.90 (4H, m, H-3", H-4"); 13C NMR (75 MHz, DMSO-d6): the adenosine moiety δ 152.7 (s, C-6), 152.0 (d, C-2), 149.7 (s, C-4), 139.3 (d, C-8), 120.1 (s, C-5), 87.9 (d, C-1'), 85.9 (d, C-4'), 73.6 (d, C-2'), 70.6 (d, C-3'), 61.6 (t, C-5'); the L-prolinol moiety δ 60.9 (t, C-1"), 59.6 (d, C-2"), 49.5, 47.7 (t, C-5"), 27.6, 26.6 (t, C-3"), 23.7, 21.3 (t, C-4").

Example 129: Preparation of N6-[2-(1,3-dihydroxy)-propyl]-adenosine

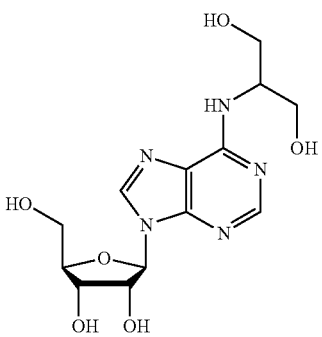

A mixture of serinol (383 mg) and 6-chloropurine riboside (300 mg) in EtOH (50 ml) was refluxed for 12 h. After evaporation of the reaction mixture, the residue was separated by column chromatography over Sephadex LH-20 gel and eluted with EtOH to yield N6-[2-(1,3-dihydroxy)-propyl]-adenosine (290 mg) as a white solid: positive ESIMS m/z 342 [M+H]+; negative ESIMS m/z 340 [M−H]−; 1H NMR (300 MHz, DMSO-d6): the adenosine moiety δ 8.36 (1H, s, H-2), 8.20 (1H, s, H-8), 7.10 (1H, brd, J=8.1 Hz, —NH), 5.88 (1H, d, J=6.0 Hz, H-1'), 5.44 (1H, d, J=6.0 Hz, —OH), 5.40 (1H, m, —OH), 5.18 (1H, d, J=4.2 Hz, —OH), 4.60 (1H, H-2'), 4.12 (1H, m, H-3'), 3.95 (1H, m, H-4'), 3.66 (1H, m, H-5'a), 3.56 (1H, m, H-5'b); the 2-(1,3-dihydroxy)-propyl moiety δ 4.75 (2H, brs, 2×—OH), 4.28 (1H, brs, H-2"), 3.56 (4H, m, H-1", H-3"); 13C NMR (75 MHz, DMSO-d6): the adenosine moiety δ 154.7 (s, C-6), 152.3 (d, C-2), 148.4 (s, C-4), 139.9 (d, C-8), 119.8 (s, C-5), 88.0 (d, C-1'), 86.0 (d, C-4'), 73.5 (d, C-2'), 70.6 (d, C-3'), 61.7 (t, C-5'); the 2-(1,3-dihydroxy)-propyl moiety δ 60.2 (t, C-1", C-3"), 53.8 (d, C-2").

Example 130: Preparation of N6-[(L)-2-(1-hydroxy-4-methyl)-pentyl]-adenosine

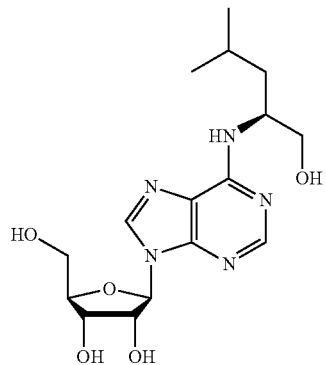

A mixture of L-leucinol (492 mg) and 6-chloropurine riboside (300 mg) in EtOH (50 ml) was refluxed for 12 h. After evaporation of the reaction mixture, the residue was separated by column chromatography over Sephadex LH-20 gel and eluted with EtOH to yield N6-[(L)-2-(1-hydroxy-4-methyl)-pentyl]-adenosine (310 mg) as a white solid: positive ESIMS m/z 368 [M+H]+ and 390 [M+Na]+; negative ESIMS m/z 366 [M−H]−; 1H NMR (300 MHz, DMSO-d6): the adenosine moiety δ 8.33 (1H, s, H-2), 8.17 (1H, s, H-8), 7.39 (1H, d, J=8.7 Hz, —NH), 5.86 (1H, d, J=6.3 Hz, H-1'), 5.44 (2H, m, 2×—OH), 5.17 (1H, d, J=4.5 Hz, —OH), 4.62 (1H, m, H-2'), 4.13 (1H, m, H-3'), 3.95 (1H, H-4'), 3.66 (1H, m, H-5'a), 3.52 (1H, m, H-5'b); the (L)-2-(1-hydroxy-4-methyl)-pentyl moiety δ 4.69 (1H, m, —OH), 4.45 (1H, m, H-2"), 3.45 (1H, m, H-1a"), 3.37 (1H, m, H-1"b), 1.55 (2H, m, H-3"), 1.42 (1H, m, H-4"), 0.86 (6H, t, J=6.6 Hz, H-5", H-6"); 13C NMR (75 MHz, DMSO-d6): the adenosine moiety δ 154.9 (s, C-6), 152.4 (d, C-2), 148.3 (s, C-4), 139.8 (d, C-8), 119.8 (s, C-5), 88.2 (d, C-1'), 86.1 (d, C-4'), 73.5 (d, C-2'), 70.8 (d, C-3'), 61.8 (t, C-5'); the (L)-2-(1-hydroxy-4-methyl)-pentyl moiety δ 63.9 (t, C-1"), 49.7 (d, C-2"), 24.5 (t, C-3"), 23.5 (d, C-4"), 22.0 (q, C-5", C-6").

Example 131: Preparation of N6-[(L)-2-(1-hydroxy-3-methyl)-pentyl]-adenosine

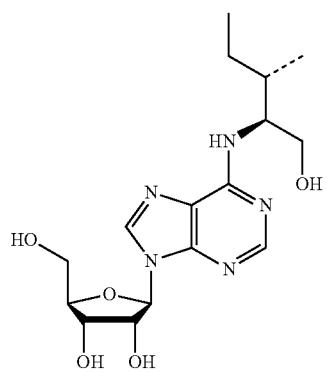

A mixture of L-isoleucinol (492 mg) and 6-chloropurine riboside (300 mg) in EtOH (50 ml) was refluxed for 12 h. After evaporation of the reaction mixture, the residue was separated by column chromatography over Sephadex LH-20 gel and eluted with EtOH to yield N⁶-[(L)-2-(1-hydroxy-3-methyl)-pentyl]-adenosine (315 mg) as a white solid: positive ESIMS m/z 368 [M+H]⁺ and 390 [M+Na]⁺; negative ESIMS m/z 366 [M−H]⁻; ¹H NMR (300 MHz, DMSO-d₆): the adenosine moiety δ 8.33 (1H, s, H-2), 8.17 (1H, s, H-8), 7.28 (1H, brd, J=9.3 Hz, —NH), 5.86 (1H, d, J=6.3 Hz, H-1'), 5.44 (2H, m, 2×—OH), 5.17 (1H, d, J=4.8 Hz, —OH), 4.62 (1H, m, H-2'), 4.13 (1H, m, H-3'), 3.95 (1H, m, H-4'), 3.66 (1H, m, H-5'a), 3.53 (1H, m, H-5'b); the (L)-2-(1-hydroxy-3-methyl)-pentyl moiety δ 4.59 (1H, m, —OH), 4.21 (1H, m, H-2"), 3.53 (2H, m, H-1"), 1.75 (1H, m, H-3"), 1.49 (1H, m, H-4-a"), 1.09 (1H, m, 4b"), 0.89 (3H, d, J=6.6 Hz, —CH₃), 0.82 (3H, t, J=7.2 Hz, C-5"); ¹³C NMR (75 MHz, DMSO-d₆): the adenosine moiety δ 155.1 (s, C-6), 152.4 (d, C-2), 148.3 (s, C-4), 139.9 (d, C-8), 119.8 (s, C-5), 88.3 (d, C-1'), 86.1 (d, C-4'), 73.6 (d, C-2'), 70.9 (d, C-3'), 61.9 (t, C-5'); the (L)-2-(1-hydroxy-3-methyl)-pentyl moiety δ 61.3 (t, C-1"), 55.7 (d, C-2"), 35.3 (t, C-3"), 25.3 (d, C-4"), 15.6 (q, C-5"), 11.4 (q, —CH₃).

Example 132: Preparation of N⁶-[(L)-2-(1-hydroxy-4-methylthioyl)-butyl]-adenosine

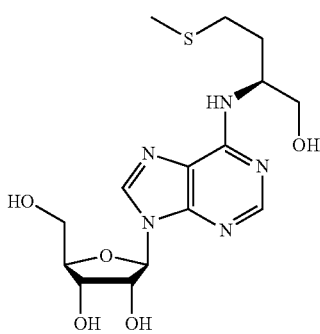

A mixture of L-methioninol (568 mg) and 6-chloropurine riboside (300 mg) in EtOH (50 ml) was refluxed for 12 h. After evaporation of the reaction mixture, the residue was separated by column chromatography over Sephadex LH-20 gel and eluted with EtOH to yield N⁶-[(L)-2-(1-hydroxy-4-methylthioyl)-butyl]-adenosine (325 mg) as a white solid: positive ESIMS m/z 386 [M+H]⁺ and 408 [M+Na]⁺; negative ESIMS m/z 384 [M−H]⁻; ¹H NMR (300 MHz, DMSO-d₆): the adenosine moiety δ 8.34 (1H, s, H-2), 8.18 (1H, s, H-8), 7.50 (1H, brd, J=8.4 Hz, —NH), 5.86 (1H, d, J=6.3 Hz, H-1'), 5.40 (2H, m, 2×—OH), 5.17 (1H, d, J=4.5 Hz, —OH), 4.60 (1H, m, H-2'), 4.13 (1H, m, H-3'), 3.94 (1H, m, H-4'), 3.65 (1H, m, H-5'a), 3.54 (1H, m, H-5'b); the (L)-2-(1-hydroxy-4-methylthioyl)-butyl moiety δ4.76 (1H, m, —OH), 4.40 (1H, m, H-2"), 3.52 (1H, m, H-1a"), 3.42 (1H, m, H-1b"), 2.48 (2H, m, H-4"), 2.0 (3H, s, —SCH₃), 1.92 (1H, m, H-3"a), 1.83 (1H, m, H-3"b); ¹³C NMR (75 MHz, DMSO-d₆): the adenosine moiety δ 154.8 (s, C-6), 152.3 (d, C-2), 148.4 (s, C-4), 139.8 (d, C-8), 119.8 (d, C-5), 88.1 (d, C-1'), 85.9 (d, C-4'), 73.5 (d, C-2'), 70.7 (d, C-3'), 61.7 (t, C-5'); the (L)-2-(1-hydroxy-4-methylthioyl)-butyl moiety δ 63.1 (t, C-1"), 50.9 (d, C-2"), 30.5 (t, C-4"), 30.3 (t, C-3"), 14.7 (q, —SCH₃).

Example 133: Preparation of N⁶-methyl-N⁶-benzyl-adenosine

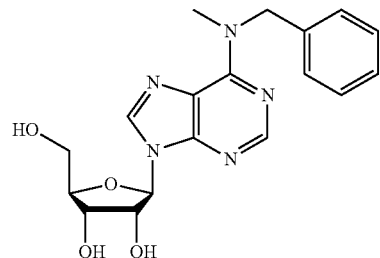

A mixture of N-methylbenzylamine (509 mg) and 6-chloropurine riboside (300 mg) in EtOH (50 ml) was refluxed for 2 h. After evaporation of the reaction mixture, the residue was separated by column chromatography over Sephadex LH-20 gel and eluted with EtOH to yield N⁶-methyl-N⁶-benzyl-adenosine (315 mg) as a white solid: positive ESIMS m/z 372 [M+H]⁺ and 394 [M+Na]⁺; negative ESIMS m/z 370 [M−H]⁻; ¹H NMR (300 MHz, DMSO-d₆): the adenosine moiety δ 8.41 (1H, s, H-2), 8.27 (1H, s, H-8), 5.95 (1H, d, J=6.0 Hz, H-1'), 5.48 (1H, d, J=6.0 Hz, —OH), 5.36 (1H, m, —OH), 5.21 (1H, d, J=4.8 Hz, —OH), 4.63 (1H, m, H-2'), 4.17 (1H, m, H-3'), 3.98 (1H, m, H-4'), 3.68 (1H, m, H-5'a), 3.56 (1H, m, H-5'b); the benzyl and methyl moieties δ 7.29 (2H, t, J=7.8 Hz, H-3", H-5"), 7.24 (2H, d, J=7.8 Hz, H-2", H-6"), 7.23 (1H, t, H-4"), 5.47 (2H, brs, H-7"), 3.33 (3H, brs, —CH₃); ¹³C NMR (75 MHz, DMSO-d₆): the adenosine moiety δ 154.2 (s, C-6), 151.9 (d, C-2), 150.2 (s, C-4), 138.9 (d, C-8), 119.6 (s, C-5), 87.8 (d, C-1'), 85.9 (d, C-4'), 73.6 (d, C-2'), 70.6 (d, C-3'), 61.6 (t, C-5'); the benzyl and methyl moieties δ 138.0 (s, C-1"), 128.6 (d, C-3", C-5"), 127.3 (d, C-2", C-6"), 127.1 (d, C-4"), 52.7 (t, C-7"), 35.7 (q, —CH₃).

Example 134: Preparation of N⁶-ethyl-N⁶-benzyl-adenosine

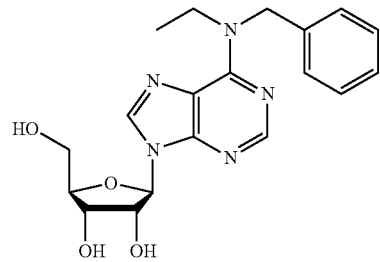

A mixture of N-methylbenzylamine (568 mg) and 6-chloropurine riboside (300 mg) in EtOH (50 ml) was refluxed for 4 h. After evaporation of the reaction mixture, the residue was separated by column chromatography over Sephadex LH-20 gel and eluted with EtOH to yield N⁶-ethyl-N⁶-benzyl-adenosine (330 mg) as a white solid: positive ESIMS m/z 386 [M+H]⁺ and 424 [M+K]⁺; negative ESIMS m/z 384 [M−H]⁻; ¹H NMR (300 MHz, DMSO-d₆): the adenosine moiety δ 8.40 (1H, s, H-2), 8.26 (1H, s, H-8), 5.94 (1H, d, J=6.0 Hz, H-1'), 5.47 (1H, d, J=6.3 Hz, —OH), 5.36 (1H, m, —OH), 5.20 (1H, d, J=4.8 Hz, —OH), 4.62 (1H, m, H-2'), 4.17 (1H, m, H-3'), 3.98 (1H, m, H-4'), 3.68 (1H, m, H-5'a), 3.57 (1H, m, H-5'b); the benzyl and ethyl moieties δ 7.32-7.20 (5H, m, H-2"~H-6"), 5.09 (2H, brs, H-7"), 4.01 (2H, brs, H-1'''), 1.15 (3H, brt, J=7.2 Hz, C-2'''); $^{13}$C NMR (75 MHz, DMSO-$d_6$): the adenosine moiety δ 153.7 (s, C-6), 151.9 (d, C-2), 150.2 (s, C-4), 139.1 (d, C-8), 119.4 (s, C-5), 87.8 (d, C-1'), 85.8 (d, C-4'), 73.5 (d, C-2'), 70.6 (d, C-3'), 61.6 (t, C-5'); the benzyl and ethyl moieties δ 138.5 (s, C-1"), 128.5 (d, C-2", C-6"), 127.3 (d, C-3", C-5"), 127.0 (d, C-4"), 50.0 (t, C-7"), 42.3 (t, C-1'''), 13.0 (q, C-2''').

Example 135: Preparation of $N^6$-methyl-$N^6$-[2-(1S,2R)-(1-hydroxy-1-phenyl)-propyl]-adenosine

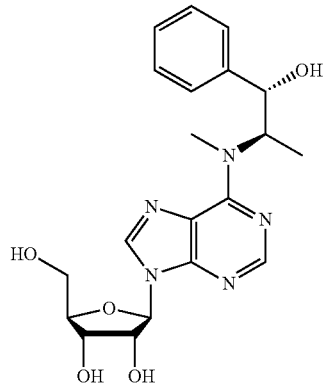

A mixture of (+)-efedrina (847 mg, the hydrochloride), 6-chloropurine riboside (300 mg) and trimethylamine (4.5 ml) in EtOH (50 ml) was refluxed for 18 h. After evaporation of the reaction mixture, the residue was separated by column chromatography over Sephadex LH-20 gel and eluted with EtOH to yield $N^6$-methyl-$N^6$-[2-(1S,2R)-(1-hydroxy-1-phenyl)-propyl]adenosine (350 mg) as a white solid: positive ESIMS m/z 416 [M+H]$^+$ and 438 [M+Na]$^+$; negative ESIMS m/z 414 [M–H]$^-$ and 450 [M+Cl]$^-$; $^1$H NMR (300 MHz, DMSO-$d_6$): the adenosine moiety δ 8.39 (1H, s, H-2), 8.21 (1H, s, H-8), 5.93 (1H, d, J=6.3 Hz, H-1'), 5.45 (2H, m, 2×—OH), 5.19 (1H, d, J=4.5 Hz, —OH), 4.60 (1H, m, H-2'), 4.16 (1H, m, H-3'), 3.98 (1H, m, H-4'), 3.68 (1H, m, H-5'a), 3.58 (1H, m, H-5'b); the 2-(1S,2R)-(1-hydroxy-1-phenyl)-propyl moiety δ 7.43 (2H, brd, J=7.5 Hz, H-2", H-6"), 7.34 (2H, t, J=7.5 Hz, H-3", H-5"), 7.25 (1H, t, J=7.5 Hz, H-4"), 6.25 (1H, brs, —OH), 5.34 (1H, brs, H-7"), 4.68 (1H, brs, H-8"), 3.14 (3H, brs, —CH$_3$), 0.98 (1H, d, J=6.3 Hz, H-9"); $^{13}$C NMR (75 MHz, DMSO-$d_6$): the adenosine moiety δ 155.2 (s, C-6), 151.5 (d, C-2), 149.7 (s, C-4), 138.1 (d, C-8), 120.0 (s, C-5), 87.8 (d, C-1'), 85.8 (d, C-4'), 73.5 (d, C-2'), 70.6 (d, C-3'), 61.6 (t, C-5'); the 2-(1S,2R)-(1-hydroxy-1-phenyl)-propyl moiety δ 143.8 (s, C-1"), 128.1 (d, C-2", C-6"), 127.3 (d, C-3", C-5"), 127.2 (d, C-4"), 74.2 (d, C-7"), 57.2 (d, C-8"), 28.4 (q, C-9"), 14.9 (q, —CH$_3$).

Example 136: Preparation of $N^6$-methyl-$N^6$-[2-(1R,2R)-(1-hydroxy-1-phenyl)-propyl]-adenosine

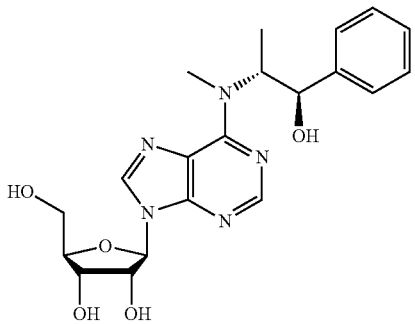

A mixture of pseudoephedrine (847 mg, the hydrochloride), 6-chloropurine riboside (300 mg) and trimethylamine (4 ml) in EtOH (50 ml) was refluxed for 6 h. After evaporation of the reaction mixture, the residue was separated by column chromatography over Sephadex LH-20 gel and eluted with EtOH to yield $N^6$-methyl-$N^6$-[2-(1R,2R)-(1-hydroxy-1-phenyl)-propyl]-adenosine (350 mg) as a white solid: positive ESIMS ink 416 [M+H]$^+$ and 438 [M+Na]$^+$; $^1$H NMR (300 MHz, DMSO-$d_6$): the adenosine moiety δ 8.39 (1H, s, H-2), 8.21 (1H, s, H-8), 5.93 (1H, d, J=6.0 Hz, H-1'), 5.43 (3H, m, 3×—OH), 4.61 (1H, m, H-2'), 4.16 (1H, m, H-3'), 3.98 (1H, m, H-4'), 3.68 (1H, m, H-5'a), 3.57 (1H, m, H-5'6); the 2-(1R,2R)-(1-hydroxy-1-phenyl)-propyl moiety δ 7.44 (2H, d, J=6.6 Hz, H-2", H-6"), 7.34 (2H, t, J=6.6 Hz, H-3", H-5"), 7.25 (1H, t, J=6.6 Hz, H-4"), 6.26 (1H, brs, —OH), 5.44 (1H, m, H-7"), 4.67 (1H, m, H-8"), 3.15 (3H, brs, —CH$_3$), 0.98 (3H, d, J=6.3 Hz, H-9"); $^{13}$C NMR (75 MHz, DMSO-$d_6$): the adenosine moiety δ 155.2 (s, C-6), 151.6 (d, C-2), 149.7 (s, C-4), 138.1 (d, C-8), 120.0 (s, C-5), 87.8 (d, C-1'), 85.8 (d, C-4'), 73.5 (d, C-2'), 70.6 (d, C-3'), 61.7 (t, C-5'); the 2-(1R,2R)-(1-hydroxy-1-phenyl)-propyl moiety δ 143.8 (s, C-1"), 128.1 (d, C-2", C-6"), 127.3 (d, C-3", C-5"), 127.2 (d, C-4"), 74.2 (d, C-7"), 57.2 (d, C-8"), 28.3 (q, —CH$_3$), 14.9 (q, C-9").

Example 137: Preparation of $N^6$-methyl-$N^6$-[(±)-2-(1-hydroxy-1-phenyl)-propyl]-adenosine

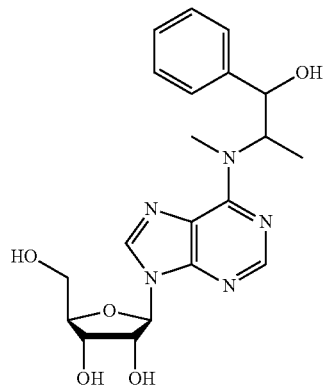

A mixture of efedrina (847 mg, the hydrochloride), 6-chloropurine riboside (300 mg) and trimethylamine (4.5 ml) in EtOH (50 ml) was refluxed for 18 h. After evaporation of the reaction mixture, the residue was separated by column chromatography over Sephadex LH-20 gel and eluted with EtOH to yield $N^6$-methyl-$N^6$-[(±)-2-(1-hydroxy-1-phenyl)-propyl]-adenosine (360 mg) as a white solid: positive ESIMS m/z 416 [M+H]$^+$ and 438 [M+Na]$^+$; negative ESIMS m/z 414 [M−H]$^−$; $^1$H NMR (300 MHz, DMSO-d$_6$): the adenosine moiety δ 8.40 (1H, s, H-2), 8.15 (1H, s, H-8), 5.88 (1H, d, J=6.3 Hz, H-1'), 5.52 (1H, m, —OH), 5.42 (1H, m, —OH), 5.17 (1H, d, J=4.5 Hz, —OH), 4.54 (1H, m, H-2'), 4.13 (1H, m, H-3'), 3.94 (1H, m, H-4'), 3.68 (1H, m, H-5'a), 3.58 (1H, m, H-5'b); the (±)-2-(1-hydroxy-1-phenyl)-propyl moiety δ 7.44 (2H, brd, J=7.5 Hz, H-2", H-6"), 7.22 (2H, t, J=7.5 Hz, H-3", H-5"), 7.14 (1H, t, J=7.5 Hz, H-4"), 6.14 (1H, brs, —OH), 5.34 (1H, brs, H-7"), 4.83 (1H, brs, H-8"), 3.08 (3H, brs, —CH$_3$), 1.22 (1H, d, J=6.3 Hz, H-9"); $^{13}$C NMR (75 MHz, DMSO-d$_6$): the adenosine moiety δ 154.1 (s, C-6), 151.6 (d, C-2), 149.8 (s, C-4), 138.5 (d, C-8), 119.8 (s, C-5), 87.9 (d, C-1'), 85.8 (d, C-4'), 73.4 (d, C-2'), 70.6 (d, C-3'), 61.6 (t, C-5'); the (±)-2-(1-hydroxy-1-phenyl)-propyl moiety δ 143.8 (s, C-1"), 127.8 (d, C-2", C-6"), 126.9 (d, C-3", C-5"), 126.5 (d, C-4"), 75.1, 73.6 (d, C-7"), 56.9 (d, C-8"), 30.1 (q, C-9"), 13.2 (q, —CH$_3$).

Example 138: Preparation of $N^6$-(2-hydroxyethyl)-$N^6$-benzyl-adenosine

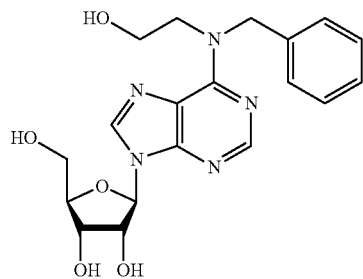

A mixture of N-benzyl-1-hydroxy-ethylamine (635 mg) and 6-chloropurine riboside (300 mg) in EtOH (50 ml) was refluxed for 6 h. After concentration, the solution was cooled to separate out $N^6$-(2-hydroxyethyl)-$N^6$-benzyl-adenosine (340 mg) as a white solid: positive ESIMS m/z 402 [M+H]$^+$ and 424 [M+Na]$^+$; $^1$H NMR (300 MHz, DMSO-d$_6$): the adenosine moiety δ 8.41 (1H, s, H-2), 8.27 (1H, s, H-8), 5.95 (1H, d, J=5.7 Hz, H-1'), 5.48 (1H, m, —OH), 5.36 (1H, m, —OH), 5.21 (1H, m, —OH), 4.63 (1H, m, H-2'), 4.17 (1H, m, H-3'), 3.99 (1H, m, H-4'), 3.66 (1H, m, H-5'a), 3.55 (1H, m, H-5'b); the benzyl moiety δ 7.30-7.23 (5H, m, H-2"~H-6"), 5.16 (2H, brs, H-7"); the 2-hydroxyethyl moiety δ 5.63 (2H, brs, H-1'''), 4.80 (1H, m, —OH), 3.68 (2H, m, H-2'''); $^{13}$C NMR (75 MHz, DMSO-d$_6$): the adenosine moiety δ 154.1 (s, C-6), 151.9 (d, C-2), 150.3 (s, C-4), 139.1 (d, C-8), 119.5 (s, C-5), 87.8 (d, C-1'), 85.8 (d, C-4'), 73.5 (d, C-2'), 70.6 (d, C-3'), 61.6 (t, C-5'); the benzyl moiety δ 138.5 (s, C-1"), 128.5 (d, C-2", C-6"), 127.2 (d, C-3", C-5"), 127.0 (d, C-4"), 52.6 (t, C-7"); the 2-hydroxyethyl moiety δ 59.8 (t, C-2'''), 48.5 (t, C-1''').

Example 139: Preparation of $N^6$-ethyl-$N^6$-(2-hydroxyethyl)-adenosine

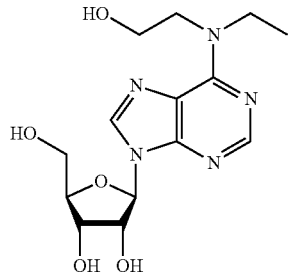

A mixture of 2-hydroxyethylamine (374 mg) and 6-chloropurine riboside (300 mg) in EtOH (50 ml) was refluxed for 7 h. The solution was cooled the solution was cooled to separate out to yield $N^6$-ethyl-$N^6$-(2-hydroxyethyl)-adenosine (285 mg) as a white solid: positive ESIMS m/z 340 [M+H]$^+$ and 362 [M+Na]$^+$; negative ESIMS m/z 338 [M−H]$^−$; $^1$H NMR (300 MHz, DMSO-d$_6$): the adenosine moiety δ 8.36 (1H, s, H-2), 8.20 (1H, s, H-8), 5.90 (1H, d, J=6.0 Hz, H-1'), 5.45 (1H, d, J=6.0 Hz, —OH), 5.38 (1H, m, —OH), 5.17 (1H, d, J=4.8 Hz, —OH), 4.76 (1H, t, J=4.8 Hz, —OH), 4.59 (1H, m, H-2'), 4.15 (1H, m, H-3'), 3.96 (1H, m, H-4'), 3.67 (3H, m, H-5'a), 3.55 (1H, m, H-5'b); the 2-hydroxyethyl and ethyl moieties δ 4.18 (2H, brm, H-1'''), 3.79 (2H, brm, H-1"), 3.67 (2H, m, H-2"), 1.18 (2H, brt, J=6.3 Hz, H-2'''); $^{13}$C NMR (75 MHz, DMSO-d$_6$): the adenosine moiety δ 153.5 (s, C-6), 151.8 (d, C-2), 150.0 (s, C-4), 138.9 (d, C-8), 119.5 (s, C-5), 87.9 (d, C-1'), 85.8 (d, C-4'), 73.5 (d, C-2'), 70.6 (d, C-3'), 61.6 (t, C-5'); the 2-hydroxyethyl and ethyl moieties δ 59.1 (t, C-2"), 50.0 (t, C-1"), 44.5 (t, C-1'''), 13.9 (q, C-2''').

Example 140: Preparation of $N^6$,$N^6$-bis(2-hydroxypropyl)-adenosine

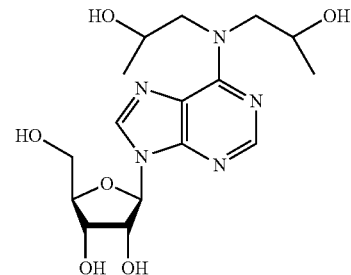

A mixture of bis(2-hydroxypropyl)amine (569 mg) and 6-chloropurine riboside (300 mg) in EtOH (50 ml) was refluxed for 7 h. After evaporation of the reaction mixture, the residue was separated by column chromatography over Sephadex LH-20 gel and eluted with EtOH to yield $N^6$,$N^6$-bis(2-hydroxypropyl)-adenosine (325 mg) as a white solid: the adenosine moiety ESIMS m/z 384 [M+H]$^+$ and 406 [M+Na]$^+$; $^1$H NMR (300 MHz, DMSO-d$_6$): the adenosine moiety δ 8.36, 8.35 (1H, s, H-2), 8.20, 8.18 (1H, s, H-8), 5.89 (1H d, J=6.0 Hz, H-1'), 5.43 (1H, d, J=6.0 Hz, —OH), 5.36 (1H, m, —OH), 5.16 (1H, d, J=4.8 Hz, —OH), 4.57 (1H, m, H-2'), 4.14 (1H, m, H-3'), 3.95 (1H, m, H-4'), 3.66

(1H, m, H-5'a), 3.55 (1H, m, H-5'b); the bis(2-hydroxypropyl) moiety δ 4.95 (1H, m, —OH), 4.76 (1H, m, —OH), 4.01 (4H, m, H-1", H-1'''), 3.74 (2H, m, H-2", H-2'''), 1.06 (6H, m, H-3", H-3'''); $^{13}$C NMR (75 MHz, DMSO-d$_6$): the adenosine moiety δ 154.3, 154.1 (s, C-6), 151.61, 151.58 (d, C-2), 150.0, 149.96 (s, C-4), 138.78, 138.65 (d, C-8), 119.74, 119.63 (s, C-5), 87.8 (d, C-1'), 85.8 (d, C-4'), 73.5 (d, C-2'), 70.6 (d, C-3'), 61.6 (t, C-5'); the bis(2-hydroxypropyl) moiety δ 66.3, 64.6 (d, C-2", C-2'''), 57.3 (t, C-1", C-1'''), 21.1 (q, C-3", C-3''').

Example 141: Preparation of N$^6$-methyl-N$^6$-cyclohexyl-adenosine

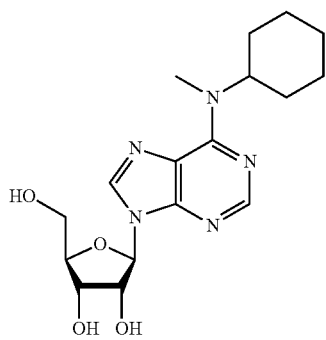

A mixture of N-methylcyclohexylamine (475 mg) and 6-chloropurine riboside (300 mg) in EtOH (50 ml) was refluxed for 6 h. After evaporation of the reaction mixture, the residue was separated by column chromatography over Sephadex LH-20 gel and eluted with EtOH to yield N$^6$-methyl-N$^6$-cyclohexyl-adenosine (305 mg) as a white solid: positive ESIMS m/z 364 [M+H]$^+$ and 386 [M+Na]$^+$; negative ESIMS m/z 362 [M–H]$^-$; $^1$H NMR (300 MHz, DMSO-d$_6$): the adenosine moiety δ 8.37 (1H, s, H-2), 8.21 (1H, s, H-6), 5.90 (1H, d, J=5.7 Hz, H-1'), 5.45 (1H, d, J=5.4 Hz, —OH), 5.39 (1H, m, —OH), 5.19 (1H, d, J=4.2 Hz, —OH), 4.57 (1H, m, H-2'), 4.14 (1H, m, H-3'), 3.96 (1H, m, H-4'), 3.67 (1H, m, H-5'a), 3.55 (1H, m, H-5'b); the cyclohexyl and methyl moieties 453.23 (4H, m, H-1", —CH$_3$), 1.80-1.10 (10H, m, H-2"~H-6"); $^{13}$C NMR (75 MHz, DMSO-d$_6$): the adenosine moiety δ 153.9 (s, C-6), 151.7 (d, C-2), 150.0 (s, C-4), 138.5 (d, C-8), 119.8 (C-5), 87.9 (d, C-1'), 85.8 (d, C-4'), 73.6 (d, C-2'), 70.6 (d, C-3'), 61.6 (t, C-5'); the cyclohexyl and methyl moieties δ 55.3 (d, C-1"), 29.5 (q, —CH$_3$), 25.4 (t, C-2", C-3", C-5", C-6"), 25.1 (t, C-4").

Example 142: Preparation of N$^6$-[(R)-1-(phenyl)-ethyl]-adenine

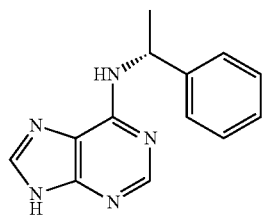 [SMILES: C[C@@H](Nc1ncnc2[nH]cnc12)c1ccccc1]

A mixture of (R)-1-phenylethylamine (708 mg) and 6-chloropurine (300 mg) in EtOH (50 ml) was refluxed for 24 h. After evaporation of the reaction mixture, the residue was separated by column chromatography over Sephadex LH-20 gel and eluted with EtOH to yield N$^6$-[(R)-1-(phenyl)-ethyl]-adenine (375 mg) as a white solid: positive ESIMS m/z 240 [M+H]$^+$, 262 [M+Na]$^+$ and 278 [M+K]$^+$; negative ESIMS m/z 238 [M–H]$^-$ and 274 [M+Cl]$^-$; $^1$H NMR (300 MHz, DMSO-d$_6$): the adenine 4511.89 (1H, brs, —NH), 8.16 (1H, s, H-2), 8.13 (1H, s, H-8), 8.01 (1H, d, J=8.4 Hz, —NH); the (R)-1-phenylethyl moiety δ 7.44 (2H, d, J=7.5 Hz, H-2', H-6'), 7.27 (2H, t, J=7.5 Hz, H-3', H-5'), 7.16 (1H, t, J=7.5 Hz, H-4'), 5.53 (1H, brs, H-7'), 1.53 (3H, d, J=6.9 Hz, H-8'); $^{13}$C NMR (75 MHz, DMSO-d$_6$): the adenine δ 153.2 (C-6), 152.3 (C-2), 151.0 (C-4), 139.2 (C-8), 117.6 (C-5); the (R)-1-phenylethyl moiety δ 145.3 (C-1'), 128.2 (C-2', C-6'), 126.5 (C-4'), 126.2 (C-3', C-5'), 48.8 (C-7'), 22.7 (C-8').

Example 143: Preparation of N$^6$-[(S)-1-(phenyl)-ethyl]-adenine

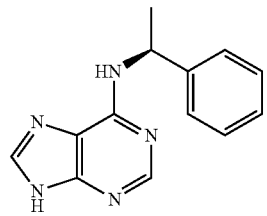 [SMILES: C[C@H](Nc1ncnc2[nH]cnc12)c1ccccc1]

A mixture of (S)-1-phenylethylamine (708 mg) and 6-chloropurine (300 mg) in EtOH (50 ml) was refluxed for 24 h. After evaporation of the reaction mixture, the residue was separated by column chromatography over Sephadex LH-20 gel and eluted with EtOH to yield N$^6$-[(S)-1-(phenyl)-ethyl]-adenine (380 mg) as a white solid: positive ESIMS m/z 240 [M+H]$^+$, 262 [M+Na]$^+$ and 278 [M+K]$^+$; negative ESIMS m/z 238 [M–H]$^-$ and 274 [M+Cl]$^-$; $^1$H NMR (300 MHz, DMSO-d$_6$): the adenine δ 12.68 (1H, brs, —NH), 8.15 (1H, s, H-2), 8.13 (1H, s, H-8), 8.02 (1H, d, J=8.4 Hz, —NH); the (S)-1-(phenyl)-ethyl moiety δ 7.43 (2H, d, J=7.2 Hz, H-2', H-6'), 7.27 (2H, t, J=7.2 Hz, H-3', H-5'), 7.16 (1H, t, J=7.2 Hz, H-4'), 5.52 (1H, brs, H-7'), 1.53 (3H, d, J=6.9 Hz, H-8'); $^{13}$C NMR (75 MHz, DMSO-d$_6$): the adenine δ 153.2 (C-6), 152.3 (C-2), 151.0 (C-4), 139.2 (C-8), 117.6 (C-5); the (S)-1-(phenyl)-ethyl moiety δ 145.4 (C-1'), 128.2 (C-2', C-6'), 126.5 (C-4'), 126.2 (C-3', C-5'), 48.8 (C-7'), 22.7 (C-8').

Example 144: Preparation of N$^6$-[(R)-1-(phenyl)-propyl]-adenine

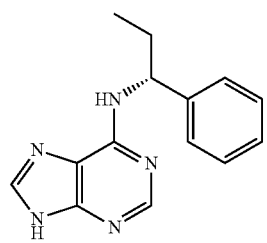 [SMILES: CC[C@@H](Nc1ncnc2[nH]cnc12)c1ccccc1]

A mixture of (R)-1-(phenyl)-propylamine (789 mg) and 6-chloropurine (300 mg) in EtOH (50 ml) was refluxed for 24 h. After evaporation of the reaction mixture, the residue was separated by column chromatography over Sephadex LH-20 gel and eluted with EtOH to yield $N^6$-[(R)-1-(phenyl)-ethyl]-adenine (395 mg) as a white solid: positive ESIMS m/z 254 [M+H]$^+$, 276 [M+Na]$^+$ and 292 [M+K]$^+$; negative ESIMS m/z 252 [M−H]$^-$, 288 [M+Cl]$^-$; $^1$H NMR (300 MHz, DMSO-d$_6$): the adenine δ 12.70 (1H, brs, —NH), 8.12 (1H, s, H-2), 8.11 (1H, s, H-8), 7.97 (1H, d, 8.4 Hz, —NH); the (R)-1-(phenyl)-propyl moiety δ 7.45 (2H, d, J=7.2 Hz, H-2', H-6'), 7.27 (2H, t, J=7.2 Hz, H-3', H-5'), 7.16 (1H, m, H-4'), 5.26 (1H, brs, H-7'), 1.93 (1H, m, H-8'a), 1.88 (1H, m, H-8'b), 0.89 (3H, t, J=7.2 Hz, H-9'); $^{13}$C NMR (75 MHz, DMSO-d$_6$): the adenine δ 153.6 (C-6), 152.3 (C-2), 150.9 (C-4), 139.1 (C-8), 117.7 (C-5); the (R)-1-(phenyl)-propyl moiety δ 144.4 (C-1'), 128.1 (C-2', C-6'), 126.7 (C-3', C-5'), 126.5 (C-4'), 55.1 (C-7'), 29.2 (C-8'), 11.4 (C-9').

Example 145: Preparation of $N^6$-[(S)-1-(phenyl)-propyl]-adenine

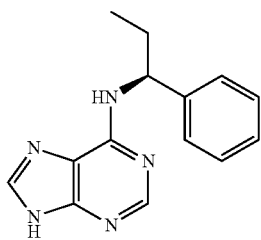 [SMILES: CC[C@H](Nc1ncnc2[nH]cnc12)c1ccccc1]

A mixture of (S)-1-(phenyl)-propylamine (789 mg) and 6-chloropurine (300 mg) in EtOH (50 ml) was refluxed for 24 h. After evaporation of the reaction mixture, the residue was separated by column chromatography over Sephadex LH-20 gel and eluted with EtOH to yield $N^6$-[(S)-1-(phenyl)-ethyl]-adenine (400 mg) as a white solid: positive ESIMS m/z 254 [M+H]$^+$, 276 [M+Na]$^+$ and 292 [M+K]$^+$; negative ESIMS m/z 252 [M−H]$^-$ and 288 [M+Cl]$^-$; $^1$H NMR (300 MHz, DMSO-d$_6$): the adenine δ 12.37 (1H, brs, —NH), 8.14 (1H, s, H-2), 8.12 (1H, s, H-8), 7.98 (1H, d, J=8.7 Hz, —NH); the (S)-1-(phenyl)-propyl moiety δ 7.46 (2H, d, J=7.2 Hz, H-2', H-6'), 7.27 (2H, t, J=7.2 Hz, H-3', H-5'), 7.16 (1H, t, J=7.2 Hz, H-4'), 5.25 (1H, brs, H-7'), 1.93 (1H, m, H-8'a), 1.82 (1H, m, H-8'b), 0.89 (3H, t, J=7.2 Hz, H-9'); $^{13}$C NMR (75 MHz, DMSO-d$_6$): the adenine δ 153.6 (C-6), 152.3 (C-2), 150.8 (C-4), 139.1 (C-8), 117.6 (C-5); the (S)-1-(phenyl)-propyl moiety δ 144.4 (C-1'), 128.1 (C-2', C-6'), 126.7 (C-3', C-5'), 126.5 (C-4'), 55.1 (C-7'), 29.3 (C-8'), 11.4 (C-9').

Example 146: Preparation of $N^6$-[(R)-1-(phenyl)-propyl]-$N^9$-(tetrahydrofuran-2-yl)-adenine

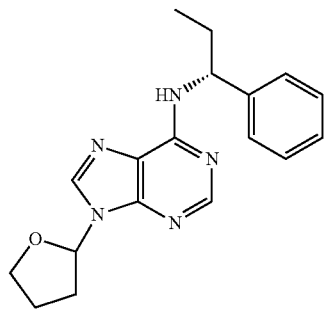 [SMILES: CC[C@@H](Nc1ncnc2c1ncn2C1CCCO1)c1ccccc1]

First step, 6-chloropurine (150 mg) was stirred with 3,4-dihydro-2H-pyrane (168 mg) for 10 min in ethyl acetate (10 ml) and subsequently, trifluoroacetic acid (160 mg) was added dropwise. The reaction mixture was stirred at room temperature for 1 h, and neutralized by the appropriate amount of aqueous ammonia. The ethyl acetate layer was washed with water (3×10 ml) and dried with sodium acetate (500 mg) for 2 h. After evaporation of the reaction mixture, the residue was separated by column chromatography over silica gel and eluted with CHCl$_3$—CH$_3$OH (200:1) to yield for 6-chloro-$N^9$-tetrahydrofuran-2-ylpurine (200 mg) as a pale yellowish solid.

Second step, a mixture of (R)-1-phenylpropylamine (362 mg) and 6-chloro-$N^9$-tetra-hydrofuran-2-ylpurine (200 mg) in EtOH (50 ml) was refluxed for 24 h. After evaporation of the reaction mixture, the residue was separated by column chromatography over silica gel and eluted with CHCl$_3$—CH$_3$OH (80:1) to yield $N^6$-[(R)-1-(phenyl)-propyl]-$N^9$-(tetrahydrofuran-2-yl)-adenine (245 mg) as a yellowish oil: positive ESIMS m/z 324 [M+H]$^+$ and 346 [M+Na]$^+$; $^1$H NMR (300 MHz, acetone-d$_6$): the $N^9$-(tetrahydrofuran-2-yl)-adenine moiety δ 8.18 (1H, s, H-2), 8.05 (1H, s, H-8), 7.03 (1H, d, J=8.1 Hz, —NH), 6.26 (1H, m, H-1'), 4.21 (1H, m, H-4'a), 3.94 (1H, m, H-4'b), 2.49 (2H, m, H-3'), 2.23 (1H, m, H-2'a), 2.00 (1H, m, H-2'b); the $N^6$—(R)-1-(phenyl)-propyl moiety δ 7.51 (2H, d, J=7.2 Hz, H-2'', H-6''), 7.29 (2H, t, J=7.2 Hz, H-3'', H-5''), 7.19 (1H, t, J=7.2 Hz, H-4''), 5.40 (1H, brs, H-7''), 2.00 (2H, m, H-8''), 0.98 (3H, t, J=7.2 Hz, H-9''); $^{13}$C NMR (75 MHz, acetone-d$_6$): the $N^9$-(tetrahydrofuran-2-yl)-adenine moiety δ 155.2 (C-6), 153.1 (C-2), 149.3 (C-4), 139.1 (C-8), 120.6 (C-5), 85.7 (C-1'), 69.5 (C-4'), 32.2 (C-2'), 24.9 (C-3'); the $N^6$—(R)-1-(phenyl)-propyl moiety δ 144.6 (C-1''), 128.7 (C-2'', C-6''), 127.3 (C-3'', C-4'', C-5''), 56.1 (C-7''), 30.0 (C-8''), 11.3 (C-9'').

Example 147: Preparation of $N^6$-[(S)-1-(phenyl)-propyl]-$N^9$-(tetrahydrofuran-2-yl)-adenine

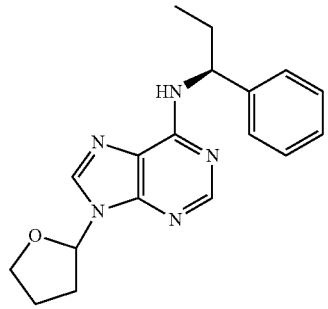 [SMILES: CC[C@H](Nc1ncnc2c1ncn2C1CCCO1)c1ccccc1]

First step, 6-chloropurine (150 mg) was stirred with 3,4-dihydro-2H-pyrane (170 mg) for 10 min in ethyl acetate (10 ml) and subsequently, trifluoroacetic acid (163 mg) was added dropwise. The reaction mixture was stirred at room temperature for 1 h, and neutralized by the appropriate amount of aqueous ammonia. The ethyl acetate layer was washed with water (3×10 ml) and dried with sodium acetate (500 mg) for 2 h. After evaporation of the reaction mixture, the residue was separated by column chromatography over silica gel and eluted with CHCl$_3$—CH$_3$OH (200:1) to yield for 6-chloro-$N^9$-tetrahydrofuran-2-ylpurine (200 mg) as a pale yellowish solid.

Second step, a mixture of (S)-1-phenylpropylamine (362 mg) 6-chloro-$N^9$-tetra-hydrofuran-2-ylpurine (200 mg) in EtOH (50 ml) was refluxed for 24 h. After evaporation of the reaction mixture, the residue was separated by column chromatography over silica gel and eluted with CHCl$_3$—CH$_3$OH (80:1) to yield $N^6$-[(S)-1-(phenyl)-propyl]-$N^9$-(tetrahydrofuran-2-yl)-adenine (242 mg) as a yellowish oil: positive ESIMS m/z 324 [M+H]+; $^1$H NMR (300 MHz, DMSO-d$_6$): the N$^9$-(tetrahydrofuran-2-yl)-adenine moiety δ 8.25 (1H, s, H-2), 8.16 20 (1H, brs, —NH), 8.16 (1H, s, H-8), 6.22 (1H, m, H-1'), 4.11 (1H, m, H-4'a), 3.87 (1H, m, H-4'b), 2.37 (2H, m, H-3'), 2.16 (1H, m, H-2'a), 1.95 (1H, m, H-2b'); the N$^6$—(S)-1-(phenyl)-propyl moiety δ 7.44 (2H, d, J=7.2 Hz, H-2", H-6"), 7.27 (2H, t, J=7.2 Hz, H-3", H-5"), 7.16 (1H, t, J=7.2 Hz, H-4"), 5.25 (1H, brs, H-7"), 1.95 (1H, m, H-8"a), 1.82 (1H, m, H-8"b), 0.89 (3H, J=7.5 Hz, H-9"); $^{13}$C NMR (75 MHz, DMSO-d$_6$): the N$^9$-(tetrahydro-furan-2-yl)-adenine moiety δ 154.2 (C-6), 152.3 (C-2), 149.0 (C-4), 138.9 (C-8), 119.5 (C-5), 84.3 (C-1'), 68.6 (C-4'), 31.1 (C-2'), 24.3 (C-3'); the N$^6$—(S)-1-(phenyl)-propyl moiety δ 144.3 (C-1"), 128.1 (C-3", C-5"), 126.7 (C-2", C-6"), 126.5 (C-4"), 55.1 (C-7"), 29.0 (C-8"), 11.4 (C-9").

Example 148: Preparation of N$^6$-(3-methoxy-4-hydroxy-benzyl)-2'-deoxy-3',5'-diacetyl adenosine

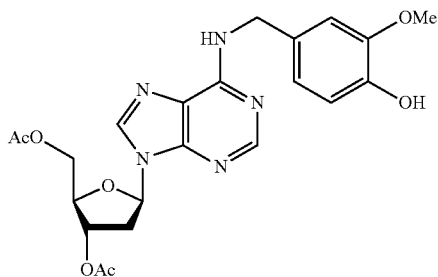 [SMILES: COc1cc(CNc2ncnc3c2ncn3[C@H]2C[C@@H](OC(C)=O)[C@@H](COC(C)=O)O2)ccc1O]

First step, a mixture of 2'-deoxy-adenosine (3.6 g), acetic anhydride (5.47 g), trimethyl (4.07 g) and DMAP (0.16 g) in anhydrous acetonitrile (40 ml) was refluxed for 8 h. Acetonitrile was removed under reduced pressure. H$_2$O (40 ml) was added to the residue, and the resulting solution was extracted with EtOAc (3×40 ml). The EtOAc of the combined organic layer was dried with sodium acetate and The EtOAc layer was filtered and the filtrate was concentrated. The residue was separated by column chromatography over silica gel and eluted with CHCl$_3$—CH$_3$OH (100:1) to yield 3',5'-diacetyl-2'-deoxy-adenosine (4.0 g).

Second step, a mixture of 3',5'-diacetyl-2'-deoxy-adenosine (1.2 g), tert-butyl nitrite (7.42 g), and tribromomethane (20 ml) was refluxed for 2 h. The excess tert-butyl nitrite was removed under reduced pressure. The residue was separated by column chromatography over silica gel and eluted with CHCl$_3$—CH$_3$OH (80:1) to yield 3',5'-diacetyl-2'-deoxy-6-bromo-adenosine (595 mg).

Third step, a mixture of 3',5'-diacetyl-2'-deoxy-6-bromo-adenosine (398 mg), 3-methoxy-4-hydroxybenzylamine (379.3 mg, the hydrochloride) and triethylamine (253 mg) in anhydrous EtOH (20 ml) was refluxed for 5 h. After evaporation, the residue was separated by column chromatography over silica gel and eluted with CHCl$_3$—CH$_3$OH (50:1) to yield N$^6$-(3-methoxy-4-hydroxy-benzyl)-2'-deoxy-3',5'-diacetyl adenosine (340 mg): $^1$H NMR (300 MHz, acetone-d$_6$): the 2'-deoxy-adenosine moiety δ 8.29 (1H, s, H-8), 8.16 (1H, s, H-2), 7.33 (1H, t, J=6.0 Hz, NH), 6.44 (1H, dd, J=7.8, 6.3 Hz, H-1'), 5.48 (1H, m, H-3'), 4.36 (1H, dd, J=6.3, 12.9 Hz, H-5'a), 4.30 (1H, dd, J=6.0, 12.9 Hz, H-5'b), 4.29 (1H, m, H-4'), 3.21 (1H, ddd, J=7.5, 7.8, 15.0 Hz, H-2'a), 2.59 (1H, ddd, J=2.4, 6.0, 15.0, H-2'b); the 3-methoxy-4-hydroxybenzyl moiety δ 7.63 (1H, brs, OH), 7.05 (1H, d, J=1.5 Hz, H-2"), 6.87 (1H, dd, J=7.8, 1.5 Hz, H-6"), 6.74 (1H, d, J=7.8 Hz, H-5"), 4.76 (2H, brs, H-7"), 3.75 (3H, s, OMe); the acetyl 62.09 (3H, s, CH$_3$CO), 2.01 (3H, s, CH$_3$CO); $^{13}$C NMR (300 MHz, acetone-d$_6$): the 2'-deoxy-adenosine moiety δ 155.9 (C-6), 153.6 (C-2), 149.1 (C-4), 139.9 (C-8), 121.2 (C-5), 85.2 (C-1'), 83.1 (C-4'), 75.6 (C-3'), 64.5 (C-5'), 37.0 (C-2'); the 3-methoxy-4-hydroxy moiety δ 148.2 (C-3"), 146.5 (C-4"), 132.0 (C-1"), 121.2 (C-2"), 115.6 (C-6"), 112.3 (C-5"), 56.1 (OMe), 44.2 (C-7"); the acetyl 6170.8, 170.7, 20.9, 20.60.

Example 149: Preparation of N$^6$-(3-methoxy-4-hydroxy-benzyl)-2'-deoxy-adenosine

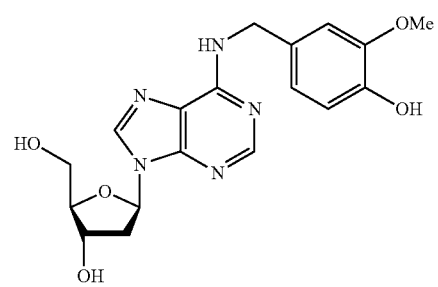 [SMILES: COc1cc(CNc2ncnc3c2ncn3[C@H]2C[C@@H](O)[C@@H](CO)O2)ccc1O]

N$^6$-(3-methoxy-4-hydroxy-benzyl)-2'-deoxy-3',5'-diacetyl adenosine (240 mg) prepared in the above example, was added to methanol-ammonia (2.0 mol/L, 5 ml). The reaction solution was stirred at room temperature for 6 h. After evaporation of the reaction mixture, the residue was separated by column chromatography over silica gel and eluted with CHCl$_3$—CH$_3$OH (10:1) to yield N$^6$-(3-methoxy-4-hydroxy-benzyl)-2'-deoxy-adenosine (200 mg): $^1$H NMR (300 MHz, acetone-d$_6$): the 2'-deoxy-adenosine moiety δ 8.25 (1H, s, H-8), 8.16 (1H, s, H-2), 7.50 (1H, t, J=6.8 Hz, NH), 6.42 (1H, dd, J=5.7, 8.7 Hz, H-1'), 4.64 (1H, m, H-3'), 4.61 (1H, m, OH), 4.09 (1H, m, H-4'), 3.80 (1H, dd, J=12.3, 2.4 Hz, H-5'a), 3.68 (1H, brd, J=12.3 Hz, H-5'b), 2.90 (1H, ddd, J=5.4, 8.7, 12.9 Hz, H-2'a), 2.33 (1H, brdd, J=4.5, 12.9 Hz, H-2'b); the 3-methoxy-4-hydroxybenzyl moiety δ 7.73 (1H, brs, OH), 7.03 (1H, d, J=0.9 Hz, H-2"), 6.85 (1H, dd, J=8.1, 0.9 Hz, H-6"), 6.73 (1H, d, J=8.1 Hz, H-5"), 5.79 (1H, brs, OH), 4.76 (2H, brs, H-7"); 3.73 (3H, s, OMe); $^{13}$C NMR (300 MHz, acetone-d$_6$): the 2'-deoxy-adenosine moiety δ 155.9 (C-6), 153.0 (C-2), 148.9 (C-4), 140.9 (C-8), 121.5 (C-5), 90.1 (C-1'), 87.4 (C-4'), 73.2 (C-3'), 63.7 (C-5'), 41.2 (C-2'); the 3-methoxy-4-hydroxybenzyl moiety δ 148.2 (C-3"), 146.5 (C-4"), 131.7 (C-1"), 121.3 (C-2"), 115.6 (C-6"), 112.3 (C-5"), 56.1 (OMe), 44.3 (C-7").

Example 150: Preparation of N$^6$-(p-methylbenzyl)-2'-deoxy-3',5'-diacetyl adenosine

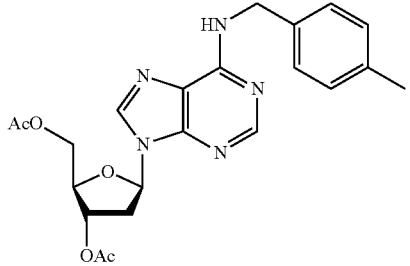 [SMILES: CC(=O)OC[C@H]1O[C@@H](n2cnc3c(NCc4ccc(C)cc4)ncnc32)C[C@H]1OC(C)=O]

A mixture of 3',5'-diacetyl-2'-deoxy-6-bromo-adenosine (500 mg) prepared in the above example, p-methylbenzylmine (304.4 mg) and triethylamine (190.6 mg) in anhydrous EtOH (40 ml) was refluxed for 5 h. After evaporation of the reaction mixture, the residue was separated by column chromatography over silica gel and eluted with CHCl$_3$—CH$_3$OH (50:1) to yield N$^6$-(p-methyl-benzyl)-2'-deoxy-3',5'-diacetyl adenosine (380 mg) as a pale yellowish solid: $^1$H NMR (300 MHz, CDCl$_3$): the 2'-deoxy-adenosine moiety δ 8.36 (1H, s, H-8), 7.82 (1H, s, H-2), 6.60 (1H, brs, NH), 6.38 (1H, dd, J=7.8, 7.2 Hz, H-1'), 5.40 (1H, m, H-3'), 4.38 (1H, m, H-5'a), 4.35 (1H, m H-5'b), 4.38 (1H, m, H-4'), 2.90 (1H, m, H-2'a), 2.56 (1H, m, H-2'b); the p-methylbenzyl moiety δ 7.23 (2H, d, J=7.5 Hz, H-2", H-6"), 7.09 (2H, d, J=7.5 Hz, H-3", H-5"), 4.80 (2H, s, H-7"), 2.30 (3H, s, Me); the acethyl moieties δ 2.10 (3H, s, CH$_3$CO), 2.05 (3H, s, CH$_3$CO); $^{13}$C NMR (300 MHz, acetone-d$_6$): the 2'-deoxy-adenosine moiety δ 155.8 (C-6), 153.6 (C-2), 149.1 (C-4), 139.9 (C-8), 121.2 (C-5), 85.2 (C-1'), 83.1 (C-4'), 75.6 (C-3'), 64.5 (C-5'), 37.1 (C-2'); the p-methylbenzyl moiety δ 137.8 (C-1"), 137.0 (C-4"), 129.7 (C-2", C-6"), 128.3 (C-3", C-5"), 44.0 (C-7"), 21.0 (Me); the acetyl moieties δ170.8, 170.7, 20.9, 20.60.

Example 151: Preparation of N$^6$-(p-methylbenzyl)-2'-deoxy-adenosine

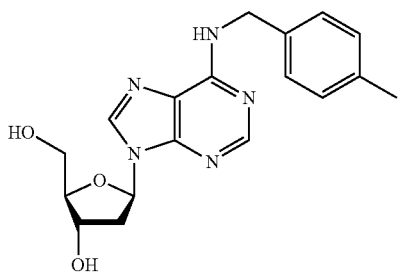 [SMILES: Cc1ccc(CNc2ncnc3c2ncn3[C@H]2C[C@@H](O)[C@@H](CO)O2)cc1]

N$^6$-(p-methylbenzyl)-2'-deoxy-3',5'-diacetyl adenosine (300 mg) prepared in the above example, was added to methanol-ammonia (2.0 mol/L, 5 ml). The reaction solution was stirred at room temperature for 6 h. After evaporation of the reaction mixture, the residue was separated by column chromatography over silica gel and eluted with CHCl$_3$—CH$_3$OH (10:1) to yield N$^6$-(p-methylbenzyl)-2'-deoxy-adenosine (240 mg): $^1$H NMR (300 MHz, DMSO-d$_6$): the 2'-deoxy-adenosine moiety δ 8.34 (2H, brs, H-8, NH), 8.18 (1H, s, H-2), 6.34 (1H, dd, J=7.5, 5.7 Hz, H-1'), 5.29 (1H, d, J=4.2 Hz, OH), 5.20 (1H, brs, OH), 4.40 (1H, m, H-4'), 3.87 (1H, m, H-3'), 3.61 (1H, m, H-5'a), 3.51 (1H, m, H-5'b), 2.72 (1H, m, H-2'a), 2.26 (1H, m, H-2'b); the p-methylbenzyl moiety δ 7.20 (2H, d, J=8.1 Hz, H-2", H-6"), 7.07 (2H, d, J=8.1 Hz, H-3", H-5"), 4.64 (2H, s, H-7"), 2.23 (3H, s, Me); $^{13}$C NMR (300 MHz, DMSO-d$_6$): the 2'-deoxy-adenosine moiety δ 154.5 (C-6), 152.3 (C-2), 148.3 (C-4), 139.5 (C-8), 119.7 (C-5), 88.0 (C-1'), 84.0 (C-4'), 71.0 (C-3'), 61.9 (C-5'), 38.9 (C-2'); the p-methylbenzyl moiety δ 137.0 (C-1"), 135.6 (C-4"), 128.7 (C-2", C-6"), 127.1 (C-3", C-5"), 42.6 (C-7"), 20.6 (Me).

Example 152: Preparation of N$^6$-(o-hydroxybenzyl)-2'-deoxy-3',5'-diacetyl adenosine

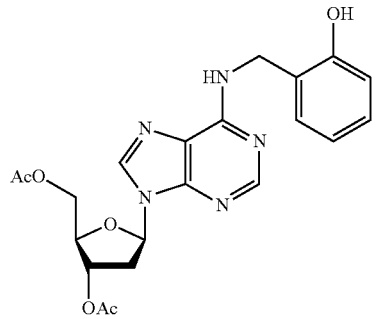 [SMILES: CC(=O)OC[C@H]1O[C@@H](n2cnc3c(NCc4ccccc4O)ncnc32)C[C@H]1OC(C)=O]

A mixture of 3',5'-diacetyl-2'-deoxy-6-bromo-adenosine (500 mg), o-hydroxy-benzylamine (400 mg, the hydrochloride) and triethylamine (318 mg) in anhydrous EtOH (40 ml) was refluxed for 5 h. After evaporation of the reaction mixture, the residue was separated by column chromatography over silica gel and eluted with CHCl$_3$—CH$_3$OH (50:1) to yield N$^6$-(o-hydroxy-benzyl)-2'-deoxy-3',5'-diacetyl adenosine (380 mg): $^1$H NMR (300 MHz, CDCl$_3$): the 2'-deoxy-adenosine moiety δ 8.41 (1H, s, H-8), 7.92 (1H, s, H-2), 7.06 (1H, brs, NH), 6.38 (1H, dd, J=7.5, 6.0 Hz, H-1'), 5.39 (1H, m, H-3'), 4.39-4.29 (3H, m, H-4', H-5'), 2.88 (1H, m, H-2'a), 2.60 (1H, m, H-2'b); the o-hydroxybenzyl moiety δ 11.2 (1H, brs, OH), 7.21-7.16 (2H, m, H-4", H-6"), 6.92 (1H, brs, J=7.8 Hz, H-3"), 6.82 (1H, brt, J=7.8 Hz, H-5"), 4.63 (2H, brd, J=6 Hz, H-7"); the acetyl δ 2.11 (3H, s, CH$_3$CO), 2.05 (3H, s, CH$_3$CO); $^{13}$C NMR (300 MHz, CDCl$_3$): the 2'-deoxy-adenosine moiety δ 153.8 (C-6), 152.1 (C-2), 148.4 (C-4), 138.2 (C-8), 120.0 (C-5), 84.6 (C-1'), 82.5 (C-4'), 74.4 (C-3'), 63.7 (C-5'), 37.5 (C-2'); the o-hydroxybenzyl moiety δ 155.8 (C-2"), 124.9 (C-1"), 131.0 (C-6"), 129.8 (C-4"), 120.0 (C-3"), 118.3 (C-5"), 41.2 (C-7"); the acetyl δ 170.4, 170.3, 20.8, 20.70.

Example 153: Preparation of N$^6$-(o-hydroxybenzyl)-2'-deoxyadenosine

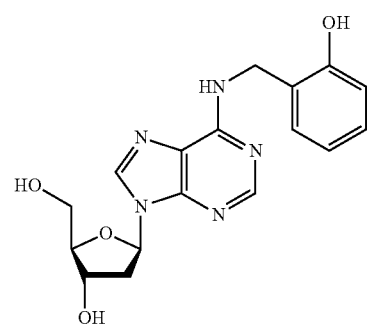 [SMILES: OC[C@H]1O[C@@H](n2cnc3c(NCc4ccccc4O)ncnc32)C[C@H]1O]

N$^6$-(o-hydroxybenzyl)-2'-deoxy-3',5'-diacetyl adenosine (280 mg) prepared in the above example, was added to methanol-ammonia (2.0 mol/L, 5 ml). The reaction solution was stirred at room temperature for 6 h. After evaporation of the reaction mixture, the residue was separated by column chromatography over silica gel and eluted with CHCl$_3$—CH$_3$OH (10:1) to yield N$^6$-(o-hydroxybenzyl)-2'-deoxyadenosine (220 mg): $^1$H NMR (300 MHz, DMSO-d$_6$): the 2'-deoxy-adenosine moiety δ 8.37 (1H, s, H-2), 8.21 (1H, s, H-8), 8.20 (1H, brs, NH), 6.35 (1H, brs, H-1'), 5.30 (1H, brs, OH), 5.18 (1H, brs, OH), 4.41 (1H, brs, H-3'), 3.87 (1H, brs, H-4'), 3.60 (1H, m, H-5'a), 3.53 (1H, m, H-5'b), 2.72 (1H, m, H-2'a), 2.28 (1H, m, H-2'b); the o-hydroxybenzyl moiety δ 9.90 (1H, brs, OH), 7.08-7.04 (2H, m, H-4", H-6"), 6.79 (1H, m, H-3"), 6.70 (1H, m, H-5"), 4.60 (2H, s, H-7"); $^{13}$C NMR (300 MHz, DMSO-d$_6$): the 2'-deoxyadenosine moiety δ 154.4 (C-6), 152.1 (C-2), 148.2 (C-4), 139.6 (C-8), 120.0 (C-5), 88.0 (C-1'), 83.9 (C-4'), 70.9 (C-3'), 61.8 (C-5'), 38.9 (C-2'); the o-hydroxybenzyl moiety δ 154.9 (C-2"), 128.1 (C-4"), 127.7 (C-6"), 125.6 (C-1"), 118.9 (C-3"), 115.3 (C-5"), 43.0 (C-7").

Example 154: Preparation of N$^6$-(3,4-methylenedioxy-benzyl)-3',5'-diacetyl-2'-deoxyadenosine

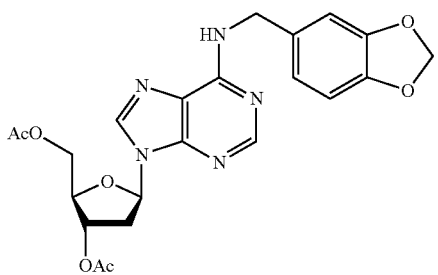 [SMILES: CC(=O)OC[C@H]1O[C@@H](n2cnc3c(NCc4ccc5c(c4)OCO5)ncnc32)C[C@H]1OC(C)=O]

A mixture of 3',5'-diacetyl-2'-deoxy-6-bromo-adenosine (420 mg), 3,4-methylene dioxy-benzylamine (320 mg, the hydrochloride) and triethylamine (267 mg) in anhydrous EtOH (30 ml) was refluxed for 5 h. After evaporation of the reaction mixture, the residue was separated by column chromatography over silica gel and eluted with CHCl$_3$—CH$_3$OH (40:1) to yield N$^6$-(3,4-methylene-dioxy-benzyl)-3',5'-diacetyl-2'-deoxyadenosine (460 mg): $^1$H NMR (300 MHz, CDCl$_3$): the 2'-deoxyadenosine moiety δ 8.34 (1H, brs, H-2), 7.86 (1H, brs, H-8), 6.62 (1H, m, NH), 6.38 (1H, dd, J=6.3, 7.5 Hz, H-1'), 5.38 (1H, m, H-3'), 4.38-4.27 (3H, m, H-4', H-5'), 2.90 (1H, m, H-2'a), 2.61-2.54 (1H, m, H-2'b); the 3,4-methylene dioxy-benzyl moiety δ 6.81 (1H, brs, H-2"), 6.78 (1H, brd, J=8.4 Hz, H-6"), 6.71 (1H, t, J=8.4 Hz, H-5"), 5.88 (2H, s, OCH$_2$O), 4.72 (2H, s, H-7"); the acetyl δ 2.09 (3H, s, CH$_3$CO), 2.04 (3H, s, CH$_3$CO); $^{13}$C NMR (300 MHz, acetone-d$_6$): the 2'-deoxy-adenosine moiety δ 155.4 (C-6), 153.3 (C-2), 149.7 (C-4), 139.7 (C-8), 120.7 (C-5), 85.0 (C-1'), 82.9 (C-4'), 75.3 (C-3'), 64.2 (C-5'), 36.7 (C-2'); the 3,4-methylenedioxy-benzyl moiety δ 148.2 (C-3"), 147.1 (C-4"), 134.5 (C-1"), 121.3 (C-6"), 108.6 (C-2"), 108.4 (C-5"), 101.5 (OCH$_2$O), 43.7 (C-7"); the acetyl 6170.5, 170.4, 20.6, 20.30.

Example 155: Preparation of N$^6$-(3,4-methylenedioxy-benzyl)-2'-deoxyadenosine

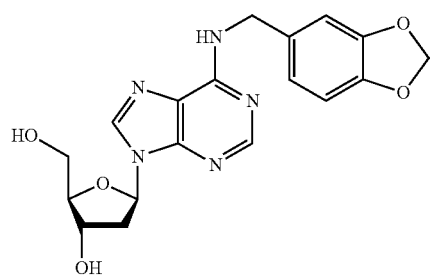 [SMILES: OC[C@H]1O[C@@H](n2cnc3c(NCc4ccc5c(c4)OCO5)ncnc32)C[C@H]1O]

N$^6$-(3,4-methylenedioxy-benzyl)-3',5'-diacetyl-2'-deoxyadenosine (190 mg) was added to methanol-ammonia (2.0 mol/L, 5 ml). The reaction solution was stirred at room temperature for 6 h. After evaporation of the reaction mixture, the residue was separated by column chromatography over silica gel and eluted with CHCl$_3$—CH$_3$OH (10:1) to yield N$^6$-(3,4-methylenedioxy-benzyl)-2'-deoxyadenosine (140 mg): $^1$H NMR (300 MHz, DMSO-d$_6$): the 2'-deoxyadenosine moiety δ 8.35 (2H, brs, H-2, NH), 8.19 (1H, s, H-8), 6.34 (1H, dd, J=6.6, 7.3 Hz, H-1'), 5.29 (1H, d, J=1.8 Hz, OH), 5.18 (1H, t, J=6.0 Hz, OH), 4.39 (1H, m, H-3'), 3.87 (1H, d, J=2.4 Hz, H-4'), 3.61 (1H, ddd, J=4.5, 4.8, 11.7 Hz, H-5'a), 3.49 (1H, ddd, J=4.5, 6.6, 11.7 Hz, H-5'b), 2.72 (1H, ddd, J=6.0, 7.8, 13.5 Hz, H-2'a), 2.24 (1H, ddd, J=2.4, 5.7, 13.5 Hz, H-2'b); the 3,4-methylenedioxy-benzyl moiety δ 6.90 (1H, s, H-6"), 6.80 (2H, s, H-2", H-5"), 5.93 (2H, s, OCH$_2$O), 4.60 (2H, s, H-7"); $^{13}$C NMR (300 MHz, DMSO-d$_6$): the 2'-deoxyadenosine moiety δ 154.4 (C-6), 152.4 (C-2), 148.3 (C-4), 139.6 (C-8), 119.8 (C-5), 88.1 (C-4'), 84.0 (C-1'), 71.0 (C-3'), 61.9 (C-5'), 42.7 (C-2'); the 3,4-methylenedioxy-benzyl moiety δ 147.2 (C-3"), 146.0 (C-4"), 134.0 (C-1"), 120.4 (C-6"), 108.0 (C-2"), 107.9 (C-5"), 100.8 (OCH$_2$O), 39.5 (C-7").

Example 156: Preparation of N$^6$-[(±)-1-(3,4,5-trimethoxyphenyl)-ethyl]-2'-deoxy-3',5'-diacetyl adenosine

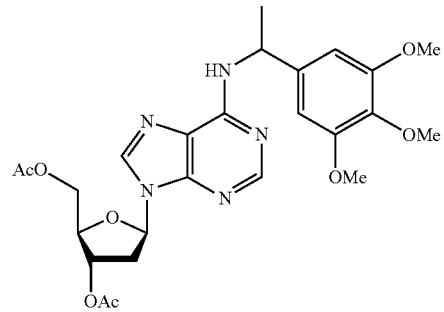 [SMILES: COc1cc(C(C)Nc2ncnc3c2ncn3[C@H]2C[C@@H](OC(C)=O)[C@@H](COC(C)=O)O2)cc(OC)c1OC]

A mixture of 3',5'-diacetyl-2'-deoxy-6-bromo-adenosine (420 mg), 1-(3,4,5-trimethoxyphenyl)-ethylamine (327 mg, the hydrochloride) and triethylamine (240 mg) in anhydrous EtOH (40 ml) was refluxed for 5 h. After evaporation of the reaction mixture, the residue was separated by column chromatography over silica gel and eluted with CHCl$_3$—CH$_3$OH (100:1) to yield N$^6$-[(±)-1-(3,4,5-trimethoxyphenyl)-ethyl]-2'-deoxy-3',5'-diacetyl adenosine (560 mg): $^1$H NMR (300 MHz, CDCl$_3$): the 2'-deoxyadenosine moiety δ 8.27 (1H, s, H-2), 7.86 (1H, s, H-8), 6.35 (1H, m, NH), 6.33 (1H, m, H-1'), 5.33 (1H, m, H-3'), 4.35-4.24 (3H, m, H-4', H-5'), 2.88 (1H, m, H-2'a), 2.51 (1H, m, H-2'b); the (±)-1-(3,4,5-tri-methoxyphenyl)-ethyl moiety δ 6.58 (2H, s, H-2", H-6"), 5.47 (1H, brs, H-7"), 3.73 (6H, s, OMe), 3.71 (3H, s, OMe), 1.53 (3H, d, J=6.6 Hz, C-8"); the acetyl δ 2.02 (3H, s), 1.97 (3H, s); $^{13}$C NMR (300 MHz, acetone-d$_6$): the 2'-deoxyadenosine moiety δ 154.7 (C-6), 153.3 (C-2), 149.6 (C-4), 139.6 (C-8), 120.5 (C-5), 84.9 (C-1'), 82.8 (C-4'), 75.2 (C-3'), 64.2 (C-5'), 36.7 (C-2'); the (±)-1-(3,4,5-trimethoxyphenyl)-ethyl moiety δ 153.9 (C-3", C-5"), 141.0 (C-1"), 137.7 (C-4"), 104.3 (C-2", C-6"), 60.1 (OMe), 56.0 (OMe), 50.2 (C-7"), 22.8 (C-8"); the acetyl 6170.5, 170.5, 20.6, 20.40.

Example 157: Preparation of $N^6$-[(±)-1-(3,4,5-trimethoxyphenyl)-ethyl]-2'-deoxy-adenosine

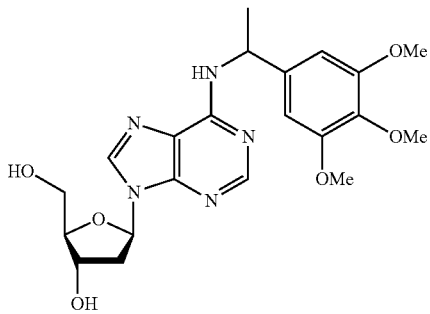 [SMILES: COc1cc(C(C)Nc2ncnc3c2ncn3[C@H]2C[C@@H](O)[C@@H](CO)O2)cc(OC)c1OC]

$N^6$-[(±)-1-(3,4,5-trimethoxyphenyl)-ethyl]-2'-deoxy-3',5'-diacetyl adenosine (240 mg) prepared in the above example, was added to methanol-ammonia (2.0 mol/L, 5 ml). The reaction solution was stirred at room temperature for 6 h. After evaporation of the reaction mixture, the residue was separated by column chromatography over silica gel and eluted with $CHCl_3$—$CH_3OH$ (10:1) to yield $N^6$-[(±)-1-(3,4,5-trimethoxyphenyl)-ethyl]-2'-deoxyadenosine (160 mg): $^1H$ NMR (300 MHz, acetone-$d_6$): the 2'-deoxyadenosine moiety δ 8.18 (1H, s, H-2), 8.17 (1H, s, H-8), 7.18 (1H, m, NH), 6.40 (1H, dd, J=5.7, 8.7, H-1'), 5.62 (1H, brs, OH), 4.62 (1H, m, H-3'), 4.42 (1H, brs, OH), 4.06 (1H, brs, H-4'), 3.75 (1H, m, H-5'a), 3.66 (1H, m, H-5'b), 2.85 (1H, m, H-2'a), 2.30 (1H, m, H-2'b); the (±)-1-(3,4,5-trimethoxyphenyl)-ethyl moiety δ 6.88 (2H, s, H-2", H-6"), 5.62 (1H, brs, H-7"), 3.79 (6H, s, OMe), 3.62 (3H, s, OMe), 1.63 (3H, d, J=6.6 Hz, C-8"); $^{13}C$ NMR (300 MHz, acetone-$d_6$): the 2'-deoxyadenosine moiety δ 155.3 (C-6), 154.3 (C-2), 149.3 (C-4), 141.2 (C-8), 121.6 (C-5), 90.2 (C-1'), 87.4 (C-4'), 73.3 (C-3'), 63.8 (C-5'), 41.2 (C-2'); the (±)-1-(3,4,5-trimethoxyphenyl)-ethyl moiety δ 152.9 (C-3", C-5"), 140.8 (C-1"), 138.3 (C-4"), 104.9 (C-2", C-6"), 60.4 (OMe), 56.5 (OMe), 50.7 (C-7"), 23.0 (C-8").

PHARMACOLOGICAL EXPERIMENTS

Example 1

$N^6$-substituted adenosine derivatives and/or $N^6$-substituted adenine derivatives potentiated sodium pentobarbital-induced sleep in mice Name of Experiment: Sub-threshold hypnotic dose sodium pentobarbital induced sleeping test Method of Experiment: Mice (n=7-10) were pretreated with test compound or vehicle, after 30 min, a maximal sub-threshold hypnotic dose of sodium pentobarbital (22 mg/kg) was given intraperitoneally (ip). (On some condition, the sub-threshold dosage of sodium pentobarbital should be optimized to the maximum dose, at which the rate of sleep onset of vehicle group is less than 10%). The criterion for sleep is that the mouse was placed on its back and exhibited a loss-of-righting reflex for more than 1 min. Following sodium pentobarbital injection, each mouse was observed 15 min for onset of sleep. The percentage of sleep onset was calculated as: (number of animals falling asleep/total number of animals)×100%. The detailed data are shown in Table 1.

TABLE 1

Intraperitoneal administration of test compounds potentiated sodium pentobarbital-induced sleep.

| Groups | Dosage (mg/kg) | Sleep rate (%) |
|---|---|---|
| control group | — | 0 |
| zolpidem | 2 | 75 |
| $N^6$-(p-hydroxybenzyl)-adenosine | 1 | 63 |
| $N^6$-(3-methxoy-4-hydroxybenzyl)-adenosine | 1 | 100 |
| $N^6$-(3,4-dihydroxybenzyl)-adenosine | 1 | 87 |
| $N^6$-(2-furanylmethyl)-adenosine | 5 | 71 |
| $N^6$-(2-thiopheneylmethyl)-adenosine | 5 | 71 |
| $N^6$-(p-trifluoromethyl)-adenosine | 5 | 57 |
| $N^6$-(3,4-methylenedioxybenzyl)-adenosine | 5 | 100 |
| $N^6$-(p-trifluoromethoxybenzyl)-adenosine | 5 | 43 |
| $N^6$-(p-fluorobenzyl)-adenosine | 5 | 71 |
| $N^6$-(4-phenyl-piperazinyl)-adenosine | 5 | 50 |
| $N^6$-(4-hydroxy-3,5-dimethoxybenzyl)-adenosine | 5 | 86 |
| $N^6$-(p-chlorobenzyl)-adenosine | 1 | 50 |
| $N^6$-(p-nitrobenzyl)-adenosine | 1 | 63 |
| $N^6$-(3-methoxy-4-hydroxybenzyl)-adenine | 1 | 38 |
| $N^6$-(o-hydroxybenzyl)-adenosine | 1 | 88 |
| $N^6$-(o-methoxybenzyl)-adenosine | 1 | 100 |
| $N^6$-(m-aminobenzyl)-adenosine | 1 | 100 |
| $N^6$-[(±)-1-(phenyl)-ethyl]-adenosine | 5 | 100 |
| $N^6$-(3,4-dihydroxybenzyl)-adenosine | 5 | 100 |
| $N^6$-(p-trifluoromethyl)-adenosine | 5 | 57 |
| $N^6$-(3,4-methylenedioxybenzyl)-adenosine | 5 | 100 |
| $N^6$-(p-trifluoromethoxybenzyl)-adenosine | 5 | 43 |
| $N^6$-(p-fluorobenzyl)-adenosine | 5 | 71 |
| N-(6-adenosine)-(L)-tryptophan | 5 | 14 |
| $N^6$-(4-hydroxy-3,5-dimethoxybenzyl)-adenosine | 5 | 86 |
| N-(6-adenosine)-5-hydroxy tryptophan | 5 | 17 |
| N-(6-adenosine)-(D)-phenylalanine | 5 | 17 |
| N-(6-adenosine)-(D)-tyrosine | 5 | 17 |
| $N^6$-[(1H-indole-3-yl)-ethyl]-adenosine | 5 | 86 |
| $N^6$-(2-thiopheneylmethyl)-adenosine | 5 | 29 |
| N-(6-adenosine)-(L)-serine | 5 | 29 |
| N-(6-adenosine)-(D)-serine | 5 | 14 |
| $N^6$-[(1H-imidazole-4-yl)-ethyl]-adenosine | 1 | 88 |
| $N^6$-[(3-hydroxy-4-methoxyphenyl)-ethyl]-adenosine | 1 | 50 |
| $N^6$-[(3-methoxy-4-hydroxyphenyl)-ethyl]-adenosine | 1 | 88 |
| $N^6$-(p-chlorobenzyl)-adenosine | 1 | 50 |
| $N^6$-(p-nitrobenzyl)-adenosine | 1 | 63 |
| $N^6$-(o-hydroxylbenzyl)-adenosine | 1 | 88 |
| $N^6$-(3,4-dimethoxybenzyl)-adenosine | 1 | 100 |
| $N^6$-(4-methoxy-3-hydroxybenzyl)-adenosine | 1 | 86 |
| $N^6$-(o-nitrobenzyl)-adenosine | 1 | 100 |

Example 2

Effects of $N^6$-substituted adenosine derivatives and/or $N^6$-substituted adenine derivatives on sodium pentobarbital-induced sleeping time in mice.

Name of Experiment: Potentiation of sodium pentobarbital sleeping time test.

Method of Experiment: Groups of 8-10 male ICR-mice with an average weight of 18-22 g were used. They were dosed orally or i.p. with the test compound or the vehicle. Thirty min after i.p. injection or 60 min after oral dosing 38 mg/kg sodium pentobarbital were injected intravenously. The latency and duration of sleep (loss of righting reflex) were recorded. The percentage of prolongation of sleeping time was calculated as: [(sleeping time of experimental group)−(sleeping time of control group)]/(sleeping time of control group)×100%. The detailed data are shown in Tables 2 and 3.

TABLE 2

The effects of intraperitoneal administration of test compounds on sodium pentobarbital-induced sleep time.

| Groups | Dosage (mg/kg) | Sleep prolonging rate (%) |
|---|---|---|
| solvent control | | |
| $N^6$-(m-methylbenzyl)-adenoisne | 1 | 84 |
| $N^6$-(p-methylbenzyl)-adenosine | 1 | 51 |
| $N^6$-(p-trifluoromethylbenzyl)-adenosine | 5 | 23 |
| $N^6$-(p-fluorobenzyl)-adenosine | 5 | 73 |
| $N^6$-(p-nitrobenzyl)-adenosine | 1 | 16 |
| $N^6$-(m-aminobenzyl)-adenosine | 1 | 101 |
| $N^6$-(p-aminobenzyl)-adenosine | 1 | 165 |
| $N^6$-(p-trifluoromethoxybenzyl)-adenosine | 5 | 44 |
| $N^6$-(3,4-dihydroxybenzyl)-adenosine | 5 | 32 |
| $N^6$-(3,4-methylenedioxybenzyl)-adenosine | 5 | 175 |
| $N^6$-(4-hydroxy-3,5-dimethoxybenzyl)-adenosine | 5 | 336 |
| $N^6$-(3,4,5-trimethoxybenzyl)-adenosine | 1 | 112 |
| $N^6$-(5-methyl-2-furanylmethyl)-adenosine | 5 | 7 |
| $N^6$-(2-thiopheneylmethyl)-adenosine | 5 | 12 |
| $N^6$-(4-phenylpiperazinyl)-adenosine | 5 | 34 |
| $N^6$-[(±)-1-(phenyl)-ethyl]-adenosine | 5 | 254 |
| $N^6$-[(3-hydroxy-4-methoxyphenyl)-ethyl]-adenosine | 1 | 1 |
| $N^6$-[(3-methoxy-4-hydroxyphenyl)-ethyl]-adenosine | 1 | 13 |
| $N^6$-[(3,4-dihydroxyphenyl)-ethyl]-adenosine | 1 | 98 |
| $N^6$-[(1H-imidazole-4-yl)-ethyl]-adenosine | 1 | 43 |
| $N^6$-[(1H-indole-3-yl)-ethyl]-adenosine | 5 | 147 |
| N-(6-adenosine)-(L)-proline | 5 | 29 |
| N-(6-adenosine)-(L)-serine | 5 | 15 |
| N-(6-adenosine)-(D)-serine | 5 | 0 |
| N-(6-adenosine)-(D)-phenylalanine | 5 | 19 |
| N-(6-adenosine)-(L)-phenylalanine | 5 | 44 |
| N-(6-adenosine)-(D)-tyrosine | 5 | 82 |
| N-(6-adenosine)-(L)-tyrosine | 5 | 66 |
| N-(6-adenosine)-(L)-tryptophan | 5 | 69 |
| N-(6-adenosine)-(D)-tryptophan | 5 | 89 |
| N-(6-adenosine)-5-hydroxy tryptophan | 5 | 60 |

TABLE 3

The effects of oral administration of test compounds on sodium pentobarbital-induced sleep time.

| Groups | Dosage (mg/kg) | Sleep prolonging rate (%) |
|---|---|---|
| solvent control | | |
| $N^6$-(3,4-dihydroxybenzyl)-adenosine | 4 | 74 |
| $N^6$-(3-methoxy-4-hydroxybenzyl)-adenosine | 4 | 87 |
| $N^6$-(p-hydroxybenzyl)-adenosine | 1 | 90 |
| $N^6$-(m-aminobenzyl)-adenosine | 5 | 50 |
| $N^6$-(p-aminobenzyl)-adenosine | 5 | 171 |
| $N^6$-(m-methylbenzyl)-adenosine | 5 | 174 |
| $N^6$-[(3,4-dihydroxyphenyl)-ethyl]-adenosine | 5 | 69 |
| $N^6$-(diphenylmethyl)-adenosine | 5 | 16 |
| $N^6$-[(±)-(6-methoxy-1,2,3,4-tetrahydro-naphthalene-1-yl)]-adenosine | 5 | 170 |
| $N^6$-[(±)-hydroxy-1,2,3,4-tetrahydro-naphthalene-1-yl)]-adenosine | 5 | 39 |
| $N^6$-[(±)-1-(cyclohexylphenyl)-methyl]-adenosine | 5 | 17 |
| $N^6$-(fluorene-9-yl)-adenosine | 5 | 53 |
| $N^6$-(3-methoxy-4-lauroyloxybenzyl)-2',3'-O-isopropylidene-adenosine-5'-laurate | 5 | 27 |
| $N^6$-(3-methoxy-4-octanoyloxy-benzyl)-adenosine-5'-caprylate | 5 | 184 |
| $N^6$-(3-methoxy-4-butanoyloxy-benzyl)-adenosine-5'-butyrate | 5 | 11 |
| $N^6$-(3-methoxy-4-butanoyloxy-benzyl)-2',3'-O-isopropylidene-adenosine-5'-butyrate | 5 | 21 |
| $N^6$-(3,4-methylenedioxy-benzyl)-2',3'-O-isopropylidene-adenosine-5'-caprylate | 5 | 4 |
| $N^6$-(3,4-methylenedioxy-benzyl)-adenosine-5'-caprylate | 5 | 26 |
| $N^6$-[(R)-1-(phenyl)-propyl]-adenosine-2',3'-O-isopropylidene-5'-acetate | 5 | 18 |
| $N^6$-(3-methoxy-4-butanoyloxy-benzyl)-adenosine | 5 | 11 |
| $N^6$-[(R)-1-(4-methylphenyl)-ethyl]-adenosine | 5 | 99 |
| $N^6$-[(S)-1-(4-methylphenyl)-ethyl]-adenosine | 5 | 19 |
| $N^6$-[(S)-1-(3-methoxyphenyl)-ethyl]-adenosine | 5 | 39 |
| $N^6$-[(R)-1-(3-methoxyphenyl)-ethyl]-adenosine | 5 | 160 |
| $N^6$-[(±)-1-(4-hydroxyphenyl)-ethyl]-adenosine | 5 | 50 |
| $N^6$-[(L)-2-(hydroxy)-1-(phenyl)-ethyl]-adenosine | 5 | 67 |
| $N^6$-[(±)-1-(1,2-diphenyl)-ethyl]-adenosine | 5 | 36 |
| $N^6$-[(±)-1-(phenyl)-propyl]-adenosine | 2.5 | 135 |
| $N^6$-[(R)-1-(phenyl)-propyl]-adenosine | 2.5 | 183 |
| $N^6$-[(S)-1-(phenyl)-propyl]-adenosine | 2.5 | 49 |
| $N^6$-[(R)-1-(4-methoxyphenyl)-ethyl]-adenosine | 5 | 66 |
| $N^6$-[(R)-1-(4-methoxyphenyl)-propyl]-adenosine | 2.5 | 86 |
| $N^6$-[(±)-1-(4-aminophenyl)-ethyl]-adenosine | 2.5 | 132 |
| $N^6$-[(±)-1-(phenyl)-butyl]-adenosine | 5 | 57 |
| $N^6$-[(±)-1-(4-methoxyphenyl)-butyl]-adenosine | 5 | 80 |
| $N^6$-(3-methoxy-4-hydroxy-benzyl)-3',5'-diacetyl-2'-deoxyadenosine | 5 | 71 |
| $N^6$-(p-methylbenzyl)-2'-deoxy-3',5'-diacetyl adenosine | 5 | 9 |

TABLE 3-continued

The effects of oral administration of test compounds on sodium pentobarbital-induced sleep time.

| Groups | Dosage (mg/kg) | Sleep prolonging rate (%) |
|---|---|---|
| $N^6$-(p-methylbenzyl)-2'-deoxyadenosine | 5 | 34 |
| $N^6$-(3,4-methylenedioxy-benzyl)-3',5'-diacetyl-2'-deoxyadenosine | 5 | 29 |
| $N^6$-[(±)-1-(3,4,5-trimethoxyphenyl)-ethyl]-adenosine-5'-caprylate | 5 | 130 |
| $N^6$-[(±)-1-(3,4,5-trimethoxyphenyl)-ethyl]-adenosine-5'-methoxy-phenyl propionate | 5 | 76 |
| N-(6-adenosine)-(D)-phenylalanine methyl ester | 5 | 2 |
| N-(6-adenosine)-(D)-tyrosine ethyl ester | 5 | 32 |
| N-(6-adenosine)-(L)-tyrosine ethyl ester | 5 | 36 |
| N-(6-adenosine)-(L)-tryptophan ethyl ester | 5 | 7 |
| N-(6-adenosine)-(D)-tryptophan ethyl ester | 5 | 16 |
| $N^6$-[(R)-1-(phenylpropyl)]-adenosine-2',3',5'-triacetate | 5 | 339 |
| $N^6$-[(1S,2S)-2-(1,3-dihydroxy-1-phenyl)-propyl]-adenosine | 5 | 33 |
| $N^6$-[(1R,2R)-2-(1,3-dihydroxy-1-phenyl)-propyl]-adenosine | 5 | 4 |
| $N^6$-[2-(1,3-dihydroxy)-propyl]-adenosine | 5 | 184 |
| $N^6$-[(L)-2-(1-hydroxy-3-methyl)-pentyl]-adenosine | 5 | 36 |
| $N^6$-[(L)-2-(1-hydroxy-4-methylthioyl)-butyl]-adenosine | 5 | 53 |
| $N^6$-{(1S,2R)-[2-hydroxy-(1,2-diphenyl)]-ethyl}-adenosine | 5 | 46 |
| $N^6$-{(1R,2S)-[2-hydroxy-(1,2-diphenyl)]-ethyl}-adenosine | 5 | 38 |
| $N^6$-methyl-$N^6$-[2-(1S,2R)-(1-hydroxy-1-phenyl)-propyl]-adenosine | 5 | 39 |
| $N^6$-methyl-$N^6$-[(±)-2-(1-hydroxy-1-phenyl)-propyl]-adenosine | 5 | 92 |
| $N^6$-[(R)-1-(phenyl)-propyl]-adenine | 5 | 42 |
| $N^6$-[(R)-1-(phenyl)-ethyl]-adenine | 5 | 21 |
| $N^6$-[(R)-1-(phenyl)-propyl]-$N^9$-(tetrahydrofuran-2-yl)-adenine | 5 | 2 |
| $N^6$-[(S)-1-(phenylpropyl)]-adenosine-2',3',5'-triacetate | 5 | 41 |
| $N^6$-[(±)-1-(3,4,5-trimethoxyphenyl)-ethyl]-adenosine-5'-decanoic ether | 5 | 2 |
| $N^6$-[(S)-1-(phenyl)-propyl]-adenosine-5'-decanoic ether | 5 | 4 |
| $N^6$-[(S)-1-(phenyl)-propyl]-adenosine-5'-propyl ether | 5 | 4 |
| $N^6$-(3,4-methylenedioxy-benzyl)-adenosine-5'-propyl ether | 5 | 36 |
| $N^6$-[(R)-1-(phenyl)-propyl]-adenosine-5'-o-nitrophenyl ether | 5 | 87 |
| $N^6$-[(R)-1-(phenyl)-propyl]-adenosine-5'-propyl ether | 5 | 318 |
| $N^6$-[(±)-1-(3,4,5-trimethoxyphenyl)-ethyl]-2'-deoxyadenosine | 5 | 9 |
| $N^6$-[(S)-1-(phenyl)-propyl)]-adenosine-5'-acetate | 5 | 24 |
| $N^6$-[(S)-1-(phenyl)-propyl]-adenosine-5'-methyl-cinnamate | 5 | 50 |
| $N^6$-[(R)-1-(phenylpropyl)]-adenosine-5'-acetate | 5 | 590 |
| $N^6$-[(±)-1-(3,4,5-trimethoxyphenyl) ethyl]-adenosine-5'-propyl ether | 5 | 14 |
| $N^6$-(4-hydroxy-3,5-dimethoxybenzyl)-adenosine | 5 | 121 |
| $N^6$-[(1H-indole-3-yl)-ethyl]-adenosine | 5 | 78 |
| $N^6$-(m-methylbenzyl)-adenosine | 5 | 136 |
| $N^6$-[(±)-1-(phenyl)-ethyl]-adenosine | 5 | 201 |
| $N^6$-methyl-$N^6$-benzyl-adenosine | 5 | 27 |
| $N^6$-ethyl-$N^6$-benzyl-adenosine | 5 | 7 |
| $N^6$-ethyl-$N^6$-(2-hydroxyethyl)-adenosine | 5 | 5 |
| $N^6$, $N^6$-Bis(2-hydroxypropyl)-adenosine | 5 | 5 |
| $N^6$-methyl-$N^6$-cyclohexyl-adenosine | 5 | 55 |
| $N^6$-[(R)-1-(4-chlorophenyl)-ethyl]-adenosine | 5 | 103 |
| $N^6$-[(S)-1-(4-chlorophenyl)-ethyl]-adenosine | 5 | 33 |
| $N^6$-[(R)-1-(4-fluorophenyl)-ethyl]-adenosine | 5 | 136 |
| $N^6$-[(S)-1-(4-fluorophenyl)-ethyl]-adenosine | 5 | 24 |
| $N^6$-(2-hydroxyethyl)-$N^6$-benzyl-adenosine | 5 | 18 |
| $N^6$-methyl-$N^6$-[2-(1R,2R)-(1-hydroxy-1-phenyl)-propyl]-adenosine | 5 | 44 |
| $N^6$-[(R)-1-(phenyl)-butyl]-adenosine | 5 | 163 |
| $N^6$-[(±)-1-(3-methoxy-4-hydroxy-phenyl)-ethyl]-adenosine | 5 | 119 |
| $N^6$-(p-nitrobenzyl)-adenosine | 5 | 29 |
| $N^6$-(o-hydroxylbenzyl)-adenosine | 5 | 92 |

The invention claimed is:
1. A compound that is an $N^6$-substituted adenosine derivative or an $N^6$-substituted adenine derivative, wherein said compound is selected from the group consisting of:
   (72) $N^6$-[(±)-1-(phenyl)-propyl]-adenosine
   (75) $N^6$-[(R)-1-(phenyl)-propyl]-adenosine
   (76) $N^6$-[(R)-1-(phenylpropyl)]-adenosine-2',3',5'-triacetate
   (77) $N^6$-[(R)-1-(phenylpropyl)]-adenosine-5'-acetate
   (78) $N^6$-[(S)-1-(phenylpropyl)]-adenosine
   (79) $N^6$-[(S)-1-(phenylpropyl)]-adenosine-2',3',5'-triacetate
   (80) $N^6$-[(S)-1-(phenylpropyl)]-adenosine-5'-acetate
   (81) $N^6$-[(S)-1-(phenyl)-propyl]-adenosine-5'-p-methyl-phenylpropionate
   (82) $N^6$-[(S)-1-(phenyl)-propyl]-adenosine-5'-methyl-cinnamate
   (85) $N^6$-[(R)-1-(phenyl)-propyl]-adenosine-5'-o-nitrophenyl ether
   (86) $N^6$-[(R)-1-(phenyl)-propyl]-adenosine-5'-propyl ether
   (87) $N^6$-[(±)-1-(phenyl)-butyl]-adenosine
   (89) $N^6$-[(R)-1-(phenyl)-butyl]-adenosine
   (90) $N^6$-[(S)-1-(phenyl)-butyl]-adenosine
   and
   (147) $N^6$-[(S)-1-(phenyl)-propyl]-$N^9$-(tetrahydrofuran-2-yl)-adenine.

2. A pharmaceutical composition comprising an effective dose of a compound according to claim 1 and pharmaceutically acceptable carrier(s).

3. A method of treating a subject having depression, insomnia, convulsion, epilepsy, Parkinson's disease, or dementia, the method comprising administering to the subject an effective dose of a compound according to claim 1.

4. A compound selected from the group consisting of:
(72) $N^6$-[(±)-1-(phenyl)-propyl]-adenosine,
(75) $N^6$-[(R)-1-(phenylpropyl)]-adenosine, and
(78) $N^6$-[(S)-1-(phenylpropyl)]-adenosine.

5. A pharmaceutical composition comprising an effective dose of a compound according to claim 4 and pharmaceutically acceptable carrier(s).

6. A method of treating a subject having depression, insomnia, convulsion, epilepsy, Parkinson's disease, or dementia, the method comprising administering to the subject an effective dose of a compound according to claim 4.

* * * * *